(12) United States Patent
Petersen et al.

(10) Patent No.: US 11,608,347 B2
(45) Date of Patent: Mar. 21, 2023

(54) OCTAHYDROPYRIDO[1,2-ALPHA]PYRAZINES AS MAGL INHIBITORS

(71) Applicant: Hoffmann-La Roche Inc., Little Falls, NJ (US)

(72) Inventors: Ann Petersen, Basel (CH); Joerg Benz, Basel (CH); Uwe Grether, Basel (CH); Benoit Hornsperger, Basel (CH); Buelent Kocer, Basel (CH); Bernd Kuhn, Basel (CH); Hans Richter, Basel (CH); Satoshi Tsuchiya, Tokyo (JP); Yangcheng Qiu, Hubei (CN); Rui Chen, Hubei (CN)

(73) Assignee: Hoffmann-La Roche Inc., Little Falls, NJ (US)

( * ) Notice: Subject to any disclaimer, the term of this patent is extended or adjusted under 35 U.S.C. 154(b) by 255 days.

(21) Appl. No.: 16/922,427

(22) Filed: Jul. 7, 2020

(65) Prior Publication Data

US 2021/0024546 A1    Jan. 28, 2021

Related U.S. Application Data

(63) Continuation of application No. PCT/EP2019/050198, filed on Jan. 7, 2019.

(30) Foreign Application Priority Data

Jan. 8, 2018   (EP) .................................. 18150649
Nov. 21, 2018  (WO) ................ PCT/CN2018/116691

(51) Int. Cl.
    *C07D 471/04*    (2006.01)
    *C07D 519/00*    (2006.01)

(52) U.S. Cl.
    CPC ......... *C07D 519/00* (2013.01); *C07D 471/04* (2013.01)

(58) Field of Classification Search
    USPC .................................................... 514/210.16
    See application file for complete search history.

(56) References Cited

U.S. PATENT DOCUMENTS

| 4,391,978 | A   | 7/1983  | Imhof et al. |
| 4,454,130 | A   | 6/1984  | Tominaga et al. |
| 4,632,925 | A   | 12/1986 | Mullin, Jr. et al. |
| 4,956,359 | A   | 9/1990  | Taylor, Jr. et al. |
| 7,488,737 | B2* | 2/2009  | Xie ................ A61P 29/00 546/183 |
| 8,614,209 | B2* | 12/2013 | Webster .......... A61P 9/00 514/214.03 |
| 10,106,556 | B2 | 10/2018 | Ikeda et al. |
| 10,610,520 | B2 | 4/2020  | Ikeda et al. |
| 11,390,610 | B2 | 7/2022  | Benz et al. |
| 11,420,961 | B2 | 8/2022  | Benz et al. |
| 2015/0018335 | A1 | 1/2015 | Cisar et al. |
| 2020/0255439 | A1 | 8/2020 | Kamata et al. |
| 2020/0299277 | A1 | 9/2020 | Benz et al. |
| 2020/0308158 | A1 | 10/2020 | Bell. et al. |
| 2020/0308190 | A1 | 10/2020 | Bell et al. |
| 2021/0024546 | A1 | 1/2021 | Petersen et al. |
| 2021/0053973 | A1* | 2/2021 | Ali .................. A61P 25/00 |
| 2021/0094943 | A1 | 4/2021 | Benz et al. |
| 2021/0094971 | A1 | 4/2021 | Grether et al. |
| 2021/0094972 | A1 | 4/2021 | Benz et al. |
| 2021/0094973 | A1 | 4/2021 | Gobbi et al. |
| 2021/0107920 | A1 | 4/2021 | Bell et al. |
| 2021/0107921 | A1 | 4/2021 | Benz et al. |
| 2021/0277020 | A1 | 9/2021 | Anselm et al. |
| 2021/0387999 | A1 | 12/2021 | Kuhn et al. |
| 2022/0098176 | A1 | 3/2022 | Benz et al. |
| 2022/0106328 | A1 | 4/2022 | Benz et al. |
| 2022/0135591 | A1 | 5/2022 | Benz et al. |
| 2022/0202963 | A1 | 6/2022 | Collin et al. |
| 2022/0213093 | A1 | 7/2022 | Benz et al. |
| 2022/0220373 | A1 | 7/2022 | Benz et al. |
| 2022/0242876 | A1 | 8/2022 | Kroll et al. |

(Continued)

FOREIGN PATENT DOCUMENTS

| EP | 3279191 A1  | 2/2018 |
| EP | 3312177 A2  | 4/2018 |
| WO | 01/07043 A1 | 2/2001 |

(Continued)

OTHER PUBLICATIONS

Mikhlina et al., Khimiya Geterotsiklicheskikh Soedinenii (1969), (3), 547-9.*

(Continued)

*Primary Examiner* — Niloofar Rahmani
(74) *Attorney, Agent, or Firm* — Carol S. Quagliato

(57) ABSTRACT

The invention provides new heterocyclic compounds having the general formula (Ie)

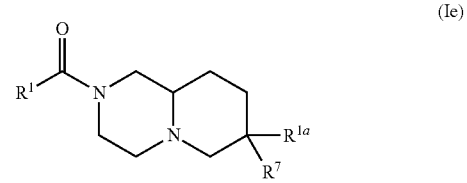

(Ie)

wherein $R^1$, $R^{1a}$ and $R^7$ are as described herein, compositions including the compounds, processes of manufacturing the compounds and methods of using the compounds.

30 Claims, No Drawings

(56) References Cited

U.S. PATENT DOCUMENTS

| | | |
|---|---|---|
| 2022/0267349 A1 | 8/2022 | Benz et al. |
| 2022/0275005 A1 | 9/2022 | Grether et al. |

FOREIGN PATENT DOCUMENTS

| | | |
|---|---|---|
| WO | 2004/00832 A1 | 12/2003 |
| WO | 2004/096763 A1 | 11/2004 |
| WO | 2005/066187 A1 | 7/2005 |
| WO | 2006/000914 A1 | 1/2006 |
| WO | 2006/001894 A1 | 1/2006 |
| WO | 2006/051410 A1 | 5/2006 |
| WO | 2007/002057 A1 | 1/2007 |
| WO | 2007/098418 A1 | 8/2007 |
| WO | 2007/117557 A2 | 10/2007 |
| WO | 2008/109336 A1 | 9/2008 |
| WO | 2009/058347 A1 | 5/2009 |
| WO | 2009/074789 A1 | 6/2009 |
| WO | 2009/112845 A1 | 9/2009 |
| WO | 2010/106333 A1 | 9/2010 |
| WO | 2011/059118 A1 | 5/2011 |
| WO | 2012/155199 A1 | 11/2012 |
| WO | 2013/028474 A1 | 2/2013 |
| WO | 2013/059118 A1 | 4/2013 |
| WO | 2013/179024 A1 | 12/2013 |
| WO | 2014/099633 A2 | 6/2014 |
| WO | 2015/179559 A2 | 11/2015 |
| WO | 2016/014975 A2 | 1/2016 |
| WO | 2016/109501 A1 | 7/2016 |
| WO | 2016/180536 A1 | 11/2016 |
| WO | 2016/185279 A1 | 11/2016 |
| WO | 2016/205590 A1 | 12/2016 |
| WO | 2017/087854 A1 | 5/2017 |
| WO | 2017/087858 A1 | 5/2017 |
| WO | 2017/087863 A | 5/2017 |
| WO | 2017/171100 A1 | 10/2017 |
| WO | 2018/134698 A1 | 7/2018 |
| WO | 2018/217809 A1 | 11/2018 |
| WO | 2019/065791 A1 | 4/2019 |
| WO | 2019/072785 A1 | 4/2019 |
| WO | 2019/105915 A1 | 6/2019 |
| WO | 2019/115660 A1 | 6/2019 |
| WO | 2019/134985 A1 | 7/2019 |
| WO | 2019/180185 A1 | 9/2019 |
| WO | 2020/035424 A1 | 2/2020 |
| WO | 2020/035425 A1 | 2/2020 |
| WO | 2020/104494 A1 | 5/2020 |
| WO | 2020/207941 A1 | 10/2020 |
| WO | 2021/005034 A1 | 1/2021 |
| WO | 2021/048036 A1 | 3/2021 |
| WO | 2021/048242 A1 | 3/2021 |
| WO | 2021/058416 A1 | 4/2021 |
| WO | 2021/058444 A1 | 4/2021 |
| WO | 2021/058445 A1 | 4/2021 |
| WO | 2022/043284 A1 | 3/2022 |
| WO | 2022/049134 A1 | 3/2022 |

OTHER PUBLICATIONS

Arata et al., Chemical & Pharmaceutical Bulletin (1973), 21(6), 1248-53.*

Likhosherstov et al., Khimiko-Farmatsevticheskii Zhurnal (1981), 15(8), 55-7.*

Brethous et al., Journal of Medicinal Chemistry (2012), 55(10), 4605-4618.*

Alpar et al., "Endocannabinoids modulate cortical development by configuring Slit2/Robo1 signaling" Nat Commun 5(4421):1-13 (Jul. 17, 2014).

Bernal-Chico et al., "Blockade of Monoacylglycerol Lipase Inhibits Oligodendrocyte Excitotoxicity and Prevents Demyelination In Vivo" GLIA 63:163-176 ( 2015).

Chanda et al., "Monoacylglycerol Lipase Activity Is a Critical Modulator of the Tone and Integrity of the Endocannabinoid System" Mol Pharmacol 78(6):996-1003 ( 2010).

Feliu et al., "2-Arachidonoylglycerol Reduces Proteoglycans and Enhances Remyelination in a Progressive Model of Demyelination" J. Neurosci. 37(35):8385-8398 (Aug. 30, 2017).

Iannotti et al., "Endocannabinoids and endocannabinoid-related mediators: Targets, metabolism and role in neurological disorders" Prog Lipid Res 62:107-128 ( 2016).

Ignatowska-Jankowska et al., "Selective Monoacylglycerol Lipase Inhibitors: Antinociceptive versus Cannabimimetic Effects in Mice" J Pharmacol Exp Ther 353:424-432 ( 2015).

International Preliminary Report on Patentability for PCT/EP2019/050198 dated Jul. 14, 2020.

International Search Report for PCT/EP2019/050198 dated Mar. 1, 2019.

Korhonen et al., "Piperazine and piperidine carboxamides and carbamates as inhibitors of fatty acid amide hydrolase (FAAH) and monoacylglycerol lipase (MAGL)"Bioorg. Med. Chem. 22:6694-6705 ( 2014).

Lleo et al., "Molecular targets of non-steroidal anti-inflammatory drugs in neurodegenerative diseases" Cell Mol Life Sci 64:1403-1418 ( 2007).

Long et al., "Selective blockade of 2-arachidonoylglycerol hydrolysis produces cannabinoid behavioral effects" Nat Chem Biol 5:37-44 ( 2009).

Moir et al., "Design, synthesis, and structure-activity relationship study of bicyclic piperazine analogs of indole-3-carboxamides as novel cannabinoid CB1 receptor agonists" Bioorg. Med. Chem. Lett. 20(24):7327-7330 (Oct. 14, 2010).

Muccioli et al., "CAY10499, a Novel Monoglyceride Lipase Inhibitor Evidenced by an Expeditious MGL Assay" Chem Bio Chem 9:2704-2710 ( 2008).

Nomura et al., "Endocannabinoid Hydrolysis Generates Brain Prostaglandins That Promote Neuroinflammation" Science 334(6057):809-813 ( 2011).

Nomura et al., "Monoacylglycerol Lipase Exerts Dual Control over Endocannabinoid and Fatty Acid Pathways to Support Prostate Cancer" Chem Biol 18(7):846-856 ( 2011).

Nomura et al., "Monoacylglycerol Lipase Regulates a Fatty Acid Network that Promotes Cancer Pathogenesis" Cell 140:49-61 ( 2010).

Qin et al., "The role of monoacylglycerol lipase (MAGL) in the cancer progress" Cell Biochem Biophys 70:33-36 ( 2014).

Saleh et al., "The Synthesis of 2,7 substituted Octahydro-2H-Pyrido[1,2-a] Pyrazines, Analogues of Quinolizidine and Piperazine Drugs" Tetrahedron 50(6):1811-1820 (Jan. 1, 1994).

U.S. Appl. No. 16/827,211.
U.S. Appl. No. 16/844,262.
U.S. Appl. No. 16/884,562.
U.S. Appl. No. 16/899,928.
U.S. Appl. No. 17/012,589.
U.S. Appl. No. 17/017,200.
U.S. Appl. No. 17/025,155.
U.S. Appl. No. 17/026,619.
U.S. Appl. No. 17/027,952.
U.S. Appl. No. 17/027,976.

Viader et al., "Reports Article Metabolic Interplay between Astrocytes and Neurons Regulates Endocannabinoid Action" Cell Rep 12(5):798-808 ( 2015).

Zhong et al., "Monoacylglycerol Lipase Inhibition Blocks Chronic Stress-Induced Depressive-Like Behaviors via Activation of mTOR Signaling" Neuropsychopharmacology 39:1763-1776 ( 2014).

Ashton, K., et al., "Design and synthesis of novel amide AKT1 inhibitors with selectivity over CDK2" Bioorg Med Chem Lett 21(18):5191-5196 (Sep. 15, 2011).

Aurora Fine Chemicals, Other Database, 1907579-56-9, (C26 H25 N3 O3), pp. 1Creation Date May 10, 2016.

Barney, C., et al., "A convenient synthesis of hindered amines and α-trifluoromethylamines from ketones" Tetrahedron Lett 31(39):5547-5550 ( 1990).

Chang, J. et al., "Highly Selective Inhibitors of Monoacylglycerol Lipase Bearing a Reactive Group that is Bio-isosteric with Endocannabinoid Substrates" Chem Biol 19(5):579-588 (May 1, 2012).

Dugar, S. et al., "A Concise and Efficient Synthesis of Substituted Morpholines" Synthesis 47(5):712-720 (Mar. 1, 2015).

(56) References Cited

OTHER PUBLICATIONS

Duncan, M., et al., "Review article: endocannabinoids and their receptors in the enteric nervous system" Aliment Pharmacol Ther 22(8):667-683 (Oct. 15, 2005).
Enamine, CAS Registry Database, 931085-56-2, (Registry No. 931085-56-2), pp. 1Creation Date Apr. 20, 2007.
Evano, G., et al., "Copper-Mediated Coupling Reactions and Their Applications in Natural Products and Designed Biomolecules Synthesis" Chem Rev 108(8):3054-3131 (Aug. 13, 2008).
Fray, M., et al., "Second generation N-(1,2-dephenylethyl)piperazines as dual serotonin and noradrenaline reuptake inhibitors: improving metabolic stability and reducing ion channel activity" Bioorg Med Chem Lett 20(12):3788-3792 (Jun. 15, 2010).
Fray, M., et al., "Structure-activity relationships of N-substituted piperazine amine reuptake inhibitors" Bioorg Med Chem Lett 16(16):4349-4353 (Aug. 15, 2006).
Gavryushin, A., et al., "Efficient Cross-Coupling of Functionalized Arylzinc Halides Catalyzed by a Nickel Chloride—Diethyl Phosphite System" Org Lett 7(22):4871-4874 (Oct. 7, 2005).
Granchi, C., et al., "A patent review of monoacylglycerol lipase (MAGL) inhibitors" Expert Opin Ther Pat 27(12):1341-1351 (Dec. 1, 2017).
Grill, M., et al., "Members of the endocannabinoid system are distinctly regulated in inflammatory bowel disease and colorectal cancer" Sci Rep 9(2358):1-13 (Feb. 20, 2019).
Haas, D., et al., "Recent Developements in Negishi Cross-Coupling Reactions" ACS Catal 6(3):1540-1552 (Feb. 3, 2016).
He, S., et al., "High-Affinity Small-Molecule Inhibitors of the Menin-Mixed Lineage Leukemia (MLL) Interaction Closely Mimic a Natural Protein-Protein Interaction" J Med Chem 57(4):1543-1556 (Feb. 27, 2014).
Heravi, M., et al., "Buchwald-Hartwig reaction: An overview" J Organometallic Chem 861:17-104 (Apr. 15, 2018).
Hutchings, K., et al., "Synthesis and antibacterial activity of the C-7 side chain of 3-aminoquinazolinediones" Bioorg Med Chem Lett 18(18):5087-5090 (Sep. 15, 2008).
"International Preliminary Report on Patentability—PCT/EP2019/057174"(dated Sep. 22, 2020—Chapter 1),:pp. 1-9 (Oct. 1, 2020).
"International Preliminary Report on Patentability—PCT/EP2019/071522" (dated Feb. 16, 2021, Chapter I),:pp. 1-9 (Feb. 25, 2021).
"International Preliminary Report on Patentability—PCT/EP2019/071520" (dated Feb. 16, 2021, Chapter I),:pp. 1-8 (Feb. 25, 2021).
"International Preliminary Report on Patentability—PCT/EP2019/081870" (dated May 25, 2021; Chapter I),:pp. 1-8 (Jun. 3, 2021).
"International Preliminary Report on Patentability—PCT/EP2020/069074" (dated Jan. 11, 2022; Chapter I),:pp. 1-8 (Jan. 20, 2022).
"International Preliminary Report on Patentability—PCT/EP2020/068320" (dated Aug. 4, 2021; Chapter II),:pp. 1-34 (Aug. 4, 2021).
"International Preliminary Report on Patentability—PCT/EP2020/059709" (dated Sep. 28, 2021; Chapter I),:pp. 1-10 (Oct. 21, 2021).
"International Search Report—PCT/EP2019/057174" (w/Written Opinion),:pp. 1-14 (dated Jul. 3, 2019).
"International Search Report—PCT/EP2019/071520" (w/Written Opinion),:pp. 1-14 (dated Sep. 17, 2019).
"International Search Report—PCT/EP2019/071522" (w/Written Opinion),:pp. 1-15 (dated Sep. 17, 2019).
"International Search Report—PCT/EP2019/081870" (w/Written Opinion),:pp. 1-12 (dated Jan. 14, 2020).
"International Search Report—PCT/EP2020/059709" (w/Written Opinion),:pp. 1-17 (dated Jun. 8, 2020).
"International Search Report—PCT/EP2020/068320" (w/Written Opinion),:pp. 1-16 (dated Aug. 13, 2020).
"International Search Report—PCT/EP2020/069074" (w/Written Opinion),:pp. 1-12 (dated Sep. 16, 2020).
"International Search Report—PCT/EP2020/074897" (w/Written Opinion),:pp. 1-15 (dated Nov. 18, 2020).
"International Search Report—PCT/EP2020/075260" (w/Written Opinion),:pp. 1-14 (dated Nov. 18, 2020).
"International Search Report—PCT/EP2020/076228" (w/Written Opinion),:pp. 1-14 (dated Nov. 12, 2020).
"International Search Report—PCT/EP2020/076346" (w/Written Opinion),:pp. 1-16 (dated Nov. 13, 2020).
"International Search Report—PCT/EP2020/076347" (w/Written Opinion),:pp. 1-16 (dated Nov. 30, 2020).
"International Search Report—PCT/EP2021/074150" (w/Written Opinion),:pp. 1-13 (dated Dec. 8, 2021).
Ishichi, Y., et al., "Novel triple reuptake inhibitors with low risk of CAD associated liabilities: design, synthesis and biological activities of 4-[(1S)-1-(3,4-dichlorophenyl)-2-methoxyethyl]piperidine and related compounds" Bioorg Med Chem 21(15):4600-4613 (Aug. 1, 2013).
Keenan, M., et al., "Design, structure-activity relationship and in vivo efficacy of piperazine analogues of fenarimol as inhibitors of Trypanosoma cruzi" Bioorg Med Chem 21(7):1756-1763 (Apr. 1, 2013).
Kitbunnadaj, R., et al., "Synthesis and structure-activity relationships of conformationally constrained histamine H(3) receptor agonists" J Med Chem 46(25):5445-5457 (Dec. 4, 2003).
Likhosherstov, A.M., et al., "Synthesis and antiarrhythmic activity of 1, 4-diazabicyclo [4. m. o] alkanyl amides of P-nitro-and P-aminobenzoic acids" Khimiko-Farmatsevticheskii Zhurnal [Russ Pharma Chem J] (English translation), 15(8):55-57 (Jan. 26, 1981).
Liu, F., et al., "Structure-Based Optimization of Pyridoxal 5'-Phosphate-Dependent Transaminase Enzyme (BioA) Inhibitors that Target Biotin Biosynthesis in Mycobacterium tuberculosis" J Med Chem 60(13):5507-5520 (Jul. 13, 2017).
Liu, Y. et al., "Discovery of 4-benzoylpiperidine and 3-(piperidin-4-yl)benzo[d]isoxazole derivatives as potential and selective GlyT1 inhibitors" RSC ADV 5(51):40964-40977 (Apr. 30, 2015).
Marquez, L., et al., "Ulcerative Colitis Induces Changes on the Expression of the Endocannabinoid System in the Human Colonic Tissue" Plos One 4(9):e6893 (1-13) (Sep. 4, 2009).
McAllister, L., et al., "Discovery of Trifluoromethyl Glycol Carbamates as Potent and Selective Covalent Monoacylglycerol Lipase (MAGL) Inhibitors for Treatment of Neuroinflammation" J Med Chem 61(7):3008-3026 (Apr. 12, 2018).
Mikhlina, E.E., et al., "The properties and some reactions of 4-oxo-1, 5-diazabicyclo [4, 4, 0] decane and 5-oxo-1, 4-diazabicyclo [4, 4, 0] decane" Kimiya Geterotsiklicheskikh Soedinenii ((English translation)), 5(3):547-549 (May 1, 1969).
Mulvihill, M., et al., "Therapeutic Potential of Monoacylglycerol Lipase Inhibitors" Life Sci 92(8-9):492-497 (Nov. 8, 2013).
Negishi, E., "Palladium- or Nickel-Catalyzed Cross Coupling. A New Selective Method for Carbon-Carbon Bond Formation" Acc Chem Res 15(11):340-348 (Nov. 1, 1982).
Patel, J. et al., "Loratadine analogues as MAGL inhibitors" Bioorg Med Chem Lett 25(7):1436-1442 (Feb. 24, 2015).
Perisetti, A., et al., "Role of cannabis in inflammatory bowel diseases" Ann Gastroenterol 33(2):134-144 (Feb. 12, 2020).
Rafinski, Z. et al., "Enantioselective Synthesis of Chromanones Bearing Quaternary Substituted Stereocenters Catalyzed by (1R)-Camphor-Derived N-Heterocyclic Carbenes" J Org Chem 80(15):7468-7476 (Aug. 7, 2015).
Scalvini, L., et al., "Monoglyceride lipase: Structure and inhibitors" Chem Phys Lipids 197:13-24 (Jul. 26, 2015).
Senter, T., et al., "Progress towards small molecule menin-mixed lineage leukemia (MLL) interaction inhibitors with in vivo utility" Bioorg Med Chem Lett 25(13):2720-2725 (Jul. 1, 2015).
Surry, D., et al., "Biaryl Phosphane Ligands in Palladium-Catalyzed Amination" Angew Chem Int Ed Engl 47(34):6338-6361 (Aug. 11, 2008).
"U.S. Appl. No. 17/749,496, filed May 20, 2022".
"U.S. Appl. No. 17/818,459, filed Aug. 9, 2022".
Ukrorgsyntez, Ltd., CAS Registry Database, 1941372-36-6, (Stereosearch—C20 H27 N3 O3), pp. 1Creation Date Jun. 29, 2016.
Venkatesh, R., et al., "Novel benzothiazine-piperazine derivatives by peptide-coupling as potential anti-proliferative agents" Bioorg Med Chem Lett 27(2):354-359 (Jan. 15, 2017).
Walsh, D., et al., "Synthesis and antiallergy activity of 4-(diarylhydroxymethyl)-1-[3-(aryloxy)propyl]piperidines and structurally related compounds" J Med Chem 32(1):105-118 (Jan. 1, 1989).

(56) References Cited

OTHER PUBLICATIONS

Wang, J., et al., "Effect of monoacylglycerol lipase inhibition on intestinal permeability in chronic stress model" Biochem Biophys Res Commun 525(4):962-967 (May 14, 2020).

Wright, K., et al., "Differential expression of cannabinoid receptors in the human colon: cannabinoids promote epithelial wound healing" Gastroenterology 129(2):437-453 (Aug. 1, 2005).

Wu, W., et al., "Synthesis and structure-activity relationships of piperidine-based melanin-concentrating hormone receptor 1 antagonists" Bioorg Med Chem Lett 16(14):3668-3673 (Jul. 15, 2006).

Yin, J., et al., "ARS2/MAGL signaling in glioblastoma stem cells promotes self-renewal and M2-like polarization of tumor-associated macrophages" Nat Commun 11(1):2978(1-15) (Jun. 12, 2020).

Zhang, P., et al., "Silyl Radical Activation of Alkyl Halides in Metallaphotoredox Catalysis: A Unique Pathway for Cross-Electrophile Coupling" J Am Chem Soc 138(26):8084-8087 (Jul. 6, 2016).

Zhang, X., et al., "Direct Aldehyde C—H Arylation and Alkylation via the Combination of Nickel, Hydrogen Atom Transfer, and Photoredox Catalysis" J Am Chem Soc 139(33):11353-11356 (Aug. 23, 2017).

\* cited by examiner

OCTAHYDROPYRIDO[1,2-ALPHA]PYRAZINES AS MAGL INHIBITORS

CROSS REFERENCE TO RELATED APPLICATIONS

This application is a continuation of International Application No. PCT/EP2019/050198, filed Jan. 7, 2019, which claims priority to International Application No. PCT/CN2018/116691, filed Nov. 21,2018, and EP Application No. 18150649.4, filed Jan. 8, 2018, the disclosure of each of which is incorporated herein by reference in its entirety.

FIELD OF THE INVENTION

The present invention relates to organic compounds useful for therapy or prophylaxis in a mammal, and in particular to monoacylglycerol lipase (MAGL) inhibitors for the treatment or prophylaxis of neuroinflammation, neurodegenerative diseases, pain, cancer, mental disorders, multiple sclerosis, Alzheimer's disease, Parkinson's disease, amyotrophic lateral sclerosis, traumatic brain injury, neurotoxicity, stroke, epilepsy, anxiety, migraine and/or depression in a mammal.

BACKGROUND OF THE INVENTION

Endocannabinoids (ECs) are signaling lipids that exert their biological actions by interacting with cannabinoid receptors (CBRs), CB1 and CB2. They modulate multiple physiological processes including neuroinflammation, neurodegeneration and tissue regeneration (Iannotti, F. A., et al., *Progress in lipid research* 2016, 62, 107-28.). In the brain, the main endocannabinoid, 2-arachidonoylglycerol (2-AG), is produced by diacyglycerol lipases (DAGL) and hydrolyzed by the monoacylglycerol lipase, MAGL. MAGL hydrolyses 85% of 2-AG; the remaining 15% being hydrolysed by ABHD6 and ABDH12 (Nomura, D. K., et al., *Science* 2011, 334, 809.). MAGL is expressed throughout the brain and in most brain cell types, including neurons, astrocytes, oligodendrocytes and microglia cells (Chanda, P. K., et al., *Molecular pharmacology* 2010, 78, 996; Viader, A., et al., *Cell reports* 2015, 12, 798.). 2-AG hydrolysis results in the formation of arachidonic acid (AA), the precursor of prostaglandins (PGs) and leukotrienes (LTs). Oxidative metabolism of AA is increased in inflamed tissues. There are two principal enzyme pathways of arachidonic acid oxygenation involved in inflammatory processes, the cyclo-oxygenase which produces PGs and the 5-lipoxygenase which produces LTs. Of the various cyclooxygenase products formed during inflammation, PGE2 is one of the most important. These products have been detected at sites of inflammation, e.g. in the cerebrospinal fluid of patients suffering from neurodegenerative disorders and are believed to contribute to inflammatory response and disease progression. Mice lacking MAGL (Mgll-/-) exhibit dramatically reduced 2-AG hydrolase activity and elevated 2-AG levels in the nervous system while other arachidonoyl-containing phospho- and neutral lipid species including anandamide (AEA), as well as other free fatty acids, are unaltered. Conversely, levels of AA and AA-derived prostaglandins and other eicosanoids, including prostaglandin E2 (PGE2), D2 (PGD2), F2 (PGF2), and thromboxane B2 (TXB2), are strongly decreased. Phospholipase $A_2$ ($PLA_2$) enzymes have been viewed as the principal source of AA, but $cPLA_2$-deficient mice have unaltered AA levels in their brain, reinforcing the key role of MAGL in the brain for AA production and regulation of the brain inflammatory process.

Neuroinflammation is a common pathological change characteristic of diseases of the brain including, but not restricted to, neurodegenerative diseases (e.g. multiple sclerosis, Alzheimer's disease, Parkinson disease, amyotrophic lateral sclerosis, traumatic brain injury, neurotoxicity, stroke, epilepsy and mental disorders such as anxiety and migraine). In the brain, production of eicosanoids and prostaglandins controls the neuroinflammation process. The pro-inflammatory agent lipopolysaccharide (LPS) produces a robust, time-dependent increase in brain eicosanoids that is markedly blunted in Mgll-/- mice. LPS treatment also induces a widespread elevation in pro-inflammatory cytokines including interleukin-1-a (IL-1-a), IL-1b, IL-6, and tumor necrosis factor-a (TNF-α) that is prevented in Mgll-/- mice.

Neuroinflammation is characterized by the activation of the innate immune cells of the central nervous system, the microglia and the astrocytes. It has been reported that anti-inflammatory drugs can suppress in preclinical models the activation of glia cells and the progression of disease including Alzheimer's disease and multiple sclerosis (Lleo A., *Cell Mol Life Sci.* 2007, 64, 1403.). Importantly, genetic and/or pharmacological disruption of MAGL activity also blocks LPS-induced activation of microglial cells in the brain (Nomura, D. K., et al., *Science* 2011, 334, 809.).

In addition, genetic and/or pharmacological disruption of MAGL activity was shown to be protective in several animal models of neurodegeneration including, but not restricted to, Alzheimer's disease, Parkinson's disease and multiple sclerosis. For example, an irreversible MAGL inhibitor has been widely used in preclinical models of neuroinflammation and neurodegeneration (Long, J. Z., et al., *Nature chemical biology* 2009, 5, 37.). Systemic injection of such inhibitor recapitulates the Mgll-/- mice phenotype in the brain, including an increase in 2-AG levels, a reduction in AA levels and related eicosanoids production, as well as the prevention of cytokines production and microglia activation following LPS-induced neuroinflammation (Nomura, D. K., et al., *Science* 2011, 334, 809.), altogether confirming that MAGL is a druggable target.

Consecutive to the genetic and/or pharmacological disruption of MAGL activity, the endogenous levels of the MAGL natural substrate in the brain, 2-AG, are increased. 2-AG has been reported to show beneficial effects on pain with, for example, anti-nociceptive effects in mice (Ignatowska-Jankowska B. et al., *J. Pharmacol. Exp. Ther.* 2015, 353, 424.) and on mental disorders, such as depression in chronic stress models (Zhong P. et al., *Neuropsychopharmacology* 2014, 39, 1763.).

Furthermore, oligodendrocytes (OLs), the myelinating cells of the central nervous system, and their precursors (OPCs) express the cannabinoid receptor 2 (CB2) on their membrane. 2-AG is the endogenous ligand of CB1 and CB2 receptors. It has been reported that both cannabinoids and pharmacological inhibition of MAGL attenuate OLs's and OPCs's vulnerability to excitotoxic insults and therefore may be neuroprotective (Bemal-Chico, A., et al., *Glia* 2015, 63, 163.). Additionally, pharmacological inhibition of MAGL increases the number of myelinating OLs in the brain of mice, suggesting that MAGL inhibition may promote differentiation of OPCs in myelinating OLs in vivo (Alpar, A., et al., *Nature communications* 2014, 5, 4421.). Inhibition of MAGL was also shown to promote remyelination and functional recovery in a mouse model of progressive multiple sclerosis (Feliu A. et al., *Journal of Neuroscience* 2017, 37 (35), 8385.).

Finally, in recent years, metabolism is talked highly important in cancer research, especially the lipid metabolism. Researchers believe that the de novo fatty acid synthesis plays an important role in tumor development. Many studies illustrated that endocannabinoids have anti-tumorigenic actions, including anti-proliferation, apoptosis induction and anti-metastatic effects. MAGL as an important decomposing enzyme for both lipid metabolism and the endocannabinoids system, additionally as a part of a gene expression signature, contributes to different aspects of tumourigenesis (Qin, H., et al., *Cell Biochem. Biophys.* 2014, 70, 33; Nomura D K et al., *Cell* 2009, 140(1), 49-61; Nomura D K et al., *Chem. Biol.* 2011, 18(7), 846-856).

Suppressing the action and/or the activation of MAGL is a promising new therapeutic strategy for the treatment or prevention of neuroinflammation, neurodegenerative diseases, pain, cancer and mental disorders. Furthermore, suppressing the action and/or the activation of MAGL is a promising new therapeutic strategy for providing neuroprotection and myelin regeneration. Accordingly, there is a high unmet medical need for new MAGL inhibitors.

SUMMARY OF THE INVENTION

In a first aspect, the present invention provides a compound of formula (e)

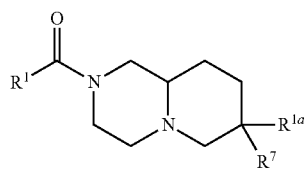
(Ie)

or a pharmaceutically acceptable salt thereof, wherein:
$R^{1a}$ is selected from the group consisting of
  (i) $C_{1-6}$-alkyl;
  (ii) $C_{1-6}$-alkoxy; and
  (iii) aryl substituted with $R^2$, $R^3$, $R^4$, $R^5$ and $R^6$, or a possible combination thereof;
$R^1$ is selected from the group consisting of
  (i) aryl substituted with $R^8$, $R^9$ and $R^{10}$; and
  (ii) heteroaryl substituted with $R^{11}$ and $R^{12}$;
each of $R^2$, $R^3$, $R^4$, $R^5$ and $R^6$ is independently selected from the group consisting of hydrogen, halogen, alkoxy, haloalkoxy, hydroxy, amino, —NH-alkyl, —N(alkyl)$_2$ and cyano;
$R^7$ is selected from the group consisting of hydrogen, halogen, alkoxy, cycloalkyloxy and hydroxy;
each of $R^8$, $R^9$, $R^{10}$, $R^{11}$ and $R^{12}$ is independently selected from the group consisting of hydrogen, hydroxy, alkoxy, cyano, alkoxyalkyl, haloalkoxy, halogen, alkyl, haloalkyl, alkylsulfanyl, amino, —NH-alkyl, —N(alkyl)$_2$, —NH-aryl, —NH-heteroaryl and a group

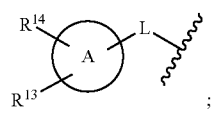

$R^{13}$ is selected from the group consisting of hydrogen, oxo, halogen, alkyl, carbamoyl, substituted carbamoyl and alkoxycarbonyl, wherein said substituted carbamoyl is substituted at the nitrogen atom with one to two alkyl substituents;
$R^{14}$ is hydrogen or halogen;
L is selected from the group consisting of a covalent bond, —CH=CH—, —O—, —CH$_2$O—, —OCH$_2$—, —CH$_2$— and —CH$_2$CH$_2$—; and
A is selected from the group consisting of aryl, heteroaryl, cycloalkyl and heterocyclyl; with the proviso that the compound of formula (e) is not (4-fluorophenyl)-[7-(4-fluorophenyl)-1,3,4,6,7,8,9,9a-octahydropyrido[1,2-a]pyrazin-2-yl]methanone.

In a further aspect, the present invention provides a process of manufacturing the compounds of formula (Ie) described herein, comprising the steps of:

a) reacting an amine 13, wherein $R^2$, $R^3$, $R^4$, $R^5$, $R^6$ and $R^7$ are as described herein,

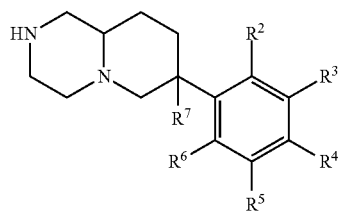
13 with an acid 14, wherein $R^1$ is as described herein

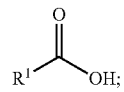
14 or b) reacting an amine 13, wherein $R^2$, $R^3$, $R^4$, $R^5$, $R^6$ and $R^7$ are as described herein,

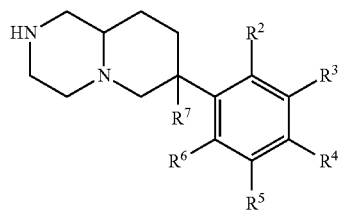
13 with an acid chloride 15, wherein $R^1$ is as described herein

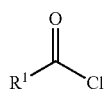
15 to form said compound of formula (e).

In a further aspect, the present invention provides a compound of formula (e), preferably a compound of formula (I), as described herein, or a pharmaceutically acceptable salt thereof, when manufactured according to the processes described herein.

In a further aspect, the present invention provides a compound of formula (e), preferably a compound of formula (I), as described herein, or a pharmaceutically acceptable salt thereof, for use as therapeutically active substance.

In a further aspect, the present invention provides a pharmaceutical composition comprising a compound of formula (Ie), preferably a compound of formula (I), described herein, or a pharmaceutically acceptable salt thereof, and a therapeutically inert carrier.

In a further aspect, the present invention provides the use of a compound of formula (Ie), preferably a compound of formula (I), as described herein, or a pharmaceutically acceptable salt thereof, for inhibiting monoacylglycerol lipase (MAGL) in a mammal.

In a further aspect, the present invention provides the use of a compound of formula (Ie), preferably a compound of formula (I), as described herein, or a pharmaceutically acceptable salt thereof, for the treatment or prophylaxis of neuroinflammation, neurodegenerative diseases, pain, cancer and/or mental disorders in a mammal.

In a further aspect, the present invention provides the use of a compound of formula (Ie), preferably a compound of formula (I), as described herein for the treatment or prophylaxis of multiple sclerosis, Alzheimer's disease, Parkinson's disease, amyotrophic lateral sclerosis, traumatic brain injury, neurotoxicity, stroke, epilepsy, anxiety, migraine, depression, cancer and/or pain in a mammal.

In a further aspect, the present invention provides a compound of formula (e), preferably a compound of formula (I), as described herein, or a pharmaceutically acceptable salt thereof, for use in a method of inhibiting monoacylglycerol lipase in a mammal.

In a further aspect, the present invention provides a compound of formula (e), preferably a compound of formula (I), as described herein, or a pharmaceutically acceptable salt thereof, for use in the treatment or prophylaxis of neuroinflammation, neurodegenerative diseases, pain, cancer and/or mental disorders in a mammal.

In a further aspect, the present invention provides a compound of formula (e), preferably a compound of formula (I), as described herein, or a pharmaceutically acceptable salt thereof, for use in the treatment or prophylaxis of multiple sclerosis, Alzheimer's disease, Parkinson's disease, amyotrophic lateral sclerosis, traumatic brain injury, neurotoxicity, stroke, epilepsy, anxiety, migraine, depression, cancer and/or pain in a mammal.

In a further aspect, the present invention provides the use of a compound of formula (Ie), preferably a compound of formula (I), as described herein, or a pharmaceutically acceptable salt thereof, for the preparation of a medicament for inhibiting monoacylglycerol lipase in a mammal.

In a further aspect, the present invention provides the use of a compound of formula (Ie), preferably a compound of formula (I), as described herein, or a pharmaceutically acceptable salt thereof, for the preparation of a medicament for the treatment or prophylaxis of neuroinflammation, neurodegenerative diseases, pain, cancer and/or mental disorders in a mammal.

In a further aspect, the present invention provides the use of a compound of formula (Ie), preferably a compound of formula (I), as described herein, or a pharmaceutically acceptable salt thereof, for the preparation of a medicament for the treatment or prophylaxis of multiple sclerosis, Alzheimer's disease, Parkinson's disease, amyotrophic lateral sclerosis, traumatic brain injury, neurotoxicity, stroke, epilepsy, anxiety, migraine, depression, cancer and/or pain in a mammal.

In a further aspect, the present invention provides a method for inhibiting monoacylglycerol lipase in a mammal, which method comprises administering an effective amount of a compound of formula (Ie), preferably of a compound of formula (I), as described herein, or of a pharmaceutically acceptable salt thereof, to the mammal.

In a further aspect, the present invention provides a method for the treatment of neuroinflammation, neurodegenerative diseases, pain, cancer and/or mental disorders in a mammal, which method comprises administering an effective amount of a compound of formula (Ie), preferably of a compound of formula (I), as described herein, or of a pharmaceutically acceptable salt thereof, to the mammal.

In a further aspect, the present invention provides a method for the prophylaxis of neuroinflammation, neurodegenerative diseases, pain, cancer and/or mental disorders in a mammal, which method comprises administering an effective amount of a compound of formula (Ie), preferably of a compound of formula (I), as described herein, or of a pharmaceutically acceptable salt thereof, to the mammal.

In a further aspect, the present invention provides a method for the treatment of multiple sclerosis, Alzheimer's disease, Parkinson's disease, amyotrophic lateral sclerosis, traumatic brain injury, neurotoxicity, stroke, epilepsy, anxiety, migraine, depression, cancer and/or pain in a mammal, which method comprises administering an effective amount of a compound of formula (Ie), preferably of a compound of formula (I), as described herein, or a pharmaceutically acceptable salt thereof, to the mammal.

In a further aspect, the present invention provides a method for the prophylaxis of multiple sclerosis, Alzheimer's disease, Parkinson's disease, amyotrophic lateral sclerosis, traumatic brain injury, neurotoxicity, stroke, epilepsy, anxiety, migraine, depression, cancer and/or pain in a mammal, which method comprises administering an effective amount of a compound of formula (Ie), preferably of a compound of formula (I), as described herein, or a pharmaceutically acceptable salt thereof, to the mammal.

DETAILED DESCRIPTION OF THE INVENTION

Definitions

Features, integers, characteristics, compounds, chemical moieties or groups described in conjunction with a particular aspect, embodiment or example of the invention are to be understood to be applicable to any other aspect, embodiment or example described herein, unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The invention is not restricted to the details of any foregoing embodiments. The invention extends to any novel one, or any novel combination, of the features disclosed in this specification (including any accompanying claims, abstract and drawings), or to any novel one, or any novel combination, of the steps of any method or process so disclosed.

The term "alkyl" refers to a mono- or multivalent, e.g., a mono- or bivalent, linear or branched saturated hydrocarbon group of 1 to 12 carbon atoms. In some preferred embodiments, the alkyl group contains 1 to 6 carbon atoms, e.g., 1,2, 3, 4, 5, or 6 carbon atoms. In other embodiments, the alkyl group contains 1 to 3 carbon atoms, e.g., 1,2 or 3 carbon atoms. Examples of such groups include, but are not limited to, methyl, ethyl, propyl, 2-propyl (isopropyl), n-butyl, iso-butyl, sec-butyl, tert-butyl, and 2,2-dimethylpropyl. In a particularly preferred embodiment, alkyl is methyl.

The term "alkoxy" refers to an alkyl group, as previously defined, attached to the parent molecular moiety via an oxygen atom. Unless otherwise specified, the alkoxy group contains 1 to 12 carbon atoms. In some embodiments, the alkoxy group contains 1 to 6 carbon atoms. In other embodiments, the alkoxy group contains 1 to 4 carbon atoms. In still other embodiments, the alkoxy group contains 1 to 3 carbon atoms. Some non-limiting examples of alkoxy groups include methoxy, ethoxy, n-propoxy, isopropoxy, n-butoxy, isobutoxy and tert-butoxy. In a preferred embodiment, alkoxy is methoxy, ethoxy or isopropoxy. In a particularly preferred embodiment, alkoxy is methoxy.

The term "alkylsulfanyl" refers to an alkyl group, as previously defined, attached to the parent molecular moiety via a sulfur atom. Unless otherwise specified, the alkylsulfanyl group contains 1 to 12 carbon atoms. In some embodiments, the alkylsulfanyl group contains 1 to 6 carbon atoms. In other embodiments, the alkylsulfanyl group contains 1 to 4 carbon atoms. In still other embodiments, the alkylsulfanyl group contains 1 to 3 carbon atoms. A preferred, yet non-limiting example of an alkylsulfanyl group is methylsulfanyl.

The term "halogen" or "halo" refers to fluoro (F), chloro (Cl), bromo (Br), or iodo (I). In a preferred embodiment, the term "halogen" or "halo" refers to fluoro (F), chloro (Cl) or bromo (Br).

The term "haloalkyl" or "haloalkoxy", respectively, refers to an alkyl or alkoxy group, as the case may be, substituted with one or more halogen atoms, wherein each of the alkyl or alkoxy is defined as described herein. In a preferred embodiment, the haloalkyl or haloalkoxy group, respectively, contains 1,2 or 3 halogen atoms, most preferably 1,2 or 3 F atoms. Examples of such groups include, but are not limited to, fluoromethyl, difluoromethyl, trifluoromethyl ($CF_3$), 2,2,2-trifluoroethyl, trifluoromethoxy, 2,2,2-trifluoroethoxy, 2,2,3,3-tetrafluoropropoxy, and the like. A particularly preferred haloalkyl group is trifluoromethyl ($CF_3$).

The term "alkoxyalkyl" refers to an alkyl group, wherein at least one of the hydrogen atoms of the alkyl group has been replaced by an alkoxy group. In a preferred embodiment, "alkoxyalkyl" refers to an alkyl group wherein 1 hydrogen atom of the alkyl group has been replaced by an alkoxy group. In a particularly preferred embodiment, alkoxyalkyl is methoxymethyl.

The terms "cycloalkyl" and "carbocycle" are used herein synonymously and refer to a saturated or partly unsaturated monocyclic or bicyclic hydrocarbon group of 3 to 10 ring carbon atoms. In some embodiments, the cycloalkyl group is a saturated monocyclic hydrocarbon group of 3 to 8 ring carbon atoms. "Bicyclic cycloalkyl" refers to cycloalkyl moieties consisting of two saturated carbocycles having two carbon atoms in common, i.e., the bridge separating the two rings is either a single bond or a chain of one or two ring atoms, and to spirocyclic moieties, i.e., the two rings are connected via one common ring atom. In a preferred embodiment, the cycloalkyl group is a saturated monocyclic hydrocarbon group of 3 to 6 ring carbon atoms, e.g., of 3, 4, 5 or 6 carbon atoms. Some non-limiting examples of cycloalkyl include cyclopropyl, cyclobutyl, cyclopentyl and cyclohexyl.

The term "heterocyclyl" refers to a saturated or partly unsaturated mono- or bicyclic ring system of 3 to 10 ring atoms, wherein 1,2, or 3 of said ring atoms are heteroatoms selected from the group consisting of N, O and S, the remaining ring atoms being carbon. Preferably, 1,2, or 3 of said ring atoms are N, the remaining ring atoms being carbon "Bicyclic heterocyclyl" refers to heterocyclic moieties consisting of two cycles having two ring atoms in common, i.e., the bridge separating the two rings is either a single bond or a chain of one or two ring atoms, and to spirocyclic moieties, i.e., the two rings are connected via one common ring atom. Some non-limiting examples of heterocyclyl include piperidyl, morpholinyl, oxetanyl and azetidinyl.

The term "aryl" refers to a monocyclic, bicyclic, or tricyclic carbocyclic ring system having a total of 6 to 14 ring members, preferably, 6 to 12 ring members, and more preferably 6 to 10 ring members, and wherein at least one ring in the system is aromatic. A particular, yet non-limiting example of aryl is phenyl.

The term "heteroaryl" refers to a mono- or multivalent, monocyclic or bicyclic ring system having a total of 5 to 12 ring members, preferably, 5 to 10 ring members, and more preferably 5 to 6 ring members, wherein at least one ring in the system is aromatic, and at least one ring in the system contains one or more heteroatoms. In one embodiment, a 5-10 membered heteroaryl comprises 1,2, 3 or 4 heteroatoms independently selected from the group consisting of O, S and N. Some non-limiting examples of heteroaryl rings include pyridyl (e.g., 2-pyridyl, 3-pyridyl and 4-pyridyl), 2,3-dihydrobenzofuranyl (e.g. 2,3-dihydrobenzofuran-7-yl), indolyl (e.g. 1H-indol-4-yl), pyrrolo[2,3-b]pyridyl (e.g. 1H-pyrrolo[2,3-b]pyridin-5-yl and 1H-pyrrolo[2,3-b]pyridin-4-yl), benzothiazolyl (e.g. 1,3-benzothiazol-5-yl), thiazolopyridyl (e.g. [1,3]thiazolo[5,4-b]pyridin-6-yl), benzothiophenyl (e.g. 1-benzothiophen-4-yl), thieno[3,2-c]pyridyl (e.g. thieno[3,2-c]pyridin-7-yl), 2,3-dihydroindolyl (e.g. 2,3-dihydroindol-4-yl), pyrazolo[3,4-b]pyridyl (e.g. pyrazolo[3,4-b]pyridin-5-yl), benzofuranyl (e.g. 1-benzofuran-4-yl), imidazo[1,2-a]pyridyl (e.g. imidazo[1,2-a]pyridin-5-yl), pyrazolyl (e.g. 1H-pyrazol-4-yl), pyridazinyl (e.g. pyridazin-3-yl) and thiazolyl (e.g. 1,3-thiazol-4-yl).

The term "amino" refers to an —$NH_2$ group.
The term "hydroxy" refers to an —OH group.
The term "cyano" refers to a —CN group.
The term "carbamoyl" refers to a group —C(O)—$NH_2$.
The term "alkoxycarbonyl" refers to a group —C(O)—O-alkyl.

The term "pharmaceutically acceptable salt" refers to those salts which retain the biological effectiveness and properties of the free bases or free acids, which are not biologically or otherwise undesirable. The salts are formed with inorganic acids such as hydrochloric acid, hydrobromic acid, sulfuric acid, nitric acid, phosphoric acid and the like, in particular hydrochloric acid, and organic acids such as acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, N-acetylcystein and the like. In addition these salts may be prepared by addition of an inorganic base or an organic base to the free acid. Salts derived from an inorganic base include, but are not limited to, the sodium, potassium, lithium, ammonium, calcium, magnesium salts and the like. Salts derived from organic bases include, but are not limited to salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, lysine, arginine, N-ethylpiperidine, piperidine, polyimine resins and the like. Particular pharmaceutically acceptable salts of compounds of formula (I) are hydrochloride salts.

The term "protecting group" (PG) denotes the group which selectively blocks a reactive site in a multifunctional compound such that a chemical reaction can be carried out selectively at another unprotected reactive site in the meaning conventionally associated with it in synthetic chemistry. Protecting groups can be removed at the appropriate point. Exemplary protecting groups are amino-protecting groups, carboxy-protecting groups or hydroxy-protecting groups. Particular protecting groups are the tert-butoxycarbonyl (Boc), benzyloxycarbonyl (Cbz), fluorenylmethoxycarbonyl (Fmoc) and benzyl (Bn). Further particular protecting groups are the tert-butoxycarbonyl (Boc) and the fluorenylmethoxycarbonyl (Fmoc). More particular protecting group is the tert-butoxycarbonyl (Boc). Exemplary protecting groups and their application in organic synthesis are described, for example, in "Protective Groups in Organic Chemistry" by T. W. Greene and P. G. M. Wutts, 5th Ed., 2014, John Wiley & Sons, N.Y.

The compounds of formula (I) can contain several asymmetric centers and can be present in the form of optically pure enantiomers, mixtures of enantiomers such as, for example, racemates, optically pure diastereoisomers, mixtures of diastereoisomers, diastereoisomeric racemates or mixtures of diastereoisomeric racemates.

According to the Cahn-Ingold-Prelog Convention, the asymmetric carbon atom can be of the "R" or "S" configuration.

The abbreviation "MAGL" refers to the enzyme monoacylglycerol lipase. The terms "MAGL" and "monoacylglycerol lipase" are used herein interchangeably.

The term "treatment" as used herein includes: (1) inhibiting the state, disorder or condition (e.g. arresting, reducing or delaying the development of the disease, or a relapse thereof in case of maintenance treatment, of at least one clinical or subclinical symptom thereof); and/or (2) relieving the condition (i.e., causing regression of the state, disorder or condition or at least one of its clinical or subclinical symptoms). The benefit to a patient to be treated is either statistically significant or at least perceptible to the patient or to the physician. However, it will be appreciated that when a medicament is administered to a patient to treat a disease, the outcome may not always be effective treatment.

The term "prophylaxis" as used herein includes: preventing or delaying the appearance of clinical symptoms of the state, disorder or condition developing in a mammal and especially a human that may be afflicted with or predisposed to the state, disorder or condition but does not yet experience or display clinical or subclinical symptoms of the state, disorder or condition.

The term "neuroinflammation" as used herein relates to acute and chronic inflammation of the nervous tissue, which is the main tissue component of the two parts of the nervous system; the brain and spinal cord of the central nervous system (CNS), and the branching peripheral nerves of the peripheral nervous system (PNS). Chronic neuroinflammation is associated with neurodegenerative diseases such as Alzheimer's disease, Parkinson's disease and multiple sclerosis. Acute neuroinflammation usually follows injury to the central nervous system immediately, e.g., as a result of traumatic brain injury (TBI).

The term "traumatic brain injury" ("TBI", also known as "intracranial injury"), relates to damage to the brain resulting from external mechanical force, such as rapid acceleration or deceleration, impact, blast waves, or penetration by a projectile.

The term "neurodegenerative diseases" relates to diseases that are related to the progressive loss of structure or function of neurons, including death of neurons. Examples of neurodegenerative diseases include, but are not limited to, multiple sclerosis, Alzheimer's disease, Parkinson's disease and amyotrophic lateral sclerosis.

The term "mental disorders" (also called mental illnesses or psychiatric disorders) relates to behavioral or mental patterns that may cause suffering or a poor ability to function in life. Such features may be persistent, relapsing and remitting, or occur as a single episode. Examples of mental disorders include, but are not limited to, anxiety and depression.

The term "pain" relates to an unpleasant sensory and emotional experience associated with actual or potential tissue damage. Examples of pain include, but are not limited to, nociceptive pain, chronic pain (including idiopathic pain), neuropathic pain, phantom pain and phsycogenic pain. A particular example of pain is neuropathic pain, which is caused by damage or disease affecting any part of the nervous system involved in bodily feelings (i.e., the somatosensory system). In one embodiment, "pain" is neuropathic pain resulting from amputation or thoracotomy.

The term "neurotoxicity" relates to toxicity in the nervous system. It occurs when exposure to natural or artificial toxic substances (neurotoxins) alter the normal activity of the nervous system in such a way as to cause damage to nervous tissue. Examples of neurotoxicity include, but are not limited to, neurotoxicity resulting from exposure to substances used in chemotherapy, radiation treatment, drug therapies, drug abuse, and organ transplants, as well as exposure to heavy metals, certain foods and food additives, pesticides, industrial and/or cleaning solvents, cosmetics, and some naturally occurring substances.

The term "mammal" as used herein includes both humans and non-humans and includes but is not limited to, humans, non-human primates, canines, felines, murines, bovines, equines, and porcines. In a particularly preferred embodiment, the term "mammal" refers to humans.

Compounds of the Invention

In a first aspect, the present invention provides a compound of formula (Ie)

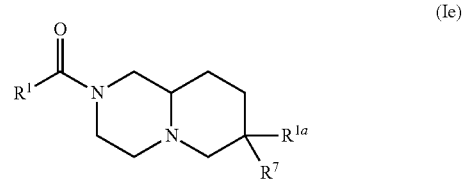

(Ie)

or a pharmaceutically acceptable salt thereof, wherein:
$R^{1a}$ is selected from the group consisting of
 (i) $C_{1-6}$-alkyl;
 (ii) $C_{1-6}$-alkoxy; and
 (iii) aryl substituted with $R^2$, $R^3$, $R^4$, $R^5$ and $R^6$, or a possible combination thereof;
$R^1$ is selected from the group consisting of
 (i) aryl substituted with $R^8$, $R^9$ and $R^{10}$; and
 (ii) heteroaryl substituted with $R^{11}$ and $R^{12}$.

each of $R^2$, $R^3$, $R^4$, $R^5$ and $R^6$ is independently selected from the group consisting of hydrogen, halogen, alkoxy, haloalkoxy, hydroxy, amino, —NH-alkyl, —N(alkyl)$_2$ and cyano;

$R^7$ is selected from the group consisting of hydrogen, halogen, alkoxy, cycloalkyloxy and hydroxy;

each of $R^8$, $R^9$, $R^{10}$, $R^{11}$ and $R^{12}$ is independently selected from the group consisting of hydrogen, hydroxy, alkoxy, cyano, alkoxyalkyl, haloalkoxy, halogen, alkyl, haloalkyl, alkylsulfanyl, amino, —NH-alkyl, —N(alkyl)$_2$, —NH-aryl, —NH-heteroaryl and a group

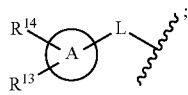

$R^{13}$ is selected from the group consisting of hydrogen, oxo, halogen, alkyl, carbamoyl, substituted carbamoyl and alkoxycarbonyl, wherein said substituted carbamoyl is substituted at the nitrogen atom with one to two alkyl substituents;

$R^{14}$ is hydrogen or halogen;

L is selected from the group consisting of a covalent bond, —CH=CH—, —O—, —CH$_2$O—, —OCH$_2$—, —CH$_2$— and —CH$_2$CH$_2$—; and A is selected from the group consisting of aryl, heteroaryl, cycloalkyl and heterocyclyl.

In one embodiment, the present invention provides a compound of formula (Ie) as defined herein, or a pharmaceutically acceptable salt thereof, wherein said compound of formula (Ie) is not (4-fluorophenyl)-[7-(4-fluorophenyl)-1,3,4,6,7,8,9,9a-octahydropyrido[1,2-a]pyrazin-2-yl]methanone.

In one embodiment, the present invention provides a compound of formula (Ie) wherein said compound of formula (Ie) is of formula (I)

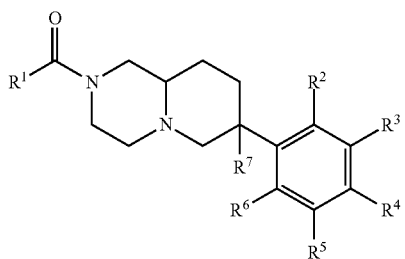

(I)

wherein:

$R^1$ is selected from the group consisting of
 (i) aryl substituted with $R^8$, $R^9$ and $R^{10}$; and
 (ii) heteroaryl substituted with $R^{11}$ and $R^{12}$, each of $R^2$, $R^3$, $R^4$, $R^5$ and $R^6$ is independently selected from the group consisting of hydrogen, halogen, alkoxy, haloalkoxy, hydroxy, amino, —NH-alkyl, —N(alkyl)$_2$ and cyano;

$R^7$ is selected from the group consisting of hydrogen, halogen, alkoxy, cycloalkyloxy and hydroxy;

each of $R^8$, $R^9$, $R^{10}$, $R^{11}$ and $R^{12}$ is independently selected from the group consisting of hydrogen, hydroxy, alkoxy, cyano, alkoxyalkyl, haloalkoxy, halogen, alkyl, haloalkyl, alkylsulfanyl, amino, —NH-alkyl, —N(alkyl)$_2$, —NH-aryl, —NH-heteroaryl and a group

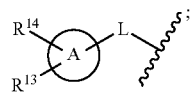

$R^{13}$ is selected from the group consisting of hydrogen, oxo, halogen, alkyl, carbamoyl, substituted carbamoyl and alkoxycarbonyl, wherein said substituted carbamoyl is substituted at the nitrogen atom with one to two alkyl substituents;

$R^{14}$ is hydrogen or halogen;

L is selected from the group consisting of a covalent bond, —CH=CH—, —O—, —CH$_2$O—, —OCH$_2$—, —CH$_2$— and —CH$_2$CH$_2$—; and A is selected from the group consisting of aryl, heteroaryl, cycloalkyl and heterocyclyl.

In one embodiment, the present invention provides a compound of formula (I), or a pharmaceutically acceptable salt thereof, wherein:

$R^1$ is selected from the group consisting of
 (i) aryl substituted with $R^8$, $R^9$ and $R^{10}$; and
 (ii) heteroaryl substituted with $R^{11}$ and $R^{12}$.

each of $R^2$, $R^3$, $R^4$, $R^5$ and $R^6$ is independently selected from the group consisting of hydrogen, halogen, alkoxy, haloalkoxy, hydroxy, amino, —NH-alkyl, —N(alkyl)$_2$ and cyano;

$R^7$ is selected from the group consisting of hydrogen, halogen and hydroxy; each of $R^8$, $R^9$, $R^{10}$, $R^{11}$ and $R^{12}$ is independently selected from the group consisting of hydrogen, hydroxy, alkoxy, cyano, alkoxyalkyl, haloalkoxy, halogen, alkyl, haloalkyl, alkylsulfanyl and a group

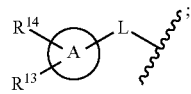

$R^{13}$ is selected from the group consisting of hydrogen, halogen, alkyl, carbamoyl, substituted carbamoyl and alkoxycarbonyl, wherein said substituted carbamoyl is substituted at the nitrogen atom with one to two alkyl substituents;

$R^{14}$ is hydrogen or halogen;

L is selected from the group consisting of a covalent bond, —CH=CH—, —O—, —CH$_2$O—, —OCH$_2$—, —CH$_2$— and —CH$_2$CH$_2$—; and A is selected from the group consisting of aryl, heteroaryl, cycloalkyl and heterocyclyl.

In one embodiment, the present invention provides a compound of formula (I), or a pharmaceutically acceptable salt thereof, wherein:

$R^1$ is selected from the group consisting of
 (i) aryl substituted with $R^8$, $R^9$ and $R^{10}$; and
 (ii) heteroaryl substituted with $R^{11}$ and $R^{12}$;

each of $R^2$, $R^3$, $R^4$, $R^5$ and $R^6$ is independently selected from the group consisting of hydrogen, halogen, alkoxy, haloalkoxy, hydroxy, amino, —NH-alkyl, —N(alkyl)$_2$ and cyano;

$R^7$ is selected from the group consisting of hydrogen, halogen and hydroxy; each of $R^8$, $R^9$, $R^{10}$, $R^{11}$ and $R^{12}$ is independently selected from the group consisting of hydrogen, hydroxy, alkoxy, cyano, alkoxyalkyl, haloalkoxy, halogen, alkyl, haloalkyl, alkylsulfanyl and a group

[Structure showing R¹⁴, R¹³ attached to ring A with linker L]

R¹³ is selected from the group consisting of hydrogen, halogen, alkyl, carbamoyl, substituted carbamoyl and alkoxycarbonyl, wherein said substituted carbamoyl is substituted at the nitrogen atom with one to two alkyl substituents;

R¹⁴ is hydrogen or halogen;

L is selected from the group consisting of a covalent bond, —CH=CH—, —O—, —CH₂O—, —OCH₂—, —CH₂— and —CH₂CH₂—; and A is selected from the group consisting of aryl, heteroaryl, cycloalkyl and heterocyclyl;

with the proviso that the compound of formula (I) is not (4-fluorophenyl)-[7-(4-fluorophenyl)-1,3,4,6,7,8,9,9a-octahydropyrido[1,2-a]pyrazin-2-yl]methanone.

In one embodiment, the compound of formula (Ie) according to the invention is a compound of formula (Ia)

(Ia)

wherein R¹, R², R³, R⁴, R⁵, R⁶ and R⁷ are as defined herein.

In one embodiment, the compound of formula (Ie) according to the invention is a compound of formula (Ib)

(Ib)

wherein R¹, R², R³, R⁴, R⁵, R⁶ and R⁷ are as defined herein.

In one embodiment, the compound of formula (Ie) according to the invention is a compound of formula (Ic)

(Ic)

wherein R, R², R³, R⁴, R⁵, R⁶ and R⁷ are as defined herein.

In one embodiment, the compound of formula (Ie) according to the invention is a compound of formula (Id)

(Id)

wherein R¹, R², R³, R⁴, R⁵, R⁶ and R⁷ are as defined herein.

In one embodiment, there is provided a compound of formula (Ie), preferably of formula (I), as described herein, or a pharmaceutically acceptable salt thereof, wherein:

R¹ is selected from the group consisting of
  (i) aryl substituted with R⁸, R⁹ and R¹⁰; and
  (ii) heteroaryl substituted with R¹¹ and R¹²;

R⁸ is selected from the group consisting of hydroxy, alkoxy, cyano, alkoxyalkyl, haloalkoxy, halogen, alkyl, haloalkyl and a group

[Structure showing R¹⁴, R¹³ attached to ring A with linker L]

R⁹ is hydrogen or halogen;

R¹⁰ is hydrogen or halogen;

R¹¹ is selected from the group consisting of hydrogen, halogen, alkyl, alkoxy and alkylsulfanyl;

R¹² is selected from the group consisting of hydrogen, halogen and alkyl;

R¹³ is selected from the group consisting of hydrogen, halogen, alkyl, carbamoyl, substituted carbamoyl and alkoxycarbonyl, wherein said substituted carbamoyl is substituted at the nitrogen atom with one to two alkyl substituents;

R¹⁴ is hydrogen or halogen;

L is selected from the group consisting of —CH=CH—, —O— and —CH₂O—; and

A is aryl or heteroaryl.

In one embodiment, there is provided a compound of formula (Ie), preferably of formula (I), as described herein, or a pharmaceutically acceptable salt thereof, wherein:

R¹ is selected from the group consisting of:
  (i) aryl substituted with R⁸, R⁹ and R¹⁰; and (ii) heteroaryl substituted with $R^{11}$ and $R^{12}$;
$R^8$ is selected from the group consisting of hydroxy, alkoxy, cyano, alkoxyalkyl, haloalkoxy, halogen, alkyl, haloalkyl and a group

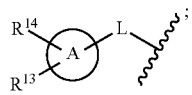

$R^9$ is hydrogen or halogen;
$R^{10}$ is hydrogen or halogen;
$R^{11}$ is selected from the group consisting of hydrogen, halogen, alkyl, alkoxy and alkylsulfanyl;
$R^{12}$ is selected from the group consisting of hydrogen, halogen and alkyl;
$R^{13}$ is selected from the group consisting of hydrogen, halogen, alkyl, carbamoyl, substituted carbamoyl and alkoxycarbonyl, wherein said substituted carbamoyl is substituted at the nitrogen atom with one to two alkyl substituents;
$R^{14}$ is hydrogen or halogen;
L is selected from the group consisting of a covalent bond, —CH=CH—, —O— and —CH$_2$O—; and
A is selected from the group consisting of aryl, heteroaryl, cycloalkyl and heterocyclyl.

In a preferred embodiment, there is provided a compound of formula (Ie), preferably of formula (I), as described herein, or a pharmaceutically acceptable salt thereof, wherein:
$R^1$ is selected from the group consisting of
(i) aryl substituted with $R^8$, $R^9$ and $R^{10}$; and
(ii) heteroaryl substituted with $R^{11}$ and $R^{12}$.
$R^8$ is selected from the group consisting of alkoxy, haloalkoxy, alkyl and a group

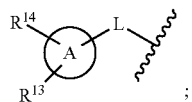

$R^9$ is halogen;
$R^{10}$ is hydrogen or halogen;
$R^{11}$ is selected from the group consisting of hydrogen, alkyl and alkylsulfanyl;
$R^{12}$ is selected from the group consisting of hydrogen, halogen and alkyl;
$R^{13}$ is hydrogen;
$R^{14}$ is hydrogen;
L is —CH$_2$O—; and
A is heteroaryl.

In a preferred embodiment, there is provided a compound of formula (e), preferably of formula (I), as described herein, or a pharmaceutically acceptable salt thereof, wherein:
$R^1$ is selected from the group consisting of
(i) aryl substituted with $R^8$, $R^9$ and $R^{10}$; and
(ii) heteroaryl substituted with $R^{11}$ and $R^{12}$;
$R^8$ is selected from the group consisting of alkoxy, haloalkoxy, alkyl and a group

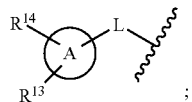

$R^9$ is halogen;
$R^{10}$ is hydrogen or halogen;
$R^{11}$ is selected from the group consisting of hydrogen, alkyl and alkylsulfanyl;
$R^{12}$ is selected from the group consisting of hydrogen, halogen and alkyl;
$R^{13}$ is hydrogen;
$R^{14}$ is hydrogen;
L is a covalent bond or —CH$_2$O—; and
A is heteroaryl or heterocyclyl.

In a particularly preferred embodiment, there is provided a compound of formula (Ie), preferably of formula (I), as described herein, or a pharmaceutically acceptable salt thereof, wherein
$R^1$ is selected from the group consisting of
(i) phenyl substituted with $R^8$, $R^9$ and $R^{10}$; and
(ii) heteroaryl substituted with $R^{11}$ and $R^{12}$, wherein said heteroaryl is selected from the group consisting of indolyl, pyrrolo[2,3-b]pyridyl, 1,3-benzothiazolyl, thiazolo[5,4-b]pyridyl and pyrazolo[3,4-b]pyridyl;
$R^8$ is selected from the group consisting of methoxy, 2,2,2-trifluoroethoxy, methyl and a group

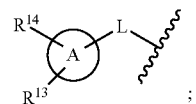

$R^9$ is Cl or Br;
$R^{10}$ is hydrogen or F;
$R^{11}$ is selected from the group consisting of hydrogen, methyl and methylsulfanyl;
$R^{12}$ is selected from the group consisting of hydrogen, Cl and methyl;
$R^{13}$ is hydrogen;
$R^{14}$ is hydrogen;
L is —CH$_2$O—; and
A is thiazolyl or pyrazolyl.

In a particularly preferred embodiment, there is provided a compound of formula (Ie), preferably of formula (I), as described herein, or a pharmaceutically acceptable salt thereof, wherein
$R^1$ is selected from the group consisting of
(i) phenyl substituted with $R^8$, $R^9$ and $R^{10}$; and
(ii) heteroaryl substituted with $R^{11}$ and $R^{12}$, wherein said heteroaryl is selected from the group consisting of indolyl, pyrrolo[2,3-b]pyridyl, 1,3-benzothiazolyl, thiazolo[5,4-b]pyridyl, 1H-indazol-5-yl, thieno[2,3-b]pyridin-5-yl, and pyrazolo[3,4-b]pyridyl;
$R^8$ is selected from the group consisting of methoxy, 2,2,2-trifluoroethoxy, methyl and a group

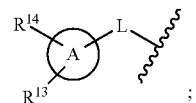

$R^9$ is Cl or Br;
$R^{10}$ is hydrogen or F;
$R^{11}$ is selected from the group consisting of hydrogen, methyl and methylsulfanyl;
$R^{12}$ is selected from the group consisting of hydrogen, Cl and methyl;

$R^{13}$ is hydrogen;
$R^{14}$ is hydrogen;
L is a covalent bond or —CH$_2$O—; and
A is thiazolyl, pyrazolyl or 2-oxa-6-azaspiro[3.3]heptan-6-yl.

In a preferred embodiment, there is provided a compound of formula (Ie), preferably of formula (I), as described herein, or a pharmaceutically acceptable salt thereof, wherein $R^1$ is phenyl substituted with $R^8$, $R^9$ and $R^{10}$, wherein $R^8$ is a group

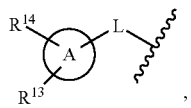

wherein the group

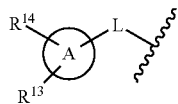

is selected from the group consisting of (1-methylpyrazol-4-yl)methoxy; thiazol-4-ylmethoxy; [4-(methylcarbamoyl)phenyl]methoxy; (1-tert-butoxycarbonylpyrazol-4-yl)methoxy; 1H-pyrazol-4-ylmethoxy; pyridazin-3-ylmethoxy; 4-pyridylmethoxy; 3-pyridylmethoxy; (Z)-2-cyclopropylvinyl; (Z)-2-[2-bromo-3-(methylcarbamoyl)phenyl]vinyl; 2-oxa-6-azaspiro[3.3]heptan-6-yl.

In a preferred embodiment, there is provided a compound of formula (Ie), as described herein, or a pharmaceutically acceptable salt thereof, wherein $R^{1a}$ is aryl substituted with $R^2$, $R^3$, $R^4$, $R^5$ and $R^6$, or a possible combination thereof, wherein $R^2$, $R^3$, $R^4$, $R^5$ and $R^6$ are as defined herein.

In a particularly preferred embodiment, there is provided a compound of formula (Ie), as described herein, or a pharmaceutically acceptable salt thereof, wherein $R^{1a}$ is phenyl substituted with $R^2$, $R^3$, $R^4$, $R^5$ and $R^6$, or a possible combination thereof, wherein $R^2$, $R^3$, $R^4$, $R^5$ and $R^6$ are as defined herein.

In a preferred embodiment, there is provided a compound of formula (Ie), preferably of formula (I), as described herein, or a pharmaceutically acceptable salt thereof, wherein $R^1$ is selected from the group consisting of.
(i) phenyl substituted with $R^8$, $R^9$ and $R^{10}$; and
(ii) heteroaryl substituted with $R^{11}$ and $R^{12}$, wherein said heteroaryl is selected from the group consisting of indolyl, pyrrolo[2,3-b]pyridyl, 1,3-benzothiazolyl, thiazolo[5,4-b]pyridyl, 1H-indazol-5-yl, thieno[2,3-b]pyridin-5-yl, and pyrazolo[3,4-b]pyridyl;
wherein $R^8$, $R^9$ $R^{10}$, $R^{11}$ and $R^{12}$ are as defined herein.

In a preferred embodiment, there is provided a compound of formula (e), preferably of formula (I), as described herein, or a pharmaceutically acceptable salt thereof, wherein $R^2$ is hydrogen.

In a preferred embodiment, there is provided a compound of formula (e), preferably of formula (I), as described herein, or a pharmaceutically acceptable salt thereof, wherein $R^3$ is selected from the group consisting of hydrogen and halogen.

In a particularly preferred embodiment, there is provided a compound of formula (Ie), preferably of formula (I), as described herein, or a pharmaceutically acceptable salt thereof, wherein $R^3$ is selected from the group consisting of hydrogen and Cl.

In a preferred embodiment, there is provided a compound of formula (Ie), preferably of formula (I), as described herein, or a pharmaceutically acceptable salt thereof, wherein $R^4$ is selected from the group consisting of hydrogen and halogen.

In a particularly preferred embodiment, there is provided a compound of formula (Ie), preferably of formula (I), as described herein, or a pharmaceutically acceptable salt thereof, wherein $R^4$ is selected from the group consisting of hydrogen, F and Cl.

In a further particularly preferred embodiment, there is provided a compound of formula (Ie), preferably of formula (I), as described herein, or a pharmaceutically acceptable salt thereof, wherein $R^4$ is selected from the group consisting of hydrogen and Cl.

In a preferred embodiment, there is provided a compound of formula (Ie), preferably of formula (I), as described herein, or a pharmaceutically acceptable salt thereof, wherein $R^5$ is hydrogen.

In a preferred embodiment, there is provided a compound of formula (Ie), preferably of formula (I), as described herein, or a pharmaceutically acceptable salt thereof, wherein $R^6$ is hydrogen.

In one embodiment, there is provided a compound of formula (Ie), preferably of formula (I), as described herein, or a pharmaceutically acceptable salt thereof, wherein $R^7$ is selected from the group consisting of hydrogen, F, methoxy and hydroxy.

In one embodiment, there is provided a compound of formula (Ie), preferably of formula (I), as described herein, or a pharmaceutically acceptable salt thereof, wherein $R^7$ is selected from the group consisting of hydrogen, F and hydroxy.

In one embodiment, there is provided a compound of formula (Ie), preferably of formula (I), as described herein, or a pharmaceutically acceptable salt thereof, wherein $R^7$ is hydroxy.

In one embodiment, there is provided a compound of formula (Ie), preferably of formula (I), as described herein, or a pharmaceutically acceptable salt thereof, wherein $R^7$ is F.

In a preferred embodiment, there is provided a compound of formula (Ie), preferably of formula (I), as described herein, or a pharmaceutically acceptable salt thereof, wherein $R^7$ is hydrogen.

In a preferred embodiment, there is provided a compound of formula (Ie), preferably of formula (I), as described herein, or a pharmaceutically acceptable salt thereof, wherein $R^2$, $R^5$, $R^6$ and $R^7$ are hydrogen and $R^3$ and $R^4$ are independently selected from the group consisting of hydrogen and halogen.

In another preferred embodiment, there is provided a compound of formula (Ie), preferably of formula (I), as described herein, or a pharmaceutically acceptable salt thereof, wherein $R^2$, $R^5$ and $R^6$ are hydrogen; $R^7$ is selected from the group consisting of hydrogen, halogen, alkoxy and hydroxy and $R^3$ and $R^4$ are independently selected from the group consisting of hydrogen and halogen.

In a particularly preferred embodiment, there is provided a compound of formula (Ie), preferably of formula (I), as described herein, or a pharmaceutically acceptable salt thereof, wherein $R^2$, $R^5$, $R^6$ and $R^7$ are hydrogen and $R^3$ and $R^4$ are independently selected from the group consisting of hydrogen and Cl.

In another particularly preferred embodiment, there is provided a compound of formula (Ie), preferably of formula (I), as described herein, or a pharmaceutically acceptable salt thereof, wherein $R^2$, $R^5$ and $R^6$ are hydrogen; $R^7$ is selected from the group consisting of hydrogen, F, methoxy and hydroxy; $R^3$ is selected from the group consisting of hydrogen and Cl; and $R^4$ is selected from the group consisting of hydrogen, F and Cl.

In one embodiment, there is provided a compound of formula (Ie), preferably of formula (I), as described herein, or a pharmaceutically acceptable salt thereof, wherein $R^8$ is selected from the group consisting of hydroxy, alkoxy, cyano, alkoxyalkyl, haloalkoxy, halogen, alkyl, haloalkyl and a group

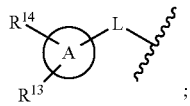

wherein A, L, $R^{13}$ and $R^{14}$ are as defined herein.

In a preferred embodiment, there is provided a compound of formula (Ie), preferably of formula (I), as described herein, or a pharmaceutically acceptable salt thereof, wherein $R^8$ is selected from the group consisting of alkoxy, haloalkoxy, alkyl and a group

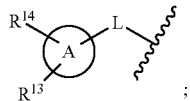

wherein A, L, $R^{13}$ and $R^{14}$ are as defined herein.

In a particularly preferred embodiment, there is provided a compound of formula (Ie), preferably of formula (I), as described herein, or a pharmaceutically acceptable salt thereof, wherein $R^8$ is selected from the group consisting of methoxy, 2,2,2-trifluoroethoxy, methyl and a group

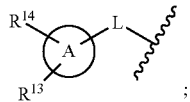

wherein A, L, $R^{13}$ and $R^{14}$ are as defined herein.

In one embodiment, there is provided a compound of formula (Ie), preferably of formula (I), as described herein, or a pharmaceutically acceptable salt thereof, wherein $R^9$ is hydrogen or halogen.

In a preferred embodiment, there is provided a compound of formula (Ie), preferably of formula (I), as described herein, or a pharmaceutically acceptable salt thereof, wherein $R^9$ is halogen.

In a particularly preferred embodiment, there is provided a compound of formula (Ie), preferably of formula (I), as described herein, or a pharmaceutically acceptable salt thereof, wherein $R^9$ is Cl or Br.

In a preferred embodiment, there is provided a compound of formula (Ie), preferably of formula (I), as described herein, or a pharmaceutically acceptable salt thereof, wherein $R^{10}$ is hydrogen or halogen.

In a particularly preferred embodiment, there is provided a compound of formula (Ie), preferably of formula (I), as described herein, or a pharmaceutically acceptable salt thereof, wherein $R^{10}$ is hydrogen or F.

In one embodiment, there is provided a compound of formula (Ie), preferably of formula (I), as described herein, or a pharmaceutically acceptable salt thereof, wherein $R^{11}$ is selected from the group consisting of hydrogen, halogen, alkyl, alkoxy and alkylsulfanyl.

In a preferred embodiment, there is provided a compound of formula (Ie), preferably of formula (I), as described herein, or a pharmaceutically acceptable salt thereof, wherein $R^{11}$ is selected from the group consisting of hydrogen, alkyl and alkylsulfanyl.

In a particularly preferred embodiment, there is provided a compound of formula (Ie), preferably of formula (I), as described herein, or a pharmaceutically acceptable salt thereof, wherein $R^{11}$ is selected from the group consisting of hydrogen, methyl and methylsulfanyl.

In a preferred embodiment, there is provided a compound of formula (Ie), preferably of formula (I), as described herein, or a pharmaceutically acceptable salt thereof, wherein $R^{12}$ is selected from the group consisting of hydrogen, halogen and alkyl.

In a particularly preferred embodiment, there is provided a compound of formula (Ie), preferably of formula (I), as described herein, or a pharmaceutically acceptable salt thereof, wherein $R^{12}$ is selected from the group consisting of hydrogen, Cl and methyl.

In one embodiment, there is provided a compound of formula (Ie), preferably of formula (I), as described herein, or a pharmaceutically acceptable salt thereof, wherein $R^{13}$ is selected from the group consisting of hydrogen, halogen, alkyl, carbamoyl, substituted carbamoyl and alkoxycarbonyl, wherein said substituted carbamoyl is substituted at the nitrogen atom with one to two alkyl substituents.

In a particularly preferred embodiment, there is provided a compound of formula (Ie), preferably of formula (I), as described herein, or a pharmaceutically acceptable salt thereof, wherein $R^{13}$ is hydrogen.

In one embodiment, there is provided a compound of formula (Ie), preferably of formula (I), as described herein, or a pharmaceutically acceptable salt thereof, wherein $R^{14}$ is hydrogen or halogen.

In a particularly preferred embodiment, there is provided a compound of formula (Ie), preferably of formula (I), as described herein, or a pharmaceutically acceptable salt thereof, wherein $R^{14}$ is hydrogen.

In one embodiment, there is provided a compound of formula (Ie), preferably of formula (I), as described herein, or a pharmaceutically acceptable salt thereof, wherein A is selected from the group consisting of aryl, heteroaryl, cycloalkyl and heterocyclyl.

In a preferred embodiment, there is provided a compound of formula (e), preferably of formula (I), as described herein, or a pharmaceutically acceptable salt thereof, wherein A is heteroaryl or heterocyclyl.

In a particularly preferred embodiment, there is provided a compound of formula (Ie), preferably of formula (I), as described herein, or a pharmaceutically acceptable salt thereof, wherein A is selected from the group consisting of thiazolyl, pyrazolyl and 2-oxa-6-azaspiro[3.3]heptan-6-yl.

In one embodiment, there is provided a compound of formula (Ie), preferably of formula (I), as described herein, or a pharmaceutically acceptable salt thereof, wherein L is selected from the group consisting of a covalent bond, —CH=CH—, —O— and —CH$_2$O—.

In a particularly preferred embodiment, there is provided a compound of formula (Ie), preferably of formula (I), as described herein, or a pharmaceutically acceptable salt thereof, wherein L is a covalent bond or —CH$_2$O—.

In one embodiment, there is provided a compound of formula (Ie), preferably of formula (I), as described herein, or a pharmaceutically acceptable salt thereof, wherein
$R^1$ is selected from the group consisting of
  (i) aryl substituted with $R^8$, $R^9$ and $R^{10}$; and
  (ii) heteroaryl substituted with $R^{11}$ and $R^{12}$;
$R^2$, $R^5$, $R^6$ and $R^7$ are hydrogen;
$R^3$ and $R^4$ are independently selected from the group consisting of hydrogen and halogen;
$R^8$ is selected from the group consisting of hydroxy, alkoxy, cyano, alkoxyalkyl, haloalkoxy, halogen, alkyl, haloalkyl and a group

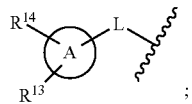

$R^9$ is hydrogen or halogen;
$R^{10}$ is hydrogen or halogen;
$R^{11}$ is selected from the group consisting of hydrogen, halogen, alkyl, alkoxy and alkylsulfanyl;
$R^{12}$ is selected from the group consisting of hydrogen, halogen and alkyl;
$R^{13}$ is selected from the group consisting of hydrogen, halogen, alkyl, carbamoyl, substituted carbamoyl and alkoxycarbonyl, wherein said substituted carbamoyl is substituted at the nitrogen atom with one to two alkyl substituents;
$R^{14}$ is hydrogen or halogen;
L is selected from the group consisting of —CH=CH—, —O— and —CH$_2$O—; and
A is aryl or heteroaryl.

In one embodiment, there is provided a compound of formula (Ie), preferably of formula (I), as described herein, or a pharmaceutically acceptable salt thereof, wherein
$R^{1a}$ is selected from the group consisting of
  (i) $C_{1-6}$-alkyl;
  (ii) $C_{1-6}$-alkoxy; and
  (iii) aryl substituted with $R^2$, $R^3$, $R^4$, $R^5$ and $R^6$, or a possible combination thereof;
$R^1$ is selected from the group consisting of
  (i) aryl substituted with $R^8$, $R^9$ and $R^{10}$; and
  (ii) heteroaryl substituted with $R^{11}$ and $R^{12}$;
$R^2$, $R^5$ and $R^6$ are hydrogen;
$R^3$ and $R^4$ are independently selected from the group consisting of hydrogen and halogen;
$R^7$ is selected from the group consisting of hydrogen, halogen, alkoxy and hydroxy;
$R^8$ is selected from the group consisting of hydroxy, alkoxy, cyano, alkoxyalkyl, haloalkoxy, halogen, alkyl, haloalkyl and a group

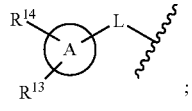

$R^9$ is hydrogen or halogen;
$R^{10}$ is hydrogen or halogen;
$R^{11}$ is selected from the group consisting of hydrogen, halogen, alkyl, alkoxy and alkylsulfanyl;

$R^{12}$ is selected from the group consisting of hydrogen, halogen and alkyl;
$R^{13}$ is selected from the group consisting of hydrogen, halogen, alkyl, carbamoyl, substituted carbamoyl and alkoxycarbonyl, wherein said substituted carbamoyl is substituted at the nitrogen atom with one to two alkyl substituents;
$R^{14}$ is hydrogen or halogen;
L is selected from the group consisting of a covalent bond, —CH=CH—, —O— and —CH$_2$O—; and
A is selected from the group consisting of aryl, heteroaryl, cycloalkyl and heterocyclyl.

In a preferred embodiment, there is provided a compound of formula (Ie), preferably of formula (I), as described herein, or a pharmaceutically acceptable salt thereof, wherein
$R^1$ is selected from the group consisting of
  (i) aryl substituted with $R^8$, $R^9$ and $R^{10}$; and
  (ii) heteroaryl substituted with $R^{11}$ and $R^{12}$;
$R^2$, $R^5$, $R^6$ and $R^7$ are hydrogen;
$R^3$ and $R^4$ are independently selected from the group consisting of hydrogen and halogen;
$R^8$ is selected from the group consisting of alkoxy, haloalkoxy, alkyl and a group

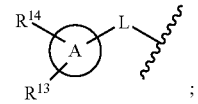

$R^9$ is halogen;
$R^{10}$ is hydrogen or halogen;
$R^{11}$ is selected from the group consisting of hydrogen, alkyl and alkylsulfanyl;
$R^{12}$ is selected from the group consisting of hydrogen, halogen and alkyl;
$R^{13}$ is hydrogen;
$R^{14}$ is hydrogen;
L is —CH$_2$O—; and
A is heteroaryl.

In another preferred embodiment, there is provided a compound of formula (Ie), preferably of formula (I), as described herein, or a pharmaceutically acceptable salt thereof, wherein
$R^{1a}$ is aryl substituted with $R^2$, $R^3$, $R^4$, $R^5$ and $R^6$, or a possible combination thereof;
$R^1$ is selected from the group consisting of
  (i) aryl substituted with $R^8$, $R^9$ and $R^{10}$; and
  (ii) heteroaryl substituted with $R^{11}$ and $R^{12}$;
$R^2$, $R^5$ and $R^6$ are hydrogen;
$R^3$ and $R^4$ are independently selected from the group consisting of hydrogen and halogen;
$R^7$ is selected from the group consisting of hydrogen, halogen, alkoxy and hydroxy;
$R^8$ is selected from the group consisting of alkoxy, haloalkoxy, alkyl and a group

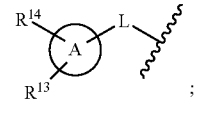

$R^9$ is halogen;
$R^{10}$ is hydrogen or halogen;

$R^{11}$ is selected from the group consisting of hydrogen, alkyl and alkylsulfanyl;
$R^{12}$ is selected from the group consisting of hydrogen, halogen and alkyl;
$R^{13}$ is hydrogen;
$R^{14}$ is hydrogen;
L is a covalent bond or —CH$_2$O—; and
A is heteroaryl or heterocyclyl.

In a particularly preferred embodiment, there is provided a compound of formula (Ie), preferably of formula (I), as described herein, or a pharmaceutically acceptable salt thereof, wherein
$R^1$ is selected from the group consisting of
  (i) phenyl substituted with $R^8$, $R^9$ and $R^{10}$; and
  (ii) heteroaryl substituted with $R^{11}$ and $R^{12}$, wherein said heteroaryl is selected from the group consisting of indolyl, pyrrolo[2,3-b]pyridyl, 1,3-benzothiazolyl, thiazolo[5,4-b]pyridyl and pyrazolo[3,4-b]pyridyl;
$R^2$, $R^5$, $R^6$ and $R^7$ are hydrogen;
$R^3$ and $R^4$ are independently selected from the group consisting of hydrogen and Cl;
$R^8$ is selected from the group consisting of methoxy, 2,2,2-trifluoroethoxy, methyl and a group

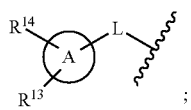

$R^9$ is Cl or Br;
$R^{10}$ is hydrogen or F;
$R^{11}$ is selected from the group consisting of hydrogen, methyl and methylsulfanyl;
$R^{12}$ is selected from the group consisting of hydrogen, Cl and methyl;
$R^{13}$ is hydrogen;
$R^{14}$ is hydrogen;
L is —CH$_2$O—; and
A is thiazolyl or pyrazolyl.

In another particularly preferred embodiment, there is provided a compound of formula (Ie), preferably of formula (I), as described herein, or a pharmaceutically acceptable salt thereof, wherein
$R^{1a}$ is phenyl substituted with $R^2$, $R^3$, $R^4$, $R^1$ and $R^6$, or a possible combination thereof;
$R^1$ is selected from the group consisting of
  (i) phenyl substituted with $R^8$, $R^9$ and $R^{10}$; and
  (ii) heteroaryl substituted with $R^{11}$ and $R^{12}$, wherein said heteroaryl is selected from the group consisting of indolyl, pyrrolo[2,3-b]pyridyl, 1,3-benzothiazolyl, thiazolo[5,4-b]pyridyl, 1H-indazol-5-yl, thieno[2,3-b]pyridin-5-yl, and pyrazolo[3,4-b]pyridyl;
$R^2$, $R^5$ and $R^6$ are hydrogen;
$R^3$ is selected from the group consisting of hydrogen and Cl;
$R^4$ is selected from the group consisting of hydrogen, F and Cl;
$R^7$ is selected from the group consisting of hydrogen, F, methoxy and hydroxy;
$R^8$ is selected from the group consisting of methoxy, 2,2,2-trifluoroethoxy, methyl and a group

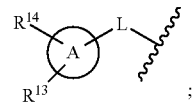

$R^9$ is Cl or Br;
$R^{10}$ is hydrogen or F;
$R^{11}$ is selected from the group consisting of hydrogen, methyl and methylsulfanyl;
$R^{12}$ is selected from the group consisting of hydrogen, Cl and methyl;
$R^{13}$ is hydrogen;
$R^{14}$ is hydrogen;
L is a covalent bond or —CH$_2$O—; and
A is thiazolyl, pyrazolyl or 2-oxa-6-azaspiro[3.3]heptan-6-yl.

In one embodiment, there is provided a compound of formula (Ie) as described herein, selected from the group consisting of:
[(7R,9aR)-7-(4-chlorophenyl)-1,3,4,6,7,8,9,9a-octahydropyrido[1,2-a]pyrazin-2-yl]-(3-phenoxyphenyl)methanone;
[(7R,9aR)-7-(4-chlorophenyl)-1,3,4,6,7,8,9,9a-octahydropyrido[1,2-a]pyrazin-2-yl]-(2-chloro-3-methylphenyl)methanone;
[(7R,9aR)-7-(4-chlorophenyl)-1,3,4,6,7,8,9,9a-octahydropyrido[1,2-a]pyrazin-2-yl]-(2-bromo-3-methoxyphenyl)methanone;
[(7R,9aR)-7-(4-chlorophenyl)-1,3,4,6,7,8,9,9a-octahydropyrido[1,2-a]pyrazin-2-yl]-(2-bromo-3-methoxyphenyl)methanone;hydrochloride;
[(7R,9aR)-7-(4-chlorophenyl)-1,3,4,6,7,8,9,9a-octahydropyrido[1,2-a]pyrazin-2-yl]-[3-(3,5-difluorophenoxy)phenyl]methanone;
[(7R,9aR)-7-phenyl-1,3,4,6,7,8,9,9a-octahydropyrido[1,2-a]pyrazin-2-yl]-(2-bromo-3-methoxyphenyl)methanone;
[(7R,9aR)-7-(4-chlorophenyl)-1,3,4,6,7,8,9,9a-octahydropyrido[1,2-a]pyrazin-2-yl]-(2-chloro-3-methoxyphenyl)methanone;
[(7R,9aR)-7-(4-chlorophenyl)-1,3,4,6,7,8,9,9a-octahydropyrido[1,2-a]pyrazin-2-yl]-(2-methoxyphenyl)methanone;
[(7R,9aR)-7-(4-chlorophenyl)-1,3,4,6,7,8,9,9a-octahydropyrido[1,2-a]pyrazin-2-yl]-[2-(trifluoromethoxy)phenyl]methanone;
[(7R,9aR)-7-(4-chlorophenyl)-1,3,4,6,7,8,9,9a-octahydropyrido[1,2-a]pyrazin-2-yl]-(2,3-dihydro-1-benzofuran-7-yl)methanone;
[(7R,9aR)-7-(4-chlorophenyl)-1,3,4,6,7,8,9,9a-octahydropyrido[1,2-a]pyrazin-2-yl]-(1H-indol-4-yl)methanone;
[(7R,9aR)-7-(4-chlorophenyl)-1,3,4,6,7,8,9,9a-octahydropyrido[1,2-a]pyrazin-2-yl]-(2-chloro-6-fluorophenyl)methanone;
[(7R,9aR)-7-(4-chlorophenyl)-1,3,4,6,7,8,9,9a-octahydropyrido[1,2-a]pyrazin-2-yl]-(2-chlorophenyl)methanone;
[(7R,9aR)-7-(4-chlorophenyl)-1,3,4,6,7,8,9,9a-octahydropyrido[1,2-a]pyrazin-2-yl]-(2-fluoro-3-methylphenyl)methanone;
[(7R,9aR)-7-(4-chlorophenyl)-1,3,4,6,7,8,9,9a-octahydropyrido[1,2-a]pyrazin-2-yl]-(4-chloro-1H-pyrrolo[2,3-b]pyridin-5-yl)methanone;
[(7R,9aR)-7-(4-chlorophenyl)-1,3,4,6,7,8,9,9a-octahydropyrido[1,2-a]pyrazin-2-yl]-(1H-pyrrolo[2,3-b]pyridin-4-yl)methanone;

[(7R,9aR)-7-(4-chlorophenyl)-1,3,4,6,7,8,9,9a-octahydropyrido[1,2-a]pyrazin-2-yl]-[2-chloro-3-(trifluoromethyl)phenyl]methanone;

[(7R,9aR)-7-(4-chlorophenyl)-1,3,4,6,7,8,9,9a-octahydropyrido[1,2-a]pyrazin-2-yl]-(2-chloro-4-fluoro-3-methylphenyl)methanone;

[(7R,9aR)-7-(4-chlorophenyl)-1,3,4,6,7,8,9,9a-octahydropyrido[1,2-a]pyrazin-2-yl]-(3-chloro-2-methylphenyl)methanone;

[(7R,9aR)-7-(4-chlorophenyl)-1,3,4,6,7,8,9,9a-octahydropyrido[1,2-a]pyrazin-2-yl]-(4-chloro-6-methylpyridin-3-yl)methanone;

[(7R,9aR)-7-(4-chlorophenyl)-1,3,4,6,7,8,9,9a-octahydropyrido[1,2-a]pyrazin-2-yl]-(2,4-dimethyl-1,3-benzothiazol-5-yl)methanone;

[(7R,9aR)-7-(4-chlorophenyl)-1,3,4,6,7,8,9,9a-octahydropyrido[1,2-a]pyrazin-2-yl]-(7-chloro-2-methylsulfanyl-[1,3]thiazolo[5,4-b]pyridin-6-yl)methanone;

[(7R,9aR)-7-(4-chlorophenyl)-1,3,4,6,7,8,9,9a-octahydropyrido[1,2-a]pyrazin-2-yl]-(1-benzothiophen-4-yl)methanone;

[(7R,9aR)-7-(4-chlorophenyl)-1,3,4,6,7,8,9,9a-octahydropyrido[1,2-a]pyrazin-2-yl]-(2-bromo-3-methylphenyl)methanone;

[(7R,9aR)-7-(4-chlorophenyl)-1,3,4,6,7,8,9,9a-octahydropyrido[1,2-a]pyrazin-2-yl]-[2-(trifluoromethyl)phenyl]methanone;

[(7R,9aR)-7-(4-chlorophenyl)-1,3,4,6,7,8,9,9a-octahydropyrido[1,2-a]pyrazin-2-yl]-(2-chloro-3-phenoxyphenyl)methanone;

[(7R,9aR)-7-phenyl-1,3,4,6,7,8,9,9a-octahydropyrido[1,2-a]pyrazin-2-yl]-(2-chloro-3-methylphenyl)methanone;

[(7R,9aR)-7-phenyl-1,3,4,6,7,8,9,9a-octahydropyrido[1,2-a]pyrazin-2-yl]-(2-chloro-3-methylphenyl)methanone;hydrochloride;

[(7R,9aR)-7-phenyl-1,3,4,6,7,8,9,9a-octahydropyrido[1,2-a]pyrazin-2-yl]-(2-chloro-5-fluoro-3-methylphenyl)methanone;

[(7R,9aR)-7-phenyl-1,3,4,6,7,8,9,9a-octahydropyrido[1,2-a]pyrazin-2-yl]-[2-bromo-3-(methoxymethyl)phenyl]methanone;

[(7R,9aR)-7-phenyl-1,3,4,6,7,8,9,9a-octahydropyrido[1,2-a]pyrazin-2-yl]-(1H-indol-4-yl)methanone;

[(7R,9aR)-7-phenyl-1,3,4,6,7,8,9,9a-octahydropyrido[1,2-a]pyrazin-2-yl]-(1-methylindol-4-yl)methanone;

[(7R,9aR)-7-phenyl-1,3,4,6,7,8,9,9a-octahydropyrido[1,2-a]pyrazin-2-yl]-(4-chloro-1H-pyrrolo[2,3-b]pyridin-5-yl)methanone;

[(7R,9aR)-7-phenyl-1,3,4,6,7,8,9,9a-octahydropyrido[1,2-a]pyrazin-2-yl]-(2-chloro-3-hydroxyphenyl)methanone;

[(7R,9aR)-7-phenyl-1,3,4,6,7,8,9,9a-octahydropyrido[1,2-a]pyrazin-2-yl]-(3-methylthieno[3,2-c]pyridin-7-yl)methanone;

[(7R,9aR)-7-phenyl-1,3,4,6,7,8,9,9a-octahydropyrido[1,2-a]pyrazin-2-yl]-(1-methyl-2,3-dihydroindol-4-yl)methanone;

[(7R,9aR)-7-phenyl-1,3,4,6,7,8,9,9a-octahydropyrido[1,2-a]pyrazin-2-yl]-(1-propan-2-ylindol-4-yl)methanone;

[(7R,9aR)-7-phenyl-1,3,4,6,7,8,9,9a-octahydropyrido[1,2-a]pyrazin-2-yl]-(2-chloro-3-propan-2-yloxyphenyl)methanone;hydrochloride;

3-[(7R,9aR)-7-phenyl-1,3,4,6,7,8,9,9a-octahydropyrido[1,2-a]pyrazine-2-carbonyl]-2-chlorobenzonitrile;

[(7R,9aR)-7-phenyl-1,3,4,6,7,8,9,9a-octahydropyrido[1,2-a]pyrazin-2-yl]-(4-chloro-1-methylpyrrolo[2,3-b]pyridin-5-yl)methanone;

[(7R,9aR)-7-phenyl-1,3,4,6,7,8,9,9a-octahydropyrido[1,2-a]pyrazin-2-yl]-[2-chloro-3-[(1-methylpyrazol-4-yl)methoxy]phenyl]methanone;

[(7R,9aR)-7-phenyl-1,3,4,6,7,8,9,9a-octahydropyrido[1,2-a]pyrazin-2-yl]-(4-chloro-1-propan-2-ylpyrrolo[2,3-b]pyridin-5-yl)methanone;

[(7S,9aS)-7-(4-chlorophenyl)-1,3,4,6,7,8,9,9a-octahydropyrido[1,2-a]pyrazin-2-yl]-(2-bromo-3-methoxyphenyl)methanone;

[(7R,9aR)-7-phenyl-1,3,4,6,7,8,9,9a-octahydropyrido[1,2-a]pyrazin-2-yl]-(4-chloro-1H-pyrazolo[3,4-b]pyridin-5-yl)methanone;

[(7R,9aR)-7-phenyl-1,3,4,6,7,8,9,9a-octahydropyrido[1,2-a]pyrazin-2-yl]-(1-benzofuran-4-yl)methanone;

[(7R,9aR)-7-phenyl-1,3,4,6,7,8,9,9a-octahydropyrido[1,2-a]pyrazin-2-yl]-(3-chloro-2-methoxypyridin-4-yl)methanone;

[(7R,9aR)-7-(4-chlorophenyl)-1,3,4,6,7,8,9,9a-octahydropyrido[1,2-a]pyrazin-2-yl]-(4-chloro-1-methylpyrrolo[2,3-b]pyridin-5-yl)methanone;

[(7R,9aR)-7-phenyl-1,3,4,6,7,8,9,9a-octahydropyrido[1,2-a]pyrazin-2-yl]-[2-chloro-3-(1,3-thiazol-4-ylmethoxy)phenyl]methanone;

4-[[3-[(7R,9aR)-7-phenyl-1,3,4,6,7,8,9,9a-octahydropyrido[1,2-a]pyrazine-2-carbonyl]-2-chlorophenoxy]methyl]-N-methylbenzamide;

[(7R,9aR)-7-(4-chlorophenyl)-1,3,4,6,7,8,9,9a-octahydropyrido[1,2-a]pyrazin-2-yl]-(4-chloro-1-methylpyrazolo[3,4-b]pyridin-5-yl)methanone;

[(7R,9aR)-7-(3,4-dichlorophenyl)-1,3,4,6,7,8,9,9a-octahydropyrido[1,2-a]pyrazin-2-yl]-(2-bromo-3-methoxyphenyl)methanone;

[(7S,9aS)-7-(3,4-dichlorophenyl)-1,3,4,6,7,8,9,9a-octahydropyrido[1,2-a]pyrazin-2-yl]-(2-bromo-3-methoxyphenyl)methanone;

[(7R,9aR)-7-(4-chlorophenyl)-1,3,4,6,7,8,9,9a-octahydropyrido[1,2-a]pyrazin-2-yl]-[2-chloro-3-(2,2,2-trifluoroethoxy)phenyl]methanone;

[(7R,9aR)-7-(4-chlorophenyl)-1,3,4,6,7,8,9,9a-octahydropyrido[1,2-a]pyrazin-2-yl]-(6-methoxypyridin-2-yl)methanone;

[(7R,9aR)-7-(4-chlorophenyl)-1,3,4,6,7,8,9,9a-octahydropyrido[1,2-a]pyrazin-2-yl]-imidazo[1,2-a]pyridin-5-yl-methanone;

tert-butyl 4-[[3-[(7R,9aR)-7-phenyl-1,3,4,6,7,8,9,9a-octahydropyrido[1,2-a]pyrazine-2-carbonyl]-2-chlorophenoxy]methyl]pyrazole-1-carboxylate;

[(7R,9aR)-7-phenyl-1,3,4,6,7,8,9,9a-octahydropyrido[1,2-a]pyrazin-2-yl]-[2-chloro-3-(1H-pyrazol-4-ylmethoxy)phenyl]methanone;hydrochloride;

[(7R,9aR)-7-phenyl-1,3,4,6,7,8,9,9a-octahydropyrido[1,2-a]pyrazin-2-yl]-[2-chloro-3-(pyridazin-3-ylmethoxy)phenyl]methanone;

[(7R,9aR)-7-phenyl-1,3,4,6,7,8,9,9a-octahydropyrido[1,2-a]pyrazin-2-yl]-[2-chloro-3-(pyridin-4-ylmethoxy)phenyl]methanone;

[(7R,9aR)-7-phenyl-1,3,4,6,7,8,9,9a-octahydropyrido[1,2-a]pyrazin-2-yl]-[2-chloro-3-(pyridin-3-ylmethoxy)phenyl]methanone;

3-[(E)-2-[4-[(7R,9aR)-7-(4-chlorophenyl)-1,3,4,6,7,8,9,9a-octahydropyrido[1,2-a]pyrazine-2-carbonyl]phenyl]vinyl]-2-bromo-N-methyl-benzamide;

3-[(E)-2-[4-[(7S,9aS)-7-(4-chlorophenyl)-1,3,4,6,7,8,9,9a-octahydropyrido[1,2-a]pyrazine-2-carbonyl]phenyl]vinyl]-2-bromo-N-methyl-benzamide;

3-[(E)-2-[4-[(7S,9aS)-7-(4-chlorophenyl)-1,3,4,6,7,8,9,9a-octahydropyrido[1,2-a]pyrazine-2-carbonyl]-3-bromophenyl]vinyl]-N-methyl-benzamide;

3-[(E)-2-[4-[(7R,9aR)-7-(4-chlorophenyl)-1,3,4,6,7,8,9,9a-octahydropyrido[1,2-a]pyrazine-2-carbonyl]-3-bromophenyl]vinyl]-N-methyl-benzamide;

[(7R,9aR)-7-(3-chloro-4-fluorophenyl)-1,3,4,6,7,8,9,9a-octahydropyrido[1,2-a]pyrazin-2-yl]-(2-chloro-3-methoxyphenyl)methanone;

[(7S,9aS)-7-(3-chloro-4-fluorophenyl)-1,3,4,6,7,8,9,9a-octahydropyrido[1,2-a]pyrazin-2-yl]-(2-chloro-3-methoxyphenyl)methanone;

[(7R,9aR)-7-(4-chlorophenyl)-1,3,4,6,7,8,9,9a-octahydropyrido[1,2-a]pyrazin-2-yl]-[2-chloro-3-[(E)-2-cyclopropylethenyl]phenyl]methanone;

[(7R,9aR)-7-(4-chlorophenyl)-1,3,4,6,7,8,9,9a-octahydropyrido[1,2-a]pyrazin-2-yl]-(4-chloro-5-methoxypyridin-3-yl)methanone;

(4-chloro-1H-pyrazolo[3,4-b]pyridin-5-yl)-[rac-(7R,9aR)-7-(3-chloro-4-fluorophenyl)-1,3,4,6,7,8,9,9a-octahydropyrido[1,2-a]pyrazin-2-yl]methanone;

[(7R,9aR)-7-(3-chloro-4-fluorophenyl)-1,3,4,6,7,8,9,9a-octahydropyrido[1,2-a]pyrazin-2-yl]-(4-chloro-1H-pyrazolo[3,4-b]pyridin-5-yl)methanone;

[(7S,9aS)-7-(3-chloro-4-fluorophenyl)-1,3,4,6,7,8,9,9a-octahydropyrido[1,2-a]pyrazin-2-yl]-(4-chloro-1H-pyrazolo[3,4-b]pyridin-5-yl)methanone;

(3-methyl-1H-indazol-5-yl)-[rac-(7R,9aR)-7-(3-chloro-4-fluorophenyl)-1,3,4,6,7,8,9,9a-octahydropyrido[1,2-a]pyrazin-2-yl]methanone;

[(7S,9aS)-7-(3-chloro-4-fluorophenyl)-1,3,4,6,7,8,9,9a-octahydropyrido[1,2-a]pyrazin-2-yl]-(3-methyl-1H-indazol-5-yl)methanone;

[(7R,9aR)-7-(3-chloro-4-fluorophenyl)-1,3,4,6,7,8,9,9a-octahydropyrido[1,2-a]pyrazin-2-yl]-(3-methyl-1H-indazol-5-yl)methanone;

(3-methyl-[1,2,4]triazolo[4,3-a]pyridin-6-yl)-[rac-(7R,9aR)-7-(3-chloro-4-fluorophenyl)-1,3,4,6,7,8,9,9a-octahydropyrido[1,2-a]pyrazin-2-yl]methanone;

(3-chloroimidazo[1,2-a]pyridin-6-yl)-[rac-(7R,9aR)-7-(3-chloro-4-fluorophenyl)-1,3,4,6,7,8,9,9a-octahydropyrido[1,2-a]pyrazin-2-yl]methanone;

(4-chlorothieno[2,3-b]pyridin-5-yl)-[rac-(7R,9aR)-7-(3-chloro-4-fluorophenyl)-1,3,4,6,7,8,9,9a-octahydropyrido[1,2-a]pyrazin-2-yl]methanone;

[(7R,9aR)-7-(3-chloro-4-fluorophenyl)-1,3,4,6,7,8,9,9a-octahydropyrido[1,2-a]pyrazin-2-yl]-(4-chlorothieno[2,3-b]pyridin-5-yl)methanone;

[(7S,9aS)-7-(3-chloro-4-fluorophenyl)-1,3,4,6,7,8,9,9a-octahydropyrido[1,2-a]pyrazin-2-yl]-(4-chlorothieno[2,3-b]pyridin-5-yl)methanone;

(4-chloro-3-methyl-[1,2]oxazolo[5,4-b]pyridin-5-yl)-[rac-(7R,9aR)-7-(3-chloro-4-fluorophenyl)-1,3,4,6,7,8,9,9a-octahydropyrido[1,2-a]pyrazin-2-yl]methanone;

[(7R,9aR)-7-(3-chloro-4-fluorophenyl)-1,3,4,6,7,8,9,9a-octahydropyrido[1,2-a]pyrazin-2-yl]-(4-chloro-3-methyl-[1,2]oxazolo[5,4-b]pyridin-5-yl)methanone;

[(7S,9aS)-7-(3-chloro-4-fluorophenyl)-1,3,4,6,7,8,9,9a-octahydropyrido[1,2-a]pyrazin-2-yl]-(4-chloro-3-methyl-[1,2]oxazolo[5,4-b]pyridin-5-yl)methanone;

(4-chloro-TH-indazol-5-yl)-[rac-(7R,9aR)-7-(3-chloro-4-fluorophenyl)-1,3,4,6,7,8,9,9a-octahydropyrido[1,2-a]pyrazin-2-yl]methanone;

[2-chloro-3-(difluoromethoxy)phenyl]-[rac-(7R,9aR)-7-(3-chloro-4-fluorophenyl)-1,3,4,6,7,8,9,9a-octahydropyrido[1,2-a]pyrazin-2-yl]methanone;

[(7S,9aS)-7-(3-chloro-4-fluorophenyl)-1,3,4,6,7,8,9,9a-octahydropyrido[1,2-a]pyrazin-2-yl]-[2-chloro-3-(difluoromethoxy)phenyl]methanone;

[(7R,9aR)-7-(3-chloro-4-fluorophenyl)-1,3,4,6,7,8,9,9a-octahydropyrido[1,2-a]pyrazin-2-yl]-[2-chloro-3-(difluoromethoxy)phenyl]methanone;

(4-chloro-3-methyl-TH-indazol-5-yl)-[rac-(7R,9aR)-7-(3-chloro-4-fluorophenyl)-1,3,4,6,7,8,9,9a-octahydropyrido[1,2-a]pyrazin-2-yl]methanone;

(4-chloro-[1,2]thiazolo[5,4-b]pyridin-5-yl)-[rac-(7R,9aR)-7-(3-chloro-4-fluorophenyl)-1,3,4,6,7,8,9,9a-octahydropyrido[1,2-a]pyrazin-2-yl]methanone;

(6-amino-4-chloropyridin-3-yl)-[rac-(7R,9aR)-7-(3-chloro-4-fluorophenyl)-1,3,4,6,7,8,9,9a-octahydropyrido[1,2-a]pyrazin-2-yl]methanone;

(4-chloro-3-methyl-1H-indazol-5-yl)-[rac-(7R,9aR)-7-(4-chlorophenyl)-7-hydroxy-3,4,6,8,9,9a-hexahydro-1H-pyrido[1,2-a]pyrazin-2-yl]methanone;

(4-chloro-3-methyl-1H-indazol-5-yl)-[rac-(7R,9aS)-7-(4-chlorophenyl)-7-hydroxy-3,4,6,8,9,9a-hexahydro-1H-pyrido[1,2-a]pyrazin-2-yl]methanone;

[(7S,9aR)-7-(4-chlorophenyl)-7-hydroxy-3,4,6,8,9,9a-hexahydro-TH-pyrido[1,2-a]pyrazin-2-yl]-(4-chloro-3-methyl-TH-indazol-5-yl)methanone;

[(7R,9aS)-7-(4-chlorophenyl)-7-hydroxy-3,4,6,8,9,9a-hexahydro-TH-pyrido[1,2-a]pyrazin-2-yl]-(4-chloro-3-methyl-TH-indazol-5-yl)methanone;

(2-chloro-3-methoxyphenyl)-[rac-(7R,9aR)-7-(4-chlorophenyl)-7-hydroxy-3,4,6,8,9,9a-hexahydro-1H-pyrido[1,2-a]pyrazin-2-yl]methanone;

[(7S,9aS)-7-(4-chlorophenyl)-7-hydroxy-3,4,6,8,9,9a-hexahydro-1H-pyrido[1,2-a]pyrazin-2-yl]-(2-chloro-3-methoxyphenyl)methanone;

[(7R,9aR)-7-(4-chlorophenyl)-7-hydroxy-3,4,6,8,9,9a-hexahydro-TH-pyrido[1,2-a]pyrazin-2-yl]-(2-chloro-3-methoxyphenyl)methanone;

(2-chloro-3-methoxyphenyl)-[rac-(7R,9aS)-7-(4-chlorophenyl)-7-hydroxy-3,4,6,8,9,9a-hexahydro-1H-pyrido[1,2-a]pyrazin-2-yl]methanone;

[(7S,9aR)-7-(4-chlorophenyl)-7-hydroxy-3,4,6,8,9,9a-hexahydro-TH-pyrido[1,2-a]pyrazin-2-yl]-(2-chloro-3-methoxyphenyl)methanone;

[(7R,9aS)-7-(4-chlorophenyl)-7-hydroxy-3,4,6,8,9,9a-hexahydro-TH-pyrido[1,2-a]pyrazin-2-yl]-(2-chloro-3-methoxyphenyl)methanone;

[2-chloro-3-(difluoromethoxy)phenyl]-[rac-(7R,9aR)-7-(4-chlorophenyl)-7-hydroxy-3,4,6,8,9,9a-hexahydro-1H-pyrido[1,2-a]pyrazin-2-yl]methanone;

[2-chloro-3-(difluoromethoxy)phenyl]-[rac-(7R,9aS)-7-(4-chlorophenyl)-7-hydroxy-3,4,6,8,9,9a-hexahydro-1H-pyrido[1,2-a]pyrazin-2-yl]methanone;

[2-chloro-3-(2-oxa-6-azaspiro[3.3]heptan-6-yl)phenyl]-[rac-(7R,9aR)-7-(4-chlorophenyl)-7-hydroxy-3,4,6,8,9,9a-hexahydro-TH-pyrido[1,2-a]pyrazin-2-yl]methanone;

[2-chloro-3-(2-oxa-6-azaspiro[3.3]heptan-6-yl)phenyl]-[rac-(7R,9aS)-7-(4-chlorophenyl)-7-hydroxy-3,4,6,8,9,9a-hexahydro-TH-pyrido[1,2-a]pyrazin-2-yl]methanone;

(2-chloro-3-methoxyphenyl)-[rac-(7R,9aR)-7-(4-chlorophenyl)-7-fluoro-3,4,6,8,9,9a-hexahydro-1H-pyrido[1,2-a]pyrazin-2-yl]methanone;

(2-chloro-3-methoxyphenyl)-[rac-(7R,9aS)-7-(4-chlorophenyl)-7-fluoro-3,4,6,8,9,9a-hexahydro-1H-pyrido[1,2-a]pyrazin-2-yl]methanone;

(2-chloro-3-methoxyphenyl)-[rac-(7R,9aR)-7-(4-chlorophenyl)-7-methoxy-3,4,6,8,9,9a-hexahydro-1H-pyrido[1,2-a]pyrazin-2-yl]methanone;

(2-chloro-3-methoxyphenyl)-[rac-(7R,9aS)-7-(4-chlorophenyl)-7-methoxy-3,4,6,8,9,9a-hexahydro-1H-pyrido[1,2-a]pyrazin-2-yl]methanone;
(2-chloro-3-methoxyphenyl)-[rac-(7R,9aS)-7-methyl-1,3,4,6,7,8,9,9a-octahydropyrido[1,2-a]pyrazin-2-yl]methanone;
(2-chloro-3-methoxyphenyl)-[rac-(7R,9aR)-7-methyl-1,3,4,6,7,8,9,9a-octahydropyrido[1,2-a]pyrazin-2-yl]methanone;
(2-chloro-3-methoxyphenyl)-[rac-(7R,9aS)-7-(2-methylpropoxy)-1,3,4,6,7,8,9,9a-octahydropyrido[1,2-a]pyrazin-2-yl]methanone; and
(1,3-dimethylthieno[2,3-c]pyrazol-5-yl)-[rac-(7R,9aR)-7-(3-chloro-4-fluorophenyl)-1,3,4,6,7,8,9,9a-octahydropyrido[1,2-a]pyrazin-2-yl]methanone;
or a pharmaceutically acceptable salt thereof.

In a preferred embodiment, there is provided a compound of formula (I) as described herein, selected from the group consisting of
[(7R,9aR)-7-(4-chlorophenyl)-1,3,4,6,7,8,9,9a-octahydropyrido[1,2-a]pyrazin-2-yl]-(3-phenoxyphenyl)methanone;
[(7R,9aR)-7-(4-chlorophenyl)-1,3,4,6,7,8,9,9a-octahydropyrido[1,2-a]pyrazin-2-yl]-(2-chloro-3-methylphenyl)methanone;
[(7R,9aR)-7-(4-chlorophenyl)-1,3,4,6,7,8,9,9a-octahydropyrido[1,2-a]pyrazin-2-yl]-(2-bromo-3-methoxyphenyl)methanone;
[(7R,9aR)-7-(4-chlorophenyl)-1,3,4,6,7,8,9,9a-octahydropyrido[1,2-a]pyrazin-2-yl]-(2-bromo-3-methoxyphenyl)methanone;hydrochloride;
[(7R,9aR)-7-(4-chlorophenyl)-1,3,4,6,7,8,9,9a-octahydropyrido[1,2-a]pyrazin-2-yl]-[3-(3,5-difluorophenoxy)phenyl]methanone;
[(7R,9aR)-7-phenyl-1,3,4,6,7,8,9,9a-octahydropyrido[1,2-a]pyrazin-2-yl]-(2-bromo-3-methoxyphenyl)methanone;
[(7R,9aR)-7-(4-chlorophenyl)-1,3,4,6,7,8,9,9a-octahydropyrido[1,2-a]pyrazin-2-yl]-(2-chloro-3-methoxyphenyl)methanone;
[(7R,9aR)-7-(4-chlorophenyl)-1,3,4,6,7,8,9,9a-octahydropyrido[1,2-a]pyrazin-2-yl]-(2-methoxyphenyl)methanone;
[(7R,9aR)-7-(4-chlorophenyl)-1,3,4,6,7,8,9,9a-octahydropyrido[1,2-a]pyrazin-2-yl]-[2-(trifluoromethoxy)phenyl]methanone;
[(7R,9aR)-7-(4-chlorophenyl)-1,3,4,6,7,8,9,9a-octahydropyrido[1,2-a]pyrazin-2-yl]-(2,3-dihydro-1-benzofuran-7-yl)methanone;
[(7R,9aR)-7-(4-chlorophenyl)-1,3,4,6,7,8,9,9a-octahydropyrido[1,2-a]pyrazin-2-yl]-(1H-indol-4-yl)methanone;
[(7R,9aR)-7-(4-chlorophenyl)-1,3,4,6,7,8,9,9a-octahydropyrido[1,2-a]pyrazin-2-yl]-(2-chloro-6-fluorophenyl)methanone;
[(7R,9aR)-7-(4-chlorophenyl)-1,3,4,6,7,8,9,9a-octahydropyrido[1,2-a]pyrazin-2-yl]-(2-chlorophenyl)methanone;
[(7R,9aR)-7-(4-chlorophenyl)-1,3,4,6,7,8,9,9a-octahydropyrido[1,2-a]pyrazin-2-yl]-(2-fluoro-3-methylphenyl)methanone;
[(7R,9aR)-7-(4-chlorophenyl)-1,3,4,6,7,8,9,9a-octahydropyrido[1,2-a]pyrazin-2-yl]-(4-chloro-1H-pyrrolo[2,3-b]pyridin-5-yl)methanone;
[(7R,9aR)-7-(4-chlorophenyl)-1,3,4,6,7,8,9,9a-octahydropyrido[1,2-a]pyrazin-2-yl]-(1H-pyrrolo[2,3-b]pyridin-4-yl)methanone;
[(7R,9aR)-7-(4-chlorophenyl)-1,3,4,6,7,8,9,9a-octahydropyrido[1,2-a]pyrazin-2-yl]-[2-chloro-3-(trifluoromethyl)phenyl]methanone;
[(7R,9aR)-7-(4-chlorophenyl)-1,3,4,6,7,8,9,9a-octahydropyrido[1,2-a]pyrazin-2-yl]-(2-chloro-4-fluoro-3-methylphenyl)methanone;
[(7R,9aR)-7-(4-chlorophenyl)-1,3,4,6,7,8,9,9a-octahydropyrido[1,2-a]pyrazin-2-yl]-(3-chloro-2-methylphenyl)methanone;
[(7R,9aR)-7-(4-chlorophenyl)-1,3,4,6,7,8,9,9a-octahydropyrido[1,2-a]pyrazin-2-yl]-(4-chloro-6-methylpyridin-3-yl)methanone;
[(7R,9aR)-7-(4-chlorophenyl)-1,3,4,6,7,8,9,9a-octahydropyrido[1,2-a]pyrazin-2-yl]-(2,4-dimethyl-1,3-benzothiazol-5-yl)methanone;
[(7R,9aR)-7-(4-chlorophenyl)-1,3,4,6,7,8,9,9a-octahydropyrido[1,2-a]pyrazin-2-yl]-(7-chloro-2-methylsulfanyl-[1,3]thiazolo[5,4-b]pyridin-6-yl)methanone;
[(7R,9aR)-7-(4-chlorophenyl)-1,3,4,6,7,8,9,9a-octahydropyrido[1,2-a]pyrazin-2-yl]-(1-benzothiophen-4-yl)methanone;
[(7R,9aR)-7-(4-chlorophenyl)-1,3,4,6,7,8,9,9a-octahydropyrido[1,2-a]pyrazin-2-yl]-(2-bromo-3-methylphenyl)methanone;
[(7R,9aR)-7-(4-chlorophenyl)-1,3,4,6,7,8,9,9a-octahydropyrido[1,2-a]pyrazin-2-yl]-[2-(trifluoromethyl)phenyl]methanone;
[(7R,9aR)-7-(4-chlorophenyl)-1,3,4,6,7,8,9,9a-octahydropyrido[1,2-a]pyrazin-2-yl]-(2-chloro-3-phenoxyphenyl)methanone;
[(7R,9aR)-7-phenyl-1,3,4,6,7,8,9,9a-octahydropyrido[1,2-a]pyrazin-2-yl]-(2-chloro-3-methylphenyl)methanone;
[(7R,9aR)-7-phenyl-1,3,4,6,7,8,9,9a-octahydropyrido[1,2-a]pyrazin-2-yl]-(2-chloro-3-methylphenyl)methanone;hydrochloride;
[(7R,9aR)-7-phenyl-1,3,4,6,7,8,9,9a-octahydropyrido[1,2-a]pyrazin-2-yl]-(2-chloro-5-fluoro-3-methylphenyl)methanone;
[(7R,9aR)-7-phenyl-1,3,4,6,7,8,9,9a-octahydropyrido[1,2-a]pyrazin-2-yl]-[2-bromo-3-(methoxymethyl)phenyl]methanone;
[(7R,9aR)-7-phenyl-1,3,4,6,7,8,9,9a-octahydropyrido[1,2-a]pyrazin-2-yl]-(1H-indol-4-yl)methanone;
[(7R,9aR)-7-phenyl-1,3,4,6,7,8,9,9a-octahydropyrido[1,2-a]pyrazin-2-yl]-(1-methylindol-4-yl)methanone;
[(7R,9aR)-7-phenyl-1,3,4,6,7,8,9,9a-octahydropyrido[1,2-a]pyrazin-2-yl]-(4-chloro-1H-pyrrolo[2,3-b]pyridin-5-yl)methanone;
[(7R,9aR)-7-phenyl-1,3,4,6,7,8,9,9a-octahydropyrido[1,2-a]pyrazin-2-yl]-(2-chloro-3-hydroxyphenyl)methanone;
[(7R,9aR)-7-phenyl-1,3,4,6,7,8,9,9a-octahydropyrido[1,2-a]pyrazin-2-yl]-(3-methylthieno[3,2-c]pyridin-7-yl)methanone;
[(7R,9aR)-7-phenyl-1,3,4,6,7,8,9,9a-octahydropyrido[1,2-a]pyrazin-2-yl]-(1-methyl-2,3-dihydroindol-4-yl)methanone;
[(7R,9aR)-7-phenyl-1,3,4,6,7,8,9,9a-octahydropyrido[1,2-a]pyrazin-2-yl]-(1-propan-2-ylindol-4-yl)methanone;
[(7R,9aR)-7-phenyl-1,3,4,6,7,8,9,9a-octahydropyrido[1,2-a]pyrazin-2-yl]-(2-chloro-3-propan-2-yloxyphenyl)methanone;hydrochloride;
3-[(7R,9aR)-7-phenyl-1,3,4,6,7,8,9,9a-octahydropyrido[1,2-a]pyrazine-2-carbonyl]-2-chlorobenzonitrile;
[(7R,9aR)-7-phenyl-1,3,4,6,7,8,9,9a-octahydropyrido[1,2-a]pyrazin-2-yl]-(4-chloro-1-methylpyrrolo[2,3-b]pyridin-5-yl)methanone;
[(7R,9aR)-7-phenyl-1,3,4,6,7,8,9,9a-octahydropyrido[1,2-a]pyrazin-2-yl]-[2-chloro-3-[(1-methylpyrazol-4-yl)methoxy]phenyl]methanone;

[(7R,9aR)-7-phenyl-1,3,4,6,7,8,9,9a-octahydropyrido[1,2-a]pyrazin-2-yl]-(4-chloro-1-propan-2-ylpyrrolo[2,3-b]pyridin-5-yl)methanone;
[(7S,9aS)-7-(4-chlorophenyl)-1,3,4,6,7,8,9,9a-octahydropyrido[1,2-a]pyrazin-2-yl]-(2-bromo-3-methoxyphenyl)methanone;
[(7R,9aR)-7-phenyl-1,3,4,6,7,8,9,9a-octahydropyrido[1,2-a]pyrazin-2-yl]-(4-chloro-1H-pyrazolo[3,4-b]pyridin-5-yl)methanone;
[(7R,9aR)-7-phenyl-1,3,4,6,7,8,9,9a-octahydropyrido[1,2-a]pyrazin-2-yl]-(1-benzofuran-4-yl)methanone;
[(7R,9aR)-7-phenyl-1,3,4,6,7,8,9,9a-octahydropyrido[1,2-a]pyrazin-2-yl]-(3-chloro-2-methoxypyridin-4-yl)methanone;
[(7R,9aR)-7-(4-chlorophenyl)-1,3,4,6,7,8,9,9a-octahydropyrido[1,2-a]pyrazin-2-yl]-(4-chloro-1-methylpyrrolo[2,3-b]pyridin-5-yl)methanone;
[(7R,9aR)-7-phenyl-1,3,4,6,7,8,9,9a-octahydropyrido[1,2-a]pyrazin-2-yl]-[2-chloro-3-(1,3-thiazol-4-ylmethoxy)phenyl]methanone;
4-[[3-[(7R,9aR)-7-phenyl-1,3,4,6,7,8,9,9a-octahydropyrido[1,2-a]pyrazine-2-carbonyl]-2-chlorophenoxy]methyl]-N-methylbenzamide;
[(7R,9aR)-7-(4-chlorophenyl)-1,3,4,6,7,8,9,9a-octahydropyrido[1,2-a]pyrazin-2-yl]-(4-chloro-1-methylpyrazolo[3,4-b]pyridin-5-yl)methanone;
[(7R,9aR)-7-(3,4-dichlorophenyl)-1,3,4,6,7,8,9,9a-octahydropyrido[1,2-a]pyrazin-2-yl]-(2-bromo-3-methoxyphenyl)methanone;
[(7S,9aS)-7-(3,4-dichlorophenyl)-1,3,4,6,7,8,9,9a-octahydropyrido[1,2-a]pyrazin-2-yl]-(2-bromo-3-methoxyphenyl)methanone;
[(7R,9aR)-7-(4-chlorophenyl)-1,3,4,6,7,8,9,9a-octahydropyrido[1,2-a]pyrazin-2-yl]-[2-chloro-3-(2,2,2-trifluoroethoxy)phenyl]methanone;
[(7R,9aR)-7-(4-chlorophenyl)-1,3,4,6,7,8,9,9a-octahydropyrido[1,2-a]pyrazin-2-yl]-(6-methoxypyridin-2-yl)methanone;
[(7R,9aR)-7-(4-chlorophenyl)-1,3,4,6,7,8,9,9a-octahydropyrido[1,2-a]pyrazin-2-yl]-imidazo[1,2-a]pyridin-5-yl)methanone;
tert-butyl 4-[[3-[(7R,9aR)-7-phenyl-1,3,4,6,7,8,9,9a-octahydropyrido[1,2-a]pyrazine-2-carbonyl]-2-chlorophenoxy]methyl]pyrazole-1-carboxylate;
[(7R,9aR)-7-phenyl-1,3,4,6,7,8,9,9a-octahydropyrido[1,2-a]pyrazin-2-yl]-[2-chloro-3-(1H-pyrazol-4-ylmethoxy)phenyl]methanone;hydrochloride;
[(7R,9aR)-7-phenyl-1,3,4,6,7,8,9,9a-octahydropyrido[1,2-a]pyrazin-2-yl]-[2-chloro-3-(pyridazin-3-ylmethoxy)phenyl]methanone;
[(7R,9aR)-7-phenyl-1,3,4,6,7,8,9,9a-octahydropyrido[1,2-a]pyrazin-2-yl]-[2-chloro-3-(pyridin-4-ylmethoxy)phenyl]methanone;
[(7R,9aR)-7-phenyl-1,3,4,6,7,8,9,9a-octahydropyrido[1,2-a]pyrazin-2-yl]-[2-chloro-3-(pyridin-3-ylmethoxy)phenyl]methanone;
[(7R,9aR)-7-(3-chloro-4-fluorophenyl)-1,3,4,6,7,8,9,9a-octahydropyrido[1,2-a]pyrazin-2-yl]-(2-chloro-3-methoxyphenyl)methanone;
(4-chloro-1H-pyrazolo[3,4-b]pyridin-5-yl)-[rac-(7R,9aR)-7-(3-chloro-4-fluorophenyl)-1,3,4,6,7,8,9,9a-octahydropyrido[1,2-a]pyrazin-2-yl]methanone;
[(7R,9aR)-7-(3-chloro-4-fluorophenyl)-1,3,4,6,7,8,9,9a-octahydropyrido[1,2-a]pyrazin-2-yl]-(4-chloro-1H-pyrazolo[3,4-b]pyridin-5-yl)methanone;

(3-methyl-1H-indazol-5-yl)-[rac-(7R,9aR)-7-(3-chloro-4-fluorophenyl)-1,3,4,6,7,8,9,9a-octahydropyrido[1,2-a]pyrazin-2-yl]methanone;
[(7R,9aR)-7-(3-chloro-4-fluorophenyl)-1,3,4,6,7,8,9,9a-octahydropyrido[1,2-a]pyrazin-2-yl]-(3-methyl-TH-indazol-5-yl)methanone;
[(7R,9aR)-7-(3-chloro-4-fluorophenyl)-1,3,4,6,7,8,9,9a-octahydropyrido[1,2-a]pyrazin-2-yl]-(4-chlorothieno[2,3-b]pyridin-5-yl)methanone;
[(7R,9aR)-7-(3-chloro-4-fluorophenyl)-1,3,4,6,7,8,9,9a-octahydropyrido[1,2-a]pyrazin-2-yl]-[2-chloro-3-(difluoromethoxy)phenyl]methanone;
(4-chloro-3-methyl-TH-indazol-5-yl)-[rac-(7R,9aR)-7-(3-chloro-4-fluorophenyl)-1,3,4,6,7,8,9,9a-octahydropyrido[1,2-a]pyrazin-2-yl]methanone;
(4-chloro-3-methyl-TH-indazol-5-yl)-[rac-(7R,9aS)-7-(4-chlorophenyl)-7-hydroxy-3,4,6,8,9,9a-hexahydro-1H-pyrido[1,2-a]pyrazin-2-yl]methanone;
[(7S,9aR)-7-(4-chlorophenyl)-7-hydroxy-3,4,6,8,9,9a-hexahydro-TH-pyrido[1,2-a]pyrazin-2-yl]-(4-chloro-3-methyl-TH-indazol-5-yl)methanone;
(2-chloro-3-methoxyphenyl)-[rac-(7R,9aR)-7-(4-chlorophenyl)-7-hydroxy-3,4,6,8,9,9a-hexahydro-1H-pyrido[1,2-a]pyrazin-2-yl]methanone;
[(7S,9aR)-7-(4-chlorophenyl)-7-hydroxy-3,4,6,8,9,9a-hexahydro-TH-pyrido[1,2-a]pyrazin-2-yl]-(2-chloro-3-methoxyphenyl)methanone;
[2-chloro-3-(difluoromethoxy)phenyl]-[rac-(7R,9aS)-7-(4-chlorophenyl)-7-hydroxy-3,4,6,8,9,9a-hexahydro-1H-pyrido[1,2-a]pyrazin-2-yl]methanone;
[2-chloro-3-(2-oxa-6-azaspiro[3.3]heptan-6-yl)phenyl]-[rac-(7R,9aS)-7-(4-chlorophenyl)-7-hydroxy-3,4,6,8,9,9a-hexahydro-TH-pyrido[1,2-a]pyrazin-2-yl]methanone;
(2-chloro-3-methoxyphenyl)-[rac-(7R,9aS)-7-(4-chlorophenyl)-7-fluoro-3,4,6,8,9,9a-hexahydro-1H-pyrido[1,2-a]pyrazin-2-yl]methanone; and
(2-chloro-3-methoxyphenyl)-[rac-(7R,9aS)-7-(4-chlorophenyl)-7-methoxy-3,4,6,8,9,9a-hexahydro-1H-pyrido[1,2-a]pyrazin-2-yl]methanone;
or a pharmaceutically acceptable salt thereof.

In a particularly preferred embodiment, there is provided a compound of formula (I) as described herein, selected from the group consisting of
[(7R,9aR)-7-(4-chlorophenyl)-1,3,4,6,7,8,9,9a-octahydropyrido[1,2-a]pyrazin-2-yl]-(2-chloro-3-methylphenyl)methanone;
[(7R,9aR)-7-(4-chlorophenyl)-1,3,4,6,7,8,9,9a-octahydropyrido[1,2-a]pyrazin-2-yl]-(2-bromo-3-methoxyphenyl)methanone;
[(7R,9aR)-7-(4-chlorophenyl)-1,3,4,6,7,8,9,9a-octahydropyrido[1,2-a]pyrazin-2-yl]-(2-chloro-3-methoxyphenyl)methanone;
[(7R,9aR)-7-(4-chlorophenyl)-1,3,4,6,7,8,9,9a-octahydropyrido[1,2-a]pyrazin-2-yl]-(1H-indol-4-yl)methanone
[(7R,9aR)-7-(4-chlorophenyl)-1,3,4,6,7,8,9,9a-octahydropyrido[1,2-a]pyrazin-2-yl]-(4-chloro-1H-pyrrolo[2,3-b]pyridin-5-yl)methanone
[(7R,9aR)-7-(4-chlorophenyl)-1,3,4,6,7,8,9,9a-octahydropyrido[1,2-a]pyrazin-2-yl]-(1H-pyrrolo[2,3-b]pyridin-4-yl)methanone
[(7R,9aR)-7-(4-chlorophenyl)-1,3,4,6,7,8,9,9a-octahydropyrido[1,2-a]pyrazin-2-yl]-(2-chloro-4-fluoro-3-methylphenyl)methanone
[(7R,9aR)-7-(4-chlorophenyl)-1,3,4,6,7,8,9,9a-octahydropyrido[1,2-a]pyrazin-2-yl]-(2,4-dimethyl-1,3-benzothiazol-5-yl)methanone

[(7R,9aR)-7-(4-chlorophenyl)-1,3,4,6,7,8,9,9a-octahydropyrido[1,2-a]pyrazin-2-yl]-(7-chloro-2-methylsulfanyl-[1,3]thiazolo[5,4-b]pyridin-6-yl)methanone

[(7R,9aR)-7-(4-chlorophenyl)-1,3,4,6,7,8,9,9a-octahydropyrido[1,2-a]pyrazin-2-yl]-(2-bromo-3-methylphenyl)methanone

[(7R,9aR)-7-phenyl-1,3,4,6,7,8,9,9a-octahydropyrido[1,2-a]pyrazin-2-yl]-(2-chloro-3-methylphenyl)methanone

[(7R,9aR)-7-(4-chlorophenyl)-1,3,4,6,7,8,9,9a-octahydropyrido[1,2-a]pyrazin-2-yl]-(4-chloro-1-methylpyrrolo[2,3-b]pyridin-5-yl)methanone

[(7R,9aR)-7-phenyl-1,3,4,6,7,8,9,9a-octahydropyrido[1,2-a]pyrazin-2-yl]-[2-chloro-3-(1,3-thiazol-4-ylmethoxy)phenyl]methanone

[(7R,9aR)-7-(4-chlorophenyl)-1,3,4,6,7,8,9,9a-octahydropyrido[1,2-a]pyrazin-2-yl]-(4-chloro-1-methylpyrazolo[3,4-b]pyridin-5-yl)methanone

[(7R,9aR)-7-(3,4-dichlorophenyl)-1,3,4,6,7,8,9,9a-octahydropyrido[1,2-a]pyrazin-2-yl]-(2-bromo-3-methoxyphenyl)methanone

[(7S,9aS)-7-(3,4-dichlorophenyl)-1,3,4,6,7,8,9,9a-octahydropyrido[1,2-a]pyrazin-2-yl]-(2-bromo-3-methoxyphenyl)methanone

[(7R,9aR)-7-(4-chlorophenyl)-1,3,4,6,7,8,9,9a-octahydropyrido[1,2-a]pyrazin-2-yl]-[2-chloro-3-(2,2,2-trifluoroethoxy)phenyl]methanone; and

[(7R,9aR)-7-phenyl-1,3,4,6,7,8,9,9a-octahydropyrido[1,2-a]pyrazin-2-yl]-[2-chloro-3-(1H-pyrazol-4-ylmethoxy)phenyl]methanone;hydrochloride;

or a pharmaceutically acceptable salt thereof.

In a particular embodiment, the present invention provides pharmaceutically acceptable salts of the compounds according to formula (e) as described herein, especially hydrochloride salts. In a further particular embodiment, the present invention provides compounds according to formula (Ie) as described herein.

Processes of Manufacturing

The preparation of compounds of formula (Ie) of the present invention may be carried out in sequential or convergent synthetic routes. Syntheses of the invention are shown in the following general schemes. The skills required for carrying out the reaction and purification of the resulting products are known to those persons skilled in the art. The substituents and indices used in the following description of the processes have the significance given herein, unless indicated to the contrary.

If one of the starting materials, intermediates or compounds of formula (Ie) contain one or more functional groups which are not stable or are reactive under the reaction conditions of one or more reaction steps, appropriate protecting groups (as described e.g., in "Protective Groups in Organic Chemistry" by T. W. Greene and P. G. M. Wutts, 5th Ed., 2014, John Wiley & Sons, N.Y.) can be introduced before the critical step applying methods well known in the art. Such protecting groups can be removed at a later stage of the synthesis using standard methods described in the literature.

If starting materials or intermediates contain stereogenic centers, compounds of formula (Ie) can be obtained as mixtures of diastereomers or enantiomers, which can be separated by methods well known in the art e.g., chiral HPLC, chiral SFC or chiral crystallization. Racemic compounds can e.g., be separated into their antipodes via diastereomeric salts by crystallization with optically pure acids or by separation of the antipodes by specific chromatographic methods using either a chiral adsorbent or a chiral eluent.

A person skilled in the art will acknowledge that in the synthesis of compounds of formula (Ie)—insofar not desired otherwise—an "orthogonal protection group strategy" will be applied, allowing the cleavage of several protective groups one at a time each without affecting other protecting groups in the molecule. The principle of orthogonal protection is well known in the art and has also been described in literature (e.g. Barany and R. B. Merrifield, *J. Am. Chem. Soc.* 1977, 99, 7363; H. Waldmann et al., *Angew. Chem. Int. Ed. Engl.* 1996, 35, 2056).

A person skilled in the art will acknowledge that the sequence of reactions may be varied depending on reactivity and nature of the intermediates.

In more detail, the compounds of formula (Ie) can be manufactured by the methods given below, by the methods given in the examples or by analogous methods. Appropriate reaction conditions for the individual reaction steps are known to a person skilled in the art. Also, for reaction conditions described in literature affecting the described reactions see for example: *Comprehensive Organic Transformations: A Guide to Functional Group Preparations, 2nd Edition*, Richard C. Larock. John Wiley & Sons, New York, N.Y. 1999). It was found convenient to carry out the reactions in the presence or absence of a solvent. There is no particular restriction on the nature of the solvent to be employed, provided that it has no adverse effect on the reaction or the reagents involved and that it can dissolve the reagents, at least to some extent. The described reactions can take place over a wide range of temperatures, and the precise reaction temperature is not critical to the invention. It is convenient to carry out the described reactions in a temperature range between −78° C. to reflux. The time required for the reaction may also vary widely, depending on many factors, notably the reaction temperature and the nature of the reagents. However, a period of from 0.5 hours to several days will usually suffice to yield the described intermediates and compounds. The reaction sequence is not limited to the one displayed in the schemes, however, depending on the starting materials and their respective reactivity, the sequence of reaction steps can be freely altered.

The following abbreviations are used in the present text:

AcOH=acetic acid, aq.=aqueous, Boc=tert-butyloxycarbonyl, BnBr=Benzylbromide, n-BuLi=n-butyllithium, n-BuOH=Butanol, CAS RN=chemical abstracts registration number, $CHCl_3$=Chloroform, CyPrI=Cyclopropyl iodide, DAST=diethylaminosulfur trifluoride, DCM=dichloromethane, DCE=1,2-dichloroethane, DCC=N,N'-dicyclohexylcarbodiimide, DIC=N,N'-diisopropylcarbodiimide, DMA=N,N-dimethylacetamide, DMAP=4-dimethylaminopyridine, DME=dimethoxyethane, DMF=N,N-dimethylformamide, EDCI=N-(3-dimethylaminopropyl)-N'-ethylcarbodiimide hydrochloride, EtOAc=ethylacetate, EtOH=ethanol, EtI=Ethyl iodide, HATU=O-(7-azabenzotriazol-1-yl)-1,1,3,3-tetramethyluronium hexafluorophosphate, HCl=hydrogen chloride, HPLC=high performance liquid chromatography, HOBt=1-hydroxybenzo-triazole, Huenig's base=$iPr_2NEt$=N-ethyl diisopropylamine, iPrI=isopropyl iodide, $K_2CO_3$=potassium carbonate, KH=potassium hydride, LDA=lithium diisopropylamide, LiHMDS=lithium bis(trimethylsilyl)amide, L-selectride=lithium tri-sec-butyl(hydrido)borate, MeOH=methanol, RT=room temperature, MeI=methyl iodide, MS=mass spectrum, MsOH=methyl sulfonic acid, NaH=sodium hydride, $NaHCO_3$=sodium hydrogen carbonate, $Na_2CO_3$=sodium carbonate, NaHMDS=sodium bis(trimethylsilyl)amide, NaOH=sodium hydroxide, $Na_2SO_4$=sodium sulfate, $NH_4Cl$=ammonium chloride, sat.=saturated, Pd/C=palladium on activated carbon, Pd(OH)$_2$=palladium hydroxyde=Pearlman's catalyst, PtO$_2$=platinum dioxide, PE=petroleum ether, PMB=4-methoxy benzyl ether, SFC=Supercritical Fluid Chromatography, TBTU=O-benzotriazol-1-yl-N,N,N',N'-tetramethyl-uronium tetrafluoroborate, TEA=triethylamine, TFA=trifluoroacetic acid, Tf$_2$NPh=N-phenyltrifluoromethanesulfonimide, Tf$_2$O=trifluoromethanesulfonic anhydride, TfOH=triflic acid, THF=tetrahydrofuran, TsOH=paratoluene sulfonic acid, T$_3$P=propylphosphonic anhydride.

Compounds of formula (I) wherein $R^1$, $R^2$, $R^3$, $R^4$, $R^5$ and $R^6$ are as defined herein and wherein $R^7$ is hydrogen may be synthesized according to the general procedure outlined in Scheme 1.

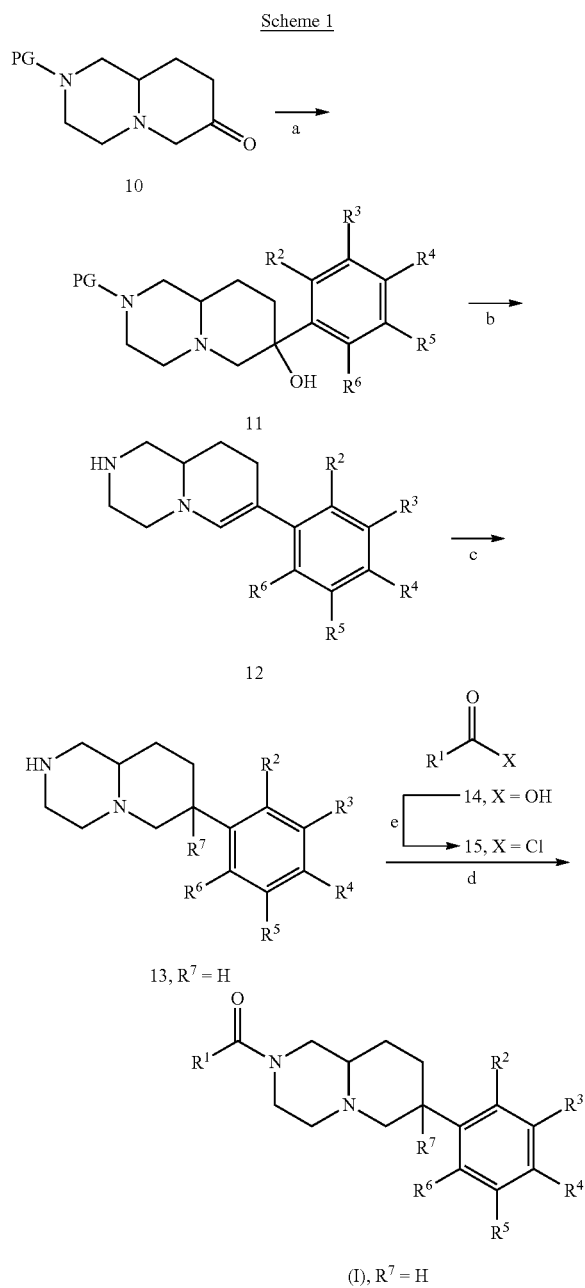

Treatment of protected ketone intermediates 10 (obtainable e.g. by the general procedure outlined in Scheme 3), wherein PG is a protective group, such as Boc (see e.g. intermediate I-1) with an aryl Grignard reagent in a solvent like diethylether or THF, preferably THF and in a temperature range between −78° C. and 25° C., preferably at 0° C. affords the corresponding tertiary alcohol intermediate 11 (Scheme 1, step a). Following dehydration reaction of the hydroxy intermediate with concomitant cleavage of the protective group PG, in presence of an acid such as HCl, TsOH or MsOH, preferably MsOH in a solvent like DCM, MeOH, EtOH, toluene or a mixture thereof, preferably in DCM and in a temperature range between 0° C. and the boiling point of the solvent, preferably at room temperature, gives the enamine intermediates 12 (Scheme 1, step b). Subsequent heterogeneous catalytic hydrogenation of the alkene using a transition metal catalyst such as PtO$_2$ or Pd/C, preferably Pd/C in presence of MgO in a solvent like MeOH, EtOH, THF or EtOAc, preferably EtOAc at around room temperature and under atmospheric pressure of hydrogen, gives the amine intermediates 13 (Scheme 1, step c, see e.g. intermediate A-1). Finally, amide coupling reaction with carboxylic acid compounds 14 (X=OH, either commercially available, or prepared by the methods described in Schemes 4, 5, 6 and 7 or in literature), wherein $R^1$ is as defined herein in connection with compounds of formula (I), can be accomplished by using coupling reagents such as, DCC, HATU, EDCI, HOBt, TBTU, T$_3$P, etc. and a base like Huenig's base, triethyl amine or DMAP in a suitable solvent solvent like N,N-dimethylformamide, DMA, DCM or dioxane, preferably between 0° C. and room temperature to give the compounds of formula (I) (Scheme 1, step d).

Alternatively, reaction of amine intermediates 13 with acid chloride compounds 15 (X=Cl, either commercially available, or prepared by treatment of the corresponding carboxylic acid compounds 14 with e.g., thionyl chloride or oxalyl chloride, neat or optionally in a solvent such as DCM, Scheme 1, step e) in an appropriate solvent such as DCM or DMF and abase, e.g. NEt$_3$, Huenig's base, pyridine or DMAP at temperatures ranging from 0° C. to the reflux temperature of the solvent also yields compounds of formula (I) (Scheme 1, step d).

Compounds of formula (I) wherein $R^1$, $R^2$, $R^3$, $R^4$, $R^5$ and $R^6$ are as defined herein and wherein $R^7$ is hydroxy, alkoxy or halogen, in particular hydroxy, methoxy or F, may be synthesized according to the general procedure outlined in Scheme 1a.

Scheme 1a

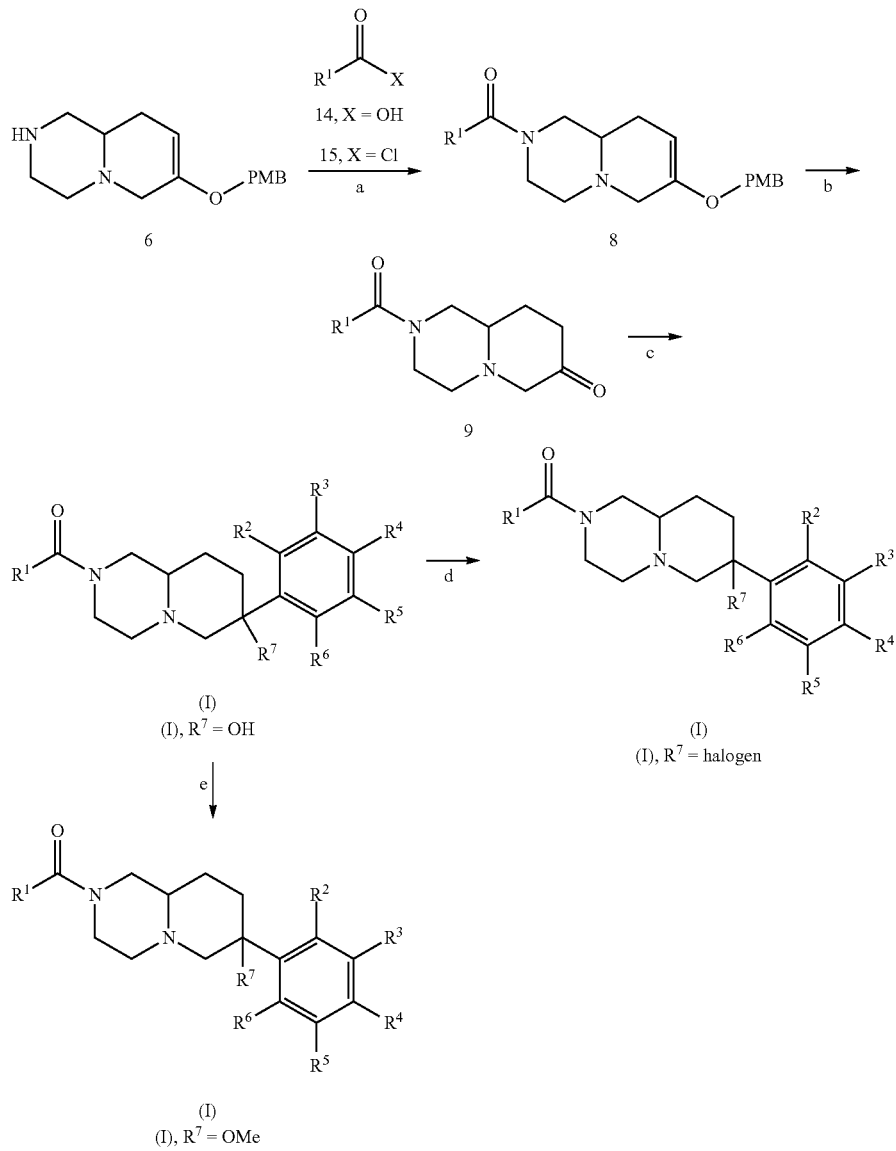

Accordingly, the PMB protected secondary amine 6 (obtainable e.g. by the general procedure outlined in Scheme 3), can be acylated with a suitable carboxylic acid 14 using coupling reagents such as, DCC, HATU, EDCI, HOBt or TBTU, preferably T$_3$P and a base like Huenig's base, triethyl amine or DMAP in a suitable solvent solvent like N,N-dimethylformamide, DMA, DCM or dioxane, preferably between 0° C. and 50° C. to afford the corresponding intermediate 8. Alternatively, reaction of amine intermediates 6 with acid chloride compounds 15 (X=Cl, either commercially available, or prepared by treatment of the corresponding carboxylic acid compounds 14 also yields the corresponding intermediate 8, wherein R$^1$ is as defined herein (Scheme 1a, step a). Removal of the PMB protective group using acidic conditions, such as treatment with neat AcOH, TfOH, MsOH, TsOH, or preferably TFA in a solvent like toluene or DCM, optionally in the presence of anisole or 1,3 dimethoxybenzene, preferably in DCM and in a temperature range between room temperature and the boiling point of the reaction mixture, preferably at room temperature gives the ketone compound 9 (see e.g. intermediate I-2, step b). Treatment of ketone intermediates 9 with a phenyl Grignard reagent in a solvent like diethylether or THF, preferably THF and in a temperature range between −78° C. and 25° C., preferably at 0° C. affords the corresponding compound of formula (I), wherein R$^1$, R$^2$, R$^3$, R$^4$, R$^5$ and R$^6$ are as defined herein and wherein R$^7$ is hydroxy (step c). The tertiary alcohol moiety of (I) may be further transformed to a halogen, preferably to F, using conditions known in the art (e.g. by reacting (I) with HCl, HBr, HI, POCl$_3$, SOCl$_2$ or PBr$_3$ or with a suitable amino sulfurane reagent such as DAST or by first converting the alcohol of (I) to a sulfonate ester, such as mesylate, in the first stage, followed by reacting said sulfonate ester with e.g. NaF), to yield compound of formula (I), wherein R$^1$, R$^2$, R$^3$, R$^4$, R and R$^6$ are as defined herein and wherein R$^7$ is halogen (Scheme 1a, step d). In addition, compounds of formula (I) wherein R$^7$ is one halogen may be transformed to compounds of formula (I) wherein $R^7$ is another halogen by methods known in the art. The tertiary alcohol moiety of (I) may be further transformed to an alkoxy, preferably to methoxy, by treatment with an appropriate base, such as NaH, KH, NaHMDS, LiHMDS or LDA, preferably with NaH in a solvent like DMF, THF, dioxane, or a mixture thereof, preferably DMF and in a temperature range between Alternatively, compounds of formula (I) wherein $R^1$, $R^2$, $R^3$, $R^4$, $R^5$ and $R^6$ are as defined herein and wherein $R^7$ is hydroxy, halogen or alkoxy, in particular hydroxy, F or methoxy, may be synthesized according to the general procedure outlined in Scheme 1b.

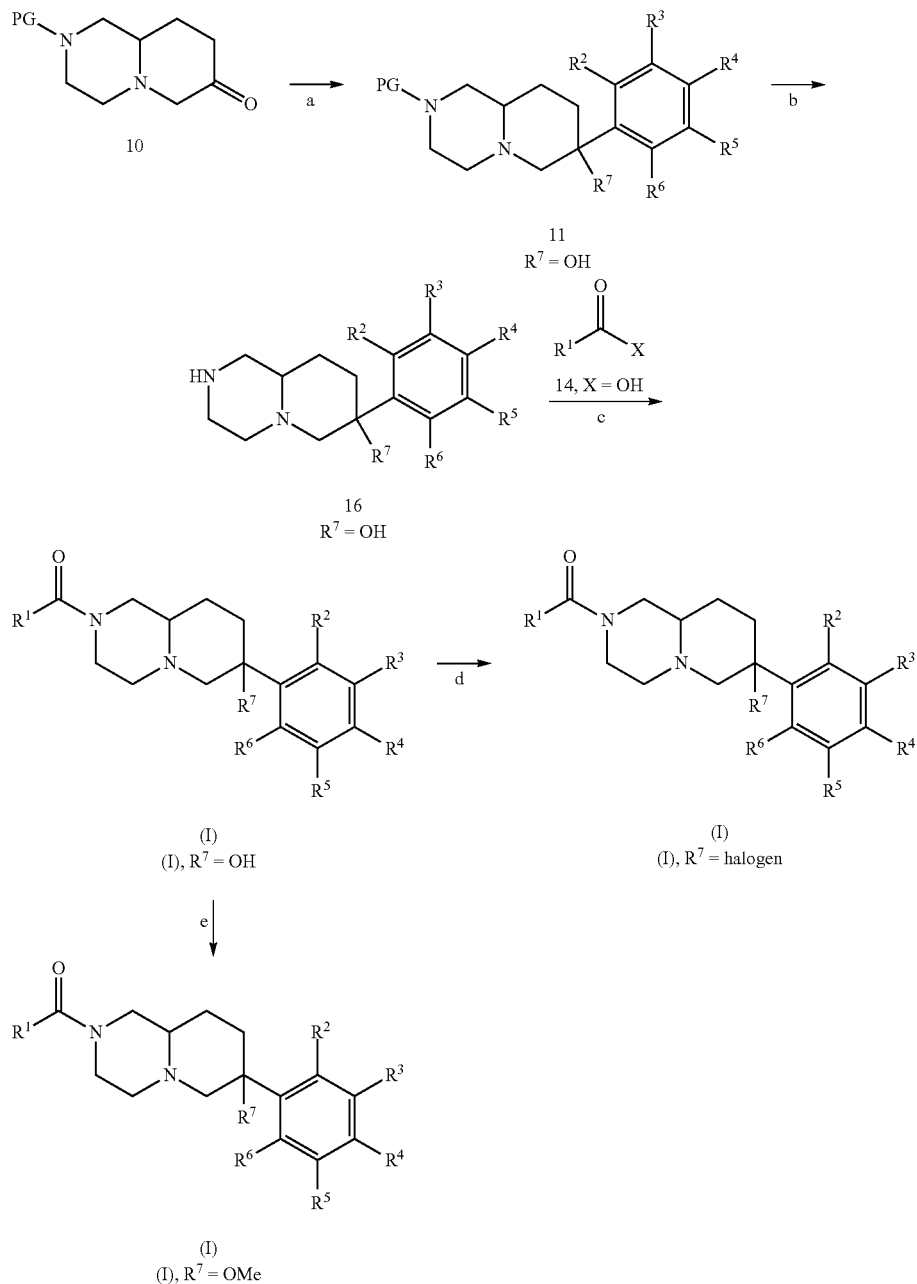

Scheme 1b

−78° C. and room temperature, preferably at 0° C., followed by addition of an electrophile, e.g. an alkyl or cycloalkyl halide, such as MeI, EtI, iPrI or CyPrI to give the corresponding compound of formula (I), wherein $R^1$, $R^2$, $R^3$, $R^4$, $R^5$ and $R^6$ are as defined herein and wherein $R^7$ is methoxy (Scheme 1a, step e).

Accordingly, treatment of protected ketone intermediate 10 (obtainable e.g. by the general procedure outlined in Scheme 3), wherein PG is a protective group, such as Boc (see e.g. intermediate I-1) with a phenyl Grignard reagent in a solvent like diethylether or THF, preferably THF and in a temperature range between −78° C. and 25° C., preferably at 0° C. affords the corresponding intermediate 11, wherein $R^2$, $R^3$, $R^4$, $R^5$ and $R^6$ are as defined herein and wherein $R^7$ is hydroxy (Scheme 1b, step a). Removal of the BOC protective group under suitable conditions, e.g. using acidic conditions, such as treatment with HCl in a solvent like EtOAc or MeOH or treatment with TFA in DCM, preferably at around room temperature affords the amine intermediates 16 (step b, see e.g. intermediate A-6). Subsequent, amide coupling reaction with carboxylic acid compounds 14, wherein $R^1$ is as defined herein, can be accomplished by using coupling reagents such as DCC, HATU, EDCI, HOBt, TBTU, T₃P, etc. and a base like Huenig's base, triethyl amine or DMAP in a suitable solvent like N,N-dimethylformamide, DMA, DCM or dioxane, preferably between 0° C. and room temperature gives compounds of formula (I) (step c). The tertiary alcohol moiety of (I) may be further transformed to a halogen, preferably to F, using conditions known in the art (e.g. by reacting (I) with HCl, HBr, HI, POCl₃, SOCl₂ or PBr₃ or with a suitable amino sulfurane reagent such as DAST or by first converting the alcohol of (I) to a sulfonate ester, such as mesylate, in the first stage, followed by reacting said sulfonate ester with e.g. NaF), to yield compound of formula (I), wherein $R^1$, $R^2$, $R^3$, $R^4$, $R^5$ and $R^6$ are as defined herein and wherein $R^7$ is halogen (Scheme 1b, step d). In addition, compounds of formula (I) wherein $R^7$ is one halogen may be transformed to compounds of formula (I) wherein $R^7$ is another halogen by methods known in the art. The tertiary alcohol moiety of (I) may be further transformed to an alkoxy, preferably to methoxy, by treatment with an appropriate base, such as NaH, KH, NaHMDS, LiHMDS or LDA, preferably with NaH in a solvent like DMF, THF, dioxane, or a mixture thereof, preferably DMF and in a temperature range between –78° C. and room temperature, preferably at 0° C., followed by addition of an electrophile, e.g. an alkyl or cycloalkyl halide, such as MeI to give the corresponding compound of formula (I), wherein $R^1$, $R^2$, $R^3$, $R^4$, $R^5$ and $R^6$ are as defined herein and wherein $R^7$ is methoxy (Scheme 1b, step e).

Alternatively, compounds of formula (I) wherein $R^1$, $R^2$, $R^3$, $R^4$, $R^5$ and $R^6$ are as defined herein and wherein $R^7$ is hydrogen may be synthesized according to the general procedure outlined in Scheme 2.

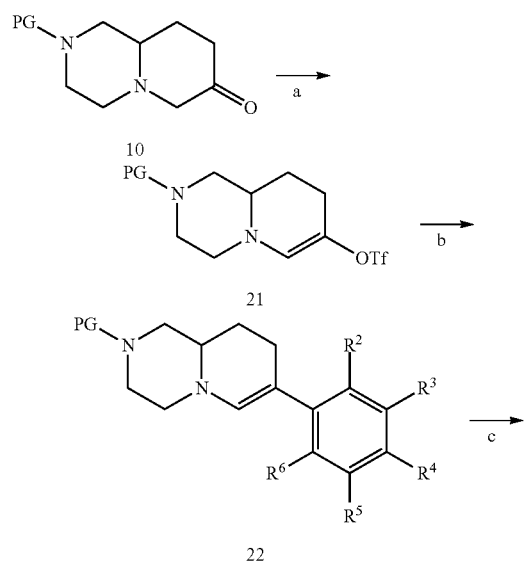

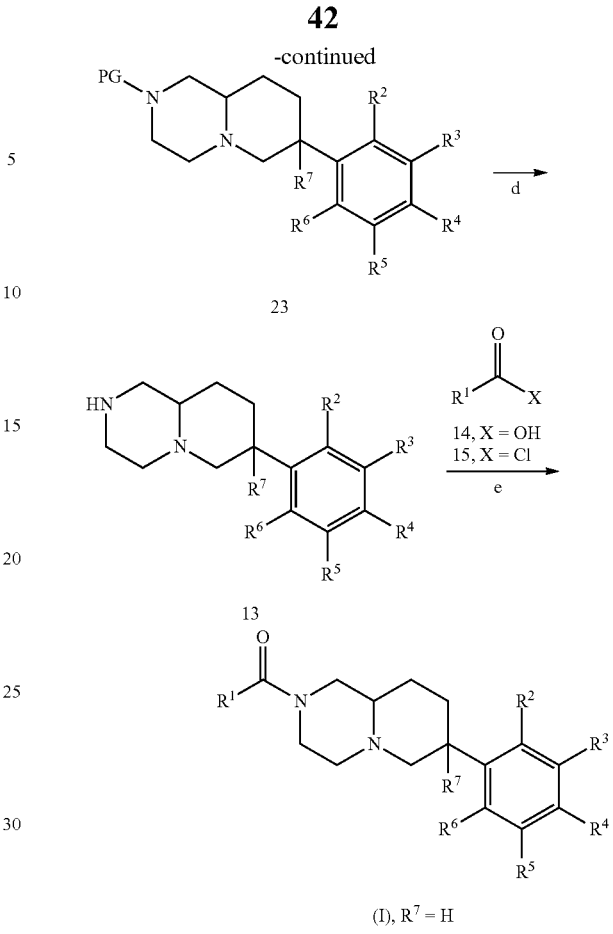

Treatment of protected ketone intermediate 10, wherein PG is a protective group, such as Boc (see e.g. intermediate I-1) with a suitable base such as NaHMDS, L-selectride, LDA or LiHMDS, preferably with LiHMDS in a solvent like dioxane, DME, THF or a mixture thereof, preferably THF and in a temperature range between –78° C. and room temperature, preferably at around –70° C., followed by addition of Tf₂O or Tf₂NPh, preferably Tf₂NPh in THF gives the corresponding vinyl triflate compounds 21 (Scheme 1, step a). Then, Suzuki cross-coupling reaction with aryl boronic acids or aryl boronic esters (e.g. pinacol or trimethylene glycol ester, either commercially available or prepared using literature procedures as described for example in "Boronic Acids—Preparation and Applications in Organic Synthesis and Medicine" by Dennis G. Hall (ed.) 1st Ed., 2005, John Wiley & Sons, New York), using a suitable catalyst (e.g., bis(triphenylphosphine)palladium (II) chloride, dichloro[1,1'-bis(diphenylphosphino)-ferrocene]palladium(II) dichloromethane adduct, tetrakis(triphenylphosphine)palladium(0) or palladium(II)acetate with triphenylphosphine) in an appropriate solvent (e.g. dioxane, DME, water, toluene, DMF or mixtures thereof) and a suitable base (e.g. Na₂CO₃, NaHCO₃, KF, K₂CO₃ or NEt₃) at temperatures between room temperature and the boiling point of the reaction mixture, yields compounds 22 (Scheme 2, step b). Subsequent heterogeneous catalytic hydrogenation of the olefin moiety using a transition metal catalyst such as PtO₂ or Pd/C, preferably Pd/C in presence of MgO in a solvent like MeOH, EtOH, THF or EtOAc, preferably EtOAc at around room temperature and under atmospheric pressure of hydrogen, gives intermediates 23 (Scheme 2, step c). Removal of the protective group under suitable conditions, e.g. using acidic conditions, such as treatment with HCl in a solvent like EtOAc or MeOH or treatment with TFA in DCM, preferably at around room temperature affords the amine intermediates 13 (Scheme 2, step d). Finally, amide coupling reaction with carboxylic acid compounds 14 (X=OH, either commercially available, or prepared by the methods described in Schemes 4, 5, 6 and 7 or in literature) or the respective acid chlorides 15, wherein $R^1$ is as defined herein, can be accomplished by using coupling reagents such as DCC, HATU, EDCI, HOBt, TBTU, $T_3P$, etc. and a base like Huenig's base, triethyl amine or DMAP in a suitable solvent solvent like N,N-dimethylformamide, DMA, DCM or dioxane, preferably between 0° C. and room temperature gives compounds of formula (I) (Scheme 2, step e).

Intermediates 10 may be synthesized by a variety of conditions, which may be exemplified by the general procedure outlined in Scheme 3.

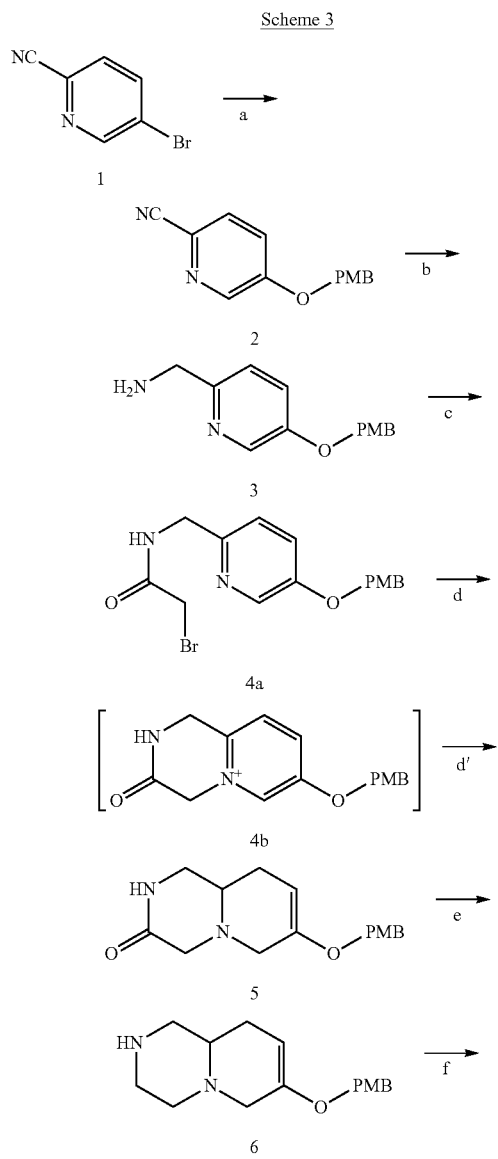

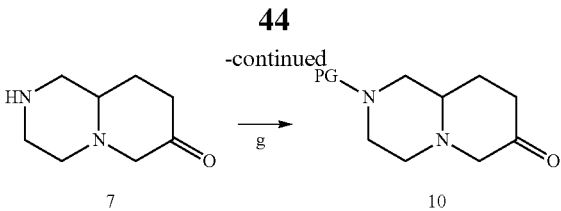

Starting from commercially available 3-bromo-6-pyridinecarbonitrile (1), a nucleophilic aromatic substitution reaction can be performed using 4-methoxybenzyl alcohol in presence of a suitable base, such as NaOH, KOH, KH, preferably with NaH in a solvent like DMF, THF, dioxane, or a mixture thereof, preferably in a mixture of DMF and THF and in a temperature range preferably between 0° C. and room temperature, to give the corresponding PMB protected compound 2 (Scheme 3, step a). Reduction of the nitrile group can be achieved using a suitable reducing agent such as borane, lithium borohydride or lithium aluminium hydride in a solvent like ether, DME, THF or a mixture thereof and in a temperature range between 0° C. and the boiling point of the solvent, or preferably using catalytic hydrogenation conditions such as Raney Nickel in a solvent like MeOH in presence of ammonium hydroxide around 50° C. and under 3.5 bar of hydrogen atmosphere, to give the corresponding amine 3 (Scheme 3, step b). Following, amide coupling reaction with bromoacetic acid using a suitable coupling agent such as DCC, DCI or preferably EDCI in a solvent like DCM, THF, DMF, DCE or $CH_3CN$, preferably DCM and in a temperature range between 0° C. and the boiling point of the solvent, preferably at room temperature gives the amide compound 4a (Scheme 3, step c). Subsequent heating of intermediate 4a in a solvent like EtOH, MeOH, preferably $CH_3CN$ and preferably around 50° C. gives the pyridinium intermediate 4b (Scheme 3, step d). Following treatment with a suitable reducing agent, such as sodium borohydride in a solvent like MeOH, preferably at around round temperature gives the lactam compound 5 (Scheme 3, step d'). Reduction of the amide using a suitable reducing agent such as borane, lithium borohydride or preferably lithium aluminium hydride in a solvent like ether, DME or a mixture thereof, preferably THF and in a temperature range between 0° C. and the boiling point of the reaction mixture, preferably at reflux, gives the corresponding amine compound 6 (Scheme 3, step e). Following removal of the PMB protective group using acidic conditions, such as treatment with neat AcOH, TfOH, MsOH, TsOH, or preferably TFA in a solvent like toluene or DCM, optionally in the presence of anisole or 1,3 dimethoxybenzene, preferably in DCM and in a temperature range between room temperature and the boiling point of the reaction mixture, preferably at room temperature gives the ketone compound 7 (Scheme 3, step f). Finally, the secondary amine in 7 is protected with a suitable protective group (Scheme 3, step g) to afford intermediate 10. Thus, for example, treatment with di-tert-butyldicarbonate optionally in presence of a base such as DMAP, TEA, $NaHCO_3$ or preferably $Na_2CO_3$ in a suitable solvent like $CH_3CN$, DCM, dioxane or THF, preferably in $CH_3CN$ and in a temperature range between 0° C. and room temperature, preferably at room temperature yields the Boc protected ketone intermediate I-1.

In one embodiment, carboxylic acid compound 14 is an intermediate of type B, C, D, E or F. Intermediates of type B, C, D, E and F can be prepared e.g., as exemplified by the synthetic procedures outlined in Schemes 4, 5, 6, 7 and 8.

Intermediates of type B, wherein $R^9$, $R^{10}$, $R^{13}$, $R^{14}$ and A are as defined herein and wherein B is aryl, in particular phenyl can be prepared by a variety of conditions, which may be exemplified by the general synthetic procedure outlined in Scheme 4.

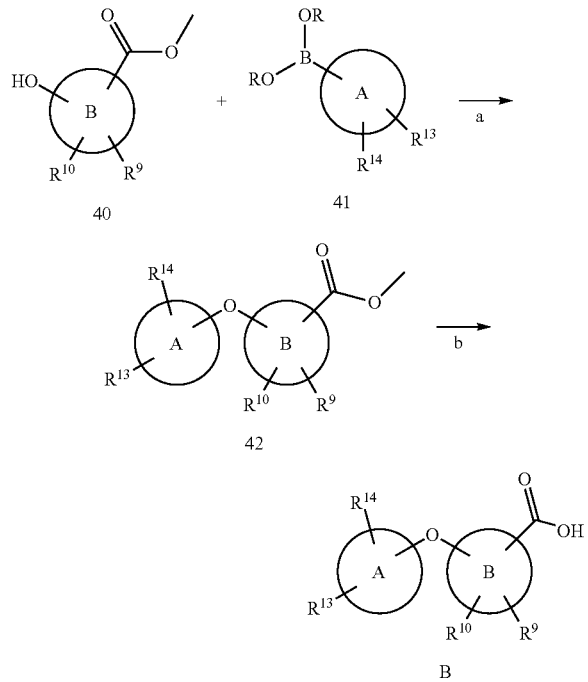

Chan-Lam coupling reaction between hydroxy aryl compounds 40, wherein B is aryl, in particular phenyl, and $R^9$ and $R^{10}$ are as defined herein, and a boronic acid 41 (R=H) or a boronic acid ester 41 (R≠H, e.g. pinacol or trimethylene glycol ester), which are either commercially available or may be prepared by methods known to the man skilled in the art, wherein A, $R^{13}$ and $R^{14}$ are as defined herein, can be performed by using a suitable catalyst, such as copper(II) acetate or copper(II) acetate monohydrate in a solvent like DCM, THF, dioxane, DME, or a mixture thereof, preferably in DCM and preferably at room temperature to give the corresponding ether intermediates 42 (Scheme 4, step a). Subsequent alkaline hydrolysis of the ester moiety with a suitable base, such as aqueous lithium, sodium or potassium hydroxide, preferably lithium hydroxide, in a solvent like MeOH, EtOH, THF or a mixture thereof and in a temperature range between 0° C. and the boiling point of the reaction mixture, preferably at around room temperature gives intermediates of type B (step b, Scheme 4).

Intermediates of type C, wherein $R^9$ and $R^{10}$ are as defined herein, $R^{8'}$ is alkoxy and B is aryl, in particular phenyl, can be prepared by a variety of conditions, which may be exemplified by the general synthetic procedure outlined in Scheme 5.

Scheme 5

Starting from halo methyl aryl compounds 50, wherein B is aryl, in particular phenyl, and $R^9$ and $R^{10}$ are as defined herein and Y is a suitable leaving group such as Cl, Br, I or OTf, an alcoholysis can be performed in the presence of a suitable base, such as $Na_2CO_3$, $K_2CO_3$, NaOH, KOH in solvent such as MeOH, EtOH, iPrOH, nBuOH, tBuOH and in a temperature range between room temperature and reflux, preferably at reflux to give the corresponding ether intermediates 51, wherein $R^{8'}$ is alkoxy and $R^9$ and $R^{10}$ are as defined herein (Scheme 5, step a). Subsequent alkaline hydrolysis with a suitable base, such as aqueous sodium or potassium hydroxide, preferably lithium hydroxide in a solvent like MeOH, EtOH, THF or a mixture thereof and in a temperature range between 0° C. and the boiling point of the solvent, preferably around room temperature gives intermediates of type C (Scheme 5, step b).

Intermediates of type D, wherein $R^{11}$ is as defined herein, $R^{12}$ is alkyl, cycloalkyl or heterocyclyl and B is heteroaryl comprising a secondary amino group, can be prepared by a variety of conditions, which may be exemplified by the general synthetic procedure outlined in Scheme 6.

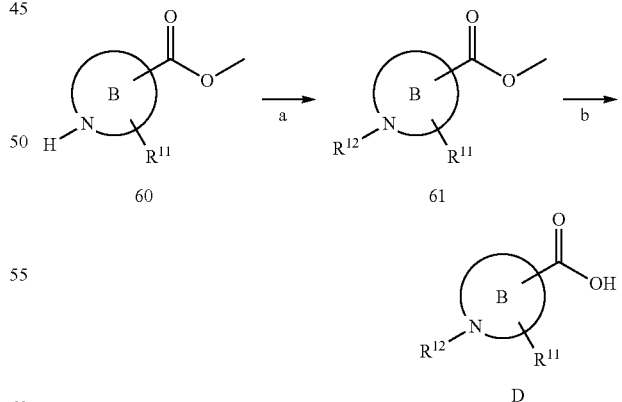

Intermediates 60, wherein $R^{11}$ is as defined herein and ring B is heteroaryl comprising a secondary amino group (i.e., "—NH—", such as in indolyl) can be N-functionalized by treatment with an appropriate base, such as NaH, KH, NaHMDS, LiHMDS or LDA, preferably with NaH in a solvent like DMF, THF, dioxane, or a mixture thereof, preferably DMF and in a temperature range between −78° C. and room temperature, preferably at 0° C., followed by addition of an electrophile, e.g. an alkyl or cycloalkyl halide, such as MeI, EtI, iPrI or CyPrI to give the corresponding N-functionalized compounds 61 (Scheme 6, step a), wherein $R^1$ is as defined herein and $R^{12}$ is alkyl, cycloalkyl or heterocyclyl. Intermediate 61 is subsequently hydrolyzed with a suitable base, such as aqueous LiOH, NaOH or KOH, preferably aqueous LiOH in a solvent like MeOH, EtOH, THF or a mixture thereof and in a temperature range between 0° C. and the boiling point of the reaction mixture, preferably at around room temperature to give carboxylic acid intermediates of type D (step b, Scheme 6).

Intermediates of type E, wherein $R^{8'}$ is alkyl, cycloalkylalkyl, arylalkyl, heteroarylalkyl or heterocyclylalkyl, $R^9$ and $R^{10}$ are as defined herein, and B is aryl, in particular phenyl, can be prepared by a variety of conditions, which may be exemplified by the general synthetic procedure outlined in Scheme 7.

Scheme 7

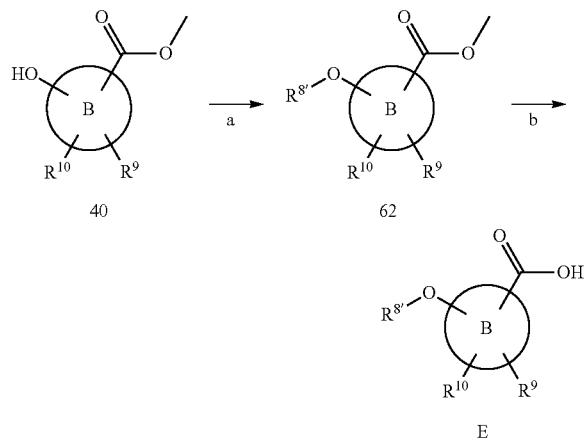

Intermediates 40, wherein B is aryl, in particular phenyl, and $R^9$ and $R^{10}$ are as defined herein, can be O-alkylated by treatment with an appropriate base, such as $Na_2CO_3$, $K_2CO_3$ or $Cs_2CO_3$ in a solvent like DMF, DCM, DCE, or a mixture thereof, preferably DMF and in a temperature range between room temperature and reflux, preferably at around 40° C., followed by addition of an electrophile, e.g. an alkyl-, cycloalkylalkyl-, arylalkyl-, heteroarylalkyl- or heterocyclylalkyl halide, such as MeI, EtI, iPrI, iodomethylcyclopropane, 4-(chloromethyl)-1-methyl-pyrazole or tert-butyl 4-(bromomethyl)pyrazole-1-carboxylate, to give the corresponding ether intermediates 62 (Scheme 7, step a), wherein $R^{8'}$ is selected from the group consisting of alkyl, cycloalkylalkyl, arylalkyl, heteroarylalkyl and heterocyclylalkyl and $R^9$ and $R^{10}$ are as defined herein. Intermediate 62 is subsequently hydrolyzed with a suitable base, such as aqueous LiOH, NaOH or KOH, preferably aqueous LiOH in a solvent like MeOH, EtOH, THF or a mixture thereof and in a temperature range between 0° C. and the boiling point of the reaction mixture, preferably at around room temperature to give carboxylic acid intermediates of type E (Scheme 7, step b).

Intermediates of type F, wherein $R^9$ and $R^{10}$ are as defined herein, B is aryl, in particular phenyl, $R^8$ is alkyl, aryl, heteroaryl, or a group —$N(R^{21}R^{22})$, wherein $R^{21}$ and $R^{22}$ are independently selected from the group consisting of hydrogen, alkyl, aryl and heteroaryl or wherein $R^{21}$ and $R^{22}$, taken together with the N-atom to which they are attached, form a mono- or bicyclic heterocycloalkyl, can be prepared by a variety of conditions, which may be exemplified by the general synthetic procedure outlined in Scheme 8.

Scheme 8

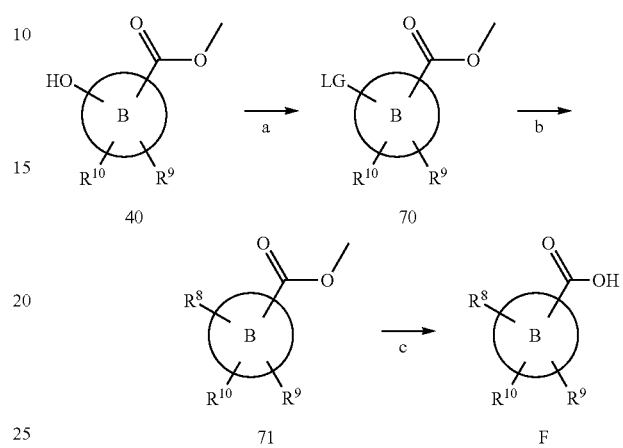

The hydroxy group of intermediates 40, wherein B is aryl, in particular phenyl, and $R^9$ and $R^{10}$ are as defined herein, can be transformed into a suitable leaving group such as a mesylate, tosylate or preferably triflate (OTf) by treatment with a suitable base such as, Huenig's base or TEA in a solvent like DMF or DCM and in a temperature range between 0° C. and room temperature, followed by addition of $Tf_2O$ or $Tf_2NPh$, preferably $Tf_2NPh$ gives the corresponding triflate compounds 70 (Scheme 8, step a). Subsequent, Suzuki cross-coupling reaction with aryl boronic acids or esters, alkyl boronic acids or esters, such as (E)-2-(2-cyclopropylvinyl)-4,4,5,5-tetramethyl-1,3,2-dioxaborolane, using a suitable catalyst (e.g. bis(triphenylphosphine)palladium (II) chloride, dichloro[1,1'-bis(diphenylphosphino)-ferrocene]palladium(II) dichloromethane adduct, tetrakis (triphenylphosphine)palladium(O) or palladium(II)acetate with triphenylphosphine) in an appropriate solvent (e.g. dioxane, DME, water, toluene, DMF or mixtures thereof) and a suitable base (e.g. $Na_2CO_3$, $NaHCO_3$, KF, $K_2CO_3$ or $NEt_3$) at temperatures between room temperature and the boiling point of the reaction mixture, yields ester compounds 71 (step b), wherein $R^8$ is selected from the group consisting of alkyl, aryl and heteroaryl, and $R^9$ and $R^{10}$ are as defined herein. Finally, alkaline hydrolysis of the ester moiety with a suitable base, such as aqueous lithium, sodium or potassium hydroxide, preferably lithium hydroxide, in a solvent like MeOH, EtOH, THF or a mixture thereof and in a temperature range between 0° C. and the boiling point of the reaction mixture, preferably at around room temperature gives intermediates of type F (step c).

Alternatively, intermediates 70, wherein B is aryl, in particular phenyl, X is a suitable leaving group such as Br, I (commercial compounds) or OTf (synthesized according to the step a described above) and $R^9$ and $R^{10}$ are as defined herein, can be transformed to intermediates 71 by applying cross-coupling reactions such as Buchwald-Hartwig. Treatment of intermediates 70 with primary or secondary amines of the type $HN(R^{21}R^{22})$, such as 2-oxa-6-azaspiro[3.3]heptane, using a suitable catalyst system such as $Pd_2(dba)_3$ and Davephos in the presence of a base such as $K_3PO_4$ in an appropriate solvent such as dioxane or toluene at temperatures ranging from room temperature up to the boiling point of the solvent, optionally applying microwave heating (Scheme 8, step b). Finally, alkaline hydrolysis of the ester moiety with a suitable base, such as aqueous lithium, sodium or potassium hydroxide, preferably lithium hydroxide, in a solvent like MeOH, EtOH, THF or a mixture thereof and in a temperature range between 0° C. and the boiling point of the reaction mixture, preferably at around room temperature gives intermediates of type F (step c).

In one aspect, the present invention provides a process of manufacturing the compounds of formula (I) described herein, comprising the steps of:

a) reacting an amine 13, wherein $R^2$, $R^3$, $R^4$, $R^5$, $R^6$ and $R^7$ are as described herein,

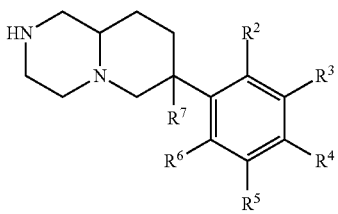
13 with an acid 14, wherein $R^1$ is as described herein

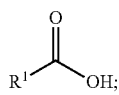
14 b) reacting an amine 13, wherein $R^2$, $R^3$, $R^4$, $R^5$, $R^6$ and $R^7$ are as described herein,

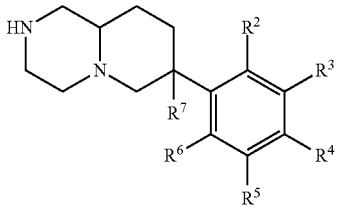
13 with an acid chloride 15, wherein $R^1$ is as described herein

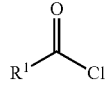
15 to form said compound of formula (I).

In one embodiment, the present invention provides a process of manufacturing the compounds of formula (I) described herein, comprising reacting an amine 13, wherein $R^2$, $R^3$, $R^4$, $R^5$, $R^6$ and $R^7$ are as described herein,

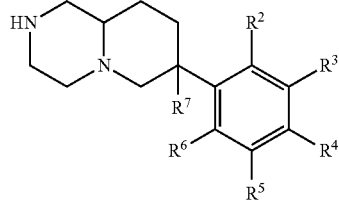
13 with an acid 14, wherein $R^1$ is as described herein

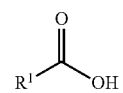
14 to form said compound of formula (I).

In one embodiment, the present invention provides a process of manufacturing the compounds of formula (I) described herein, comprising reacting an amine 13, wherein $R^2$, $R^3$, $R^4$, $R^5$, $R^6$ and $R^7$ are as described herein,

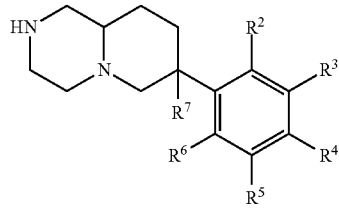
13 with an acid chloride 15, wherein $R^1$ is as described herein

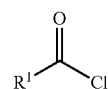
15 to form said compound of formula (I).

In one aspect, the present invention provides a compound of formula (I) as described herein, when manufactured according to any one of the processes described herein.

MAGL Inhibitory Activity

Compounds of the present invention are MAGL inhibitors. Thus, in one aspect, the present invention provides the use of compounds of formula (I) as described herein for inhibiting MAGL in a mammal.

In a further aspect, the present invention provides compounds of formula (I) as described herein for use in a method of inhibiting MAGL in a mammal.

In a further aspect, the present invention provides the use of compounds of formula (I) as described herein for the preparation of a medicament for inhibiting MAGL in a mammal.

In a further aspect, the present invention provides a method for inhibiting MAGL in a mammal, which method comprises administering an effective amount of a compound of formula (I) as described herein to the mammal.

Compounds were profiled for MAGL inhibitory activity by measuring the enzymatic activity of MAGL by following the hydrolysis of 4-nitrophenylacetate resulting in 4-nitrophenol, which absorbs at 405-412 nm (G. G. Muccioli, G. Labar, D. M. Lambert, *Chem. Bio. Chem.* 2008, 9, 2704-2710). This assay is hereinafter abbreviated "4-NPA assay".

The 4-NPA assay was carried out in 384 well assay plates (black with clear bottom, non-binding surface treated, Corning Ref. 3655) in a total volume of 40 µL. Compound dilutions were made in 100% DMSO (VWR Chemicals 23500.297) in a polypropylene plate in 3-fold dilution steps to give a final concentration range in the assay from 25 µM to 1.7 nM. 1 µL compound dilutions (100% DMSO) were added to 19 µL MAGL (recombinant wild-type) in assay buffer (50 mM TRIS (GIBCO, 15567-027), 1 mM EDTA (Fluka, 03690-100 ml)). The plate was shaken for 1 min at 2000 rpm (Variomag Teleshake) and then incubated for 15 min at RT. To start the reaction, 20 µL 4-Nitrophenlyacetate (Sigma N-8130) in assay buffer with 6% EtOH was added. The final concentrations in the assay were 1 nM MAGL and 300 µM 4-Nitrophenylacetate. After shaking (1 min, 2000 rpm) and 5 min incubation at RT, the absorbance at 405 nm was measured for a first time (Molecular Devices, SpectraMax Paradigm). A second measurement was then done after incubation for 80 min at RT. From the two measurements, the slope was calculated by substracting the first from the second measurement.

Alternatively, compounds were profiled for MAGL inhibitory activity by determining the enzymatic activity by following the hydrolysis of the natural substrate, 2-arachidonoylglycerol, resulting in arachidonic acid, which can be followed by mass spectrometry. This assay is hereinafter abbreviated "2-AG assay".

The 2-AG assay was carried out in 384 well assay plates (PP, Greiner Cat #784201) in a total volume of 20 µL. Compound dilutions were made in 100% DMSO (VWR Chemicals 23500.297) in a polypropylene plate in 3-fold dilution steps to give a final concentration range in the assay from 12.5 µM to 0.8 µM. 0.25 µL compound dilutions (100% DMSO) were added to 9 µL MAGL in assay buffer (50 mM TRIS (GIBCO, 15567-027), 1 mM EDTA (Fluka, 03690-100 ml), 0.01% (v/v) Tween. After shaking, the plate was incubated for 15 min at RT. To start the reaction, 10 µL 2-arachidonoylglycerol in assay buffer was added. The final concentrations in the assay was 50 µM MAGL and 8 µM 2-arachidonoylglyerol. After shaking and 30 min incubation at RT, the reaction was quenched by the addition of 40 µL of acetonitrile containing 4 µM of d8-arachidonic acid. The amount of arachidonic acid was traced by an online SPE system (Agilent Rapidfire) coupled to a triple quadrupole mass spectrometer (Agilent 6460). A C18 SPE cartridge (G9205A) was used in an acetonitrile/water liquid setup. The mass spectrometer was operated in negative electrospray mode following the mass transitions 303.1→259.1 for arachidonic acid and 311.1→267.0 for d8-arachidonic acid. The activity of the compounds was calculated based on the ratio of intensities [arachidonic acid/d8-arachidonic acid].

TABLE 1

| Example | Name | Structure | IC$_{50}$ MAGL [µM] |
|---|---|---|---|
| 1 | [(7R,9aR)-7-(4-chlorophenyl)-1,3,4,6,7,8,9,9a-octahydropyrido[1,2-a]pyrazin-2-yl]-(3-phenoxyphenyl)methanone | 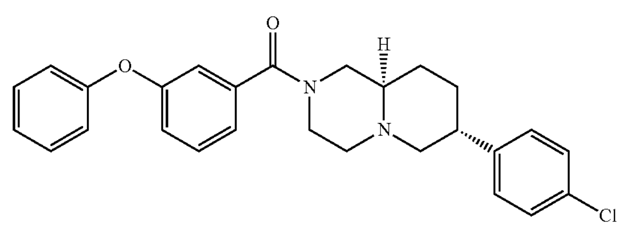 [SMILES: O=C(c1cccc(Oc2ccccc2)c1)N1CCN2C[C@@H](c3ccc(Cl)cc3)CC[C@@H]2C1] | 1.160 |
| 2 | [(7R,9aR)-7-(4-chlorophenyl)-1,3,4,6,7,8,9,9a-octahydropyrido[1,2-a]pyrazin-2-yl]-(2-chloro-3-methylphenyl)methanone | 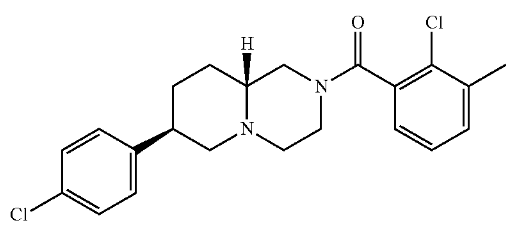 [SMILES: Cc1cccc(C(=O)N2CCN3C[C@@H](c4ccc(Cl)cc4)CC[C@@H]3C2)c1Cl] | 0.063 |
| 3 | [(7R,9aR)-7-(4-chlorophenyl)-1,3,4,6,7,8,9,9a-octahydropyrido[1,2-a]pyrazin-2-yl]-(2-bromo-3-methoxyphenyl)methanone | 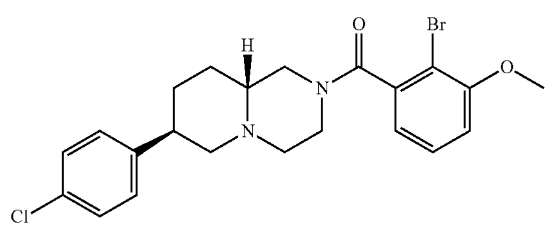 [SMILES: COc1cccc(C(=O)N2CCN3C[C@@H](c4ccc(Cl)cc4)CC[C@@H]3C2)c1Br] | 0.030 |

TABLE 1-continued

| Example | Name | Structure | IC$_{50}$ MAGL [µM] |
|---|---|---|---|
| 4 | [(7R,9aR)-7-(4-chlorophenyl)-1,3,4,6,7,8,9,9a-octahydropyrido[1,2-a]pyrazin-2-yl]-[3-(3,5-difluorophenoxy)phenyl]methanone | 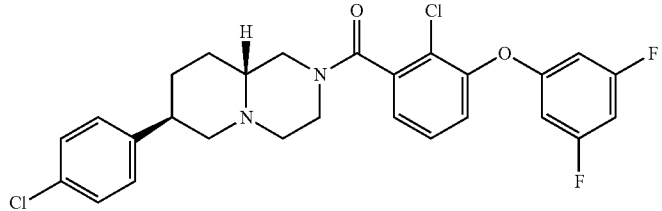 [SMILES: O=C(c1cccc(Oc2cc(F)cc(F)c2)c1Cl)N1CCN2C[C@@H](c3ccc(Cl)cc3)CC[C@@H]2C1] | 3.960 |
| 5 | [(7R,9aR)-7-phenyl-1,3,4,6,7,8,9,9a-octahydropyrido[1,2-a]pyrazin-2-yl]-(2-bromo-3-methoxyphenyl)methanone | 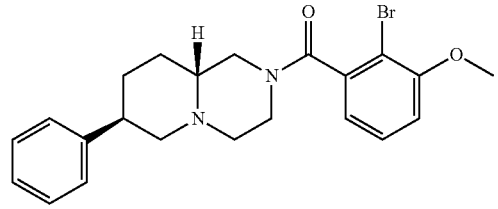 | 0.150 |
| 6 | [(7R,9aR)-7-(4-chlorophenyl)-1,3,4,6,7,8,9,9a-octahydropyrido[1,2-a]pyrazin-2-yl]-(2-chloro-3-methoxyphenyl)methanone | 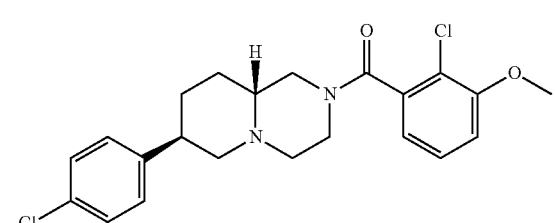 | 0.043 |
| 7 | [(7R,9aR)-7-(4-chlorophenyl)-1,3,4,6,7,8,9,9a-octahydropyrido[1,2-a]pyrazin-2-yl]-(2-methoxyphenyl)methanone | 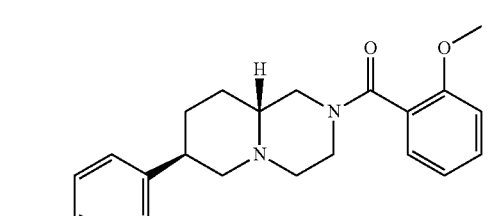 | 3.780 |
| 8 | [(7R,9aR)-7-(4-chlorophenyl)-1,3,4,6,7,8,9,9a-octahydropyrido[1,2-a]pyrazin-2-yl]-[2-(trifluoromethoxy)phenyl]methanone | 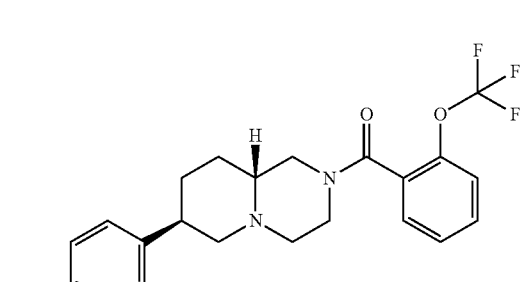 | 3.360 |
| 9 | [(7R,9aR)-7-(4-chlorophenyl)-1,3,4,6,7,8,9,9a-octahydropyrido[1,2-a]pyrazin-2-yl]-(2,3-dihydro-1-benzofuran-7-yl)methanone | 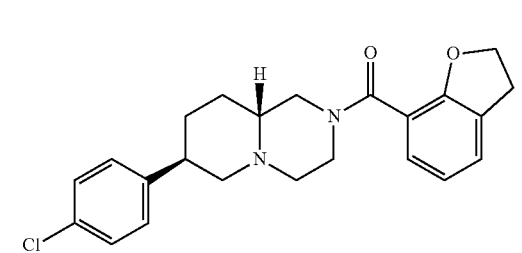 [SMILES: O=C(c1cccc2c1OCC2)N1CCN2C[C@@H](c3ccc(Cl)cc3)CC[C@@H]2C1] | 1.740 |

TABLE 1-continued

| Example | Name | Structure | IC$_{50}$ MAGL [μM] |
|---------|------|-----------|---------------------|
| 10 | [(7R,9aR)-7-(4-chlorophenyl)-1,3,4,6,7,8,9,9a-octahydropyrido[1,2-a]pyrazin-2-yl]-(1H-indol-4-yl)methanone | 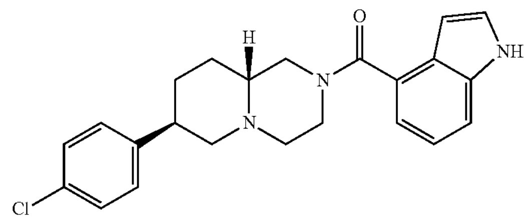 [SMILES: O=C(c1cccc2[nH]ccc12)N1CCN2C[C@@H](c3ccc(Cl)cc3)CC[C@@H]2C1] | 0.198 |
| 11 | [(7R,9aR)-7-(4-chlorophenyl)-1,3,4,6,7,8,9,9a-octahydropyrido[1,2-a]pyrazin-2-yl]-(2-chloro-6-fluorophenyl)methanone | 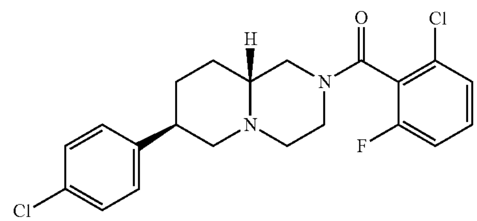 [SMILES: O=C(c1c(F)cccc1Cl)N1CCN2C[C@@H](c3ccc(Cl)cc3)CC[C@@H]2C1] | 1.170 |
| 12 | [(7R,9aR)-7-(4-chlorophenyl)-1,3,4,6,7,8,9,9a-octahydropyrido[1,2-a]pyrazin-2-yl]-(2-chlorophenyl)methanone | 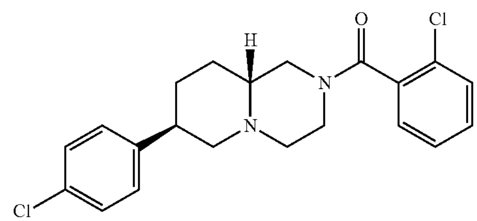 [SMILES: O=C(c1ccccc1Cl)N1CCN2C[C@@H](c3ccc(Cl)cc3)CC[C@@H]2C1] | 0.360 |
| 13 | [(7R,9aR)-7-(4-chlorophenyl)-1,3,4,6,7,8,9,9a-octahydropyrido[1,2-a]pyrazin-2-yl]-(2-fluoro-3-methylphenyl)methanone | 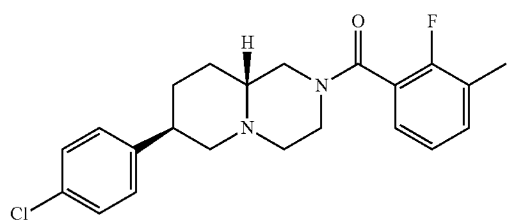 [SMILES: Cc1cccc(C(=O)N2CCN3C[C@@H](c4ccc(Cl)cc4)CC[C@@H]3C2)c1F] | 0.190 |
| 14 | [(7R,9aR)-7-(4-chlorophenyl)-1,3,4,6,7,8,9,9a-octahydropyrido[1,2-a]pyrazin-2-yl]-(4-chloro-1H-pyrrolo[2,3-b]pyridin-5-yl)methanone | 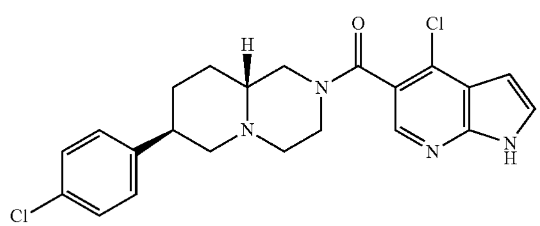 [SMILES: O=C(c1cnc2[nH]ccc2c1Cl)N1CCN2C[C@@H](c3ccc(Cl)cc3)CC[C@@H]2C1] | 0.134 |
| 15 | [(7R,9aR)-7-(4-chlorophenyl)-1,3,4,6,7,8,9,9a-octahydropyrido[1,2-a]pyrazin-2-yl]-(1H-pyrrolo[2,3-b]pyridin-4-yl)methanone | 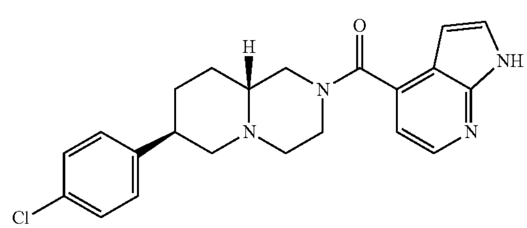 [SMILES: O=C(c1ccnc2[nH]ccc12)N1CCN2C[C@@H](c3ccc(Cl)cc3)CC[C@@H]2C1] | 0.290 |
| 16 | [(7R,9aR)-7-(4-chlorophenyl)-1,3,4,6,7,8,9,9a-octahydropyrido[1,2-a]pyrazin-2-yl]-[2-chloro-3-(trifluoromethyl)phenyl]methanone | 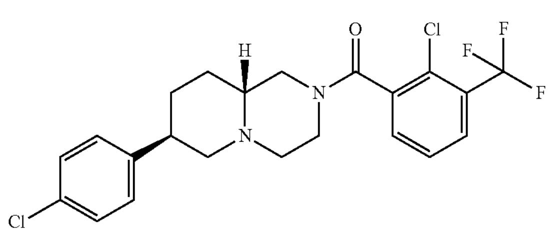 [SMILES: O=C(c1cccc(C(F)(F)F)c1Cl)N1CCN2C[C@@H](c3ccc(Cl)cc3)CC[C@@H]2C1] | 0.560 |

TABLE 1-continued

| Example | Name | Structure | IC$_{50}$ MAGL [μM] |
|---|---|---|---|
| 17 | [(7R,9aR)-7-(4-chlorophenyl)-1,3,4,6,7,8,9,9a-octahydropyrido[1,2-a]pyrazin-2-yl]-(2-chloro-4-fluoro-3-methylphenyl)methanone | 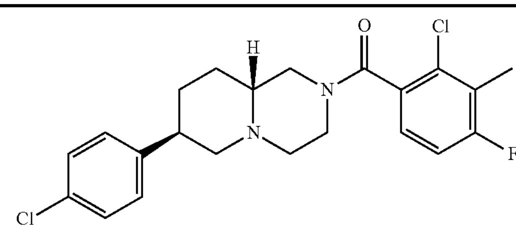 | 0.120 |
| 18 | [(7R,9aR)-7-(4-chlorophenyl)-1,3,4,6,7,8,9,9a-octahydropyrido[1,2-a]pyrazin-2-yl]-(3-chloro-2-methylphenyl)methanone | 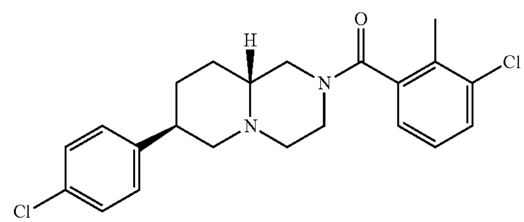 [SMILES: Cc1c(Cl)cccc1C(=O)N1CCN2C[C@@H](c3ccc(Cl)cc3)CC[C@@H]2C1] | 0.570 |
| 19 | [(7R,9aR)-7-(4-chlorophenyl)-1,3,4,6,7,8,9,9a-octahydropyrido[1,2-a]pyrazin-2-yl]-(4-chloro-6-methylpyridin-3-yl)methanone | 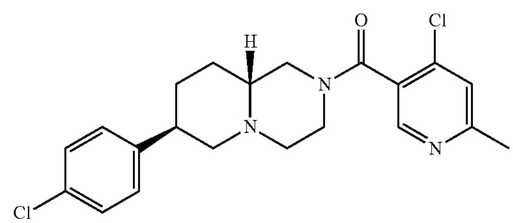 [SMILES: Cc1cc(Cl)c(C(=O)N2CCN3C[C@@H](c4ccc(Cl)cc4)CC[C@@H]3C2)cn1] | 1.620 |
| 20 | [(7R,9aR)-7-(4-chlorophenyl)-1,3,4,6,7,8,9,9a-octahydropyrido[1,2-a]pyrazin-2-yl]-(2,4-dimethyl-1,3-benzothiazol-5-yl)methanone | 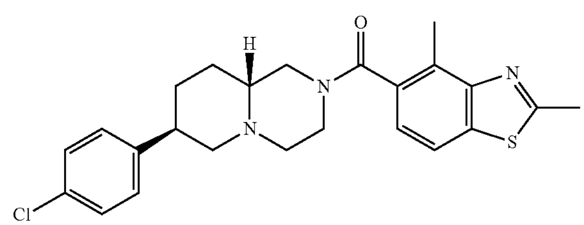 [SMILES: Cc1nc2c(C)c(C(=O)N3CCN4C[C@@H](c5ccc(Cl)cc5)CC[C@@H]4C3)ccc2s1] | 0.110 |
| 21 | [(7R,9aR)-7-(4-chlorophenyl)-1,3,4,6,7,8,9,9a-octahydropyrido[1,2-a]pyrazin-2-yl]-(7-chloro-2-methylsulfanyl-[1,3]thiazolo[5,4-b]pyridin-6-yl)methanone | 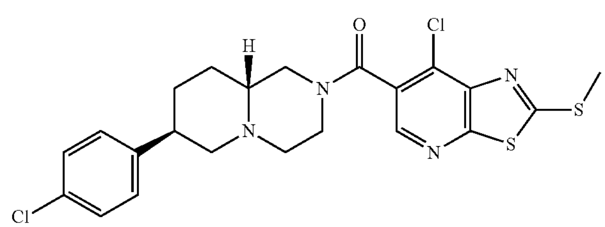 [SMILES: CSc1nc2c(Cl)c(C(=O)N3CCN4C[C@@H](c5ccc(Cl)cc5)CC[C@@H]4C3)cnc2s1] | 0.130 |
| 22 | [(7R,9aR)-7-(4-chlorophenyl)-1,3,4,6,7,8,9,9a-octahydropyrido[1,2-a]pyrazin-2-yl]-(1-benzothiophen-4-yl)methanone | 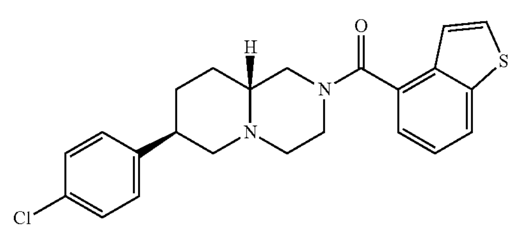 [SMILES: O=C(c1cccc2sccc12)N1CCN2C[C@@H](c3ccc(Cl)cc3)CC[C@@H]2C1] | 1.200 |
| 23 | [(7R,9aR)-7-(4-chlorophenyl)-1,3,4,6,7,8,9,9a-octahydropyrido[1,2-a]pyrazin-2-yl]-(2-bromo-3-methylphenyl)methanone | 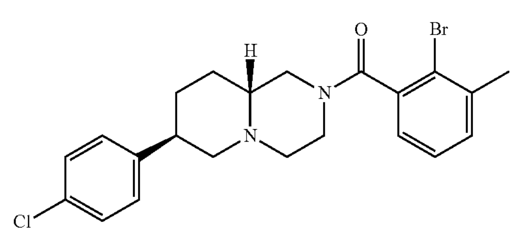 | 0.072 |

TABLE 1-continued

| Example | Name | Structure | IC$_{50}$ MAGL [µM] |
|---|---|---|---|
| 24 | [(7R,9aR)-7-(4-chlorophenyl)-1,3,4,6,7,8,9,9a-octahydropyrido[1,2-a]pyrazin-2-yl]-[2-(trifluoromethyl)phenyl]methanone | 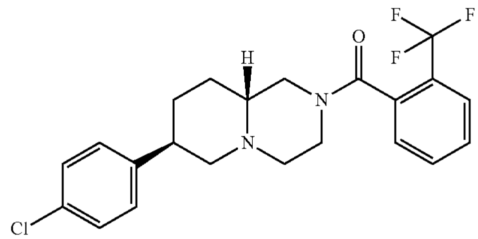 [SMILES: O=C(c1ccccc1C(F)(F)F)N1CCN2C[C@@H](c3ccc(Cl)cc3)CC[C@@H]2C1] | 0.740 |
| 25 | [(7R,9aR)-7-(4-chlorophenyl)-1,3,4,6,7,8,9,9a-octahydropyrido[1,2-a]pyrazin-2-yl]-(2-chloro-3-phenoxyphenyl)methanone | 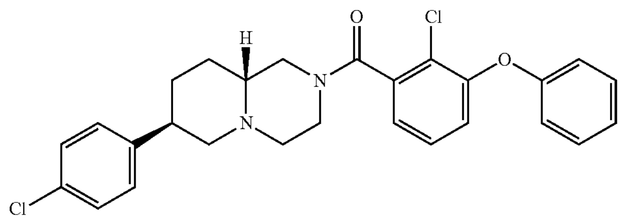 [SMILES: O=C(c1cccc(Oc2ccccc2)c1Cl)N1CCN2C[C@@H](c3ccc(Cl)cc3)CC[C@@H]2C1] | 0.750 |
| 26 | [(7R,9aR)-7-phenyl-1,3,4,6,7,8,9,9a-octahydropyrido[1,2-a]pyrazin-2-yl]-(2-chloro-3-methylphenyl)methanone | 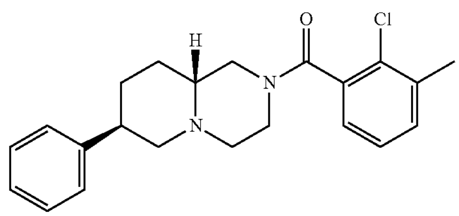 [SMILES: Cc1cccc(C(=O)N2CCN3C[C@@H](c4ccccc4)CC[C@@H]3C2)c1Cl] | 0.250 |
| 27 | [(7R,9aR)-7-phenyl-1,3,4,6,7,8,9,9a-octahydropyrido[1,2-a]pyrazin-2-yl]-(2-chloro-5-fluoro-3-methylphenyl)methanone | 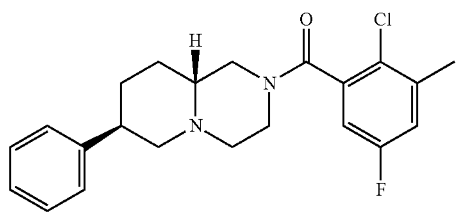 [SMILES: Cc1cc(F)cc(C(=O)N2CCN3C[C@@H](c4ccccc4)CC[C@@H]3C2)c1Cl] | 0.260 |
| 28 | [(7R,9aR)-7-phenyl-1,3,4,6,7,8,9,9a-octahydropyrido[1,2-a]pyrazin-2-yl]-[2-bromo-3-(methoxymethyl)phenyl]methanone | 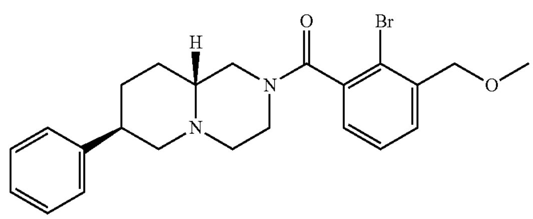 [SMILES: COCc1cccc(C(=O)N2CCN3C[C@@H](c4ccccc4)CC[C@@H]3C2)c1Br] | 3.120 |
| 29 | [(7R,9aR)-7-phenyl-1,3,4,6,7,8,9,9a-octahydropyrido[1,2-a]pyrazin-2-yl]-(1H-indol-4-yl)methanone | 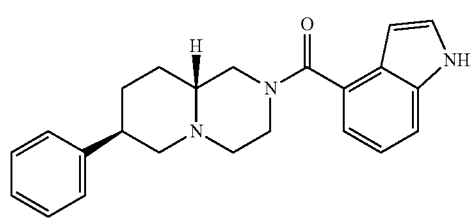 [SMILES: O=C(c1cccc2[nH]ccc12)N1CCN2C[C@@H](c3ccccc3)CC[C@@H]2C1] | 0.880 |
| 30 | [(7R,9aR)-7-phenyl-1,3,4,6,7,8,9,9a-octahydropyrido[1,2-a]pyrazin-2-yl]-(1-methylindol-4-yl)methanone | 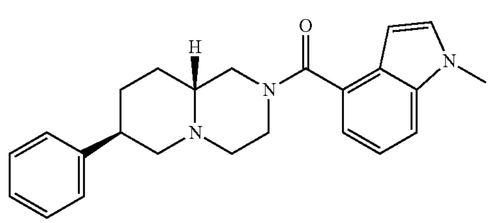 [SMILES: Cn1ccc2c(C(=O)N3CCN4C[C@@H](c5ccccc5)CC[C@@H]4C3)cccc21] | 0.350 |

TABLE 1-continued

| Example | Name | Structure | IC$_{50}$ MAGL [µM] |
|---|---|---|---|
| 31 | [(7R,9aR)-7-phenyl-1,3,4,6,7,8,9,9a-octahydropyrido[1,2-a]pyrazin-2-yl]-(4-chloro-1H-pyrrolo[2,3-b]pyridin-5-yl)methanone | 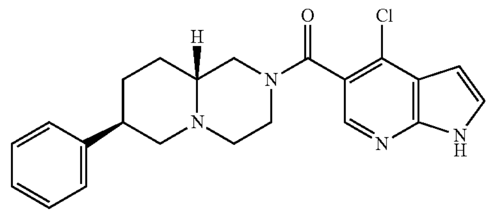 [SMILES: O=C(c1cnc2[nH]ccc2c1Cl)N1CCN2C[C@@H](c3ccccc3)CC[C@@H]2C1] | 0.890 |
| 32 | [(7R,9aR)-7-phenyl-1,3,4,6,7,8,9,9a-octahydropyrido[1,2-a]pyrazin-2-yl]-(2-chloro-3-hydroxyphenyl)methanone | 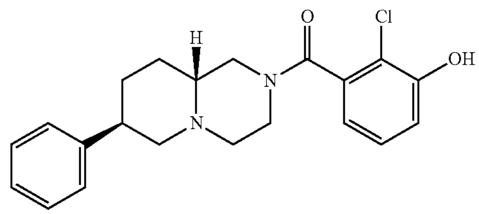 [SMILES: O=C(c1cccc(O)c1Cl)N1CCN2C[C@@H](c3ccccc3)CC[C@@H]2C1] | 3.050 |
| 33 | [(7R,9aR)-7-phenyl-1,3,4,6,7,8,9,9a-octahydropyrido[1,2-a]pyrazin-2-yl]-(1-methyl-2,3-dihydroindol-4-yl)methanone | 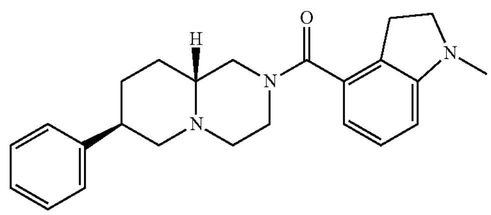 [SMILES: CN1CCc2c(C(=O)N3CCN4C[C@@H](c5ccccc5)CC[C@@H]4C3)cccc21] | 3.460 |
| 34 | [(7R,9aR)-7-phenyl-1,3,4,6,7,8,9,9a-octahydropyrido[1,2-a]pyrazin-2-yl]-(1-propan-2-ylindol-4-yl)methanone | 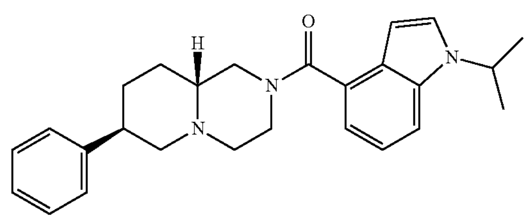 [SMILES: CC(C)n1ccc2c(C(=O)N3CCN4C[C@@H](c5ccccc5)CC[C@@H]4C3)cccc21] | 2.260 |
| 35 | [(7R,9aR)-7-phenyl-1,3,4,6,7,8,9,9a-octahydropyrido[1,2-a]pyrazin-2-yl]-(2-chloro-3-propan-2-yloxyphenyl)methanone;hydrochloride | 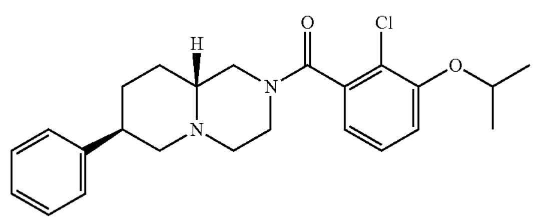 [SMILES: CC(C)Oc1cccc(C(=O)N2CCN3C[C@@H](c4ccccc4)CC[C@@H]3C2)c1Cl] | 0.790 |
| 36 | 3-[(7R,9aR)-7-phenyl-1,3,4,6,7,8,9,9a-octahydropyrido[1,2-a]pyrazine-2-carbonyl]-2-chlorobenzonitrile | 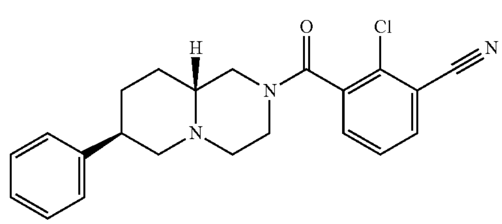 [SMILES: N#Cc1cccc(C(=O)N2CCN3C[C@@H](c4ccccc4)CC[C@@H]3C2)c1Cl] | 1.180 |
| 37 | [(7R,9aR)-7-phenyl-1,3,4,6,7,8,9,9a-octahydropyrido[1,2-a]pyrazin-2-yl]-(4-chloro-1-methylpyrrolo[2,3-b]pyridin-5-yl)methanone | 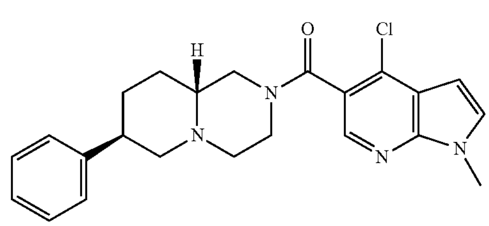 [SMILES: Cn1ccc2c(Cl)c(C(=O)N3CCN4C[C@@H](c5ccccc5)CC[C@@H]4C3)cnc21] | 0.680 |

TABLE 1-continued

| Example | Name | Structure | IC$_{50}$ MAGL [μM] |
|---|---|---|---|
| 38 | [(7R,9aR)-7-phenyl-1,3,4,6,7,8,9,9a-octahydropyrido[1,2-a]pyrazin-2-yl]-[2-chloro-3-[(1-methylpyrazol-4-yl)methoxy]phenyl]methanone | 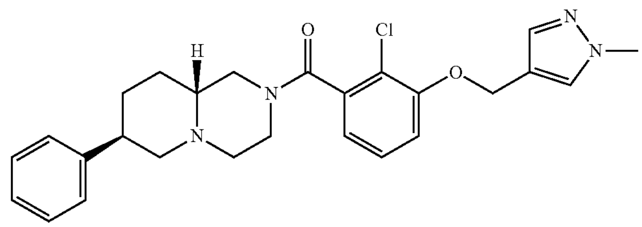 [SMILES: Cn1cc(COc2cccc(C(=O)N3CCN4C[C@@H](c5ccccc5)CC[C@@H]4C3)c2Cl)cn1] | 4.610 |
| 39 | [(7R,9aR)-7-phenyl-1,3,4,6,7,8,9,9a-octahydropyrido[1,2-a]pyrazin-2-yl]-(4-chloro-1-propan-2-ylpyrrolo[2,3-b]pyridin-5-yl)methanone | 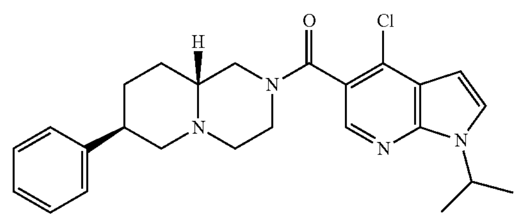 [SMILES: CC(C)n1ccc2c(Cl)c(C(=O)N3CCN4C[C@@H](c5ccccc5)CC[C@@H]4C3)cnc21] | 2.168 |
| 40 | [(7S,9aS)-7-(4-chlorophenyl)-1,3,4,6,7,8,9,9a-octahydropyrido[1,2-a]pyrazin-2-yl]-(2-bromo-3-methoxyphenyl)methanone | 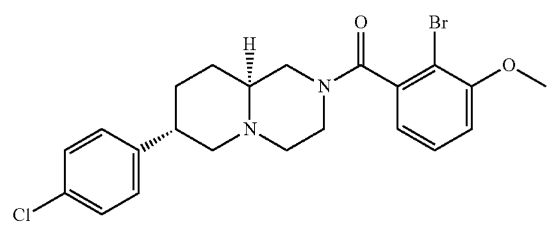 [SMILES: COc1cccc(C(=O)N2CCN3C[C@H](c4ccc(Cl)cc4)CC[C@H]3C2)c1Br] | 0.409 |
| 41 | [(7R,9aR)-7-phenyl-1,3,4,6,7,8,9,9a-octahydropyrido[1,2-a]pyrazin-2-yl]-(3-chloro-2-methoxypyridin-4-yl)methanone | 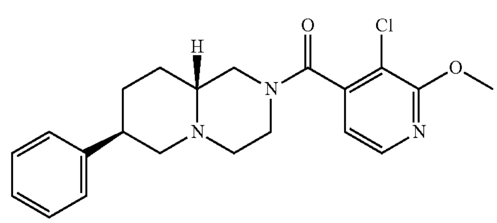 | 2.990 |
| 42 | [(7R,9aR)-7-(4-chlorophenyl)-1,3,4,6,7,8,9,9a-octahydropyrido[1,2-a]pyrazin-2-yl]-(4-chloro-1-methylpyrrolo[2,3-b]pyridin-5-yl)methanone | 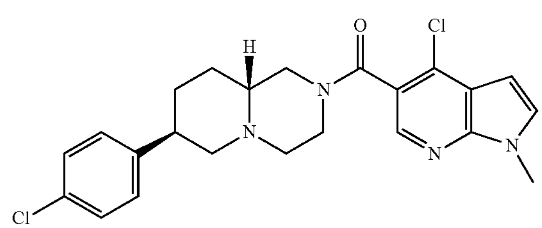 [SMILES: Cn1ccc2c(Cl)c(C(=O)N3CCN4C[C@@H](c5ccc(Cl)cc5)CC[C@@H]4C3)cnc21] | 0.071 |
| 43 | [(7R,9aR)-7-phenyl-1,3,4,6,7,8,9,9a-octahydropyrido[1,2-a]pyrazin-2-yl]-[2-chloro-3-(1,3-thiazol-4-ylmethoxy)phenyl]methanone | 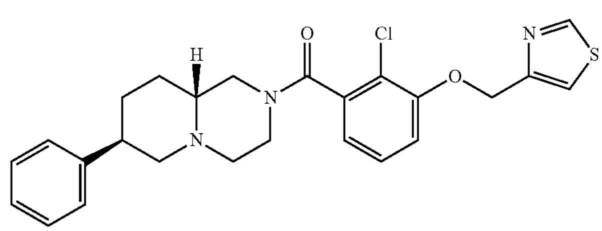 [SMILES: O=C(c1cccc(OCc2cscn2)c1Cl)N1CCN2C[C@@H](c3ccccc3)CC[C@@H]2C1] | 0.185 |

TABLE 1-continued

| Example | Name | Structure | IC₅₀ MAGL [μM] |
|---|---|---|---|
| 44 | 4-[[3-[(7R,9aR)-7-phenyl-1,3,4,6,7,8,9,9a-octahydropyrido[1,2-a]pyrazine-2-carbonyl]-2-chlorophenoxy]methyl]-N-methylbenzamide | 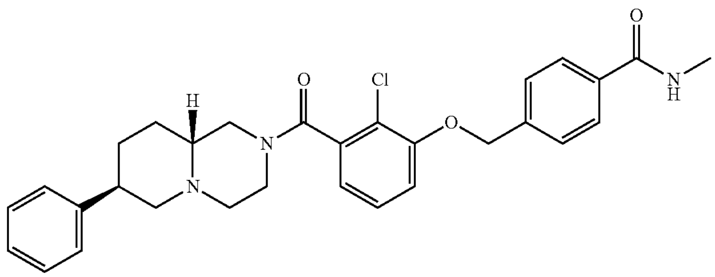 [SMILES: CNC(=O)c1ccc(COc2cccc(C(=O)N3CCN4C[C@@H](c5ccccc5)CC[C@@H]4C3)c2Cl)cc1] | 1.401 |
| 45 | [(7R,9aR)-7-(4-chlorophenyl)-1,3,4,6,7,8,9,9a-octahydropyrido[1,2-a]pyrazin-2-yl]-(4-chloro-1-methylpyrazolo[3,4-b]pyridin-5-yl)methanone | 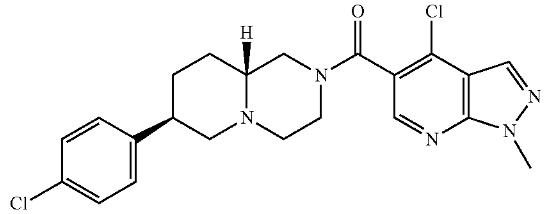 [SMILES: Cn1ncc2c(Cl)c(C(=O)N3CCN4C[C@@H](c5ccc(Cl)cc5)CC[C@@H]4C3)cnc21] | 0.161 |
| 46 | [(7R,9aR)-7-(3,4-dichlorophenyl)-1,3,4,6,7,8,9,9a-octahydropyrido[1,2-a]pyrazin-2-yl]-(2-bromo-3-methoxyphenyl)methanone | 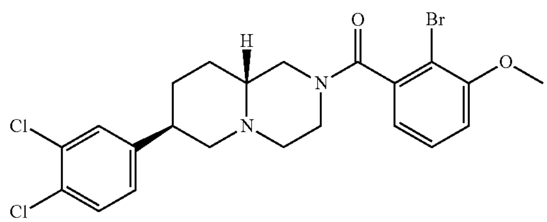 [SMILES: COc1cccc(C(=O)N2CCN3C[C@@H](c4ccc(Cl)c(Cl)c4)CC[C@@H]3C2)c1Br] | 0.003 |
| 47 | [(7S,9aS)-7-(3,4-dichlorophenyl)-1,3,4,6,7,8,9,9a-octahydropyrido[1,2-a]pyrazin-2-yl]-(2-bromo-3-methoxyphenyl)methanone | 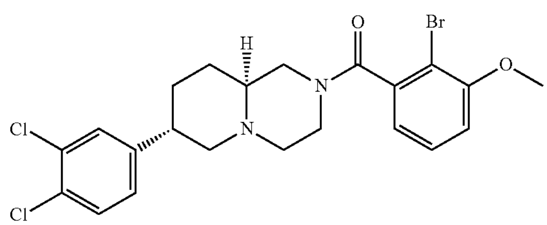 [SMILES: COc1cccc(C(=O)N2CCN3C[C@H](c4ccc(Cl)c(Cl)c4)CC[C@H]3C2)c1Br] | 0.100 |
| 48 | [(7R,9aR)-7-(4-chlorophenyl)-1,3,4,6,7,8,9,9a-octahydropyrido[1,2-a]pyrazin-2-yl]-[2-chloro-3-(2,2,2-trifluoroethoxy)phenyl]methanone | 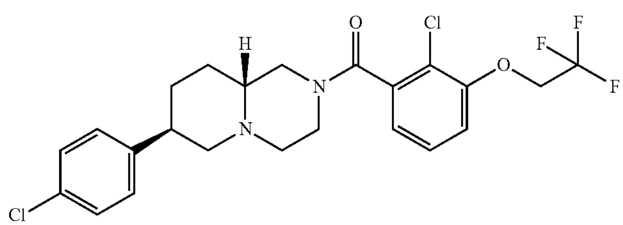 [SMILES: O=C(c1cccc(OCC(F)(F)F)c1Cl)N1CCN2C[C@@H](c3ccc(Cl)cc3)CC[C@@H]2C1] | 0.223 |
| 49 | [(7R,9aR)-7-(4-chlorophenyl)-1,3,4,6,7,8,9,9a-octahydropyrido[1,2-a]pyrazin-2-yl]-imidazo[1,2-a]pyridin-5-ylmethanone | 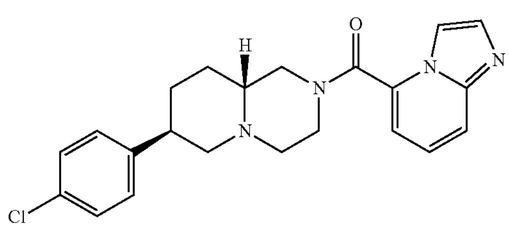 [SMILES: O=C(c1cccc2nccn12)N1CCN2C[C@@H](c3ccc(Cl)cc3)CC[C@@H]2C1] | 3.699 |

TABLE 1-continued

| Example | Name | Structure | IC$_{50}$ MAGL [µM] |
|---|---|---|---|
| 50 | tert-butyl 4-[[3-[(7R,9aR)-7-phenyl-1,3,4,6,7,8,9,9a-octahydropyrido[1,2-a]pyrazine-2-carbonyl]-2-chlorophenoxy]methyl]pyrazole-1-carboxylate | 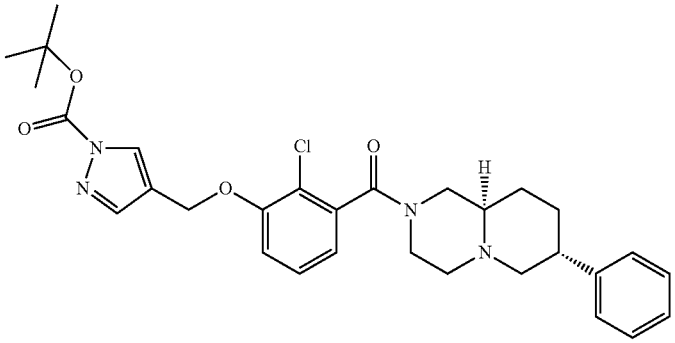 [SMILES: CC(C)(C)OC(=O)n1cc(COc2cccc(C(=O)N3CCN4C[C@@H](c5ccccc5)CC[C@@H]4C3)c2Cl)cn1] | 0.624 |
| 51 | [(7R,9aR)-7-phenyl-1,3,4,6,7,8,9,9a-octahydropyrido[1,2-a]pyrazin-2-yl]-[2-chloro-3-(1H-pyrazol-4-ylmethoxy)phenyl]methanone; hydrochloride | 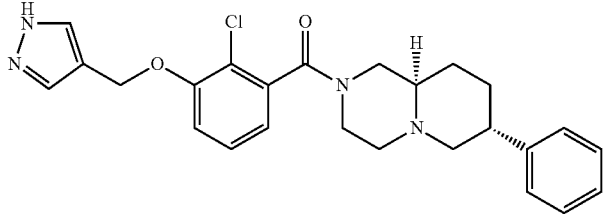 [SMILES: O=C(c1cccc(OCc2cn[nH]c2)c1Cl)N1CCN2C[C@@H](c3ccccc3)CC[C@@H]2C1] | 0.208 |
| 52 | [(7R,9aR)-7-phenyl-1,3,4,6,7,8,9,9a-octahydropyrido[1,2-a]pyrazin-2-yl]-[2-chloro-3-(pyridazin-3-ylmethoxy)phenyl]methanone | 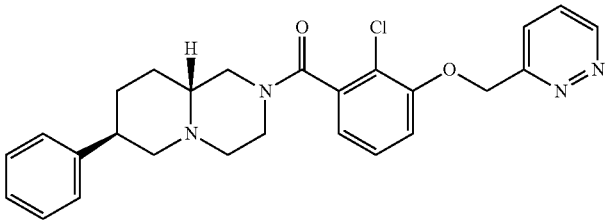 [SMILES: O=C(c1cccc(OCc2cccnn2)c1Cl)N1CCN2C[C@@H](c3ccccc3)CC[C@@H]2C1] | 1.160 |
| 53 | [(7R,9aR)-7-phenyl-1,3,4,6,7,8,9,9a-octahydropyrido[1,2-a]pyrazin-2-yl]-[2-chloro-3-(pyridin-4-ylmethoxy)phenyl]methanone | 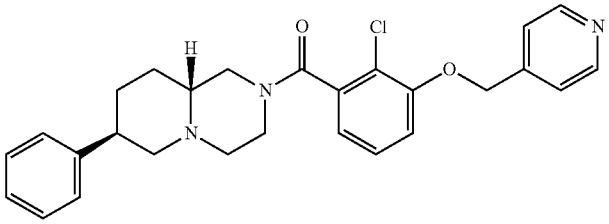 [SMILES: O=C(c1cccc(OCc2ccncc2)c1Cl)N1CCN2C[C@@H](c3ccccc3)CC[C@@H]2C1] | 0.391 |
| 54 | [(7R,9aR)-7-phenyl-1,3,4,6,7,8,9,9a-octahydropyrido[1,2-a]pyrazin-2-yl]-[2-chloro-3-(pyridin-3-ylmethoxy)phenyl]methanone | 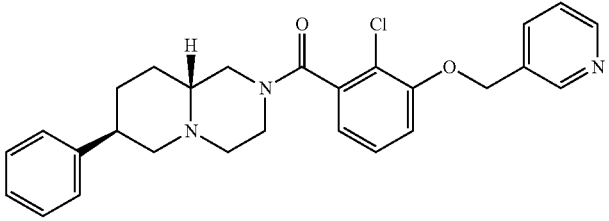 [SMILES: O=C(c1cccc(OCc2cccnc2)c1Cl)N1CCN2C[C@@H](c3ccccc3)CC[C@@H]2C1] | 1.150 |
| 55 | [(7R,9aR)-7-(3-chloro-4-fluorophenyl)-1,3,4,6,7,8,9,9a-octahydropyrido[1,2-a]pyrazin-2-yl]-(2-chloro-3-methoxyphenyl)methanone | 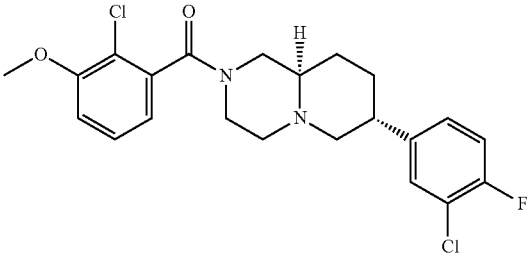 [SMILES: COc1cccc(C(=O)N2CCN3C[C@@H](c4ccc(F)c(Cl)c4)CC[C@@H]3C2)c1Cl] | 0.0002* |

TABLE 1-continued

| Example | Name | Structure | IC$_{50}$ MAGL [µM] |
|---|---|---|---|
| 56 | [(7S,9aS)-7-(3-chloro-4-fluorophenyl)-1,3,4,6,7,8,9,9a-octahydropyrido[1,2-a]pyrazin-2-yl]-(2-chloro-3-methoxyphenyl)methanone | 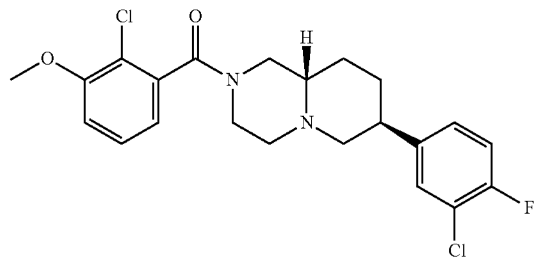 [SMILES: COc1cccc(C(=O)N2CCN3C[C@H](c4ccc(F)c(Cl)c4)CC[C@H]3C2)c1Cl] | 0.2026* |
| 57 | [(7R,9aR)-7-(4-chlorophenyl)-1,3,4,6,7,8,9,9a-octahydropyrido[1,2-a]pyrazin-2-yl]-[2-chloro-3-[(E)-2-cyclopropylethenyl]phenyl]methanone | 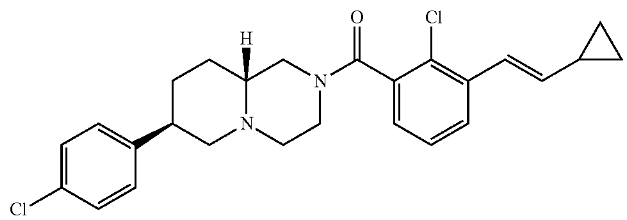 [SMILES: O=C(c1cccc(/C=C/C2CC2)c1Cl)N1CCN2C[C@@H](c3ccc(Cl)cc3)CC[C@@H]2C1] | 0.0613* |
| 58 | [(7R,9aR)-7-(4-chlorophenyl)-1,3,4,6,7,8,9,9a-octahydropyrido[1,2-a]pyrazin-2-yl]-(4-chloro-5-methoxypyridin-3-yl)methanone | 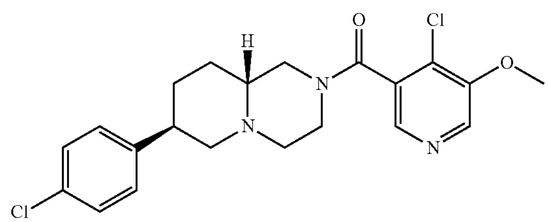 [SMILES: COc1cncc(C(=O)N2CCN3C[C@@H](c4ccc(Cl)cc4)CC[C@@H]3C2)c1Cl] | 0.1146* |
| 59 | (4-chloro-1H-pyrazolo[3,4-b]pyridin-5-yl)-[rac-(7R,9aR)-7-(3-chloro-4-fluorophenyl)-1,3,4,6,7,8,9,9a-octahydropyrido[1,2-a]pyrazin-2-yl]methanone | 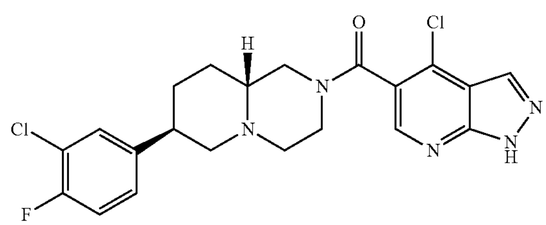 [SMILES: O=C(c1cnc2[nH]ncc2c1Cl)N1CCN2C[C@@H](c3ccc(F)c(Cl)c3)CC[C@@H]2C1] | 0.0895* |
| 59-A | [(7R,9aR)-7-(3-chloro-4-fluorophenyl)-1,3,4,6,7,8,9,9a-octahydropyrido[1,2-a]pyrazin-2-yl]-(4-chloro-1H-pyrazolo[3,4-b]pyridin-5-yl)methanone | 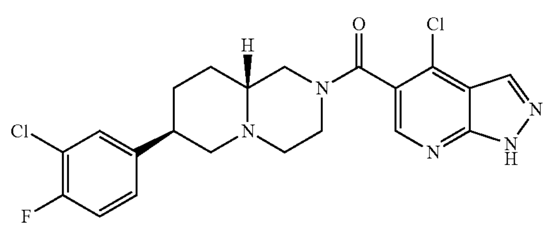 [SMILES: O=C(c1cnc2[nH]ncc2c1Cl)N1CCN2C[C@@H](c3ccc(F)c(Cl)c3)CC[C@@H]2C1] | 0.0310* |
| 59-B | [(7S,9aS)-7-(3-chloro-4-fluorophenyl)-1,3,4,6,7,8,9,9a-octahydropyrido[1,2-a]pyrazin-2-yl]-(4-chloro-1H-pyrazolo[3,4-b]pyridin-5-yl)methanone | 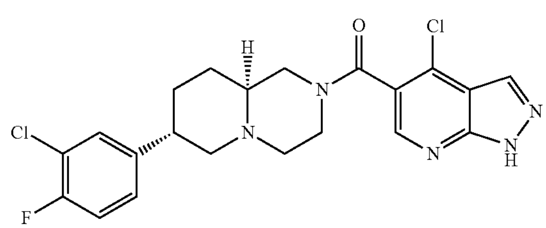 [SMILES: O=C(c1cnc2[nH]ncc2c1Cl)N1CCN2C[C@H](c3ccc(F)c(Cl)c3)CC[C@H]2C1] | 0.1635* |

TABLE 1-continued

| Example | Name | Structure | IC$_{50}$ MAGL [µM] |
|---|---|---|---|
| 60 | (3-methyl-1H-indazol-5-yl)-[rac-(7R,9aR)-7-(3-chloro-4-fluorophenyl)-1,3,4,6,7,8,9,9a-octahydropyrido[1,2-a]pyrazin-2-yl]methanone | 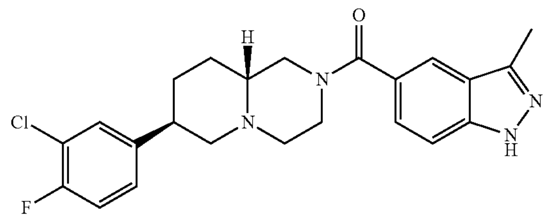 [SMILES: Cc1n[nH]c2ccc(C(=O)N3CCN4C[C@@H](c5ccc(F)c(Cl)c5)CC[C@@H]4C3)cc12] | 0.0901* |
| 60-A | [(7S,9aS)-7-(3-chloro-4-fluorophenyl)-1,3,4,6,7,8,9,9a-octahydropyrido[1,2-a]pyrazin-2-yl]-(3-methyl-1H-indazol-5-yl)methanone | 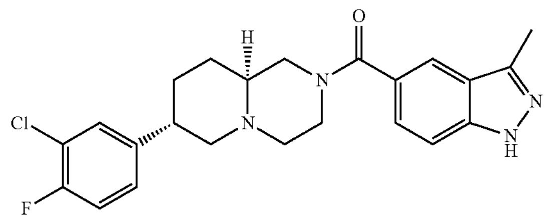 [SMILES: Cc1n[nH]c2ccc(C(=O)N3CCN4C[C@H](c5ccc(F)c(Cl)c5)CC[C@H]4C3)cc12] | 0.2724* |
| 60-B | [(7R,9aR)-7-(3-chloro-4-fluorophenyl)-1,3,4,6,7,8,9,9a-octahydropyrido[1,2-a]pyrazin-2-yl]-(3-methyl-1H-indazol-5-yl)methanone | 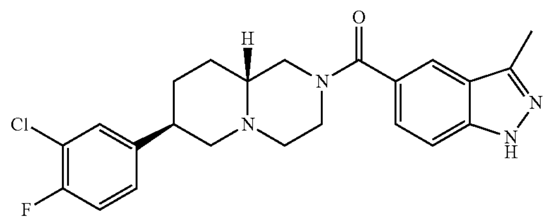 [SMILES: Cc1n[nH]c2ccc(C(=O)N3CCN4C[C@@H](c5ccc(F)c(Cl)c5)CC[C@@H]4C3)cc12] | 0.1113* |
| 61 | (3-methyl-[1,2,4]triazolo[4,3-a]pyridin-6-yl)-[rac-(7R,9aR)-7-(3-chloro-4-fluorophenyl)-1,3,4,6,7,8,9,9a-octahydropyrido[1,2-a]pyrazin-2-yl]methanone | 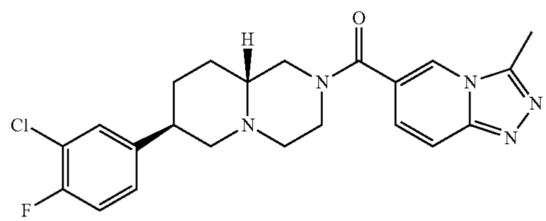 [SMILES: Cc1nnc2ccc(C(=O)N3CCN4C[C@@H](c5ccc(F)c(Cl)c5)CC[C@@H]4C3)cn12] | 4.1667* |
| 62 | (3-chloroimidazo[1,2-a]pyridin-6-yl)-[rac-(7R,9aR)-7-(3-chloro-4-fluorophenyl)-1,3,4,6,7,8,9,9a-octahydropyrido[1,2-a]pyrazin-2-yl]methanone | 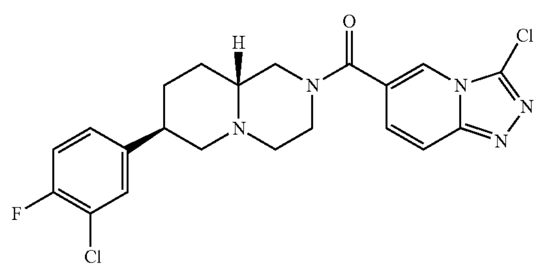 [SMILES: O=C(c1ccc2nnc(Cl)n2c1)N1CCN2C[C@@H](c3ccc(F)c(Cl)c3)CC[C@@H]2C1] | 1.0374* |
| 63 | (4-chlorothieno[2,3-b]pyridin-5-yl)-[rac-(7R,9aR)-7-(3-chloro-4-fluorophenyl)-1,3,4,6,7,8,9,9a-octahydropyrido[1,2-a]pyrazin-2-yl]methanone | 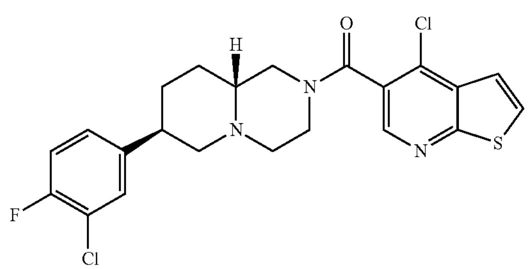 [SMILES: O=C(c1cnc2sccc2c1Cl)N1CCN2C[C@@H](c3ccc(F)c(Cl)c3)CC[C@@H]2C1] | 0.0032* |

TABLE 1-continued

| Example | Name | Structure | IC$_{50}$ MAGL [μM] |
|---|---|---|---|
| 63-A | [(7R,9aR)-7-(3-chloro-4-fluorophenyl)-1,3,4,6,7,8,9,9a-octahydropyrido[1,2-a]pyrazin-2-yl]-(4-chlorothieno[2,3-b]pyridin-5-yl)methanone | 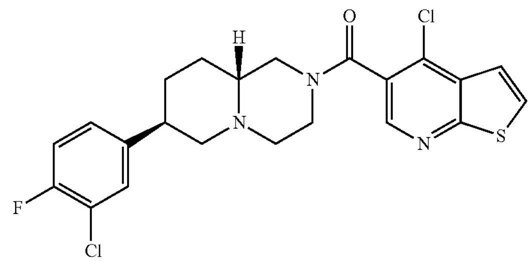 [SMILES: O=C(c1cnc2sccc2c1Cl)N1CCN2C[C@@H](c3ccc(F)c(Cl)c3)CC[C@@H]2C1] | 0.0024* |
| 63-B | [(7S,9aS)-7-(3-chloro-4-fluorophenyl)-1,3,4,6,7,8,9,9a-octahydropyrido[1,2-a]pyrazin-2-yl]-(4-chlorothieno[2,3-b]pyridin-5-yl)methanone | 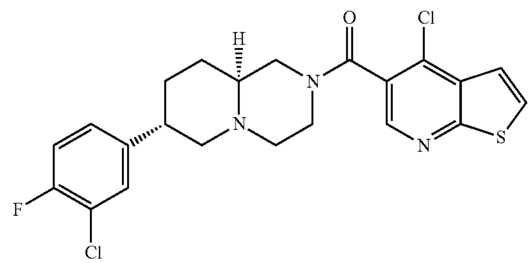 [SMILES: O=C(c1cnc2sccc2c1Cl)N1CCN2C[C@H](c3ccc(F)c(Cl)c3)CC[C@H]2C1] | 0.0175* |
| 64 | (4-chloro-3-methyl-[1,2]oxazolo[5,4-b]pyridin-5-yl)-[rac-(7R,9aR)-7-(3-chloro-4-fluorophenyl)-1,3,4,6,7,8,9,9a-octahydropyrido[1,2-a]pyrazin-2-yl]methanone | 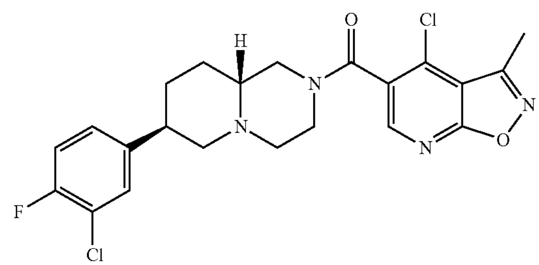 [SMILES: Cc1noc2ncc(C(=O)N3CCN4C[C@@H](c5ccc(F)c(Cl)c5)CC[C@@H]4C3)c(Cl)c12] | 0.0580* |
| 64-A | [(7R,9aR)-7-(3-chloro-4-fluorophenyl)-1,3,4,6,7,8,9,9a-octahydropyrido[1,2-a]pyrazin-2-yl]-(4-chloro-3-methyl-[1,2]oxazolo[5,4-b]pyridin-5-yl)methanone | 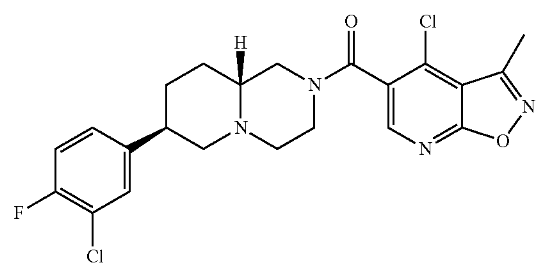 [SMILES: Cc1noc2ncc(C(=O)N3CCN4C[C@@H](c5ccc(F)c(Cl)c5)CC[C@@H]4C3)c(Cl)c12] | 0.0393* |
| 64-B | [(7S,9aS)-7-(3-chloro-4-fluorophenyl)-1,3,4,6,7,8,9,9a-octahydropyrido[1,2-a]pyrazin-2-yl]-(4-chloro-3-methyl-[1,2]oxazolo[5,4-b]pyridin-5-yl)methanone | 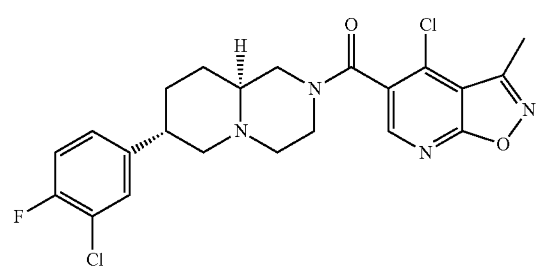 [SMILES: Cc1noc2ncc(C(=O)N3CCN4C[C@H](c5ccc(F)c(Cl)c5)CC[C@H]4C3)c(Cl)c12] | 6.2391* |
| 65 | (4-chloro-1H-indazol-5-yl)-[rac-(7R,9aR)-7-(3-chloro-4-fluorophenyl)-1,3,4,6,7,8,9,9a-octahydropyrido[1,2-a]pyrazin-2-yl]methanone | 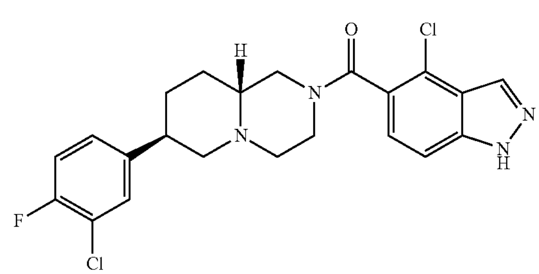 [SMILES: O=C(c1ccc2[nH]ncc2c1Cl)N1CCN2C[C@@H](c3ccc(F)c(Cl)c3)CC[C@@H]2C1] | 0.0114* |

TABLE 1-continued

| Example | Name | Structure | IC$_{50}$ MAGL [μM] |
|---|---|---|---|
| 66 | [2-chloro-3-(difluoromethoxy)phenyl]-[rac-(7R,9aR)-7-(3-chloro-4-fluorophenyl)-1,3,4,6,7,8,9,9a-octahydropyrido[1,2-a]pyrazin-2-yl]methanone | 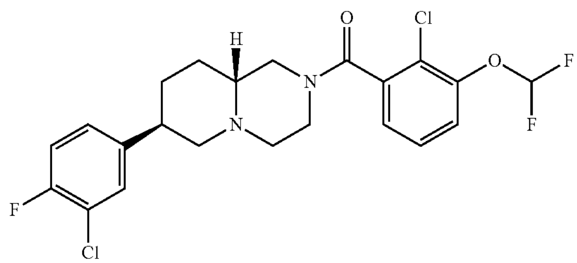 [SMILES: O=C(c1cccc(OC(F)F)c1Cl)N1CCN2C[C@@H](c3ccc(F)c(Cl)c3)CC[C@@H]2C1] | 0.0260* |
| 66-A | [(7S,9aS)-7-(3-chloro-4-fluorophenyl)-1,3,4,6,7,8,9,9a-octahydropyrido[1,2-a]pyrazin-2-yl]-[2-chloro-3-(difluoromethoxy)phenyl]methanone | 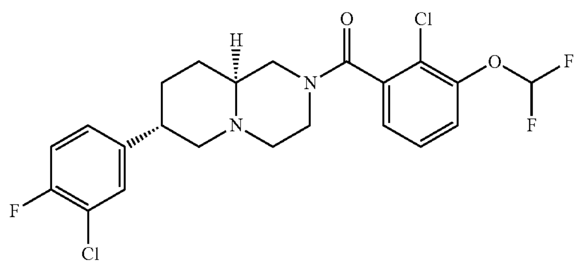 [SMILES: O=C(c1cccc(OC(F)F)c1Cl)N1CCN2C[C@H](c3ccc(F)c(Cl)c3)CC[C@H]2C1] | 0.0976* |
| 66-B | [(7R,9aR)-7-(3-chloro-4-fluorophenyl)-1,3,4,6,7,8,9,9a-octahydropyrido[1,2-a]pyrazin-2-yl]-[2-chloro-3-(difluoromethoxy)phenyl]methanone | 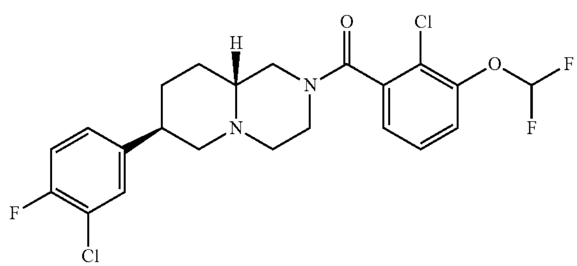 [SMILES: O=C(c1cccc(OC(F)F)c1Cl)N1CCN2C[C@@H](c3ccc(F)c(Cl)c3)CC[C@@H]2C1] | 0.0130* |
| 67 | (4-chloro-3-methyl-1H-indazol-5-yl)-[rac-(7R,9aR)-7-(3-chloro-4-fluorophenyl)-1,3,4,6,7,8,9,9a-octahydropyrido[1,2-a]pyrazin-2-yl]methanone | 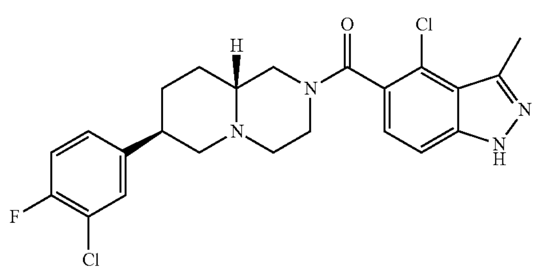 [SMILES: Cc1n[nH]c2ccc(C(=O)N3CCN4C[C@@H](c5ccc(F)c(Cl)c5)CC[C@@H]4C3)c(Cl)c12] | 0.0061* |
| 68 | (4-chloro-[1,2]thiazolo[5,4-b]pyridin-5-yl)-[rac-(7R,9aR)-7-(3-chloro-4-fluorophenyl)-1,3,4,6,7,8,9,9a-octahydropyrido[1,2-a]pyrazin-2-yl]methanone | 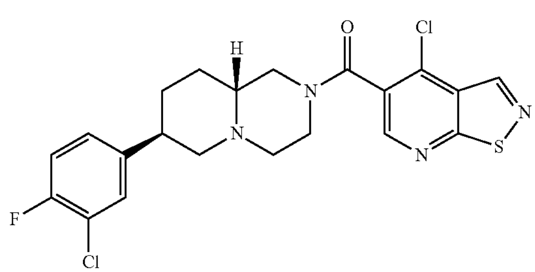 [SMILES: O=C(c1cnc2sncc2c1Cl)N1CCN2C[C@@H](c3ccc(F)c(Cl)c3)CC[C@@H]2C1] | 0.1186* |

TABLE 1-continued

| Example | Name | Structure | IC$_{50}$ MAGL [μM] |
|---|---|---|---|
| 69 | (6-amino-4-chloropyridin-3-yl)-[rac-(7R,9aR)-7-(3-chloro-4-fluorophenyl)-1,3,4,6,7,8,9,9a-octahydropyrido[1,2-a]pyrazin-2-yl]methanone | 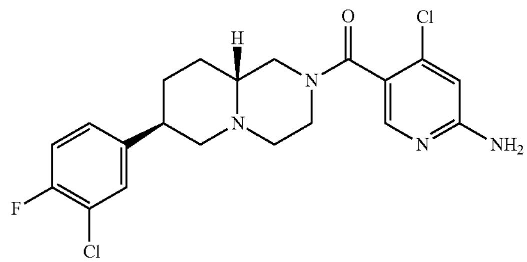 [SMILES: Nc1cc(Cl)c(C(=O)N2CCN3C[C@@H](c4ccc(F)c(Cl)c4)CC[C@@H]3C2)cn1] | 0.0731* |
| 70 | (4-chloro-3-methyl-1H-indazol-5-yl)-[rac-(7R,9aR)-7-(4-chlorophenyl)-7-hydroxy-3,4,6,8,9,9a-hexahydro-1H-pyrido[1,2-a]pyrazin-2-yl]methanone | 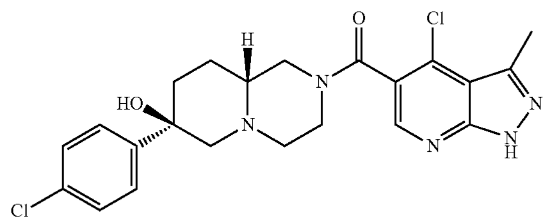 [SMILES: Cc1n[nH]c2ncc(C(=O)N3CCN4C[C@](O)(c5ccc(Cl)cc5)CC[C@@H]4C3)c(Cl)c12] | 0.6385* |
| 71 | (4-chloro-3-methyl-1H-indazol-5-yl)-[rac-(7R,9aS)-7-(4-chlorophenyl)-7-hydroxy-3,4,6,8,9,9a-hexahydro-1H-pyrido[1,2-a]pyrazin-2-yl]methanone | 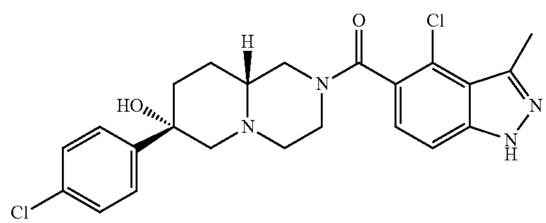 [SMILES: Cc1n[nH]c2ccc(C(=O)N3CCN4C[C@@](O)(c5ccc(Cl)cc5)CC[C@@H]4C3)c(Cl)c12] | 0.0382* |
| 71-A | [(7S,9aR)-7-(4-chlorophenyl)-7-hydroxy-3,4,6,8,9,9a-hexahydro-1H-pyrido[1,2-a]pyrazin-2-yl]-(4-chloro-3-methyl-1H-indazol-5-yl)methanone | 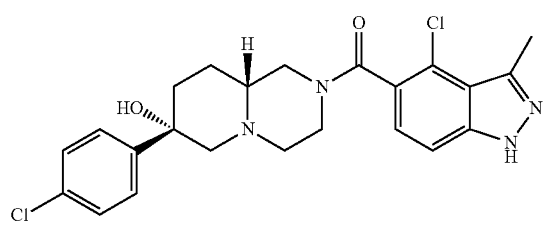 [SMILES: Cc1n[nH]c2ccc(C(=O)N3CCN4C[C@@](O)(c5ccc(Cl)cc5)CC[C@@H]4C3)c(Cl)c12] | 0.0301* |
| 71-B | [(7R,9aS)-7-(4-chlorophenyl)-7-hydroxy-3,4,6,8,9,9a-hexahydro-1H-pyrido[1,2-a]pyrazin-2-yl]-(4-chloro-3-methyl-1H-indazol-5-yl)methanone | 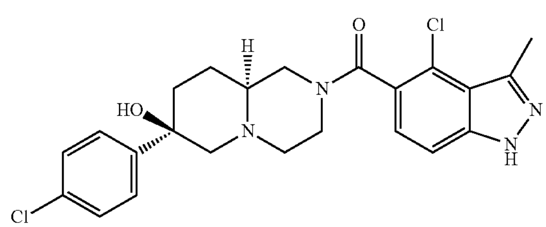 [SMILES: Cc1n[nH]c2ccc(C(=O)N3CCN4C[C@](O)(c5ccc(Cl)cc5)CC[C@H]4C3)c(Cl)c12] | 0.0995* |
| 72 | (2-chloro-3-methoxyphenyl)-[rac-(7R,9aR)-7-(4-chlorophenyl)-7-hydroxy-3,4,6,8,9,9a-hexahydro-1H-pyrido[1,2-a]pyrazin-2-yl]methanone | 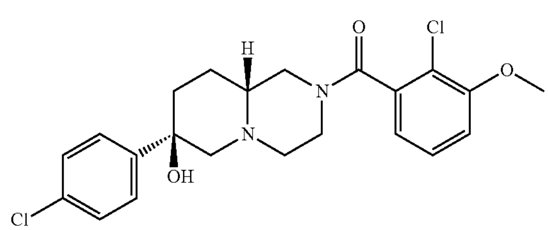 [SMILES: COc1cccc(C(=O)N2CCN3C[C@](O)(c4ccc(Cl)cc4)CC[C@@H]3C2)c1Cl] | 2.1173* |

TABLE 1-continued

| Example | Name | Structure | IC$_{50}$ MAGL [μM] |
|---|---|---|---|
| 72-A | [(7S,9aS)-7-(4-chlorophenyl)-7-hydroxy-3,4,6,8,9,9a-hexahydro-1H-pyrido[1,2-a]pyrazin-2-yl]-(2-chloro-3-methoxyphenyl)methanone | 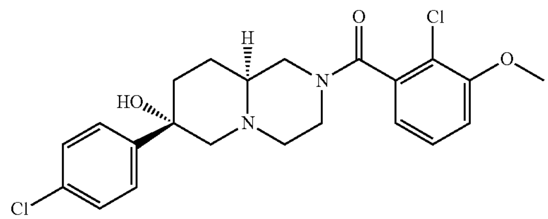 | 11.8555* |
| 72-B | [(7R,9aR)-7-(4-chlorophenyl)-7-hydroxy-3,4,6,8,9,9a-hexahydro-1H-pyrido[1,2-a]pyrazin-2-yl]-(2-chloro-3-methoxyphenyl)methanone | 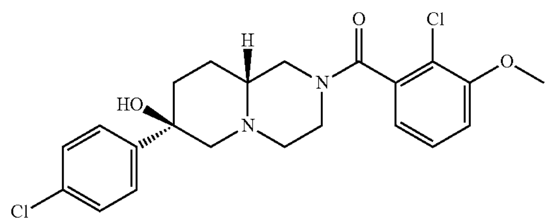 [SMILES: COc1cccc(C(=O)N2CCN3C[C@](O)(c4ccc(Cl)cc4)CC[C@@H]3C2)c1Cl] | 10.6205* |
| 73 | (2-chloro-3-methoxyphenyl)-[rac-(7R,9aS)-7-(4-chlorophenyl)-7-hydroxy-3,4,6,8,9,9a-hexahydro-1H-pyrido[1,2-a]pyrazin-2-yl]methanone | 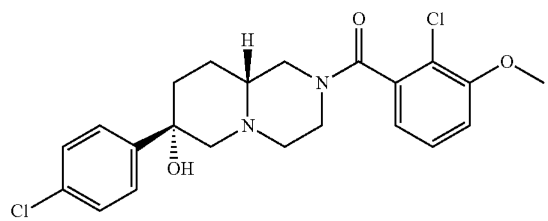 [SMILES: COc1cccc(C(=O)N2CCN3C[C@@](O)(c4ccc(Cl)cc4)CC[C@@H]3C2)c1Cl] | 0.0072* |
| 73-A | [(7S,9aR)-7-(4-chlorophenyl)-7-hydroxy-3,4,6,8,9,9a-hexahydro-1H-pyrido[1,2-a]pyrazin-2-yl]-(2-chloro-3-methoxyphenyl)methanone | 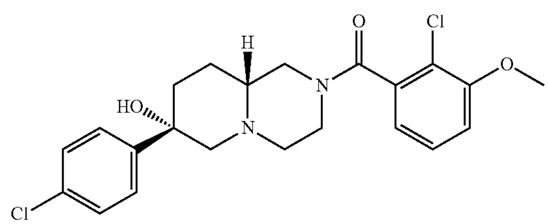 [SMILES: COc1cccc(C(=O)N2CCN3C[C@@](O)(c4ccc(Cl)cc4)CC[C@@H]3C2)c1Cl] | 0.0185* |
| 73-B | [(7R,9aS)-7-(4-chlorophenyl)-7-hydroxy-3,4,6,8,9,9a-hexahydro-1H-pyrido[1,2-a]pyrazin-2-yl]-(2-chloro-3-methoxyphenyl)methanone | 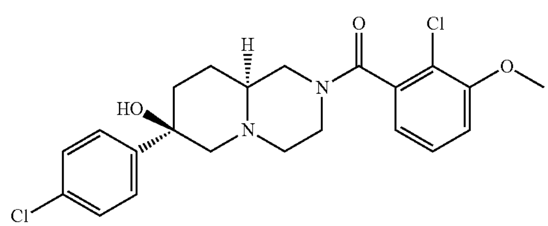 [SMILES: COc1cccc(C(=O)N2CCN3C[C@](O)(c4ccc(Cl)cc4)CC[C@H]3C2)c1Cl] | 0.1555* |
| 74 | [2-chloro-3-(difluoromethoxy)phenyl]-[rac-(7R,9aR)-7-(4-chlorophenyl)-7-hydroxy-3,4,6,8,9,9a-hexahydro-1H-pyrido[1,2-a]pyrazin-2-yl]methanone | 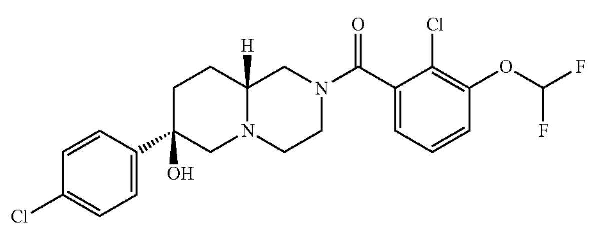 [SMILES: O=C(c1cccc(OC(F)F)c1Cl)N1CCN2C[C@](O)(c3ccc(Cl)cc3)CC[C@@H]2C1] | 9.0203* |
| 75 | [2-chloro-3-(difluoromethoxy)phenyl]-[rac-(7R,9aS)-7-(4-chlorophenyl)-7-hydroxy-3,4,6,8,9,9a-hexahydro-1H-pyrido[1,2-a]pyrazin-2-yl]methanone | 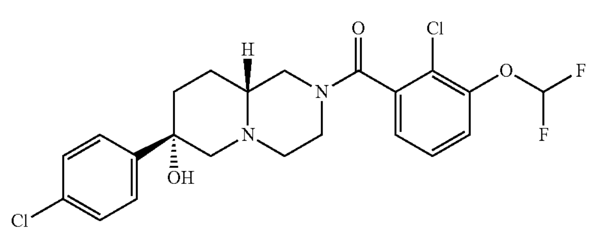 [SMILES: O=C(c1cccc(OC(F)F)c1Cl)N1CCN2C[C@@](O)(c3ccc(Cl)cc3)CC[C@@H]2C1] | 0.0676* |

TABLE 1-continued

| Example | Name | Structure | IC$_{50}$ MAGL [μM] |
|---|---|---|---|
| 76 | [2-chloro-3-(2-oxa-6-azaspiro[3.3]heptan-6-yl)phenyl]-[rac-(7R,9aR)-7-(4-chlorophenyl)-7-hydroxy-3,4,6,8,9,9a-hexahydro-1H-pyrido[1,2-a]pyrazin-2-yl]methanone | 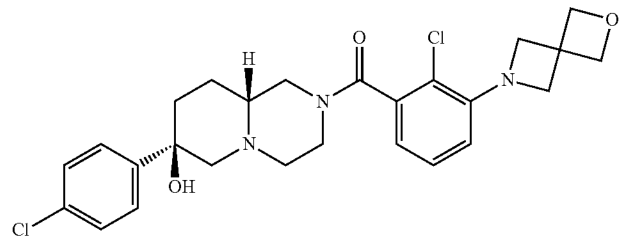 [SMILES: O=C(c1cccc(N2CC3(COC3)C2)c1Cl)N1CCN2C[C@](O)(c3ccc(Cl)cc3)CC[C@@H]2C1] | 1.6830* |
| 77 | [2-chloro-3-(2-oxa-6-azaspiro[3.3]heptan-6-yl)phenyl]-[rac-(7R,9aS)-7-(4-chlorophenyl)-7-hydroxy-3,4,6,8,9,9a-hexahydro-1H-pyrido[1,2-a]pyrazin-2-yl]methanone | 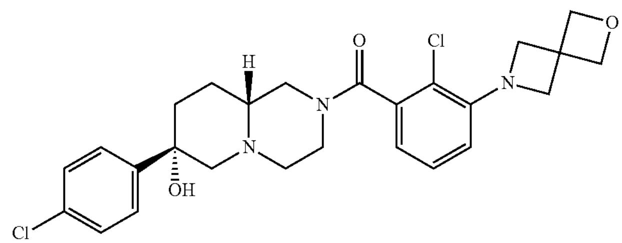 [SMILES: O=C(c1cccc(N2CC3(COC3)C2)c1Cl)N1CCN2C[C@@](O)(c3ccc(Cl)cc3)CC[C@@H]2C1] | 0.0397* |
| 78 | (2-chloro-3-methoxyphenyl)-[rac-(7R,9aR)-7-(4-chlorophenyl)-7-fluoro-3,4,6,8,9,9a-hexahydro-1H-pyrido[1,2-a]pyrazin-2-yl]methanone | 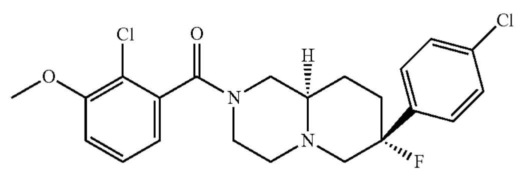 [SMILES: COc1cccc(C(=O)N2CCN3C[C@](F)(c4ccc(Cl)cc4)CC[C@@H]3C2)c1Cl] | 0.5220* |
| 79 | (2-chloro-3-methoxyphenyl)-[rac-(7R,9aS)-7-(4-chlorophenyl)-7-fluoro-3,4,6,8,9,9a-hexahydro-1H-pyrido[1,2-a]pyrazin-2-yl]methanone | 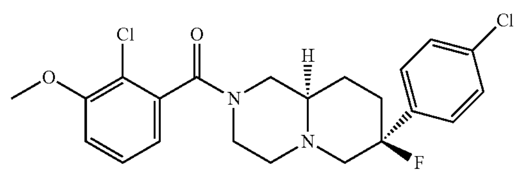 [SMILES: COc1cccc(C(=O)N2CCN3C[C@@](F)(c4ccc(Cl)cc4)CC[C@@H]3C2)c1Cl] | 0.0057* |
| 80 | (2-chloro-3-methoxyphenyl)-[rac-(7R,9aR)-7-(4-chlorophenyl)-7-methoxy-3,4,6,8,9,9a-hexahydro-1H-pyrido[1,2-a]pyrazin-2-yl]methanone | 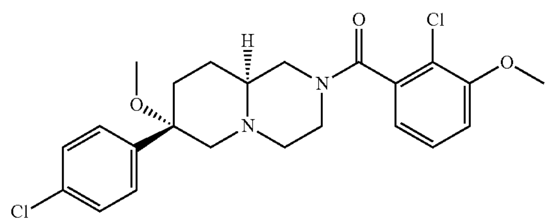 [SMILES: COc1cccc(C(=O)N2CCN3C[C@@](OC)(c4ccc(Cl)cc4)CC[C@H]3C2)c1Cl] | 10.9580* |
| 81 | (2-chloro-3-methoxyphenyl)-[rac-(7R,9aS)-7-(4-chlorophenyl)-7-methoxy-3,4,6,8,9,9a-hexahydro-1H-pyrido[1,2-a]pyrazin-2-yl]methanone | 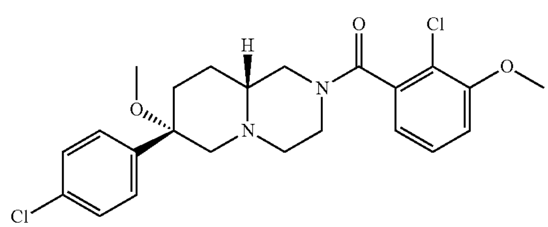 [SMILES: COc1cccc(C(=O)N2CCN3C[C@@](OC)(c4ccc(Cl)cc4)CC[C@@H]3C2)c1Cl] | 0.0425* |
| 82 | (2-chloro-3-methoxyphenyl)-[rac-(7R,9aS)-7-methyl-1,3,4,6,7,8,9,9a-octahydropyrido[1,2-a]pyrazin-2-yl]methanone | 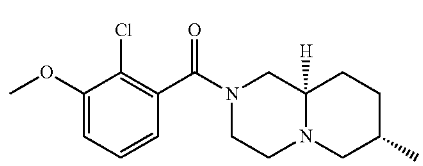 | 0.3505* |

TABLE 1-continued

| Example | Name | Structure | IC$_{50}$ MAGL [μM] |
|---|---|---|---|
| 83 | (2-chloro-3-methoxyphenyl)-[rac-(7R,9aR)-7-methyl-1,3,4,6,7,8,9,9a-octahydropyrido[1,2-a]pyrazin-2-yl]methanone | 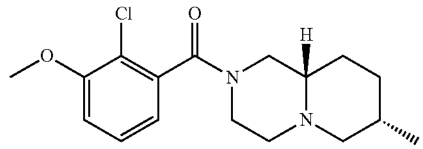 | 0.8667* |
| 84 | (2-chloro-3-methoxyphenyl)-[rac-(7R,9aS)-7-(2-methylpropoxy)-1,3,4,6,7,8,9,9a-octahydropyrido[1,2-a]pyrazin-2-yl]methanone | 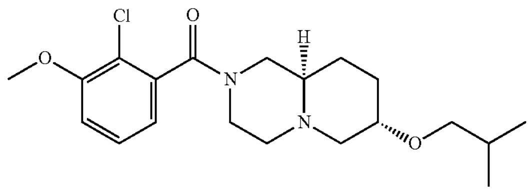 [SMILES: COc1cccc(C(=O)N2CCN3C[C@@H](OCC(C)C)CC[C@@H]3C2)c1Cl] | 0.8013* |
| 85 | (1,3-dimethylthieno[2,3-c]pyrazol-5-yl)-[rac-(7R,9aR)-7-(3-chloro-4-fluorophenyl)-1,3,4,6,7,8,9,9a-octahydropyrido[1,2-a]pyrazin-2-yl]methanone | 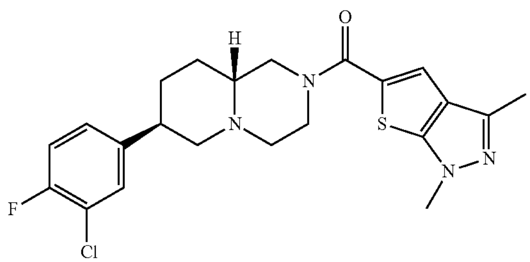 [SMILES: Cc1nn(C)c2sc(C(=O)N3CCN4C[C@@H](c5ccc(F)c(Cl)c5)CC[C@@H]4C3)cc12] | 1.3121* |

*measured in 2-AG assay; if nothing else is indicated (i.e. *), the activity was measured in the 4-NPA assay.

In one aspect, the present invention provides compounds of formula (Ie) and their pharmaceutically acceptable salts as described herein, wherein said compounds of formula (Ie) and their pharmaceutically acceptable salts have IC$_{50}$'s for MAGL inhibition below 25 μM, preferably below 10 μM, more preferably below 5 μM as measured in the MAGL assay described herein.

In one embodiment, compounds of formula (Ie) and their pharmaceutically acceptable salts as described herein have IC$_{50}$ (MAGL inhibition) values between 0.000001 μM and 25 μM, particular compounds have IC$_{50}$ values between 0.000005 μM and 10 μM, further particular compounds have IC$_{50}$ values between 0.00005 μM and 5 μM, as measured in the MAGL assay described herein.

In one embodiment, the present invention provides compounds of formula (Ie) and their pharmaceutically acceptable salts as described herein, wherein said compounds of formula (I) and their pharmaceutically acceptable salts have an IC$_{50}$ for MAGL below 25 μM, preferably below 10 μM, more preferably below 5 μM.

In one embodiment, the present invention provides compounds of formula (Ie) and their pharmaceutically acceptable salts as described herein, wherein said compounds of formula (Ie) and their pharmaceutically acceptable salts have an IC$_{50}$ for MAGL below 25 μM, preferably below 10 μM, more preferably below 5 μM as measured in an assay comprising the steps of:
  a) providing a solution of a compound formula (e), or a pharmaceutically acceptable salt thereof, in DMSO;
  b) providing a solution of MAGL (recombinant wild-type) in assay buffer (50 mM tris(hydroxymethyl) aminomethane; 1 mM ethylenediaminetetraacetic acid);
  c) adding 1 μL of compound solution from step a) to 19 μL of MAGL solution from step b);
  d) shaking the mixture for 1 min at 2000 rpm;
  e) incubating for 15 min at RT;
  f) adding 20 μL of a solution of 4-nitrophenlyacetate in assay buffer (50 mM tris(hydroxymethyl)aminomethane; 1 mM ethylenediaminetetraacetic acid, 6% EtOH);
  g) shaking the mixture for 1 min at 2000 rpm;
  h) incubating for 5 min at RT;
  i) measuring the absorbance of the mixture at 405 nm a first time;
  j) incubating a further 80 min at RT;
  k) measuring the absorbance of the mixture at 405 nm a second time;
  l) substracting the absorbance measured under i) from the absorbance measured under k) and calculating the slope of absorbance;
wherein:
  i) the concentration of the compound of formula (Ie), or the pharmaceutically acceptable salt thereof in the assay after step f) is in the range of 25 μM to 1.7 nM;
  ii) the concentration of MAGL in the assay after step f) is 1 nM;
  iii) the concentration of 4-nitrophenylacetate in the assay after step f) is 300 μM; and
  iv) steps a) to l) are repeated for at least 3 times, each time with a different concentration of the compound of formula (Ie), or the pharmaceutically acceptable salt thereof.

Using the Compounds of the Invention

In one aspect, the present invention provides compounds of formula (Ie), preferably a compound of formula (I), as described herein, or a pharmaceutically acceptable salt thereof, for use as therapeutically active substance.

In a further aspect, the present invention provides the use of compounds of formula (Ie), preferably a compound of formula (I), as described herein, or a pharmaceutically acceptable salt thereof, for the treatment or prophylaxis of neuroinflammation, neurodegenerative diseases, pain, cancer and/or mental disorders in a mammal.

In one embodiment, the present invention provides the use of compounds of formula (Ie), preferably a compound of formula (I), as described herein, or a pharmaceutically acceptable salt thereof, for the treatment or prophylaxis of neuroinflammation and/or neurodegenerative diseases in a mammal.

In one embodiment, the present invention provides the use of compounds of formula (Ie), preferably a compound of formula (I), as described herein, or a pharmaceutically acceptable salt thereof, for the treatment or prophylaxis of neurodegenerative diseases in a mammal.

In one embodiment, the present invention provides the use of compounds of formula (Ie), preferably a compound of formula (I), as described herein, or a pharmaceutically acceptable salt thereof, for the treatment or prophylaxis of cancer in a mammal.

In one aspect, the present invention provides the use of compounds of formula (e), preferably of a compound of formula (I), as described herein, or a pharmaceutically acceptable salt thereof, for the treatment or prophylaxis of multiple sclerosis, Alzheimer's disease, Parkinson's disease, amyotrophic lateral sclerosis, traumatic brain injury, neurotoxicity, stroke, epilepsy, anxiety, migraine, depression, cancer and/or pain in a mammal.

In a preferred embodiment, the present invention provides the use of compounds of formula (Ie), preferably of a compound of formula (I), as described herein, or a pharmaceutically acceptable salt thereof, for the treatment or prophylaxis of multiple sclerosis, Alzheimer's disease and/or Parkinson's disease in a mammal.

In a particularly preferred embodiment, the present invention provides the use of compounds of formula (Ie), preferably of a compound of formula (I), as described herein, or a pharmaceutically acceptable salt thereof, for the treatment or prophylaxis of multiple sclerosis in a mammal.

In one aspect, the present invention provides compounds of formula (Ie), preferably a compound of formula (I), as described herein, or a pharmaceutically acceptable salt thereof, for use in the treatment or prophylaxis of neuroinflammation, neurodegenerative diseases, pain, cancer and/or mental disorders in a mammal.

In one embodiment, the present invention provides compounds of formula (Ie), preferably a compound of formula (I), as described herein, or a pharmaceutically acceptable salt thereof, for use in the treatment or prophylaxis of neuroinflammation and/or neurodegenerative diseases in a mammal.

In one embodiment, the present invention provides compounds of formula (Ie), preferably a compound of formula (I), as described herein, or a pharmaceutically acceptable salt thereof, for use in the treatment or prophylaxis of cancer in a mammal.

In one embodiment, the present invention provides compounds of formula (Ie), preferably a compound of formula (I), as described herein, or a pharmaceutically acceptable salt thereof, for use in the treatment or prophylaxis of neurodegenerative diseases in a mammal.

In one aspect, the present invention provides compounds of formula (Ie), preferably a compound of formula (I), as described herein, or a pharmaceutically acceptable salt thereof, for use in the treatment or prophylaxis of multiple sclerosis, Alzheimer's disease, Parkinson's disease, amyotrophic lateral sclerosis, traumatic brain injury, neurotoxicity, stroke, epilepsy, anxiety, migraine, depression, cancer and/or pain in a mammal.

In a preferred embodiment, the present invention provides compounds of formula (Ie), preferably a compound of formula (I), as described herein, or a pharmaceutically acceptable salt thereof, for use in the treatment or prophylaxis of multiple sclerosis, Alzheimer's disease and/or Parkinson's disease in a mammal.

In a particularly preferred embodiment, the present invention provides compounds of formula (Ie), preferably a compound of formula (I), as described herein, or a pharmaceutically acceptable salt thereof, for use in the treatment or prophylaxis of multiple sclerosis in a mammal.

In one aspect, the present invention provides the use of compounds of formula (Ie), preferably a compound of formula (I), as described herein, or a pharmaceutically acceptable salt thereof, for the preparation of a medicament for the treatment or prophylaxis of neuroinflammation, neurodegenerative diseases, pain, cancer and/or mental disorders in a mammal.

In one embodiment, the present invention provides the use of compounds of formula (Ie), preferably a compound of formula (I), as described herein, or a pharmaceutically acceptable salt thereof, for the preparation of a medicament for the treatment or prophylaxis of neuroinflammation and/or neurodegenerative diseases in a mammal.

In one embodiment, the present invention provides the use of compounds of formula (Ie), preferably a compound of formula (I), as described herein, or a pharmaceutically acceptable salt thereof, for the preparation of a medicament for the treatment or prophylaxis of neurodegenerative diseases in a mammal.

In one embodiment, the present invention provides the use of compounds of formula (Ie), preferably a compound of formula (I), as described herein, or a pharmaceutically acceptable salt thereof, for the preparation of a medicament for the treatment or prophylaxis of cancer in a mammal.

In a further aspect, the present invention provides the use of compounds of formula (Ie), preferably a compound of formula (I), as described herein, or a pharmaceutically acceptable salt thereof, for the preparation of a medicament for the treatment or prophylaxis of multiple sclerosis, Alzheimer's disease, Parkinson's disease, amyotrophic lateral sclerosis, traumatic brain injury, neurotoxicity, stroke, epilepsy, anxiety, migraine, depression, cancer and/or pain in a mammal.

In a preferred embodiment, the present invention provides the use of compounds of formula (Ie), preferably a compound of formula (I), as described herein, or a pharmaceutically acceptable salt thereof, for the preparation of a medicament for the treatment or prophylaxis of multiple sclerosis, Alzheimer's disease and/or Parkinson's disease in a mammal.

In a particularly preferred embodiment, the present invention provides the use of compounds of formula (Ie), preferably a compound of formula (I), as described herein, or a pharmaceutically acceptable salt thereof, for the preparation of a medicament for the treatment or prophylaxis of multiple sclerosis in a mammal.

In one aspect, the present invention provides a method for the treatment of neuroinflammation, neurodegenerative diseases, pain, cancer and/or mental disorders in a mammal, which method comprises administering an effective amount of a compound of formula (Ie), preferably of a compound of formula (I), as described herein, or a pharmaceutically acceptable salt thereof, to the mammal.

In one embodiment, the present invention provides a method for the treatment of neuroinflammation and/or neurodegenerative diseases in a mammal, which method comprises administering an effective amount of a compound of formula (Ie), preferably of a compound of formula (I), as described, or a pharmaceutically acceptable salt thereof, herein to the mammal.

In one embodiment, the present invention provides a method for the treatment of neurodegenerative diseases in a mammal, which method comprises administering an effective amount of a compound of formula (Ie), preferably of a compound of formula (I), as described, or a pharmaceutically acceptable salt thereof, herein to the mammal.

In one aspect, the present invention provides a method for the treatment of multiple sclerosis, Alzheimer's disease, Parkinson's disease, amyotrophic lateral sclerosis, traumatic brain injury, neurotoxicity, stroke, epilepsy, anxiety, migraine, depression and/or pain in a mammal, which method comprises administering an effective amount of a compound of formula (Ie), preferably a compound of formula (I), as described herein, or a pharmaceutically acceptable salt thereof, to the mammal.

In a preferred embodiment, the present invention provides a method for the treatment of multiple sclerosis, Alzheimer's disease and/or Parkinson's disease in a mammal, which method comprises administering an effective amount of a compound of formula (Ie), preferably a compound of formula (I), as described herein, or a pharmaceutically acceptable salt thereof, to the mammal.

In a particularly preferred embodiment, the present invention provides a method for the treatment of multiple sclerosis in a mammal, which method comprises administering an effective amount of a compound of formula (Ie), preferably a compound of formula (I), as described herein, or a pharmaceutically acceptable salt thereof, to the mammal.

In one aspect, the present invention provides a method for the prophylaxis of neuroinflammation, neurodegenerative diseases, pain, cancer and/or mental disorders in a mammal, which method comprises administering an effective amount of a compound of formula (Ie), preferably of a compound of formula (I), as described herein, or a pharmaceutically acceptable salt thereof, to the mammal.

In one embodiment, the present invention provides a method for the prophylaxis of neuroinflammation and/or neurodegenerative diseases in a mammal, which method comprises administering an effective amount of a compound of formula (Ie), preferably a compound of formula (I), as described, or a pharmaceutically acceptable salt thereof, herein to the mammal.

In one embodiment, the present invention provides a method for the prophylaxis of neurodegenerative diseases in a mammal, which method comprises administering an effective amount of a compound of formula (Ie), preferably of a compound of formula (I), as described, or a pharmaceutically acceptable salt thereof, herein to the mammal.

In one aspect, the present invention provides a method for the prophylaxis of multiple sclerosis, Alzheimer's disease, Parkinson's disease, amyotrophic lateral sclerosis, traumatic brain injury, neurotoxicity, stroke, epilepsy, anxiety, migraine, depression and/or pain in a mammal, which method comprises administering an effective amount of a compound of formula (Ie), preferably a compound of formula (I), as described herein, or a pharmaceutically acceptable salt thereof, to the mammal.

In a preferred embodiment, the present invention provides a method for the prophylaxis of multiple sclerosis, Alzheimer's disease and/or Parkinson's disease in a mammal, which method comprises administering an effective amount of a compound of formula (Ie), preferably a compound of formula (I), as described herein, or a pharmaceutically acceptable salt thereof, to the mammal.

In a particularly preferred embodiment, the present invention provides a method for the prophylaxis of multiple sclerosis in a mammal, which method comprises administering an effective amount of a compound of formula (e), preferably a compound of formula (I), as described herein, or a pharmaceutically acceptable salt thereof, to the mammal.

Pharmaceutical Compositions and Administration

In one aspect, the present invention provides a pharmaceutical composition comprising a compound of formula (Ie), preferably a compound of formula (I), described herein, or a pharmaceutically acceptable salt thereof, and a therapeutically inert carrier.

The compounds of formula (Ie) and their pharmaceutically acceptable salts can be used as medicaments (e.g. in the form of pharmaceutical preparations). The pharmaceutical preparations can be administered internally, such as orally (e.g. in the form of tablets, coated tablets, dragées, hard and soft gelatin capsules, solutions, emulsions or suspensions), nasally (e.g. in the form of nasal sprays) or rectally (e.g. in the form of suppositories). However, the administration can also be effected parentally, such as intramuscularly or intravenously (e.g. in the form of injection solutions).

The compounds of formula (Ie) and their pharmaceutically acceptable salts can be processed with pharmaceutically inert, inorganic or organic adjuvants for the production of tablets, coated tablets, dragées and hard gelatin capsules. Lactose, corn starch or derivatives thereof, talc, stearic acid or its salts etc. can be used, for example, as such adjuvants for tablets, dragées and hard gelatin capsules.

Suitable adjuvants for soft gelatin capsules are, for example, vegetable oils, waxes, fats, semi-solid substances and liquid polyols, etc.

Suitable adjuvants for the production of solutions and syrups are, for example, water, polyols, saccharose, invert sugar, glucose, etc.

Suitable adjuvants for injection solutions are, for example, water, alcohols, polyols, glycerol, vegetable oils, etc.

Suitable adjuvants for suppositories are, for example, natural or hardened oils, waxes, fats, semi-solid or liquid polyols, etc.

Moreover, the pharmaceutical preparations can contain preservatives, solubilizers, viscosity-increasing substances, stabilizers, wetting agents, emulsifiers, sweeteners, colorants, flavorants, salts for varying the osmotic pressure, buffers, masking agents or antioxidants. They can also contain still other therapeutically valuable substances.

The dosage can vary in wide limits and will, of course, be fitted to the individual requirements in each particular case. In general, in the case of oral administration a daily dosage of about 0.1 mg to 20 mg per kg body weight, preferably about 0.5 mg to 4 mg per kg body weight (e.g. about 300 mg per person), divided into preferably 1-3 individual doses, which can consist, for example, of the same amounts, should be appropriate. It will, however, be clear that the upper limit given herein can be exceeded when this is shown to be indicated.

EXAMPLES

The invention will be more fully understood by reference to the following examples. The claims should not, however, be construed as limited to the scope of the examples.

In case the preparative examples are obtained as a mixture of enantiomers, the pure enantiomers can be separated by methods described herein or by methods known to the man skilled in the art, such as e.g., chiral chromatography (e.g., chiral SFC) or crystallization.

All reaction examples and intermediates were prepared under an argon atmosphere if not specified otherwise.

Intermediate I-1 tert-Butyl 7-oxo-3,4,6,8,9,9a-hexahydro-1H-pyrido [1,2-a]pyrazine-2-carboxylate

Step [A] 5-[(4-methoxyphenyl)methoxy]pyridine-2-carbonitrile

To a solution of (4-methoxyphenyl)methanol (75.5 g, 546.4 mmol) in DMF (1000 mL) cooled at 0° C. was added 65% NaH dispersion in mineral oil (32.8 g, 819.6 mmol) portionwise and the mixture was stirred at this temperature for 30 min. Then, 3-bromo-6-pyridinecarbonitrile (CAS RN 97483-77-7, 100.0 g, 546.4 mmol) was added in portions and the reaction mixture was stirred at room temperature for 2 hours. The mixture was poured into a sat. NH$_4$Cl aq. solution (3000 mL), filtered and washed with EtOAc (3×200 mL). The combined organic layers were dried over Na$_2$SO$_4$, filtered and concentrated in vacuo to give the crude title compound (112 g, 85.3%) as a pink solid; MS (ESI): m/z=241.1 [M+H]$^+$.

Step [B] [5-[(4-methoxyphenyl)methoxyl]-2-pyridyl]methanamine

To a solution of 5-[(4-methoxyphenyl)methoxy]pyridine-2-carbonitrile (50.0 g, 208.1 mmol) in methanol (2000 mL) was added Raney Nickel (10.0 g, 170.4 mmol) followed by ammonium hydroxide (20.0 mL, 266.7 mmol). The reaction mixture was then heated to 50° C. under 3.5 bar of H$_2$ atmosphere for 12 hours. The mixture was filtered and the resulting filtrate was concentrated in vacuo to give the crude title compound (50 g, 98.3% yield) as a dark red solid; MS (ESI): m/z=245.3 [M+H]$^+$.

Step [C] 2-bromo-N-[[5-[(4-methoxyphenyl) methoxyl]-2-pyridyl]methyl]acetamide

To a solution of [5-[(4-methoxyphenyl)methoxy]-2-pyridyl]methanamine (43.6 g, 178.5 mmol) in DCM (200 mL) cooled at 0° C. was added EDCI (34.1 g, 178.5 mmol) followed by bromoacetic acid (24.8 g, 178.5 mmol) in portions and the reaction mixture was stirred at room temperature for 1 hour. The mixture was poured into a sat. NaHCO$_3$ aq. solution (200 mL). The organic layer was separated, washed with more sat. NaHCO$_3$ aq. solution (3×50 mL), brine (50 mL), dried over Na$_2$SO$_4$ and concentrated in vacuo to give the crude title compound (60.6 g, 93% yield) as a dark red oil; MS (ESI): m/z=367.2 [M+2]$^+$.

Step [D] 7-[(4-methoxyphenyl)methoxyl]-1,2,4,6,9,9a-hexahydropyrido[1,2-a]pyrazin-3-one 2-bromo-N-[[5-[(4-methoxyphenyl)methoxy]-2-pyridyl] methyl]acetamide (11.60 g, 31.76 mmol, 1 eq) was dissolved in CH$_3$CN (150 mL) and stirred at 50° C. for 12 hours.

The reaction mixture was concentrated in vacuo to remove the solvent, the residue was re-dissolved in MeOH (150 mL) and cooled to 0° C. Then, sodium borohydride (12.01 g, 317.5 mmol) was carefully added to the reaction mixture which was stirred at room temperature for 12 hours. The mixture was evaporated to dryness and the residue was purified by silica gel flash chromatography eluting with a 1 to 10% MeOH in DCM gradient to give the crude product. This material was then triturated with EtOAc (50 mL), filtered and further dried under high vacuum to give the title compound (3.1 g, 33.9%) as a yellow solid; MS (ESI): m/z=289.1 [M+H]$^+$.

Step [E] 7-[(4-methoxyphenyl)methoxyl]-2,3,4,6,9, 9a-hexahydro-1H-pyrido[1,2-a]pyrazine To a solution of 7-[(4-methoxyphenyl)methoxy]-1,2,4,8, 9,9a-hexahydropyrido [1,2-a] pyrazin-3-one (3.10 g, 10.7 mmol) in THF (100 mL) cooled at 0° C., was carefully added LiAlH$_4$ (1.02 g, 26.9 mmol) and the reaction mixture was heated to 80° C. for 2 hours. The mixture was cooled to 0° C., quenched with water (4 mL) and a 20% aq. NaHCO$_3$ solution (4 mL). The mixture was filtered, washed with THF (3×20 mL) and the resulting filtrate was concentrated in vacuo to give the crude title compound (2.9 g, 98%) as a yellow solid; MS (ESI): m/z=275.3 [M+H]$^+$.

Step [F] tert-butyl 7-oxo-3,4,6,8,9,9a-hexahydro-H-pyrido[1,2-a]pyrazine-2-carboxylate To a solution of 7-[(4-methoxyphenyl)methoxy]-2,3,4,8, 9,9a-hexahydro-1H-pyrido [1,2-a]pyrazine (2.9 g, 10.6 mmol) in DCM (50 mL) was added TFA (10.0 mL, 10.57 mmol), and the reaction mixture was stirred at room temperature for 1 hour. The mixture was concentrated in vacuo to remove the solvent, the residue was re-dissolved in CH$_3$CN (50 mL) and cooled to 0° C. Then, Na$_2$CO$_3$ (3.3 g, 31.13 mmol) followed by di-tert-butyldicarbonate (6.8 g, 31.1 mmol) were added and the reaction mixture was stirred at room temperature for 12 hours. The mixture was diluted with water (100 mL) and extracted with EtOAc (3×100 mL). The combined organic layers were washed with water (3×30 mL), brine (50 mL), dried over Na$_2$SO$_4$ and concentrated in vacuo. The residue was purified by silica gel flash chromatography eluting with a 10 to 30% of EtOAc in PE to give the title compound (2.62 g, 99.3%) as a light yellow solid.

Intermediate I-2

2-(2-Chloro-3-methoxybenzoyl)-3,4,6,8,9,9a-hexahydro-1H-pyrido[1,2-a]pyrazin-7-one Step [A] (2-Chloro-3-methoxphenyl)-[7-[(4-methoxphenyl)methoxy]-1,3,4,6,9,9a-hexahydropyrido[1,2-a]pyrazin-2-yl]methanone To a solution of 2-chloro-3-methoxybenzoic acid (2.94 g, 15.75 mmol) and 7-[(4-methoxyphenyl)methoxy]-2,3,4,6,9, 9a-hexahydro-1H-pyrido[1,2-a]pyrazine (Intermediate I-1 [E], 3.6 g, 13.12 mmol) in DMF (50 mL) cooled at 0° C. was added TEA (5.6 mL, 39.36 mmol) followed by T$_3$P (9.06 g, 19.68 mmol), then the reaction mixture was heated to 50° C. for 12 hours. The reaction was diluted with water (100 mL) and extracted with EtOAc (2×80 mL). The combined organic layer was washed with water (2×50 mL) and brine (50 mL), dried over Na$_2$SO$_4$, filtered and concentrated in vacuo. The residue was purified by silica flash chromatography, eluting with a 50 to 100% EtOAc-heptane gradient to give the title compound (3.9 g, 67.1%) as a yellow solid; MS (ESI): m/z=443.2 [M+H]$^+$.

Step [B] 2-(2-Chloro-3-methoxybenzoyl)-3,4,6,8,9,9a-hexahydro-1H-pyrido[1,2-a]pyrazin-7-one To a solution of (2-chloro-3-methoxy-phenyl)-[7-[(4-methoxyphenyl)methoxy]-1,3,4,6,9,9a-hexahydropyrido[1,2-a]pyrazin-2-yl]methanone (3.9 g, 8.8 mmol) in DCM (50 mL) cooled to 0° C. was added TFA (3.39 mL, 44 mmol), then the reaction mixture was stirred at room temperature for 1 hour. The mixture was concentrated in vacuo, the residue taken up in EtOAc, poured into a saturated aq. NaHCO$_3$ solution (100 mL) and the aqueous layer was extracted with EtOAc (2×50 mL). Combined organics were washed with brine, dried over Na$_2$SO$_4$, filtered and evaporated. The residue was purified by silica gel flash chromatography, eluting with a 50 to 100% EtOAc-heptane gradient to give the title compound (2.1 g, 73.9%) as a light yellow foam. MS (ESI): m/z=341.2 [M+H$_2$O+H]$^+$.

Intermediate I-3

2-[2-chloro-3-(difluoromethoxy)benzoyl]-3,4,6,8,9,9a-hexahydro-1H-pyrido[1,2-a]pyrazin-7-one Intermediate 1-3 was prepared in analogy to intermediate 1-2, but using in step [A] 2-chloro-3-(difluoromethoxy)benzoic acid (CAS RN 1427432-41-4) to give the title compound as an off-white foam. MS (ESI): m/z=377.2 [M+H$_2$O+H]$^+$.

Intermediate I-4

2-[2-chloro-3-(2-oxa-6-azaspiro[3.3]heptan-6-yl)benzoyl]-3,4,6,8,9,9a-hexahydro-1H-pyrido[1,2-a]pyrazin-7-one Intermediate 1-4 was prepared in analogy to intermediate I-2, but using in step [A] 2-chloro-3-(2-oxa-6-azaspiro[3.3]heptan-6-yl)benzoic acid (Intermediate E-1) to give the title compound as a colorless foam. MS (ESI): m/z=408.3 [M+H$_2$O+H]$^+$.

Intermediate A-1

(7R,9aR)-7-(4-Chlorophenyl)octahydro-1H-pyrido[1,2-a]pyrazine

Step [A] tert-butyl 7-(4-chlorophenyl)-7-hydroxy-3,4,6,8,9,9a-hexahydro-1H-pyrido[1,2-a]pyrazine-2-carboxylate To a solution of tert-butyl 7-oxo-3,4,6,8,9,9a-hexahydro-1H-pyrido[1,2-a] pyrazine-2-carboxylate (Intermediate I-1, 1.0 g, 3.93 mmol) in THF (30 mL) cooled at 0° C. was added 4-chlorophenylmagnesium bromide (1M solution in THF, 7.08 mL, 7.08 mmol) and the reaction mixture was stirred at room temperature for 2 hours. The mixture was poured into a saturated NH$_4$Cl aq. solution (100 mL) and extracted with EtOAc (3×50 mL). The combined organic phase was washed with brine, dried over Na$_2$SO$_4$, filtered and concentrated in vacuo. The residue was purified by silica flash chromatography, eluting with a 5% to 25% EtOAc-PE gradient to give the title compound (0.820 g, 56.8%) as a light yellow oil; MS (ESI): m/z=367.1 [M+H]$^+$.

Step [B] 7-(4-chlorophenyl)-2,3,4,8,9,9a-hexahydro-1H-pyrido[1,2-a]pyrazine

To a solution of tert-butyl 7-(4-chlorophenyl)-7-hydroxy-3,4,6,8,9,9a-hexahydro-1H-pyrido [1,2-a]pyrazine-2-carboxylate (0.820 g, 2.24 mmol) in DCM (25 mL) was added methane sulfonic acid (5.0 mL, 164 mmol) and the reaction mixture was stirred at 20° C. for 48 hours. The mixture was poured into a sat. NaHCO$_3$ aq. solution (100 mL) and extracted with DCM (3×50 mL). The combined organic phase was washed with brine, dried over Na$_2$SO$_4$, filtered and concentrated in vacuo to give the crude title compound (0.560 g,) as a light yellow oil; MS (ESI): m/z=249.1 [M+H]$^+$.

Step [C] rac-(7R,9aR)-7-(4-chlorophenyl)-2,3,4,6,7,8,9,9a-octahydro-1H-pyrido[1,2-a]pyrazine To a solution of 7-(4-chlorophenyl)-2,3,4,8,9,9a-hexahydro-1H-pyrido[1,2-a]pyrazine (0.560 g, ~2.24 mmol) and magnesium oxide (0.272 g, 6.75 mmol) in EtOAc (60 mL) was added Pd/C (0.250 g, 2.25 mmol) and the mixture was stirred at room temperature under H$_2$ atmosphere for 4 hours. The mixture was filtered and the filtrate was concentrated in vacuo. The residue was purified by preparative HPLC (MeCN and 0.1% of TFA in water, 0~30%) and the solution containing product was basified with a sat. NaHCO$_3$ aq. solution to pH-8, followed by extraction with EtOAc. The organic phase dried over Na$_2$SO$_4$, filtered and concentrated in vacuo to give the title compound (0.180 g, 31.8%) as an off-white foam; MS (ESI): m/z=251.1 [M+H]$^+$.

Step [D] (7R,9aR)-7-(4-chlorophenyl)-2,3,4,6,7,8,9,9a-octahydro-1H-pyrido[1,2-a]pyrazine 7-(4-Chlorophenyl)-2,3,4,6,7,8,9,9a-octahydro-1H-pyrido[1,2-a]pyrazine (0.16 g, 0.640 mmol) was separated by preparative chiral HPLC (Daicel Chiralpak) to give (7R,9aR)-7-(4-chlorophenyl)-2,3,4,6,7,8,9,9a-octahydro-1H-pyrido[1,2-a]pyrazine (0.064 g, 36.3%) as light yellow solid; MS (ESI): m/z=251.0 [M+H]$^+$.

Intermediate A-2

(7S,9aS)-7-(4-Chlorophenyl)octahydro-1H-pyrido[1,2-a]pyrazine 7-(4-Chlorophenyl)-2,3,4,6,7,8,9,9a-octahydro-1H-pyrido[1,2-a]pyrazine (Intermediate A-1[C], 0.16 g, 0.64 mmol) was separated by preparative chiral HPLC (Daicel Chiralpack AY) to give the title compound (0.061 g, 33%) as a light yellow solid; MS (ESI): m/z=251.0 [M+H]$^+$.

Intermediate A-3

(7R,9aR)-7-Phenyloctahydro-1H-pyrido[1,2-a]pyrazine

Intermediate A-3 was prepared in analogy to intermediate A-1, but using in step [A] phenylmagnesium bromide (1M solution in THF) to give the title compound as a white solid. MS (ESI): m/z=217.2 [M+H]$^+$.

Intermediate A-4 rac-(7R,9aR)-7-(3,4-Dichlorophenyl)-2,3,4,6,7,8,9,9a-octahydro-1H-pyrido[1,2-a]pyrazine

Step [A] tert-butyl 7-(trifluoromethylsulfonyloxy)-1,3,4,8,9,9a-hexahydropyrido[1,2-a]pyrazine-2-carboxylate To a solution of tert-butyl 7-oxo-3,4,6,8,9,9a-hexahydro-1H-pyrido[1,2-a]pyrazine-2-carboxylate (Intermediate I-1, 0.5 g, 1.97 mmol) in THF (10 mL) cooled at −78° C. was added a 1M solution of lithium bis(trimethylsilyl)amide in THF (2.36 mL, 2.36 mmol) dropwise and the reaction mixture was stirred at this temperature for 1 hour. A solution of N-phenyl trifluoromethanesulfonimide (0.77 g, 2.16 mmol) in THF (5 mL) was then added dropwise to the mixture which was warmed up to room temperature and stirred for another 3 hours. The mixture was poured into a sat. Na$_2$CO$_3$ aq. solution (50 mL) and extracted with EtOAc (3×50 mL). The combined organic layers were washed with brine, dried over Na$_2$SO$_4$, filtered and the filtrate was concentrated in vacuo. The residue was purified by silica gel flash chromatography, eluting with a 10 to 35% EtOAc in PE gradient to give the title compound (0.62 g, 81.6%) as a yellow oil; MS (ESI): m/z=331.5 [M+H]$^+$.

Step [B] tert-butyl 7-(3,4-dichlorophenyl)-1,3,4,8,9,9a-hexahydropyrido[1,2-a]pyrazine-2-carboxylate In a sealed tube, 3,4-dichlorophenylboronic acid (0.296 g, 1.55 mmol), tert-butyl 7-(trifluoromethylsulfonyloxy)-1,3,4,8,9,9a-hexahydropyrido[1,2-a]pyrazine-2-carboxylate (0.6 g, 1.55 mmol), sodium carbonate (0.658 g, 6.21 mmol) were mixed in dioxane (16 mL) and water (4 mL). Then, tetrakis(triphenylphosphine)palladium (0.179 g, 0.160 mmol) was added and the reaction mixture was heated to 110° C. for 12 hours. The mixture was filtered and the resulting filtrate concentrated in vacuo. The residue was purified by silica gel flash chromatography, eluting with a 10 to 25% EtOAc in PE gradient to give the title compound (0.27 g, 45.4%) as a light yellow oil; MS (ESI): m/z=383.1 [M+H]$^+$.

Step [C] tert-butyl 7-(3,4-dichlorophenyl)-1,3,4,6,7,8,9,9a-octahydropyrido[1,2-a]pyrazine-2-carboxylate To a solution of tert-butyl 7-(3,4-dichlorophenyl)-1,3,4,8,9,9a-hexahydropyrido[1,2-a] pyrazine-2-carboxylate (0.24 g, 0.630 mmol) and magnesium oxide (0.32 g, 7.94 mmol) in EtOAc (50 mL) was added Pd/C (0.16 g, 1.76 mmol) and the mixture was stirred at room temperature under H$_2$ atmosphere for 4 hours. The mixture was filtered and the filtrate was concentrated in vacuo to give the crude title compound (0.25 g) as a light yellow oil; MS (ESI): m/z=385.1 [M+H]$^+$.

Step [D] rac-(7R,9aR)-7-(3,4-dichlorophenyl)-2,3,4,6,7,8,9,9a-octahydro-1H-pyrido[1,2-a]pyrazine To a solution of tert-butyl 7-(3,4-dichlorophenyl)-1,3,4,6,7,8,9,9a-octahydropyrido[1,2-a] pyrazine-2-carboxylate (0.25 g, ~0.630 mmol) was added 4M HCl in dioxane (10 mL) and the reaction mixture was stirred at room temperature for 1 hour. The solution was concentrated in vacuo and the residue was purified by prep-HPLC (MeCN and 0.1% of TFA in water, 0~30%) to give the title compound (0.093 g, 35.9%) as an off-white solid as TFA salt; MS (ESI): m/z=285.0 [M+H]$^+$.

Intermediate A-5 rac-(7R,9aR)-7-(3-Chloro-4-fluoro-phenyl)-2,3,4,6,7,8,9,9a-octahydro-1H-pyrido[1,2-a]pyrazine Intermediate A-5 was prepared in analogy to intermediate A-4, but using in step [B] 3-chloro-4-fluorophenylboronic acid to give the title compound as an off-white solid as TFA salt; MS (ESI): m/z=269.3 [M+H]$^+$.

Intermediate A-6 rac-(7R,9aR)-7-(4-chlorophenyl)-1,2,3,4,6,8,9,9a-octahydropyrido[1,2-a]pyrazin-7-ol Step [A] tert-Butyl 7-(4-chlorophenyl)-7-hydroxy-3,4,6,8,9,9a-hexahydro-1H-pyrido[1,2-a]pyrazine-2-carboxylate To a solution of tert-butyl 7-oxo-3,4,6,8,9,9a-hexahydro-1H-pyrido[1,2-a] pyrazine-2-carboxylate (Intermediate A-1, 0.5 g, 1.97 mmol) in THF (15 mL) cooled at 0° C. was added a 1M solution of 4-chlorophenylmagnesium bromide in THF (3.54 mL, 3.54 mmol) dropwise while keeping the temperature below 5° C., then the reaction mixture was stirred at room temperature overnight. The mixture was diluted with EtOAc, poured into a sat. NH$_4$Cl aq. solution (10 mL) and extracted with EtOAc (25 mL). The organic layer was washed with brine (10 mL), dried over Na$_2$SO$_4$, filtered and concentrated in vacuo. The residue was purified by silica gel flash chromatography, eluting with a 0 to 50% EtOAc-heptane gradient to give the title compound (0.164 g, 22.7%) as a pink solid; MS (ESI): m/z=367.4 [M+H]$^+$.

Step [B] 7-(4-chlorophenyl)-1,2,3,4,6,8,9,9a-octahydropyrido[1,2-a]pyrazin-7-ol

To a solution of tert-butyl 7-(4-chlorophenyl)-7-hydroxy-3,4,6,8,9,9a-hexahydro-1H-pyrido[1,2-a]pyrazine-2-carboxylate (0.164 g, 0.447 mmol) in dioxane (1.2 mL) was added 4M HCl in dioxane (1.12 mL, 4.47 mmol) and the reaction mixture was stirred at room temperature for 4 hours. The solvent was evaporated to dryness and further dried on the high vacuum to give the crude title compound (0.160 g) as a yellow oil as the hydrochloride salt. MS: 267.2 (M+H+).

Step [C] rac-(7R,9aR)-7-(4-chlorophenyl)-1,2,3,4,6,8,9,9a-octahydropyrido[1,2-a]pyrazin-7-ol 7-(4-chlorophenyl)-1,2,3,4,6,8,9,9a-octahydropyrido[1,2-a]pyrazin-7-ol (0.160 g) was separated by preparative preparative HPLC to give the title compound (0.030 g, 25.2%) as a yellow foam; MS (ESI): m/z=267.2 [M+H]$^+$.

Intermediate A-7 rac-(7R,9aS)-7-(4-chlorophenyl)-1,2,3,4,6,8,9,9a-octahydropyrido[1,2-a]pyrazin-7-ol 7-(4-chlorophenyl)-1,2,3,4,6,8,9,9a-octahydropyrido[1,2-a]pyrazin-7-ol (Intermediate A-6[B], 0.160 g) was separated by preparative HPLC to give the title compound (0.020 g, 15.9%) as a yellow oil; MS (ESI): m/z=267.2 [M+H]$^+$.

Intermediate B-1

2-Chloro-3-(3,5-difluorophenoxy)benzoic Acid

Step [A] methyl 2-chloro-3-(3,5-difluorophenoxy)benzoate

In a flask, methyl 2-chloro-3-hydroxy-benzoate (0.1 g, 0.53 mmol), 3,5-difluorophenylboronic acid (0.083 g, 0.53 mmol), copper(II) acetate (0.095 g, 0.53 mmol), triethylamine (0.07 mL, 0.53 mmol) and molecular sieves were mixed in DCM (10 mL) and the reaction mixture was stirred at room temperature for 20 hours. The reaction mixture was filtered, washed with DCM and the filtrate was concentrated in vacuo. The residue was purified by silica gel flash chromatography, eluting with a 0 to 10% EtOAc-heptane gradient to give the title compound (0.035 g, 21%) as a colorless liquid.

[B] 2-chloro-3-(3,5-difluorophenoxy)benzoic Acid

To a stirred solution of methyl 2-chloro-3-(3,5-difluorophenoxy)benzoate (0.03 g, 0.1 mmol) in a mixture of THF (2 mL), water (2 mL) and methanol (2 mL) was added LiOH (0.021 g, 0.5 mmol) and the reaction mixture was stirred at room temperature overnight. The mixture was diluted with water and extracted with ethyl acetate. The aqueous layer was acidified to pH 3 with 2N aqueous HCl solution and extracted with ethyl acetate. The combined organic layers were washed with brine, dried over $Na_2SO_4$, filtered and concentrated in vacuo to give the crude title compound (0.02 g, 69%) as off white solid.

Intermediate B-2

2-Chloro-3-phenoxy-benzoic Acid

Intermediate B-2 was prepared in analogy to intermediate B-1, but using in step [A]phenylboronic acid to give the title compound as a light yellow solid.

Intermediate C-1

2-Bromo-3-(methoxymethyl)benzoic Acid

Step [A] methyl 2-bromo-3-(methoxymethyl)benzoate

A mixture of methyl 2-bromo-3-(bromomethyl)benzoate (CAS RN 750585-90-1, 0.05 g, 0.162 mmol) and $K_2CO_3$ (0.22 g, 0.162 mmol) in MeOH (2 mL) was heated to 80° C. for 2 hours. The solvent was removed under vacuum, the residue taken up in EtOAc and washed with water. The organic phase was washed with brine, dried over $Na_2SO_4$, filtered and concentrated in vacuo. The residue was purified by silica gel flash chromatography, eluting with a 0 to 40% EtOAc-heptane gradient to give the title compound (0.035 g, 83%) as a colorless oil.

Step [B] 2-bromo-3-(methoxymethyl)benzoic Acid

To a solution of methyl 2-bromo-3-(methoxymethyl)benzoate (0.032 g, 0.124 mmol) in THF (0.5 mL) was added a 1M LiOH aqueous solution (0.247 mL, 0.247 mmol) and the reaction mixture was stirred at room temperature for 5 hours. The mixture was diluted with EtOAc, poured into 1M HCl and the aqueous layer was extracted with EtOAc. Combined organics were washed with brine, dried over $Na_2SO_4$, filtered and concentrated in vacuo to give the crude title compound (0.023 g, 76%) as colorless solid. MS (ESI): m/z=243.2 [M−H]⁻.

Intermediate D-1

4-Chloro-1-methylpyrrolo[2,3-b]pyridine-5-carboxylic acid

Step [A] ethyl 4-chloro-1-methylpyrrolo[2,3-b]pyridine-5-carboxylate

To a solution of ethyl 4-chloro-1H-pyrrolo[2,3-b]pyridine-5-carboxylate (0.050 g, 0.223 mmol) in DMF (0.5 mL) cooled to 0° C. with an ice bath was added 65% NaH dispersion in mineral oil (0.011 g, 0.289 mmol) and the reaction was stirred at this temperature for 10 minutes. Then, methyl iodide (0.018 mL, 0.289 mmol) was added and the reaction mixture was stirred at room temperature for 1 hour. The mixture was diluted with EtOAc, poured into a sat. $NH_4Cl$ aq. solution and the aqueous layer was extracted with EtOAc. Combined organics were washed with brine, dried over $Na_2SO_4$, filtered and evaporated. The residue was purified by silica gel flash chromatography, eluting with a 0-30% EtOAc-heptane gradient to give the title compound (0.042 g, 79%) as a colorless oil. MS (ESI): m/z=239.2 [M+H]⁺.

Step [B] 4-chloro-1-methylpyrrolo[2,3-b]pyridine-5-carboxylic acid

To a solution of ethyl 4-chloro-1-methyl-1H-pyrrolo[2,3-b]pyridine-5-carboxylate (0.04 g, 0.168 mmol) in THF (1 mL) was added a 1M aqueous solution of LiOH (0.335 mL, 0.335 mmol) and the mixture was stirred at room temperature overnight. The mixture was diluted with EtOAc, poured into a 1M HCl aq. solution and the aqueous layer was extracted with EtOAc. Combined organics were washed with brine, dried over $Na_2SO_4$, filtered and evaporated to dryness to afford the crude title compound (0.028 g, 79%) as a white solid. MS (ESI): m/z=211.1 [M+H]⁺.

Intermediate D-2

4-Chloro-1-propan-2-ylpyrrolo[2,3-b]pyridine-5-carboxylic acid

Step [A] ethyl 4-chloro-1-propan-2-ylpyrrolo[2,3-b]pyridine-5-carboxylate

To a solution of ethyl 4-chloro-1H-pyrrolo[2,3-b]pyridine-5-carboxylate (0.050 g, 0.223 mmol) in DMF (0.5 mL) cooled to 0° C. with an ice bath was added 65% NaH dispersion in mineral oil (0.010 g, 0.267 mmol) and the reaction was stirred at this temperature for 10 minutes. Then, 2-iodopropane (0.027 mL, 0.267 mmol) was added and the reaction mixture was stirred at room temperature for 1 hour. The mixture was diluted with EtOAc, poured into water and the aqueous layer was extracted with EtOAc. Combined organics were washed with brine, dried over $Na_2SO_4$, filtered and evaporated. The residue was purified by silica gel flash chromatography, eluting with a 0-30% EtOAc-heptane gradient to give the title compound (0.034 g, 57%) as a colorless oil. MS (ESI): m/z=267.3 [M+H]⁺.

Step [B] 4-chloro-1-propan-2-ylpyrrolo[2,3-b]pyridine-5-carboxylic acid

To a solution of ethyl 4-chloro-1-propan-2-ylpyrrolo[2,3-b]pyridine-5-carboxylate (0.032 g, 0.120 mmol) in THF (1 mL) was added a 1M aqueous solution of LiOH (0.240 mL, 0.240 mmol) and the reaction mixture was heated to 40° C. for 6 hours. The mixture was diluted with EtOAc, poured into a 1M HCl aq. solution and the aqueous layer was extracted with EtOAc. The combined organic layers were washed with brine, dried over $Na_2SO_4$ and concentrated in vacuo to afford the crude title compound (0.028 g, 97%) as a white solid. MS (ESI): m/z=239.2 [M+H]⁺.

Intermediate D-3

1-Isopropylindole-4-carboxylic acid

Intermediate D-3 was prepared in analogy to intermediate D-2, but using in step [A] methyl 1H-indole-4-carboxylate to give the title compound as a white solid.

Intermediate E-1

2-Chloro-3-propan-2-yloxybenzoic acid

Step [A] methyl 2-chloro-3-propan-2-yloxybenzoate

To a solution of methyl 2-chloro-3-hydroxybenzoate (0.1 g, 0.536 mmol) in DMF (1 mL) was added $Cs_2CO_3$ (0.210 g, 0.643 mmol) followed by 2-iodopropane (0.080 mL, 0.804 mmol) dropwise and the reaction mixture was heated to 40° C. for 2 hours. The mixture was diluted with EtOAc, poured into water and the aqueous layer was extracted with EtOAc. Combined organics were washed with brine, dried over $Na_2SO_4$, filtered and evaporated. The residue was purified by silica gel flash chromatography, eluting with a 0 to 20% EtOAc-heptane gradient to give the title compound (0.111 g, 91%) as a colorless liquid. MS (ESI): m/z=229.1 $[M+H]^+$.

Step [B] 2-Chloro-3-propan-2-yloxybenzoic acid was prepared in analogy to intermediate D-2[B] to give the title compound as a white solid. MS (ESI): m/z=215.1 $[M+H]^+$.

Intermediate E-2

2-Chloro-3-[(1-methylpyrazol-4-yl)methoxy]benzoic acid

Intermediate E-2 was prepared in analogy to intermediate E-1, but using in step [A]4-(chloromethyl)-1-methyl-1H-pyrazole hydrochloride (CAS RN 735241-98-2) to give the title compound as a white solid. MS (ESI): m/z=267.3 $[M+H]^+$.

Intermediate E-3

2-Chloro-3-(1,3-thiazol-4-ylmethoxy)benzoic acid

Intermediate E-3 was prepared in analogy to intermediate E-1, but using in step [A]4-(chloromethyl)thiazole hydrochloride (CAS RN 7709-58-2) to give the title compound as a white solid. MS (ESI): m/z=270.1 $[M+H]^+$.

Intermediate E-4

2-Chloro-3-[[4-(methylcarbamoyl)phenyl]methoxy]benzoic acid

Intermediate E-4 was prepared in analogy to intermediate E-1, but using in step [A]4-(chloromethyl)-N-methylbenzamide (CAS RN 220875-88-7) to give the title compound as a white solid; MS (ESI): m/z=320.1 $[M+H]^+$.

Intermediate E-5

2-Chloro-3-(2,2,2-trifluoroethoxy)benzoic acid

Intermediate E-5 was prepared in analogy to intermediate E-1, but using in step [A]1,1,1-trifluoro-2-iodoethane to give the title compound as a white solid; MS (ESI): m/z=253.2 $[M-H]^-$.

Intermediate F-1

2-Chloro-3-(2-oxa-6-azaspiro[3.3]heptan-6-yl)benzoic acid

Step [A] Methyl 2-chloro-3-(2-oxa-6-azaspiro[3.3]heptan-6-yl)benzoate

In a sealed tube, methyl 3-bromo-2-chlorobenzoate (CAS RN 871224-19-0, 0.250 g, 1 mmol), 2-oxa-6-azaspiro[3.3]heptane (CAS RN 174-78-7, 0.199 g, 2 mmol), $K_3PO_4$ (0.425 g, 2 mmol), $Pd_2(dba)_3$ (0.092 g, 0.1 mmol) and DavePhos (0.059 g, 0.150 mmol) were combined in Toluene (4 mL). The reaction mixture was degassed with Argon and then heated to 100° C. overnight. The mixture was evaporated to dryness and the residue purified by silica gel flash chromatography, eluting with a 0 to 50% EtOAc-heptane gradient to give the title compound (0.21 g, 78.3%) as a dark red oil. MS (ESI): m/z=268.3 $[M+H]^+$.

Step [B] 2-Chloro-3-(2-oxa-6-azaspiro[3.3]heptan-6-yl)benzoic acid

To a solution of methyl 2-chloro-3-(2-oxa-6-azaspiro[3.3]heptan-6-yl)benzoate (0.21 g, 0.784 mmol) in THF (5 mL) was added a 1M LiOH aq. solution (1.57 mL, 1.57 mmol) and the reaction mixture was heated to 50° C. for 4 hours. The mixture was acidified to pH 4 with a 1M HCl aq. solution, poured into 2-methyltetrahydrofuran (50 mL) and then $Na_2SO_4$ was added in excess. The mixture was stirred vigorously for 1 hour, filtered and concentrated in vacuo to give the crude title compound (0.233 g, 93.7%) as a light yellow solid. MS (ESI): m/z=254.2 $[M+H]^+$.

Intermediate F-2

(E)-2-chloro-3-(2-cyclopropylvinyl)benzoic acid

Step [A] methyl 2-chloro-3-(trifluoromethylsulfonyloxy)benzoate

To a solution of methyl 2-chloro-3-hydroxybenzoate (CAS RN 1125632-11-2, 0.1 g, 0.536 mmol) in DCM (1 mL) was added TEA (0.090 mL, 0.643 mmol) followed by 1,1,1-trifluoro-N-phenyl-N-((trifluoromethyl)sulfonyl)methanesulfonamide (0.307 g, 0.858 mmol) and the reaction mixture was stirred at room temperature for 6 hours. The reaction was diluted with DCM, poured into water and the aqueous layer was extracted with DCM. Combined organics were washed with brine, dried over $Na_2SO_4$, filtered and evaporated. The residue was purified by silica gel flash chromatography, eluting with a 0 to 100% EtOAc-heptane gradient to give the title compound (0.15 g, 87.8%) as a colorless oil. MS (ESI): m/z=319.0 $[M+H]^+$.

Step [B] methyl (E)-2-chloro-3-(2-cyclopropylvinyl)benzoate

In a sealed tube, methyl 2-chloro-3-(trifluoromethylsulfonyloxy)benzoate (0.1 g, 0.314 mmol) and (E)-2-(2-cyclopropylvinyl)-4,4,5,5-tetramethyl-1,3,2-dioxaborolane (CAS RN 849061-99-0, 0.067 g, 0.345 mmol) were mixed in DMF (1 mL). Then, bis(triphenylphosphine)palladium (II) chloride (0.022 g, 0.031 mmol), followed by a 1M $Na_2CO_3$ aq. solution (0.941 mL, 0.941 mmol) were added and the reaction mixture was heated to 80° C. overnight. The mixture was diluted with EtOAc, filtered through a plug of Dicalite and washed with EtOAc. The filtrate was washed with brine, dried over $Na_2SO_4$, filtered and evaporated in vacuo. The residue was purified by silica gel flash chromatography, eluting with a 0 to 20% EtOAc-heptane gradient to give the title compound (0.022, 29%) as an off-white solid; MS (ESI): m/z=237.1 $[M+H]^+$.

Step [C] (E)-2-chloro-3-(2-cyclopropylvinyl)benzoic acid

To a solution of methyl (E)-2-chloro-3-(2-cyclopropylvinyl)benzoate (0.022 g, 0.093 mmol) in THF (0.75 mL) was added a 1M LiOH aq. solution (0.279 mL, 0.279 mmol) and the reaction mixture was stirred at 50° C. overnight. The mixture was acidified with 2M HCl aq. solution and the aqueous layer was extracted with EtOAc. Combined organics were washed with brine, dried over $Na_2SO_4$, filtered and concentrated in vacuo to give the crude title compound (0.018, 87%) as a light yellow solid; MS (ESI): m/z=233.1 $[M+H]^+$.

Example 1

[(7R,9aR)-7-(4-Chlorophenyl)-1,3,4,6,7,8,9,9a-octahydropyrido[1,2-a]pyrazin-2-yl]-(3-phenoxyphenyl)methanone In a flask, (7R,9aR)-7-(4-chlorophenyl)octahydro-1H-pyrido[1,2-a]pyrazine (Intermediate A-1, 0.04 g, 0.160 mmol), 3-phenoxybenzoic acid (0.034 g, 0.160 mmol) and HATU (0.073 g, 0.191 mmol) were mixed in DMF (0.5 mL). Then, Hünig's base (0.084 mL, 0.479 mmol) was added and the reaction mixture was stirred at room temperature for 2 hours. The reaction was diluted with EtOAc, poured into water and the aqueous layer was extracted with EtOAc. The combined organic layers were washed with brine, dried over $Na_2SO_4$, filtered and concentrated in vacuo. The residue was purified by silica gel flash chromatography eluting with a 0 to 100% EtOAc-heptane gradient to give the title compound (0.05 g, 70%) as a colorless amorphous solid; MS (ESI): m/z=447.2 $[M+H]^+$.

The following examples listed in Table 2 were prepared in analogy to the procedures described for the preparation of example 1 by using the indicated intermediates and/or commercial compounds and using the mentioned purification method such as preparative HPLC (Gemini NX column), silica gel flash chromatography or preparative chiral HPLC (Daicel Chiralpack column).

TABLE 2

| Ex | Name Aspect Purification method | Intermediates | MS, m/z $[M+H]^+$ or $[M-H]^-$ |
|---|---|---|---|
| 2 | [(7R,9aR)-7-(4-Chlorophenyl)-1,3,4,6,7,8,9,9a-octahydropyrido[1,2-a]pyrazin-2-yl]-(2-chloro-3-methylphenyl)methanone Colorless amorphous Flash chromatography | Intermediate A-1 and 2-chloro-3-methylbenzoic acid | 403.2 |
| 3 | [(7R,9aR)-7-(4-Chlorophenyl)-1,3,4,6,7,8,9,9a-octahydropyrido[1,2-a]pyrazin-2-yl]-(2-bromo-3-methoxyphenyl)methanone Colorless amorphous Flash chromatography | Intermediate A-1 and 2-bromo-3-methoxybenzoic acid | 465.2 |
| 4 | [(7R,9aR)-7-(4-Chlorophenyl)-1,3,4,6,7,8,9,9a-octahydropyrido[1,2-a]pyrazin-2-yl]-[3-(3,5-difluorophenoxy)phenyl]methanone Colorless amorphous Flash chromatography | Intermediate A-1 and Intermediate B-1 | 483.2 |
| 5 | [(7R,9aR)-7-Phenyl-1,3,4,6,7,8,9,9a-octahydropyrido[1,2-a]pyrazin-2-yl]-(2-bromo-3-methoxyphenyl)methanone Off-white solid Flash chromatography | Intermediate A-3 and 2-bromo-3-methoxybenzoic acid | 431.2 |
| 6 | [(7R,9aR)-7-(4-Chlorophenyl)-1,3,4,6,7,8,9,9a-octahydropyrido[1,2-a]pyrazin-2-yl]-(2-chloro-3-methoxyphenyl)methanone Colorless amorphous Flash chromatography | Intermediate A-1 and 2-chloro-3-methoxybenzoic acid | 419.2 |
| 7 | [(7R,9aR)-7-(4-Chlorophenyl)-1,3,4,6,7,8,9,9a-octahydropyrido[1,2-a]pyrazin-2-yl]-(2-methoxyphenyl)methanone Orange solid Preparative HPLC | Intermediate A-1 and 2-methoxybenzoic acid | 385.2 |
| 8 | [(7R,9aR)-7-(4-Chlorophenyl)-1,3,4,6,7,8,9,9a-octahydropyrido[1,2-a]pyrazin-2-yl]-[2-(trifluoromethoxy)phenyl]methanone Colorless foam Preparative HPLC | Intermediate A-1 and 2-trifluoromethoxybenzoic acid | 439.2 |
| 9 | [(7R,9aR)-7-(4-Chlorophenyl)-1,3,4,6,7,8,9,9a-octahydropyrido[1,2-a]pyrazin-2-yl]-(2,3-dihydro-1-benzofuran-7-yl)methanone Colorless foam Preparative HPLC | Intermediate A-1 and 2,3-dihydro-benzofuran-7-carboxylic acid | 397.2 |
| 10 | [(7R,9aR)-7-(4-Chlorophenyl)-1,3,4,6,7,8,9,9a-octahydropyrido[1,2-a]pyrazin-2-yl]-(1H-indol-4-yl)methanone Off white solid Preparative HPLC | Intermediate A-1 and 1H-indole-4-carboxylic acid | 394.2 |
| 11 | [(7R,9aR)-7-(4-Chlorophenyl)-1,3,4,6,7,8,9,9a-octahydropyrido[1,2-a]pyrazin-2-yl]-(2-chloro-6-fluorophenyl)methanone Colorless solid Flash chromatography | Intermediate A-1 and 2-chloro-6-fluorobenzoic acid | 407.2 |
| 12 | [(7R,9aR)-7-(4-Chlorophenyl)-1,3,4,6,7,8,9,9a-octahydropyrido[1,2-a]pyrazin-2-yl]-(2-chlorophenyl)methanone Colorless solid Flash chromatography | Intermediate A-1 and 2-chlorobenzoic acid | 389.2 |
| 13 | [(7R,9aR)-7-(4-Chlorophenyl)-1,3,4,6,7,8,9,9a-octahydropyrido[1,2-a]pyrazin-2-yl]-(2-fluoro-3-methylphenyl)methanone Colorless amorphous Preparative HPLC | Intermediate A-1 and 2-fluoro-3-methylbenzoic acid | 387.2 |
| 14 | [(7R,9aR)-7-(4-Chlorophenyl)- | Intermediate A-1 | 429.2 |

TABLE 2-continued

| Ex | Name Aspect Purification method | Intermediates | MS, m/z [M + H]+ or [M − H]− |
|---|---|---|---|
| | 1,3,4,6,7,8,9,9a-octahydropyrido[1,2-a]pyrazin-2-yl]-(4-chloro-1H-pyrrolo[2,3-b]pyridin-5-yl)methanone<br>White solid<br>Preparative HPLC | and 4-chloro-1H-pyrrolo[2,3-b]pyridine-5-carboxylic acid (CAS RN 920966-03-6) | |
| 15 | [(7R,9aR)-7-(4-Chlorophenyl)-1,3,4,6,7,8,9,9a-octahydropyrido[1,2-a]pyrazin-2-yl]-(1H-pyrrolo[2,3-b]pyridin-4-yl)methanone<br>Colorless amorphous<br>Preparative HPLC | Intermediate A-1 and 1H-Pyrrolo[2,3-b]pyridine-4-carboxylic acid (CAS RN 479553-01-0) | 395.2 |
| 16 | [(7R,9aR)-7-(4-Chlorophenyl)-1,3,4,6,7,8,9,9a-octahydropyrido[1,2-a]pyrazin-2-yl]-[2-chloro-3-(trifluoromethyl)phenyl]methanone<br>Colorless solid<br>Flash chromatography | Intermediate A-1 and 2-chloro-3-trifluorobenzoic acid | 457.2 |
| 17 | [(7R,9aR)-7-(4-Chlorophenyl)-1,3,4,6,7,8,9,9a-octahydropyrido[1,2-a]pyrazin-2-yl]-(2-chloro-4-fluoro-3-methylphenyl)methanone<br>Colorless solid<br>Flash chromatography | Intermediate A-1 and 2-chloro-4-fluoro-3-methylbenzoic acid | 421.2 |
| 18 | [(7R,9aR)-7-(4-Chlorophenyl)-1,3,4,6,7,8,9,9a-octahydropyrido[1,2-a]pyrazin-2-yl]-(3-chloro-2-methylphenyl)methanone<br>Off-white solid<br>Flash chromatography | Intermediate A-1 and 3-chloro-2-methylbenzoic acid | 403.2 |
| 19 | [(7R,9aR)-7-(4-Chlorophenyl)-1,3,4,6,7,8,9,9a-octahydropyrido[1,2-a]pyrazin-2-yl]-(4-chloro-6-methylpyridin-3-yl)methanone<br>Off-white amorphous<br>Preparative HPLC | Intermediate A-1 and 4-Chloro-6-methyl-nicotinic acid | 404.2 |
| 20 | [(7R,9aR)-7-(4-Chlorophenyl)-1,3,4,6,7,8,9,9a-octahydropyrido[1,2-a]pyrazin-2-yl]-(2,4-dimethyl-1,3-benzothiazol-5-yl)methanone<br>Colorless foam<br>Flash chromatography | Intermediate A-1 and 2,4-dimethyl-1,3-benzothiazole-5-carboxylic acid (CAS RN 305381-76-4) | 440.2 |
| 21 | [(7R,9aR)-7-(4-Chlorophenyl)-1,3,4,6,7,8,9,9a-octahydropyrido[1,2-a]pyrazin-2-yl]-(7-chloro-2-methylsulfanyl-[1,3]thiazolo[5,4-b]pyridin-6-yl)methanone<br>Off-white solid<br>Flash chromatography | Intermediate A-1 and 7-chloro-2-methylsulfanyl-thiazolo[5,4-b]pyridine-6-carboxylic acid (CAS RN 457949-02-9) | 493.1 |
| 22 | [(7R,9aR)-7-(4-Chlorophenyl)-1,3,4,6,7,8,9,9a-octahydropyrido[1,2-a]pyrazin-2-yl]-(1-benzothiophen-4-yl)methanone<br>Light brown oil<br>Flash chromatography | Intermediate A-1 and Benzo[b]thiophene-4-carboxylic acid | 411.2 |
| 23 | [(7R,9aR)-7-(4-Chlorophenyl)-1,3,4,6,7,8,9,9a-octahydropyrido[1,2-a]pyrazin-2-yl]-(2-bromo-3-methylphenyl)methanone<br>Off-white oil<br>Flash chromatography | Intermediate A-1 and 2-bromo-3-methylbenzoic acid | 449.1 |
| 24 | [(7R,9aR)-7-(4-Chlorophenyl)-1,3,4,6,7,8,9,9a-octahydropyrido[1,2-a]pyrazin-2-yl]-[2-(trifluoromethyl)phenyl]methanone<br>Off-white oil<br>Flash chromatography | Intermediate A-1 and trifluoromethylbenzoic acid | 423.2 |
| 25 | [(7R,9aR)-7-(4-Chlorophenyl)-1,3,4,6,7,8,9,9a-octahydropyrido[1,2-a]pyrazin-2-yl]-(2-chloro-3-phenoxyphenyl)methanone<br>Colorless solid<br>Flash chromatography | Intermediate A-1 and Intermediate B-2 | 481.2 |
| 26 | [(7R,9aR)-7-Phenyl-1,3,4,6,7,8,9,9a-octahydropyrido[1,2-a]pyrazin-2-yl]-(2-chloro-3-methylphenyl)methanone<br>Off-white solid<br>Flash chromatography | Intermediate A-3 and 2-chloro-3-methylbenzoic acid | 369.2 |
| 27 | [(7R,9aR)-7-Phenyl-1,3,4,6,7,8,9,9a-octahydropyrido[1,2-a]pyrazin-2-yl]-(2-chloro-5-fluoro-3-methylphenyl)methanone<br>Light brown amorphous<br>Flash chromatography | Intermediate A-3 and 2-chloro-5-fluoro-3-methylbenzoic acid | 387.2 |
| 28 | [(7R,9aR)-7-Phenyl-1,3,4,6,7,8,9,9a-octahydropyrido[1,2-a]pyrazin-2-yl]-[2-bromo-3-(methoxymethyl)phenyl]methanone<br>Orange amorphous<br>Flash chromatography | Intermediate A-3 and Intermediate C-1 | 443.3 |
| 29 | [(7R,9aR)-7-Phenyl-1,3,4,6,7,8,9,9a-octahydropyrido[1,2-a]pyrazin-2-yl]-(1H-indol-4-yl)methanone<br>Light yellow solid<br>Flash chromatography | Intermediate A-3 and 1H-indole-4-carboxylic acid | 360.3 |
| 30 | [(7R,9aR)-7-Phenyl-1,3,4,6,7,8,9,9a-octahydropyrido[1,2-a]pyrazin-2-yl]-(1-methylindol-4-yl)methanone<br>Light yellow amorphous<br>Flash chromatography | Intermediate A-3 and 1-methyl-1H-indole-4-carboxylic acid (CAS RN 90924-06-4) | 374.3 |
| 31 | [(7R,9aR)-7-Phenyl-1,3,4,6,7,8,9,9a-octahydropyrido[1,2-a]pyrazin-2-yl]-(4-chloro-1H-pyrrolo[2,3-b]pyridin-5-yl)methanone<br>Off-white solid<br>Preparative HPLC | Intermediate A-3 and 4-chloro-1H-pyrrolo[2,3-b]pyridine-5-carboxylic acid (CAS RN 920966-03-6) | 395.3 |
| 32 | [(7R,9aR)-7-Phenyl-1,3,4,6,7,8,9,9a-octahydropyrido[1,2-a]pyrazin-2-yl]-(2-chloro-3-hydroxyphenyl)methanone<br>White solid<br>Preparative HPLC | Intermediate A-3 and 2-chloro-3-hydroxybenzoic acid (CAS RN 51786-10-8) | 371.3 |
| 33 | [(7R,9aR)-7-Phenyl-1,3,4,6,7,8,9,9a-octahydropyrido[1,2-a]pyrazin-2-yl]-(1-methyl-2,3-dihydroindol-4-yl)methanone<br>White solid<br>Preparative HPLC | Intermediate A-3 And 1-methylindoline-4-carboxylic acid (CAS RN 168899-63-6) | 376.4 |
| 34 | [(7R,9aR)-7-Phenyl-1,3,4,6,7,8,9,9a-octahydropyrido[1,2-a]pyrazin-2-yl]-(1-propan-2-ylindol-4-yl)methanone<br>White amorphous<br>Flash chromatography | Intermediate A-3 and Intermediate D-3 | 402.4 |
| 35 | [(7R,9aR)-7-Phenyl-1,3,4,6,7,8,9,9a-octahydropyrido[1,2-a]pyrazin-2-yl]-(2-chloro-3-propan-2-yloxyphenyl)methanone<br>Off-white solid<br>Flash chromatography | Intermediate A-3 and Intermediate E-1 | 413.4 |
| 36 | 3-[(7R,9aR)-7-Phenyl-1,3,4,6,7,8,9,9a- | Intermediate A-3 and | 380.3 |

TABLE 2-continued

| Ex | Name Aspect Purification method | Intermediates | MS, m/z [M + H]+ or [M − H]− |
|---|---|---|---|
| | octahydropyrido[1,2-a]pyrazine-2-carbonyl]-2-chlorobenzonitrile Colorless amorphous Flash chromatography | 2-chloro-3-cyanobenzoic acid (CAS RN 1261499-34-6) | |
| 37 | [(7R,9aR)-7-Phenyl-1,3,4,6,7,8,9,9a-octahydropyrido[1,2-a]pyrazin-2-yl]-(4-chloro-1-methylpyrrolo[2,3-b]pyridin-5-yl)methanone Off-white amorphous Flash Chromatography | Intermediate A-3 and Intermediate D-1 | 409.3 |
| 38 | [(7R,9aR)-7-Phenyl-1,3,4,6,7,8,9,9a-octahydropyrido[1,2-a]pyrazin-2-yl]-[2-chloro-3-[(1-methylpyrazol-4-yl)methoxy]phenyl]methanone Colorless gum Preparative HPLC | Intermediate A-3 and Intermediate E-2 | 465.4 |
| 39 | [(7R,9aR)-7-Phenyl-1,3,4,6,7,8,9,9a-octahydropyrido[1,2-a]pyrazin-2-yl]-(4-chloro-1-propan-2-ylpyrrolo[2,3-b]pyridin-5-yl)methanone White solid Flash chromatography | Intermediate A-3 and Intermediate D-2 | 437.4 |
| 40 | [(7S,9aS)-7-(4-Chlorophenyl)-1,3,4,6,7,8,9,9a-octahydropyrido[1,2-a]pyrazin-2-yl]-(2-bromo-3-methoxyphenyl)methanone Off-white amorphous Flash chromatography | Intermediate A-2 and 2-bromo-3-methoxybenzoic acid (CAS RN 88377-29-1) | 465.3 |
| 41 | [(7R,9aR)-7-phenyl-1,3,4,6,7,8,9,9a-octahydropyrido[1,2-a]pyrazin-2-yl]-(3-chloro-2-methoxypyridin-4-yl)methanone Off-white solid Flash chromatography | Intermediate A-3 and 3-chloro-2-methoxy-isonicotinic acid (CAS RN 1211584-06-3) | 386.2 |
| 42 | R7R,9aR)-7-(4-chlorophenyl)-1,3,4,6,7,8,9,9a-octahydropyrido[1,2-a]pyrazin-2-yl]-(4-chloro-1-methylpyrrolo[2,3-b]pyridin-5-yl)methanone White solid Flash chromatography | Intermediate A-1 and Intermediate D-2 | 443.0 |
| 43 | [(7R,9aR)-7-phenyl-1,3,4,6,7,8,9,9a-octahydropyrido[1,2-a]pyrazin-2-yl]-[2-chloro-3-(1,3-thiazol-4-ylmethoxy)phenyl]methanone Colorless foam Flash chromatography | Intermediate A-3 and Intermediate E-3 | 468.3 |
| 44 | 4-[[3-[(7R,9aR)-7-phenyl-1,3,4,6,7,8,9,9a-octahydropyrido[1,2-a]pyrazine-2-carbonyl]-2-chlorophenoxy]methyl]-N-methylbenzamide Colorless solid Flash chromatography | Intermediate A-3 and Intermediate E-4 | 518.3 |
| 45 | (7R,9aR)-7-(4-chlorophenyl)-1,3,4,6,7,8,9,9a-octahydropyrido[1,2-a]pyrazin-2-yl]-(4-chloro-1-methylpyrazolo[3,4-b]pyridin-5-yl)methanone Off-white amorphous Flash chromatography | Intermediate A-1 and 4-chloro-1-methyl-1H-pyrazolo[3,4-b]pyridine-5-carboxylic acid (CAS RN 675111-88-3) | 444.3 |
| 48 | [(7R,9aR)-7-(4-chlorophenyl)-1,3,4,6,7,8,9,9a-octahydropyrido[1,2-a]pyrazin-2-yl]42-chloro-3-(2,2,2-trifluoroethoxy)phenyl]methanone Colorless solid Flash chromatography | Intermediate A-1 and Intermediate E-5 | 487.2 |
| 49 | [(7R,9aR)-7-(4-chlorophenyl)-1,3,4,6,7,8,9,9a-octahydropyrido[1,2-a]pyrazin-2-yl]-imidazo[1,2-a]pyridin-5-ylmethanone Colorless amorphous Preparative HPLC | Intermediate A-1 and imidazo[1,2-a]pyridine-5-carboxylic acid (CAS RN 479028-72-3) | 395.2 |
| 57 | [(7R,9aR)-7-(4-chlorophenyl)-1,3,4,6,7,8,9,9a-octahydropyrido[1,2-a]pyrazin-2-yl]-[2-chloro-3-[(E)-2-cyclopropyl-ethenyl]phenyl]methanone Colorless amorphous | Intermediate A-1 and Intermediate F-2 | 455.2 |
| 58 | [(7R,9aR)-7-(4-chlorophenyl)-1,3,4,6,7,8,9,9a-octahydropyrido[1,2-a]pyrazin-2-yl]-(4-chloro-5-methoxypyridin-3-yl)methanone Off-white solid Preparative HPLC | Intermediate A-1 and 4-chloro-5-methoxynicotinic acid | 420.2 |
| 59 | (4-chloro-1H-pyrazolo[3,4-b]pyridin-5-yl)-[rac-(7R,9aR)-7-(3-chloro-4-fluorophenyl)-1,3,4,6,7,8,9,9a-octahydropyrido[1,2-a]pyrazin-2-yl]methanone Off-white solid Preparative HPLC | Intermediate A-5 and 4-chloro-1H-pyrazolo[3,4-b]pyridine-(CAS RN 1780768-22-0) | 448.1 |
| 59-A | [(7R,9aR)-7-(3-chloro-4-fluorophenyl)-1,3,4,6,7,8,9,9a-octahydropyrido[1,2-a]pyrazin-2-yl]-(4-chloro-1H-pyrazolo[3,4-b]pyridin-5-yl)methanone Colorless amorphous | SFC separation of example 59 | 448.2 |
| 59-B | [(7S,9aS)-7-(3-chloro-4-fluorophenyl)-1,3,4,6,7,8,9,9a-octahydropyrido[1,2-a]pyrazin-2-yl]-(4-chloro-1H-pyrazolo[3,4-b]pyridin-5-yl)methanone Colorless amorphous | SFC separation of example 59 | 448.2 |
| 60 | (3-methyl-1H-indazol-5-yl)-[rac-(7R,9aR)-7-(3-chloro-4-fluorophenyl)-1,3,4,6,7,8,9,9a-octahydropyrido[1,2-a]pyrazin-2-yl]methanone Off-white solid Preparative HPLC | Intermediate A-5 and 3-methyl-1H-indazole-5-carboxylic acid (CAS RN 885223-58-5) | 427.2 |
| 60-A | [(7S,9aS)-7-(3-chloro-4-fluorophenyl)-1,3,4,6,7,8,9,9a-octahydropyrido[1,2-a]pyrazin-2-yl]-(3-methyl-1H-indazol-5-yl)methanone Colorless amorphous | SFC separation of example 60 | 427.2 |
| 60-B | [(7R,9aR)-7-(3-chloro-4-fluorophenyl)-1,3,4,6,7,8,9,9a-octahydropyrido[1,2-a]pyrazin-2-yl]-(3-methyl-1H-indazol-5-yl)methanone Colorless amorphous | SFC separation of example 60 | 427.2 |
| 61 | (3-methyl-[1,2,4]triazolo[4,3-a]pyridin-6-yl)-[rac-(7R,9aR)-7-(3-chloro-4-fluorophenyl)-1,3,4,6,7,8,9,9a- | Intermediate A-5 and 3-methyl-[1,2, | 428.2 |

TABLE 2-continued

| Ex | Name Aspect Purification method | Intermediates | MS, m/z [M + H]+ or [M − H]− |
|---|---|---|---|
| | octahydropyrido[1,2-a]pyrazin-2-yl]methanone White foam Preparative HPLC | 4]triazolo[4,3-a]pyridine-6-carboxylic acid (CAS RN 1031619-88-1) | |
| 62 | (3-chloroimidazo[1,2-a]pyridin-6-yl)-[rac-(7R,9aR)-7-(3-chloro-4-fluorophenyl)-1,3,4,6,7,8,9,9a-octahydropyrido[1,2-a]pyrazin-2-yl]methanone Orange waxy solid Flash chromatography | Intermediate A-5 and 3-chloro-imidazo[1,2-a]pyridine-6-carboxylic acid (CAS RN 900019-39-8 | 447.1 |
| 63 | (4-chlorothieno[2,3-b]pyridin-5-yl)-[rac-(7R,9aR)-7-(3-chloro-4-fluorophenyl)-1,3,4,6,7,8,9,9a-octahydropyrido[1,2-a]pyrazin-2-yl]methanone White solid Preparative HPLC | Intermediate A-5 and 4-chlorothieno[2,3-b]pyridine-5-carboxylic acid (CAS RN 700844-19-5) | 464.1 |
| 63-A | [(7R,9aR)-7-(3-chloro-4-fluorophenyl)-1,3,4,6,7,8,9,9a-octahydropyrido[1,2-a]pyrazin-2-yl]-(4-chlorothieno[2,3-b]pyridin-5-yl)methanone Colorless amorphous | SFC separation of example 63 | 464.2 |
| 63-B | [(7S,9aS)-7-(3-chloro-4-fluorophenyl)-1,3,4,6,7,8,9,9a-octahydropyrido[1,2-a]pyrazin-2-yl]-(4-chlorothieno[2,3-b]pyridin-5-yl)methanone Colorless amorphous | SFC separation of example 63 | 464.1 |
| 64 | (4-chloro-3-methyl-[1,2]oxazolo[5,4-b]pyridin-5-yl)-[rac-(7R,9aR)-7-(3-chloro-4-fluorophenyl)-1,3,4,6,7,8,9,9a-octahydropyrido[1,2-a]pyrazin-2-yl]methanone Yellow solid Preparative HPLC | Intermediate A-5 and 4-chloro-3-methyl-[1,2]oxazolo[5,4-b]pyridine-5-carboxylic acid (CAS RN 1936101-21-1) | 463.2 |
| 64-A | [(7R,9aR)-7-(3-chloro-4-fluorophenyl)-1,3,4,6,7,8,9,9a-octahydropyrido[1,2-a]pyrazin-2-yl]-(4-chloro-3-methyl-[1,2]oxazolo[5,4-b]pyridin-5-yl)methanone Colorless amorphous | SFC separation of example 64 | 463.3 |
| 64-B | [(7S,9aS)-7-(3-chloro-4-fluorophenyl)-1,3,4,6,7,8,9,9a-octahydropyrido[1,2-a]pyrazin-2-yl]-(4-chloro-3-methyl-[1,2]oxazolo[5,4-b]pyridin-5-yl)methanone Colorless amorphous | SFC separation of example 64 | 463.3 |
| 65 | (4-chloro-1H-indazol-5-yl)-[rac-(7R,9aR)-7-(3-chloro-4-fluorophenyl)-1,3,4,6,7,8,9,9a-octahydropyrido[1,2-a]pyrazin-2-yl]methanone Colorless foam | Intermediate A-5 and 4-chloro-1H-indazole-5-carboxylic acid (CAS RN 1890325-99-1) | 447.2 |
| 66 | [2-chloro-3-(difluoromethoxy)phenyl]-[rac-(7R,9aR)-7-(3-chloro-4-fluorophenyl)-1,3,4,6,7,8,9,9a-octahydropyrido[1,2-a]pyrazin-2-yl]methanone Colorless amorphous Preparative HPLC | Intermediate A-5 and 2-chloro-3-(difluoromethoxy)benzoic acid (CAS RN 1427432-41-4) | 473.3 |
| 66-A | [(7S,9aS)-7-(3-chloro-4-fluorophenyl)-1,3,4,6,7,8,9,9a-octahydropyrido[1,2-a]pyrazin-2-yl]-[2-chloro-3-(difluoromethoxy)phenyl]methanone Red amorphous | SFC separation of example 66 | 473.3 |
| 66-B | [(7R,9aR)-7-(3-chloro-4-fluorophenyl)-1,3,4,6,7,8,9,9a-octahydropyrido[1,2-a]pyrazin-2-yl]-[2-chloro-3-(difluoromethoxy)phenyl]methanone Red amorphous | SFC separation of example 66 | 473.3 |
| 67 | (4-chloro-3-methyl-1H-indazol-5-yl)-[rac-(7R,9aR)-7-(3-chloro-4-fluorophenyl)-1,3,4,6,7,8,9,9a-octahydropyrido[1,2-a]pyrazin-2-yl]methanone White solid Preparative HPLC | Intermediate A-5 and 4-chloro-3-methyl-1H-indazole-5-carboxylic acid (CAS RN 1895008-64-6) | 461.3 |
| 68 | (4-chloro-[1,2]thiazolo[5,4-b]pyridin-5-yl)-[rac-(7R,9aR)-7-(3-chloro-4-fluorophenyl)-1,3,4,6,7,8,9,9a-octahydropyrido[1,2-a]pyrazin-2-yl]methanone Yellow solid Preparative HPLC | Intermediate A-5 and methyl-4-chloro-[1,2]thiazolo[5,4-b]pyridine-5-carboxylate (CAS RN 2139258-59-4) after ester hydrolysis. | 465.3 |
| 69 | (6-amino-4-chloropyridin-3-yl)-[rac-(7R,9aR)-7-(3-chloro-4-fluorophenyl)-1,3,4,6,7,8,9,9a-octahydropyrido[1,2-a]pyrazin-2-yl]methanone White solid Preparative HPLC | Intermediate A-5 and 6-amino-4-chloro-3-pyridine-carboxylic acid (CAS RN 1060808-94-7) | 423.3 |
| 70 | (4-chloro-3-methyl-1H-indazol-5-yl)-[rac-(7R,9aR)-7-(4-chlorophenyl)-7-hydroxy-3,4,6,8,9,9a-hexahydro-1H-Pyrido[1,2-a]pyrazin-2-yl]methanone White solid Preparative HPLC | Intermediate A-6 and 4-chloro-3-methyl-1H-indazole-5-carboxylic acid (CAS RN 1895008-64-6) | 459.4 |
| 71 | (4-chloro-3-methyl-1H-indazol-5-yl)-[rac-(7R,9aS)-7-(4-chlorophenyl)-7-hydroxy-3,4,6,8,9,9a-hexahydro-1H-Pyrido[1,2-a]pyrazin-2-yl]methanone White solid Preparative HPLC | Intermediate A-7 and 4-chloro-3-methyl-1H-indazole-5-carboxylic acid (CAS RN 1895008-64-6) | 459.4 |
| 71-A | [(7S,9aR)-7-(4-chlorophenyl)-7-hydroxy-3,4,6,8,9,9a-hexahydro-1H-pyrido[1,2-a]pyrazin-2-yl]-(4-chloro-3- | SFC separation of EX 71 | 459.3 |

TABLE 2-continued

| Ex | Name Aspect Purification method | Intermediates | MS, m/z [M + H]+ or [M − H]− |
|---|---|---|---|
| 71-B | methyl-1H-indazol-5-yl)methanone White solid [(7R,9aS)-7-(4-chlorophenyl)-7-hydroxy-3,4,6,8,9,9a-hexahydro-1H-pyrido[1,2-a]pyrazin-2-yl]-(4-chloro-3-methyl-1H-indazol-5-yl)methanone White solid | SFC separation of EX 71 | 459.3 |

Examples 46 and 47

[(7R,9aR)-7-(3,4-dichlorophenyl)-1,3,4,6,7,8,9,9a-octahydropyrido[1,2-a]pyrazin-2-yl]-(2-bromo-3-methoxyphenyl)methanone and [(7S,9aS)-7-(3,4-dichlorophenyl)-1,3,4,6,7,8,9,9a-octahydropyrido[1,2-a]pyrazin-2-yl]-(2-bromo-3-methoxyphenyl)methanone In a flask, rac-(7R,9aR)-7-(3,4-dichlorophenyl)-2,3,4,6,7,8,9,9a-octahydro-1H-pyrido[1,2-a]pyrazine (Intermediate A-4, 0.085 g, 0.210 mmol), propylphosphonic anhydride 50% solution in DMF (0.108 g, 0.230 mmol) and 2-bromo-3-methoxy-benzoic acid (0.052 g, 0.220 mmol) were mixed in DMF (2 mL) and cooled to 0° C. with an ice bath. Then, Huenig's base (0.09 mL, 0.530 mmol) was added and the reaction mixture stirred at room temperature for 12 hours. The mixture was diluted with a sat. $Na_2CO_3$ aq. solution (10 mL) and extracted with EtOAc (3×10 mL). The combined organic phases were washed with brine, dried over $Na_2SO_4$, filtered and concentrated in vacuo. The residue was purified by silica gel flash chromatography, eluting with a 50 to 100% EtOAc-heptane gradient to give rac-(7R,9aR)-[7-(3,4-dichlorophenyl)-1,3,4,6,7,8,9,9a-octahydropyrido[1,2-a]pyrazin-2-yl]-(2-bromo-3-methoxy-phenyl)methanone (0.042 g, 39.6%) as an off-white solid. This material was separated by preparative chiral HPLC (DAICEL CHIRALCEL OD(250 mm*50 mm, 10 um), eluent: 0.1% $NH_3.H_2O$ IPA, 60%) to give respectively [(7S,9aS)-7-(3,4-dichlorophenyl)-1,3,4,6,7,8,9,9a-octahydropyrido[1,2-a]pyrazin-2-yl]-(2-bromo-3-methoxy-phenyl)methanone (Example 47, 0.014 g, 33.7%) and [(7R,9aR)-7-(3,4-dichlorophenyl)-1,3,4,6,7,8,9,9a-octahydropyrido[1,2-a]pyrazin-2-yl]-(2-bromo-3-methoxy-phenyl)methanone (Example 46, 0.015 g, 34.8%) as white solids; MS (ESI): m/z=499.2 [M+3H]+.

The following examples listed in Table 3 were prepared in analogy to the procedure described for the preparation of examples 46 and 47 by reacting the indicated intermediates and commercial compounds and using the mentioned purification method such as preparative HPLC (Gemini NX column), silica gel flash chromatography or chiral separation method such as preparative chiral HPLC or SFC.

TABLE 3

| Ex | Name Aspect Purification method | Intermediates | MS, m/z [M + H]+ or [M − H]− |
|---|---|---|---|
| 55 | [(7R,9aR)-7-(3-chloro-4-fluorophenyl)-1,3,4,6,7,8,9,9a-octahydropyrido[1,2-a]pyrazin-2-yl]-(2-chloro-3-methoxyphenyl)methanone Light yellow solid Preparative chiral HPLC | Intermediate A-5 and 2-chloro-3-methoxy-benzoic acid | 437.2 |
| 56 | [(7S,9aS)-7-(3-chloro-4-fluorophenyl)-1,3,4,6,7,8,9,9a-octahydropyrido[1,2-a]pyrazin-2-yl]-(2-chloro-3-methoxyphenyl)methanone Light yellow solid Preparative chiral HPLC | Intermediate A-5 and 2-chloro-3-methoxy-benzoic acid | 437.2 |

,

Example 50 tert-Butyl 4-[[3-[(7R,9aR)-7-phenyl-1,3,4,6,7,8,9,9a-octahydropyrido[1,2-a]pyrazine-2-carbonyl]-2-chlorophenoxy]methyl]pyrazole-1-carboxylate To a solution of [(7R,9aR)-7-phenyl-1,3,4,6,7,8,9,9a-octahydropyrido[1,2-a]pyrazin-2-yl]-(2-chloro-3-hydroxyphenyl)methanone (example 32, 0.04 g, 0.108 mmol) and $K_2CO_3$ (0.045 g, 0.324 mmol) in DMF (1 mL) was added tert-butyl 4-(bromomethyl)-1H-pyrazole-1-carboxylate (42.2 mg, 162 µmol, Eq: 1.5) followed by KI (0.002 g, 0.011 mmol) and the reaction mixture was stirred to 60° C. overnight. The mixture was diluted with EtOAc, poured into a saturated aq. $NaHCO_3$ solution and the aqueous layer was extracted with EtOAc. Combined organics were washed with brine, dried over $Na_2SO_4$, filtered and evaporated. The residue was purified by silica gel flash chromatography, eluting with a 0 to 100% EtOAc-heptane gradient to give the title compound (0.035 g, 59%) as a white foam. MS (ESI): m/z=551.5 [M+H]+.

Example 51

[(7R,9aR)-7-Phenyl-1,3,4,6,7,8,9,9a-octahydropyrido[1,2-a]pyrazin-2-yl]-[2-chloro-3-(1H-pyrazol-4-ylmethoxy)phenyl]methanone To a solution of tert-butyl 4-[[3-[(7R,9aR)-7-phenyl-1,3,4,6,7,8,9,9a-octahydropyrido[1,2-a]pyrazine-2-carbonyl]-2-chlorophenoxy]methyl]pyrazole-1-carboxylate (Example 50, 0.032 g, 0.058 mmol) in MeOH (1 mL) was added 4M HCl in dioxane (0.073 mL, 0.290 mmol) and the reaction mixture was stirred at room temperature for 3 hours. The solvent was evaporated to dryness and the residue triturated in diisopropylether, filtered off and further dried on the high vacuum to give the title compound (0.02 g, 66%) as a white solid as the hydrochloride salt. MS: 451.4 (M+H+).

The following examples listed in Table 4 were prepared in analogy to the procedures described for the preparation of example 50 by reacting example 32 and the indicated commercial compounds and using the mentioned purification method such as preparative HPLC (Gemini NX column) or silica gel flash chromatography.

TABLE 4

| Ex | Name Aspect Purification method | Intermediates | MS, m/z [M + H]+ or [M − H]− |
|---|---|---|---|
| 52 | [(7R,9aR)-7-phenyl-1,3,4,6,7,8,9,9a-octahydropyrido[1,2-a]pyrazin-2-yl]-[2-chloro-3-(pyridazin-3-ylmethoxy)phenyl]methanone<br>Off white foam<br>Flash chromatography | 3-(chloro-methyl)pyridazine hydrochloride (CAS RN 27349-66-2) | 463.3 |
| 53 | [(7R,9aR)-7-phenyl-1,3,4,6,7,8,9,9a-octahydropyrido[1,2-a]pyrazin-2-yl]-[2-chloro-3-(pyridin-4-ylmethoxy)phenyl]methanone<br>Off white solid<br>Flash chromatography | 4-(chloro-methyl)pyridine hydrochloride (CAS RN 10445-91-7) | 462.4 |
| 54 | [(7R,9aR)-7-phenyl-1,3,4,6,7,8,9,9a-octahydropyrido[1,2-a]pyrazin-2-yl]-[2-chloro-3-(pyridin-3-ylmethoxy)phenyl]methanone<br>Colorless amorphous<br>Preparative HPLC | 3-(chloro-methyl)pyridine hydrochloride (CAS RN 3099-31-8) | 462.3 |

Examples 72 and 73

(2-Chloro-3-methoxyphenyl)-[rac-(7R,9aR)-7-(4-chlorophenyl)-7-hydroxy-3,4,6,8,9,9a-hexahydro-1H-pyrido[1,2-a]pyrazin-2-yl]methanone and (2-chloro-3-methoxyphenyl)-[rac-(7R,9aS)-7-(4-chlorophenyl)-7-hydroxy-3,4,6,8,9,9a-hexahydro-1H-pyrido[1,2-a]pyrazin-2-yl]methanone To a solution of 2-(2-chloro-3-methoxy-benzoyl)-3,4,6,8,9,9a-hexahydro-1H-pyrido[1,2-a]pyrazin-7-one (Intermediate I-2, 0.2 g, 0.620 mmol) in THF (10 mL) cooled at 0° C. was added a 1M solution of 4-chlorophenylmagnesium bromide in THF (1.86 mL, 1.86 mmol) dropwise while keeping the temperature below 5° C., then the reaction mixture was stirred at room temperature for 3 hours. The mixture was diluted with EtOAc, poured into a sat. NH$_4$Cl aq. solution (30 mL) and extracted with EtOAc (2×30 mL). The combined organic layer was washed with water (2×30 mL), brine (10 mL), dried over Na$_2$SO$_4$, filtered and concentrated in vacuo. The residue was purified by preparative HPLC to give respectively (2-chloro-3-methoxyphenyl)-[rac-(7R,9aR)-7-(4-chlorophenyl)-7-hydroxy-3,4,6,8,9,9a-hexahydro-1H-pyrido[1,2-a]pyrazin-2-yl]methanone (Example 72) and (2-chloro-3-methoxyphenyl)-[rac-(7R,9aS)-7-(4-chlorophenyl)-7-hydroxy-3,4,6,8,9,9a-hexahydro-1H-pyrido[1,2-a]pyrazin-2-yl]methanone (Example 73) as light yellow solids; MS (ESI): m/z=435.3 [M+H]+.

Examples 72-A and 72-B

[(7S,9aS)-7-(4-chlorophenyl)-7-hydroxy-3,4,6,8,9,9a-hexahydro-1H-pyrido[1,2-a]pyrazin-2-yl]-(2-chloro-3-hydroxy-phenyl)methanone and [(7R,9aR)-7-(4-chlorophenyl)-7-hydroxy-3,4,6,8,9,9a-hexahydro-1H-pyrido[1,2-a]pyrazin-2-yl]-(2-chloro-3-hydroxy-phenyl)methanone (2-Chloro-3-methoxyphenyl)-[rac-(7R,9aR)-7-(4-chlorophenyl)-7-hydroxy-3,4,6,8,9,9a-hexahydro-1H-pyrido[1,2-a]pyrazin-2-yl]methanone (Example 72) was separated by preparative chiral HPLC (DAICEL CHIRALCEL AY-3 (50× 4.6 mm, 3 um), eluent: 0.05% DEA in MeOH, 40%) to give respectively [(7S,9aS)-7-(4-chlorophenyl)-7-hydroxy-3,4,6,8,9,9a-hexahydro-1H-pyrido[1,2-a]pyrazin-2-yl]-(2-chloro-3-hydroxy-phenyl)methanone (Example 72-A, 0.009 g, 4.2%) and [(7R,9aR)-7-(4-chlorophenyl)-7-hydroxy-3,4,6,8,9,9a-hexahydro-1H-pyrido[1,2-a]pyrazin-2-yl]-(2-chloro-3-hydroxy-phenyl)methanone (Example 72-B, 0.012 g, 3.2%) as light yellow solids; MS (ESI): m/z=435.1 [M+H]+.

Examples 73-A and 73-B

[(7S,9aR)-7-(4-chlorophenyl)-7-hydroxy-3,4,6,8,9,9a-hexahydro-1H-pyrido[1,2-a]pyrazin-2-yl]-(2-chloro-3-hydroxy-phenyl)methanone and [(7R,9aS)-7-(4-chlorophenyl)-7-hydroxy-3,4,6,8,9,9a-hexahydro-1H-pyrido[1,2-a]pyrazin-2-yl]-(2-chloro-3-hydroxy-phenyl)methanone (2-Chloro-3-methoxyphenyl)-[rac-(7R,9aS)-7-(4-chlorophenyl)-7-hydroxy-3,4,6,8,9,9a-hexahydro-1H-pyrido[1,2-a]pyrazin-2-yl]methanone (Example 73) was separated by preparative chiral HPLC (DAICEL CHIRALCEL AD-3(50× 4.6 mm, 3 um), eluent: 0.05% DEA in MeOH, 40%) to give respectively [(7S,9aR)-7-(4-chlorophenyl)-7-hydroxy-3,4,6,8,9,9a-hexahydro-1H-pyrido[1,2-a]pyrazin-2-yl]-(2-chloro-3-methoxy-phenyl)methanone (Example 73-A, 0.004 g, 1.4%) and [(7R,9aS)-7-(4-chlorophenyl)-7-hydroxy-3,4,6,8,9,9a-hexahydro-1H-pyrido[1,2-a]pyrazin-2-yl]-(2-chloro-3-methoxy-phenyl)methanone (Example 73-B, 0.002 g, 0.7%) as light yellow solids; MS (ESI): m/z=435.3 [M+H]+.

The following examples listed in Table 5 were prepared in analogy to the procedure described for the preparation of examples 72 and 73 by reacting the indicated intermediates and commercial compounds and using the mentioned purification method such as preparative HPLC (Gemini NX column), silica gel flash chromatography or chiral separation method such as preparative chiral HPLC or SFC.

TABLE 5

| Ex | Name Aspect Purification method | Intermediates | MS, m/z [M + H]+ or [M − H]− |
|---|---|---|---|
| 74 | [2-chloro-3-(difluoromethoxy)phenyl]-[rac-(7R,9aR)-7-(4-chlorophenyl)-7-hydroxy-3,4,6,8,9,9a-hexahydro-1H-pyrido [1,2-a]pyrazin-2-yl]methanone<br>White foam<br>Preparative HPLC | Intermediate 1-3 and 4-chlorophenyl-magnesium bromide | 471.2 |
| 75 | [2-chloro-3-(difluoromethoxy)phenyl]-[rac-(7R,9aS)-7-(4-chlorophenyl)-7-hydroxy-3,4,6,8,9,9a-hexahydro-1H-pyrido [1,2-a]pyrazin-2-yl]methanone<br>White foam<br>Preparative HPLC | Intermediate 1-3 and 4-chlorophenyl-magnesium bromide | 471.2 |
| 76 | [2-chloro-3-(2-oxa-6-azaspiro[3.3]heptan-6-yl)phenyl]-[rac-(7R,9aR)-7-(4-chlorophenyl)-7-hydroxy-3,4,6,8,9,9a-hexahydro-1H-pyrido [1,2-a]pyrazin-2-yl]methanone<br>Colorless amorphous<br>Preparative HPLC | Intermediate 1-4 and 4-chlorophenyl-magnesium bromide | 502.3 |
| 77 | [2-chloro-3-(2-oxa-6-azaspiro[3.3]heptan-6-yl)phenyl]-[rac-(7R,9aS)-7-(4-chlorophenyl)-7- | Intermediate 1-4 and 4-chlorophenyl- | 502.3 |

TABLE 5-continued

| Ex | Name<br>Aspect<br>Purification method | Intermediates | MS, m/z<br>[M + H]+<br>or<br>[M − H]− |
|---|---|---|---|
| | hydroxy-3,4,6,8,9,9a-hexahydro-1H-<br>pyrido [1,2-a]pyrazin-2-<br>yl]methanone<br>Colorless amorphous<br>Preparative HPLC | magnesium<br>bromide | |

Example 78

(2-Chloro-3-methoxyphenyl)-[rac-(7R,9aR)-7-(4-chlorophenyl)-7-fluoro-3,4,6,8,9,9a-hexahydro-1H-pyrido[1,2-a]pyrazin-2-yl]methanone To a solution of (2-chloro-3-methoxyphenyl)-[rac-(7R,9aS)-7-(4-chlorophenyl)-7-hydroxy-3,4,6,8,9,9a-hexahydro-1H-pyrido[1,2-a]pyrazin-2-yl]methanone (Example 73, 0.2 g, 0.460 mmol) in DCM (1 mL) cooled at −78° C., was carefully added DAST (1.11 g, 6.89 mmol) dropwise and the reaction mixture was stirred at this temperature for 3 hours. The mixture was diluted with DCM, poured into a sat. $Na_2CO_3$ aq. solution (30 mL) and the aqueous layer was extracted with DCM (3×30 mL). Combined organics were washed with water (2×20 mL), brine (20 mL), dried over $Na_2SO_4$ and concentrated in vacuo. The residue was purified by preparative HPLC to give the title compound (0.023 g, 10.8%) as a pink solid; MS (ESI): m/z=437.2 [M+H]+.

Example 79

(2-Chloro-3-methoxyphenyl)-[rac-(7R,9aS)-7-(4-chlorophenyl)-7-fluoro-3,4,6,8,9,9a-hexahydro-1H-pyrido[1,2-a]pyrazin-2-yl]methanone Example 79 was prepared in analogy to example 78, but using (2-chloro-3-methoxyphenyl)-[rac-(7R,9aR)-7-(4-chlorophenyl)-7-hydroxy-3,4,6,8,9,9a-hexahydro-1H-pyrido[1,2-a]pyrazin-2-yl]methanone (Example 72) to give the title compound (0.010 g, 4.8%) as a light yellow solid; MS (ESI): m/z=437.2 [M+H]+.

Example 80

(2-Chloro-3-methoxyphenyl)-[rac-(7R,9aR)-7-(4-chlorophenyl)-7-methoxy-3,4,6,8,9,9a-hexahydro-1H-pyrido[1,2-a]pyrazin-2-yl]methanone To a solution of (2-chloro-3-methoxyphenyl)-[rac-(7R,9aR)-7-(4-chlorophenyl)-7-hydroxy-3,4,6,8,9,9a-hexahydro-1H-pyrido[1,2-a]pyrazin-2-yl]methanone (Example 72, 0.190 g, 0.440 mmol) in THF (1 mL) cooled at 0° C., was added 65% NaH dispersion in mineral oil (0.035 g, 0.870 mmol) and the reaction mixture was stirred for 30 minutes. Then, MeI (0.186 g, 1.31 mmol) was added and the reaction mixture was stirred at room temperature for 12 hours. The mixture was diluted with EtOAc, poured into a sat. $NH_4Cl$ aq. solution (20 mL) and the aqueous layer was extracted with EtOAc (3×20 mL). The combined organic layer was washed with water (2×10 mL), brine (10 mL), dried over $Na_2SO_4$ and concentrated in vacuo. The residue was purified by preparative HPLC to give the title compound (0.037 g, 18.6%) as a white solid; MS (ESI): m/z=449.3 [M+H]+.

Example 81

(2-Chloro-3-methoxyphenyl)-[rac-(7R,9aS)-7-(4-chlorophenyl)-7-methoxy-3,4,6,8,9,9a-hexahydro-1H-pyrido[1,2-a]pyrazin-2-yl]methanone Example 81 was prepared in analogy to example 80, but using (2-chloro-3-methoxyphenyl)-[rac-(7R,9aS)-7-(4-chlorophenyl)-7-hydroxy-3,4,6,8,9,9a-hexahydro-1H-pyrido[1,2-a]pyrazin-2-yl]methanone (Example 73) to give the title compound (0.015 g, 7.1%) as a white solid; MS (ESI): m/z=449.2 [M+H]*.

Example 82 and 83

(2-Chloro-3-methoxyphenyl)-[rac-(7R,9aS)-7-methyl-1,3,4,6,7,8,9,9a-octahydropyrido[1,2-a]pyrazin-2-yl]methanone and (2-Chloro-3-methoxyphenyl)-[rac-(7R,9aR)-7-methyl-1,3,4,6,7,8,9,9a-octahydropyrido[1,2-a]pyrazin-2-yl]methanone Step [A] (2-Chloro-3-methoxyphenyl)(7-methylene-hexahydro-1H-pyrido[1,2-a]pyrazin-2(6H)-yl)methanone To a solution of methyltriphenylphosphonium bromide (0.283 g, 1.02 mmol) in THF (10 mL) cooled at 0° C., was added a 1M solution of lithium bis(trimethylsilyl)amide (1.39 mL, 1.39 mmol) in THF dropwise and the reaction mixture was stirred for 1 hour. Then, a solution of 2-(2-chloro-3-methoxy-benzoyl)-3,4,6,8,9,9a-hexahydro-1H-pyrido[1,2-a]pyrazin-7-one (Intermediate I-2, 0.3 g, 0.930 mmol) in THF (5 mL) was added dropwise then the mixture was allowed to warm up to room temperature and stirred for 2 hours. The mixture was diluted with EtOAC, poured into a sat. $NH_4Cl$ aq. solution (10 mL) and extracted with EtOAc (3×5 mL). The combined organic phase was washed with brine, dried over $Na_2SO_4$, filtered and concentrated in vacuo. The residue was purified by preparative HPLC to give the title compound (0.080 g, 26.8%) as a light yellow oil. MS (ESI): m/z=321.0 [M+H]+.

Step [B] (2-Chloro-3-methoxphenyl)-[rac-(7R,9aS)-7-methyl-1,3,4,6,7,8,9,9a-octahydropyrido[1,2-a]pyrazin-2-yl]methanone and (2-Chloro-3-methoxyphenyl)-[rac-(7R,9aR)-7-methyl-1,3,4,6,7,8,9,9a-octahydropyrido[1,2-a]pyrazin-2-yl]methanone To a solution of (2-Chloro-3-methoxy-phenyl)-(7-methylene-3,4,6,8,9,9a-hexahydro-1H-pyrido[1,2-a]pyrazin-2-yl)methanone (0.6 g, 0.190 mmol) and magnesium oxide (0.038 g, 0.940 mmol) in EtOAc (5 mL) was added wet Pd/C (CAS RN 7440-05-3, 0.030 g) and the reaction mixture was stirred at room temperature under $H_2$ atmosphere for 4 hours. The mixture was filtered off and the filtrate was concentrated in vacuo. The residue was purified by preparative HPLC to give respectively (2-chloro-3-methoxyphenyl)-[rac-(7R,9aS)-7-methyl-1,3,4,6,7,8,9,9a-octahydropyrido[1,2-a]pyrazin-2-yl]methanone (Example 82, 0.019 g, 31.4%) and (2-Chloro-3-methoxyphenyl)-[rac-(7R,9aR)-7-methyl-1,3,4,6,7,8,9,9a-octahydropyrido[1,2-a]pyrazin-2- yl]methanone (Example 83, 0.008 g, 12.4%) as white solids; MS (ESI): m/z=323.1 [M+H]+.

Example 84

(2-Chloro-3-methoxyphenyl)-[rac-(7R,9aS)-7-(2-methylpropoxy)-1,3,4,6,7,8,9,9a-octahydropyrido[1,2-a]pyrazin-2-yl]methanone Step [A] (2-Chloro-3-methoxy-phenyl)-[rac-(7R,9aS)-7-[(4-methoxyphenyl)methoxy]-9a-methyl]-3,4,6,7,8,9-hexahydro-1H-pyrido[1,2-a]pyrazin-2-yl]methanone To a solution of (2-chloro-3-methoxy-phenyl)-[7-[(4-methoxyphenyl)methoxy]-1,3,4,6,9,9a-hexahydropyrido[1,2-a]pyrazin-2-yl]methanone (Intermediate 1-2 [A], 0.6 g, 1.35 mmol) and magnesium oxide (0.120 g, 1.35 mmol) in methanol (10 mL) was added wet Pd/C (CAS RN 7440-05-3, 0.06 g) and the reaction mixture was stirred under $H_2$ atmosphere at room temperature for 12 hours. The mixture was filtered off and the filtrate was concentrated in vacuo to get the crude title compound (0.6 g, 99.5%) as a yellow oil; MS (ESI): m/z=445.3 [M+H]+.

Step [B] (2-Chloro-3-methoxy-phenyl)-[rac-(7R,9aS)-7-hydroxy-9a-methyl-3,4,6,7,8,9-hexahydro-1H-pyrido[1,2-a]pyrazin-2-yl]methanone To a solution of 2-chloro-3-methoxy-phenyl)-[rac-(7R,9aS)-7-[(4-methoxyphenyl)methoxy]-9a-methyl-3,4,6,7,8,9-hexahydro-1H-pyrido[1,2-a]pyrazin-2-yl]methanone (0.5 g, 1.12 mmol) and para-toluene sulfonamide (0.104 g, 0.560 mmol) in 1,4-dioxane (10 mL) was added triflic acid (0.084.g, 0.560 mmol) dropwise and the reaction mixture was stirred at room temperature for 12 hours. The mixture was concentrated in vacuo and the residue purified by silica gel flash chromatography to give the crude title compound (0.45 g) as a colorless solid; MS (ESI): m/z=325.1 [M+H]+.

Step [C] (2-Chloro-3-methoxy-phenyl)-[rac-(7R,9aS)-9a-methyl-7-(2-methylallyloxy)-3,4,6,7,8,9-hexahydro-1H-pyrido[1,2-a]pyrazin-2-yl]methanone To a solution of (2-chloro-3-methoxy-phenyl)-[rac-(7R,9aS)-7-hydroxy-9a-methyl-3,4,6,7,8,9-hexahydro-1H-pyrido[1,2-a]pyrazin-2-yl]methanone (0.1 g, crude) in DMF (1 mL) cooled at 0° C., was added 65% NaH dispersion in mineral oil (0.015 g, 0.370 mmol) portionwise and the reaction mixture was stirred for 30 minutes. Then, 3-bromo-2-methylpropene (0.125 g, 0.920 mmol) was added and the reaction mixture was stirred at room temperature for 12 hours. The mixture was diluted with EtOAc, poured into water (10 mL) and extracted with EtOAc (2×20 mL). The combined organic layer was washed with water (2×10 mL), brine (10 mL), dried over $Na_2SO_4$ and concentrated in vacuo to give the crude title compound (0.1 g, 85.7%) as a colorless solid; MS (ESI): m/z=379.3 [M+H]+.

Step [D] (2-Chloro-3-methoxyphenyl)-[rac-(7R,9aS)-7-(2-methylpropoxy)-1,3,4,6,7,8,9,9a-octahydropyrido[1,2-a]pyrazin-2-yl]methanone To a solution of (2-chloro-3-methoxy-phenyl)-[rac-(7R,9aS)-9a-methyl-7-(2-methylallyloxy)-3,4,6,7,8,9-hexahydro-1H-pyrido[1,2-a]pyrazin-2-yl]methanone (0.1 g, 0.260 mmol) and magnesium oxide (0.03 g, 0.750 mmol) in methanol (10 mL) was added wet Pd/C (CAS RN 7440-05-3, 0.01 g) and the reaction mixture was stirred under $H_2$ atmosphere at room temperature for 12 hours. The mixture was filtered off and the filtrate was concentrated in vacuo. The residue was purified by preparative HPLC to give the title compound (0.033 g, 31.9%) as a colorless solid; MS (ESI): m/z=381.1 [M+H]+.

Example 85

(1,3-Dimethylthieno[2,3-c]pyrazol-5-yl)-[rac-(7R,9aR)-7-(3-chloro-4-fluorophenyl)-1,3,4,6,7,8,9,9a-octahydropyrido[1,2-a]pyrazin-2-yl]methanone Example 85 is prepared in analogy to e.g. Example 60, starting from Intermediate A-5 and 1,3-dimethylthieno[2,3-c]pyrazole-5-carboxylic acid.

Example 86

A compound of formula (I) can be used in a manner known per se as the active ingredient for the production of tablets of the following composition:

|  | Per tablet |
| --- | --- |
| Active ingredient | 200 mg |
| Microcrystalline cellulose | 155 mg |
| Corn starch | 25 mg |
| Talc | 25 mg |
| Hydroxypropylmethylcellulose | 20 mg |
|  | 425 mg |

Example 87

A compound of formula (I) can be used in a manner known per se as the active ingredient for the production of capsules of the following composition:

|  | Per capsule |
| --- | --- |
| Active ingredient | 100.0 mg |
| Corn starch | 20.0 mg |
| Lactose | 95.0 mg |
| Talc | 4.5 mg |
| Magnesium stearate | 0.5 mg |
|  | 220.0 mg |

The invention claimed is:
1. A compound of formula (Ie):

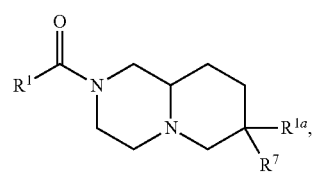

or a pharmaceutically acceptable salt thereof, wherein:
$R^{1a}$ is selected from the group consisting of
(i) $C_{1-6}$-alkyl;
(ii) $C_{1-6}$-alkoxy; and (iii) aryl substituted with $R^2$, $R^3$, $R^4$, $R^5$, and $R^6$, or a combination thereof;

$R^1$ is selected from the group consisting of
(i) aryl substituted with $R^8$, $R^9$, and $R^{10}$; and
(ii) heteroaryl substituted with $R^{11}$ and $R^{12}$;

each of $R^2$, $R^3$, $R^4$, $R^5$, and $R^6$ is independently selected from the group consisting of hydrogen, halogen, alkoxy, haloalkoxy, hydroxy, amino, —NH-alkyl, —N(alkyl)$_2$, and cyano;

$R^7$ is selected from the group consisting of hydrogen, halogen, alkoxy, cycloalkyloxy, and hydroxy;

each of $R^8$, $R^9$, $R^{10}$, $R^{11}$, and $R^{12}$ is independently selected from the group consisting of hydrogen, hydroxy, alkoxy, cyano, alkoxyalkyl, haloalkoxy, halogen, alkyl, haloalkyl, alkylsulfanyl, amino, —NH-alkyl, —N(alkyl)$_2$, —NH-aryl, —NH-heteroaryl, and a group

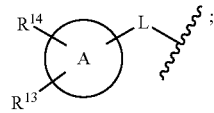

$R^{13}$ is selected from the group consisting of hydrogen, halogen, alkyl, oxo, carbamoyl, substituted carbamoyl, and alkoxycarbonyl, wherein said substituted carbamoyl is substituted at the nitrogen atom with one to two alkyl substituents;

$R^{14}$ is hydrogen or halogen;

L is selected from the group consisting of a covalent bond, —CH=CH—, —O—, —CH$_2$—, —OCH$_2$—, —CH$_2$— and —CH$_2$CH$_2$—; and A is selected from the group consisting of aryl, heteroaryl, cycloalkyl and heterocyclyl;

wherein the compound of formula (Ie) is not (4-fluorophenyl)-[7-(4-fluorophenyl)-1,3,4,6,7,8,9,9a-octahydropyrido[1,2-a]pyrazin-2-yl]methanone.

2. The compound of claim 1, wherein said compound is a compound of formula (I):

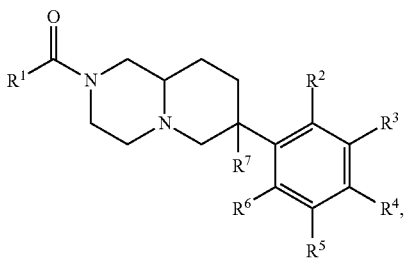

or a pharmaceutically acceptable salt thereof, wherein:
$R^1$ is selected from the group consisting of:
(i) aryl substituted with $R^8$, $R^9$, and $R^{10}$; and
(ii) heteroaryl substituted with $R^{11}$ and $R^{12}$, each of $R^2$, $R^3$, $R^4$, $R^5$ and $R^6$ is independently selected from the group consisting of hydrogen, halogen, alkoxy, haloalkoxy, hydroxy, amino, —NH-alkyl, —N(alkyl)$_2$, and cyano;

$R^7$ is selected from the group consisting of hydrogen, halogen, alkoxy, cycloalkyloxy, and hydroxy;

each of $R^8$, $R^9$, $R^{10}$, $R^{11}$, and $R^{12}$ is independently selected from the group consisting of hydrogen, hydroxy, alkoxy, cyano, alkoxyalkyl, haloalkoxy, halogen, alkyl, haloalkyl, alkylsulfanyl, amino, —NH-alkyl, —N(alkyl)$_2$, —NH-aryl, —NH-heteroaryl, and a group

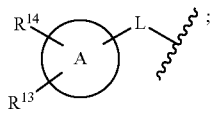

$R^{13}$ is selected from the group consisting of hydrogen, halogen, alkyl, carbamoyl, substituted carbamoyl, and alkoxycarbonyl, wherein said substituted carbamoyl is substituted at the nitrogen atom with one to two alkyl substituents;

$R^{14}$ is hydrogen or halogen;

L is selected from the group consisting of a covalent bond, —CH=CH—, —O—, —CH$_2$O—, —OCH$_2$—, —CH$_2$—, and —CH$_2$CH$_2$—; and A is selected from the group consisting of aryl, heteroaryl, cycloalkyl, and heterocyclyl.

3. The compound of claim 1, wherein said compound is a compound of formula (Ia)

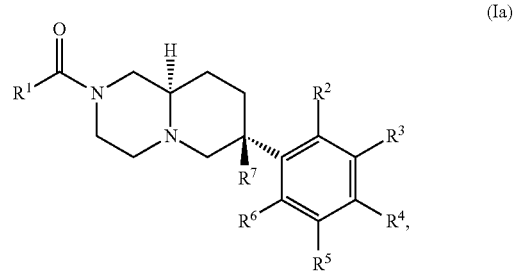

or a pharmaceutically acceptable salt thereof, wherein $R^1$, $R^2$, $R^3$, $R^4$, $R^5$, $R^6$ and $R^7$ are as defined in claim 1.

4. The compound of claim 1, wherein said compound is a compound of formula (Ib)

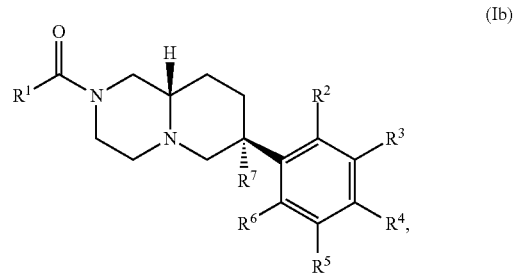

or a pharmaceutically acceptable salt thereof, wherein $R^1$, $R^2$, $R^3$, $R^4$, $R^5$, $R^6$ and $R^7$ are as defined in claim 1.

5. The compound of claim 1, wherein said compound is a compound of formula (Ic):

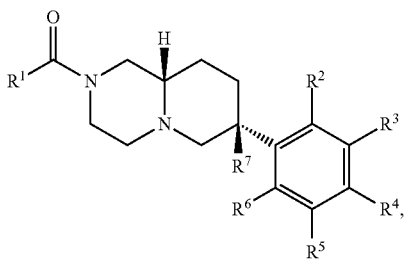

(Ic)

or a pharmaceutically acceptable salt thereof, wherein $R^1$, $R^2$, $R^3$, $R^4$, $R^5$, $R^6$ and $R^7$ are as defined in claim 1.

6. The compound of claim 1, wherein said compound is a compound of formula (Id):

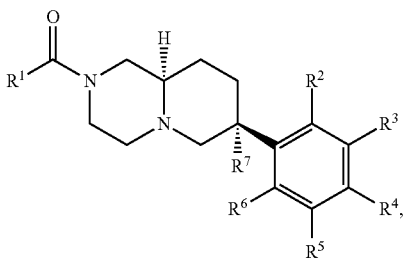

(Id)

or a pharmaceutically acceptable salt thereof, wherein $R^1$, $R^2$, $R^3$, $R^4$, $R^5$, $R^6$ and $R^7$ are as defined in claim 1.

7. The compound of claim 1, or a pharmaceutically acceptable salt thereof, wherein:
$R^1$ is selected from the group consisting of
(i) aryl substituted with $R^8$, $R^9$ and $R^{10}$; and
(ii) heteroaryl substituted with $R^{11}$ and $R^{12}$;
$R^8$ is selected from the group consisting of hydroxy, alkoxy, cyano, alkoxyalkyl, haloalkoxy, halogen, alkyl, haloalkyl, and a group

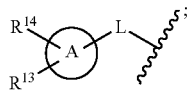

$R^9$ is hydrogen or halogen;
$R^{10}$ is hydrogen or halogen;
$R^{11}$ is selected from the group consisting of hydrogen, halogen, alkyl, alkoxy, and alkylsulfanyl;
$R^{12}$ is selected from the group consisting of hydrogen, halogen, and alkyl;
$R^{13}$ is selected from the group consisting of hydrogen, halogen, alkyl, carbamoyl, substituted carbamoyl, and alkoxycarbonyl, wherein said substituted carbamoyl is substituted at the nitrogen atom with one to two alkyl substituents;
$R^{14}$ is hydrogen or halogen;
L is selected from the group consisting of a covalent bond, —CH=CH—, —O—, and —CH$_2$O—; and
A is selected from the group consisting of aryl, heteroaryl, cycloalkyl and heterocyclyl.

8. The compound of claim 1, or a pharmaceutically acceptable salt thereof, wherein:
$R^1$ is selected from the group consisting of
(i) aryl substituted with $R^8$, $R^9$ and $R^{10}$; and
(ii) heteroaryl substituted with $R^{11}$ and $R^{12}$;
$R^8$ is selected from the group consisting of alkoxy, haloalkoxy, alkyl and a group

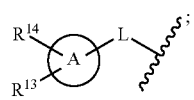

$R^9$ is halogen;
$R^{10}$ is hydrogen or halogen;
$R^{11}$ is selected from the group consisting of hydrogen, alkyl and alkylsulfanyl;
$R^{12}$ is selected from the group consisting of hydrogen, halogen and alkyl;
$R^{13}$ is hydrogen;
$R^{14}$ is hydrogen;
L is a covalent bond or —CH$_2$O—; and
A is heteroaryl or heterocyclyl.

9. The compound of claim 1, or a pharmaceutically acceptable salt thereof, wherein:
$R^1$ is selected from the group consisting of:
(i) phenyl substituted with $R^8$, $R^9$, and $R^{10}$; and
(ii) heteroaryl substituted with $R^{11}$ and $R^{12}$, wherein said heteroaryl is selected from the group consisting of indolyl, pyrrolo[2,3-b]pyridyl, 1,3-benzothiazolyl, thiazolo[5,4-b]pyridyl, 1H-indazol-5-yl, thieno[2,3-b]pyridin-5-yl, and pyrazolo[3,4-b]pyridyl;
$R^8$ is selected from the group consisting of methoxy, 2,2,2-trifluoroethoxy, methyl, and a group

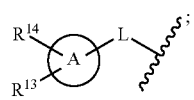

$R^9$ is Cl or Br;
$R^{10}$ is hydrogen or F;
$R^{11}$ is selected from the group consisting of hydrogen, methyl, and methylsulfanyl;
$R^{12}$ is selected from the group consisting of hydrogen, Cl, and methyl;
$R^{13}$ is hydrogen;
$R^{14}$ is hydrogen;
L is a covalent bond or —CH$_2$O—; and
A is thiazolyl, pyrazolyl, or 2-oxa-6-azaspiro[3.3]heptan-6-yl.

10. The compound of claim 1, or a pharmaceutically acceptable salt thereof, wherein $R^2$ is hydrogen.

11. The compound claim 1, or a pharmaceutically acceptable salt thereof, wherein $R^3$ is selected from the group consisting of hydrogen and halogen.

12. The compound of claim 1, wherein $R^3$ is selected from the group consisting of hydrogen and Cl.

13. The compound of claim 1, or a pharmaceutically acceptable salt thereof, wherein $R^4$ is selected from the group consisting of hydrogen and halogen.

14. The compound of claim 1, or a pharmaceutically acceptable salt thereof, wherein $R^4$ is selected from the group consisting of hydrogen, F and Cl.

15. The compound of claim 1, or a pharmaceutically acceptable salt thereof, wherein $R^5$ is hydrogen.

16. The compound of claim 1, or a pharmaceutically acceptable salt thereof, wherein $R^6$ is hydrogen.

17. The compound of claim 1, or a pharmaceutically acceptable salt thereof, wherein $R^7$ is selected from the group consisting of hydrogen, F, methoxy, and hydroxy.

18. The compound of claim 1, or a pharmaceutically acceptable salt thereof, wherein:
   $R^2$ is hydrogen;
   $R^3$ is selected from the group consisting of hydrogen and halogen;
   $R^4$ is selected from the group consisting of hydrogen and halogen;
   $R^5$ is hydrogen;
   $R^6$ is hydrogen; and
   $R^7$ is selected from the group consisting of hydrogen, F, methoxy, and hydroxy.

19. The compound of claim 1, or a pharmaceutically acceptable salt thereof, wherein
   $R^{1a}$ is selected from the group consisting of
      (i) $C_{1-6}$-alkyl;
      (i) $C_{1-6}$-alkoxy; and
      (ii) aryl substituted with $R^2$, $R^3$, $R^4$, $R^5$ and $R^6$, or a possible combination thereof;
   $R^1$ is selected from the group consisting of
      (i) aryl substituted with $R^8$, $R^9$ and $R^{10}$; and
      (ii) heteroaryl substituted with $R^{11}$ and $R^{12}$;
   $R^2$, $R^5$, and $R^6$ are hydrogen;
   $R^3$ and $R^4$ are independently selected from the group consisting of hydrogen and halogen;
   $R^7$ is selected from the group consisting of hydrogen, halogen, alkoxy, and hydroxy;
   $R^8$ is selected from the group consisting of hydroxy, alkoxy, cyano, alkoxyalkyl, haloalkoxy, halogen, alkyl, haloalkyl, and a group

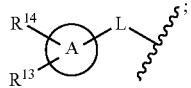

$R^9$ is hydrogen or halogen;
   $R^{10}$ is hydrogen or halogen;
   $R^{11}$ is selected from the group consisting of hydrogen, halogen, alkyl, alkoxy, and alkylsulfanyl;
   $R^{12}$ is selected from the group consisting of hydrogen, halogen, and alkyl;
   $R^{13}$ is selected from the group consisting of hydrogen, halogen, alkyl, carbamoyl, substituted carbamoyl, and alkoxycarbonyl, wherein said substituted carbamoyl is substituted at the nitrogen atom with one to two alkyl substituents;
   $R^{14}$ is hydrogen or halogen;
   L is selected from the group consisting of a covalent bond, —CH=CH—, —O— and —CH$_2$O—; and
   A is selected from the group consisting of aryl, heteroaryl, cycloalkyl, and heterocyclyl.

20. The compound of claim 1, or a pharmaceutically acceptable salt thereof, wherein:
   $R^{1a}$ is aryl substituted with $R^2$, $R^3$, $R^4$, $R^5$, and $R^6$, or a possible combination thereof;
   $R^1$ is selected from the group consisting of:
      (i) aryl substituted with $R^8$, $R^9$, and $R^{10}$; and
      (ii) heteroaryl substituted with $R^{11}$ and $R^{12}$;
   $R^2$, $R^5$, and $R^6$ are hydrogen;
   $R^3$ and $R^4$ are independently selected from the group consisting of hydrogen and halogen;
   $R^7$ is selected from the group consisting of hydrogen, halogen, alkoxy, and hydroxy;
   $R^8$ is selected from the group consisting of alkoxy, haloalkoxy, alkyl, and a group

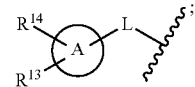

$R^9$ is halogen;
   $R^{10}$ is hydrogen or halogen;
   $R^{11}$ is selected from the group consisting of hydrogen, alkyl, and alkylsulfanyl;
   $R^{12}$ is selected from the group consisting of hydrogen, halogen, and alkyl;
   $R^{13}$ is hydrogen;
   $R^{14}$ is hydrogen;
   L is a covalent bond or —CH$_2$O—; and
   A is heteroaryl or heterocyclyl.

21. The compound of claim 1, or a pharmaceutically acceptable salt thereof, wherein:
   $R^{1a}$ is phenyl substituted with $R^2$, $R^3$, $R^4$, $R^5$, and $R^6$, or a possible combination thereof;
   $R^1$ is selected from the group consisting of
      (i) phenyl substituted with $R^8$, $R^9$, and $R^{10}$; and
      (ii) heteroaryl substituted with $R^{11}$ and $R^{12}$, wherein said heteroaryl is selected from the group consisting of indolyl, pyrrolo[2,3-b]pyridyl, 1,3-benzothiazolyl, thiazolo[5,4-b]pyridyl, 1H-indazol-5-yl, thieno[2,3-b]pyridin-5-yl, and pyrazolo[3,4-b]pyridyl;
   $R^2$, $R^5$, and $R^6$ are hydrogen;
   $R^3$ is selected from the group consisting of hydrogen and Cl;
   $R^4$ is selected from the group consisting of hydrogen, F and Cl;
   $R^7$ is selected from the group consisting of hydrogen, F, methoxy, and hydroxy;
   $R^8$ is selected from the group consisting of methoxy, 2,2,2-trifluoroethoxy, methyl, and a group

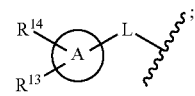

$R^9$ is Cl or Br;
   $R^{10}$ is hydrogen or F;
   $R^{11}$ is selected from the group consisting of hydrogen, methyl, and methylsulfanyl;
   $R^{12}$ is selected from the group consisting of hydrogen, Cl, and methyl;
   $R^{13}$ is hydrogen;
   $R^{14}$ is hydrogen;
   L is a covalent bond or —CH$_2$O—; and
   A is thiazolyl, pyrazolyl, or 2-oxa-6-azaspiro[3.3]heptan-6-yl.

22. The compound of claim 1, selected from the group consisting of:
   [(7R,9aR)-7-(4-chlorophenyl)-1,3,4,6,7,8,9,9a-octahydropyrido[1,2-a]pyrazin-2-yl]-(3-phenoxyphenyl)methanone;
   [(7R,9aR)-7-(4-chlorophenyl)-1,3,4,6,7,8,9,9a-octahydropyrido[1,2-a]pyrazin-2-yl]-(2-chloro-3-methylphenyl)methanone;

[(7R,9aR)-7-(4-chlorophenyl)-1,3,4,6,7,8,9,9a-octahydropyrido[1,2-a]pyrazin-2-yl]-(2-bromo-3-methoxyphenyl)methanone;
[(7R,9aR)-7-(4-chlorophenyl)-1,3,4,6,7,8,9,9a-octahydropyrido[1,2-a]pyrazin-2-yl]-(2-bromo-3-methoxyphenyl)methanone;hydrochloride;
[(7R,9aR)-7-(4-chlorophenyl)-1,3,4,6,7,8,9,9a-octahydropyrido[1,2-a]pyrazin-2-yl]-[3-(3,5-difluorophenoxy)phenyl]methanone;
[(7R,9aR)-7-phenyl-1,3,4,6,7,8,9,9a-octahydropyrido[1,2-a]pyrazin-2-yl]-(2-bromo-3-mrethoxyphenyl)methanone;
[(7R,9aR)-7-(4-chlorophenyl)-1,3,4,6,7,8,9,9a-octahydropyrido[1,2-a]pyrazin-2-yl]-(2-chloro-3-methoxyphenyl)methanone;
[(7R,9aR)-7-(4-chlorophenyl)-1,3,4,6,7,8,9,9a-octahydropyrido[1,2-a]pyrazin-2-yl]-(2-methoxyphenyl)methanone;
[(7R,9aR)-7-(4-chlorophenyl)-1,3,4,6,7,8,9,9a-octahydropyrido[1,2-a]pyrazin-2-yl]-[2-(trifluoromethoxy)phenyl]methanone;
[(7R,9aR)-7-(4-chlorophenyl)-1,3,4,6,7,8,9,9a-octahydropyrido[1,2-a]pyrazin-2-yl]-(2,3-dihydro-1-benzofuran-7-yl)methanone;
[(7R,9aR)-7-(4-chlorophenyl)-1,3,4,6,7,8,9,9a-octahydropyrido[1,2-a]pyrazin-2-yl]-(1H-indol-4-yl)methanone;
[(7R,9aR)-7-(4-chlorophenyl)-1,3,4,6,7,8,9,9a-octahydropyrido[1,2-a]pyrazin-2-yl]-(2-chloro-6-fluorophenyl)methanone;
[(7R,9aR)-7-(4-chlorophenyl)-1,3,4,6,7,8,9,9a-octahydropyrido[1,2-a]pyrazin-2-yl]-(2-chlorophenyl)methanone;
[(7R,9aR)-7-(4-chlorophenyl)-1,3,4,6,7,8,9,9a-octahydropyrido[1,2-a]pyrazin-2-yl]-(2-fluoro-3-methylphenyl)methanone;
[(7R,9aR)-7-(4-chlorophenyl)-1,3,4,6,7,8,9,9a-octahydropyrido[1,2-a]pyrazin-2-yl]-(4-chloro-1H-pyrrolo[2,3-b]pyridin-5-yl)methanone;
[(7R,9aR)-7-(4-chlorophenyl)-1,3,4,6,7,8,9,9a-octahydropyrido[1,2-a]pyrazin-2-yl]-(1H-pyrrolo[2,3-b]pyridin-4-yl)methanone;
[(7R,9aR)-7-(4-chlorophenyl)-1,3,4,6,7,8,9,9a-octahydropyrido[1,2-a]pyrazin-2-yl]-[2-chloro-3-(trifluoromethyl)phenyl]methanone;
[(7R,9aR)-7-(4-chlorophenyl)-1,3,4,6,7,8,9,9a-octahydropyrido[1,2-a]pyrazin-2-yl]-(2-chloro-4-fluoro-3-methylphenyl)methanone;
[(7R,9aR)-7-(4-chlorophenyl)-1,3,4,6,7,8,9,9a-octahydropyrido[1,2-a]pyrazin-2-yl]-(3-chloro-2-methylphenyl)methanone;
[(7R,9aR)-7-(4-chlorophenyl)-1,3,4,6,7,8,9,9a-octahydropyrido[1,2-a]pyrazin-2-yl]-(4-chloro-6-methylpyridin-3-yl)methanone;
[(7R,9aR)-7-(4-chlorophenyl)-1,3,4,6,7,8,9,9a-octahydropyrido[1,2-a]pyrazin-2-yl]-(2,4-dimethyl-1,3-benzothiazol-5-yl)methanone;
[(7R,9aR)-7-(4-chlorophenyl)-1,3,4,6,7,8,9,9a-octahydropyrido[1,2-a]pyrazin-2-yl]-(7-chloro-2-methylsulfanyl-[1,3]thiazolo[5,4-b]pyridin-6-yl)methanone;
[(7R,9aR)-7-(4-chlorophenyl)-1,3,4,6,7,8,9,9a-octahydropyrido[1,2-a]pyrazin-2-yl]-(1-benzothiophen-4-yl)methanone;
[(7R,9aR)-7-(4-chlorophenyl)-1,3,4,6,7,8,9,9a-octahydropyrido[1,2-a]pyrazin-2-yl]-(2-bromo-3-methylphenyl)methanone;
[(7R,9aR)-7-(4-chlorophenyl)-1,3,4,6,7,8,9,9a-octahydropyrido[1,2-a]pyrazin-2-yl]-[2-(trifluoromethyl)phenyl]methanone;
[(7R,9aR)-7-(4-chlorophenyl)-1,3,4,6,7,8,9,9a-octahydropyrido[1,2-a]pyrazin-2-yl]-(2-chloro-3-phenoxyphenyl)methanone;
[(7R,9aR)-7-phenyl-1,3,4,6,7,8,9,9a-octahydropyrido[1,2-a]pyrazin-2-yl]-(2-chloro-3-methylphenyl)methanone;
[(7R,9aR)-7-phenyl-1,3,4,6,7,8,9,9a-octahydropyrido[1,2-a]pyrazin-2-yl]-(2-chloro-3-methylphenyl)methanone;hydrochloride;
[(7R,9aR)-7-phenyl-1,3,4,6,7,8,9,9a-octahydropyrido[1,2-a]pyrazin-2-yl]-(2-chloro-5-fluoro-3-methylphenyl)methanone;
[(7R,9aR)-7-phenyl-1,3,4,6,7,8,9,9a-octahydropyrido[1,2-a]pyrazin-2-yl]-[2-bromo-3-(methoxymethyl)phenyl]methanone;
[(7R,9aR)-7-phenyl-1,3,4,6,7,8,9,9a-octahydropyrido[1,2-a]pyrazin-2-yl]-(1H-indol-4-yl)methanone;
[(7R,9aR)-7-phenyl-1,3,4,6,7,8,9,9a-octahydropyrido[1,2-a]pyrazin-2-yl]-(1-methylindol-4-yl)methanone;
[(7R,9aR)-7-phenyl-1,3,4,6,7,8,9,9a-octahydropyrido[1,2-a]pyrazin-2-yl]-(4-chloro-1H-pyrrolo[2,3-b]pyridin-5-yl)methanone;
[(7R,9aR)-7-phenyl-1,3,4,6,7,8,9,9a-octahydropyrido[1,2-a]pyrazin-2-yl]-(2-chloro-3-hydroxyphenyl)methanone;
[(7R,9aR)-7-phenyl-1,3,4,6,7,8,9,9a-octahydropyrido[1,2-a]pyrazin-2-yl]-(3-methylthieno[3,2-c]pyridin-7-yl)methanone;
[(7R,9aR)-7-phenyl-1,3,4,6,7,8,9,9a-octahydropyrido[1,2-a]pyrazin-2-yl]-(1-methyl-2,3-dihydroindol-4-yl)methanone;
[(7R,9aR)-7-phenyl-1,3,4,6,7,8,9,9a-octahydropyrido[1,2-a]pyrazin-2-yl]-(1-propan-2-ylindol-4-yl)methanone;
[(7R,9aR)-7-phenyl-1,3,4,6,7,8,9,9a-octahydropyrido[1,2-a]pyrazin-2-yl]-(2-chloro-3-propan-2-yloxyphenyl)methanone;hydrochloride;
3-[(7R,9aR)-7-phenyl-1,3,4,6,7,8,9,9a-octahydropyrido[1,2-a]pyrazine-2-carbonyl]-2-chlorobenzonitrile;
[(7R,9aR)-7-phenyl-1,3,4,6,7,8,9,9a-octahydropyrido[1,2-a]pyrazin-2-yl]-(4-chloro-1-methylpyrrolo[2,3-b]pyridin-5-yl)methanone;
[(7R,9aR)-7-phenyl-1,3,4,6,7,8,9,9a-octahydropyrido[1,2-a]pyrazin-2-yl]-[2-chloro-3-[(1-methylpyrazol-4-yl)methoxy]phenyl]methanone;
[(7R,9aR)-7-phenyl-1,3,4,6,7,8,9,9a-octahydropyrido[1,2-a]pyrazin-2-yl]-(4-chloro-1-propan-2-ylpyrrolo[2,3-b]pyridin-5-yl)methanone;
[(7S,9aS)-7-(4-chlorophenyl)-1,3,4,6,7,8,9,9a-octahydropyrido[1,2-a]pyrazin-2-yl]-(2-bromo-3-methoxyphenyl)methanone;
[(7R,9aR)-7-phenyl-1,3,4,6,7,8,9,9a-octahydropyrido[1,2-a]pyrazin-2-yl]-(4-chloro-1H-pyrazolo[3,4-b]pyridin-5-yl)methanone;
[(7R,9aR)-7-phenyl-1,3,4,6,7,8,9,9a-octahydropyrido[1,2-a]pyrazin-2-yl]-(1-benzofuran-4-yl)methanone;
[(7R,9aR)-7-phenyl-1,3,4,6,7,8,9,9a-octahydropyrido[1,2-a]pyrazin-2-yl]-(3-chloro-2-methoxypyridin-4-yl)methanone;
[(7R,9aR)-7-(4-chlorophenyl)-1,3,4,6,7,8,9,9a-octahydropyrido[1,2-a]pyrazin-2-yl]-(4-chloro-1-methylpyrrolo[2,3-b]pyridin-5-yl)methanone;

[(7R,9aR)-7-phenyl-1,3,4,6,7,8,9,9a-octahydropyrido[1,2-a]pyrazin-2-yl]-[2-chloro-3-(1,3-thiazol-4-ylmethoxy)phenyl]methanone;
4-[[3-[(7R,9aR)-7-phenyl-1,3,4,6,7,8,9,9a-octahydropyrido[1,2-a]pyrazine-2-carbonyl]-2-chlorophenoxy]methyl]-N-methylbenzamide;
[(7R,9aR)-7-(4-chlorophenyl)-1,3,4,6,7,8,9,9a-octahydropyrido[1,2-a]pyrazin-2-yl]-(4-chloro-1-methylpyrazolo[3,4-b]pyridin-5-yl)methanone;
[(7R,9aR)-7-(3,4-dichlorophenyl)-1,3,4,6,7,8,9,9a-octahydropyrido[1,2-a]pyrazin-2-yl]-(2-bromo-3-methoxyphenyl)methanone;
[(7S,9aS)-7-(3,4-dichlorophenyl)-1,3,4,6,7,8,9,9a-octahydropyrido[1,2-a]pyrazin-2-yl]-(2-bromo-3-methoxyphenyl)methanone;
[(7R,9aR)-7-(4-chlorophenyl)-1,3,4,6,7,8,9,9a-octahydropyrido[1,2-a]pyrazin-2-yl]-[2-chloro-3-(2,2,2-trifluoroethoxy)phenyl]methanone;
[(7R,9aR)-7-(4-chlorophenyl)-1,3,4,6,7,8,9,9a-octahydropyrido[1,2-a]pyrazin-2-yl]-(6-methoxypyridin-2-yl)methanone;
[(7R,9aR)-7-(4-chlorophenyl)-1,3,4,6,7,8,9,9a-octahydropyrido[1,2-a]pyrazin-2-yl]-imidazo[1,2-a]pyridin-5-ylmethanone;
tert-butyl 4-[[3-[(7R,9aR)-7-phenyl-1,3,4,6,7,8,9,9a-octahydropyrido[1,2-a]pyrazine-2-carbonyl]-2-chlorophenoxy]methyl]pyrazole-1-carboxylate;
[(7R,9aR)-7-phenyl-1,3,4,6,7,8,9,9a-octahydropyrido[1,2-a]pyrazin-2-yl]-[2-chloro-3-(1H-pyrazol-4-ylmethoxy)phenyl]methanone;hydrochloride;
[(7R,9aR)-7-phenyl-1,3,4,6,7,8,9,9a-octahydropyrido[1,2-a]pyrazin-2-yl]-[2-chloro-3-(pyridazin-3-ylmethoxy)phenyl]methanone;
[(7R,9aR)-7-phenyl-1,3,4,6,7,8,9,9a-octahydropyrido[1,2-a]pyrazin-2-yl]-[2-chloro-3-(pyridin-4-ylmethoxy)phenyl]methanone;
[(7R,9aR)-7-phenyl-1,3,4,6,7,8,9,9a-octahydropyrido[1,2-a]pyrazin-2-yl]-[2-chloro-3-(pyridin-3-ylmethoxy)phenyl]methanone;
3-[(E)-2-[4-[(7R,9aR)-7-(4-chlorophenyl)-1,3,4,6,7,8,9,9a-octahydropyrido[1,2-a]pyrazine-2-carbonyl]phenyl]vinyl]-2-bromo-N-methyl-benzamide;
3-[(E)-2-[4-[(7S,9aS)-7-(4-chlorophenyl)-1,3,4,6,7,8,9,9a-octahydropyrido[1,2-a]pyrazine-2-carbonyl]phenyl]vinyl]-2-bromo-N-methyl-benzamide;
3-[(E)-2-[4-[(7S,9aS)-7-(4-chlorophenyl)-1,3,4,6,7,8,9,9a-octahydropyrido[1,2-a]pyrazine-2-carbonyl]-3-bromo-phenyl]vinyl]-N-methyl-benzamide;
3-[(E)-2-[4-[(7R,9aR)-7-(4-chlorophenyl)-1,3,4,6,7,8,9,9a-octahydropyrido[1,2-a]pyrazine-2-carbonyl]-3-bromo-phenyl]vinyl]-N-methyl-benzamide;
[(7R,9aR)-7-(3-chloro-4-fluorophenyl)-1,3,4,6,7,8,9,9a-octahydropyrido[1,2-a]pyrazin-2-yl]-(2-chloro-3-methoxyphenyl)methanone;
[(7S,9aS)-7-(3-chloro-4-fluorophenyl)-1,3,4,6,7,8,9,9a-octahydropyrido[1,2-a]pyrazin-2-yl]-(2-chloro-3-methoxyphenyl)methanone;
[(7R,9aR)-7-(4-chlorophenyl)-1,3,4,6,7,8,9,9a-octahydropyrido[1,2-a]pyrazin-2-yl]-[2-chloro-3-[(E)-2-cyclopropylethenyl]phenyl]methanone;
[(7R,9aR)-7-(4-chlorophenyl)-1,3,4,6,7,8,9,9a-octahydropyrido[1,2-a]pyrazin-2-yl]-(4-chloro-5-methoxypyridin-3-yl)methanone;
(4-chloro-1H-pyrazolo[3,4-b]pyridin-5-yl)-[rac-(7R,9aR)-7-(3-chloro-4-fluorophenyl)-1,3,4,6,7,8,9,9a-octahydropyrido[1,2-a]pyrazin-2-yl]methanone;
[(7R,9aR)-7-(3-chloro-4-fluorophenyl)-1,3,4,6,7,8,9,9a-octahydropyrido[1,2-a]pyrazin-2-yl]-(4-chloro-1H-pyrazolo[3,4-b]pyridin-5-yl)methanone;
[(7S,9aS)-7-(3-chloro-4-fluorophenyl)-1,3,4,6,7,8,9,9a-octahydropyrido[1,2-a]pyrazin-2-yl]-(4-chloro-1H-pyrazolo[3,4-b]pyridin-5-yl)methanone;
(3-methyl-1H-indazol-5-yl)-[rac-(7R,9aR)-7-(3-chloro-4-fluorophenyl)-1,3,4,6,7,8,9,9a-octahydropyrido[1,2-a]pyrazin-2-yl]methanone;
[(7S,9aS)-7-(3-chloro-4-fluorophenyl)-1,3,4,6,7,8,9,9a-octahydropyrido[1,2-a]pyrazin-2-yl]-(3-methyl-1H-indazol-5-yl)methanone;
[(7R,9aR)-7-(3-chloro-4-fluorophenyl)-1,3,4,6,7,8,9,9a-octahydropyrido[1,2-a]pyrazin-2-yl]-(3-methyl-1H-indazol-5-yl)methanone;
(3-methyl-[1,2,4]triazolo[4,3-a]pyridin-6-yl)-[rac-(7R,9aR)-7-(3-chloro-4-fluorophenyl)-1,3,4,6,7,8,9,9a-octahydropyrido[1,2-a]pyrazin-2-yl]methanone;
(3-chloroimidazo[1,2-a]pyridin-6-yl)-[rac-(7R,9aR)-7-(3-chloro-4-fluorophenyl)-1,3,4,6,7,8,9,9a-octahydropyrido[1,2-a]pyrazin-2-yl]methanone;
(4-chlorothieno[2,3-b]pyridin-5-yl)-[rac-(7R,9aR)-7-(3-chloro-4-fluorophenyl)-1,3,4,6,7,8,9,9a-octahydropyrido[1,2-a]pyrazin-2-yl]methanone;
[(7R,9aR)-7-(3-chloro-4-fluorophenyl)-1,3,4,6,7,8,9,9a-octahydropyrido[1,2-a]pyrazin-2-yl]-(4-chlorothieno[2,3-b]pyridin-5-yl)methanone;
[(7S,9aS)-7-(3-chloro-4-fluorophenyl)-1,3,4,6,7,8,9,9a-octahydropyrido[1,2-a]pyrazin-2-yl]-(4-chlorothieno[2,3-b]pyridin-5-yl)methanone;
(4-chloro-3-methyl-[1,2]oxazolo[5,4-b]pyridin-5-yl)-[rac-(7R,9aR)-7-(3-chloro-4-fluorophenyl)-1,3,4,6,7,8,9,9a-octahydropyrido[1,2-a]pyrazin-2-yl]methanone;
[(7R,9aR)-7-(3-chloro-4-fluorophenyl)-1,3,4,6,7,8,9,9a-octahydropyrido[1,2-a]pyrazin-2-yl]-(4-chloro-3-methyl-[1,2]oxazolo[5,4-b]pyridin-5-yl)methanone;
[(7S,9aS)-7-(3-chloro-4-fluorophenyl)-1,3,4,6,7,8,9,9a-octahydropyrido[1,2-a]pyrazin-2-yl]-(4-chloro-3-methyl-[1,2]oxazolo[5,4-b]pyridin-5-yl)methanone;
(4-chloro-1H-indazol-5-yl)-[rac-(7R,9aR)-7-(3-chloro-4-fluorophenyl)-1,3,4,6,7,8,9,9a-octahydropyrido[1,2-a]pyrazin-2-yl]methanone;
[2-chloro-3-(difluoromethoxy)phenyl]-[rac-(7R,9aR)-7-(3-chloro-4-fluorophenyl)-1,3,4,6,7,8,9,9a-octahydropyrido[1,2-a]pyrazin-2-yl]methanone;
[(7S,9aS)-7-(3-chloro-4-fluorophenyl)-1,3,4,6,7,8,9,9a-octahydropyrido[1,2-a]pyrazin-2-yl]-[2-chloro-3-(difluoromethoxy)phenyl]methanone;
[(7R,9aR)-7-(3-chloro-4-fluorophenyl)-1,3,4,6,7,8,9,9a-octahydropyrido[1,2-a]pyrazin-2-yl]-[2-chloro-3-(difluoromethoxy)phenyl]methanone;
(4-chloro-3-methyl-1H-indazol-5-yl)-[rac-(7R,9aR)-7-(3-chloro-4-fluorophenyl)-1,3,4,6,7,8,9,9a-octahydropyrido[1,2-a]pyrazin-2-yl]methanone;
(4-chloro-[1,2]thiazolo[5,4-b]pyridin-5-yl)-[rac-(7R,9aR)-7-(3-chloro-4-fluoro phenyl)-1,3,4,6,7,8,9,9a-octahydropyrido[1,2-a]pyrazin-2-yl]methanone;
(6-amino-4-chloropyridin-3-yl)-[rac-(7R,9aR)-7-(3-chloro-4-fluorophenyl)-1,3,4,6,7,8,9,9a-octahydropyrido[1,2-a]pyrazin-2-yl]methanone;
(4-chloro-3-methyl-1H-indazol-5-yl)-[rac-(7R,9aR)-7-(4-chlorophenyl)-7-hydroxy-3,4,6,8,9,9a-hexahydro-1H-pyrido[1,2-a]pyrazin-2-yl]methanone;
(4-chloro-3-methyl-1H-indazol-5-yl)-[rac-(7R,9aS)-7-(4-chlorophenyl)-7-hydroxy-3,4,6,8,9,9a-hexahydro-1H-pyrido[1,2-a]pyrazin-2-yl]methanone;

[(7S,9aR)-7-(4-chlorophenyl)-7-hydroxy-3,4,6,8,9,9a-hexahydro-1H-pyrido[1,2-a]pyrazin-2-yl]-(4-chloro-3-methyl-1H-indazol-5-yl)methanone;
[(7R,9aS)-7-(4-chlorophenyl)-7-hydroxy-3,4,6,8,9,9a-hexahydro-1H-pyrido[1,2-a]pyrazin-2-yl]-(4-chloro-3-methyl-1H-indazol-5-yl)methanone;
(2-chloro-3-methoxyphenyl)-[rac-(7R,9aR)-7-(4-chlorophenyl)-7-hydroxy-3,4,6,8,9,9a-hexahydro-1H-pyrido[1,2-a]pyrazin-2-yl]methanone;
[(7S,9aS)-7-(4-chlorophenyl)-7-hydroxy-3,4,6,8,9,9a-hexahydro-1H-pyrido[1,2-a]pyrazin-2-yl]-(2-chloro-3-methoxyphenyl)methanone;
[(7R,9aR)-7-(4-chlorophenyl)-7-hydroxy-3,4,6,8,9,9a-hexahydro-1H-pyrido[1,2-a]pyrazin-2-yl]-(2-chloro-3-methoxyphenyl)methanone;
(2-chloro-3-methoxyphenyl)-[rac-(7R,9aS)-7-(4-chlorophenyl)-7-hydroxy-3,4,6,8,9,9a-hexahydro-1H-pyrido[1,2-a]pyrazin-2-yl]methanone;
[(7S,9aR)-7-(4-chlorophenyl)-7-hydroxy-3,4,6,8,9,9a-hexahydro-1H-pyrido[1,2-a]pyrazin-2-yl]-(2-chloro-3-methoxyphenyl)methanone;
[(7R,9aS)-7-(4-chlorophenyl)-7-hydroxy-3,4,6,8,9,9a-hexahydro-1H-pyrido[1,2-a]pyrazin-2-yl]-(2-chloro-3-methoxyphenyl)methanone;
[2-chloro-3-(difluoromethoxy)phenyl]-[rac-(7R,9aR)-7-(4-chlorophenyl)-7-hydroxy-3,4,6,8,9,9a-hexahydro-1H-pyrido[1,2-a]pyrazin-2-yl]methanone;
[2-chloro-3-(difluoromethoxy)phenyl]-[rac-(7R,9aS)-7-(4-chlorophenyl)-7-hydroxy-3,4,6,8,9,9a-hexahydro-1H-pyrido[1,2-a]pyrazin-2-yl]methanone;
[2-chloro-3-(2-oxa-6-azaspiro[3.3]heptan-6-yl)phenyl]-[rac-(7R,9aR)-7-(4-chlorophenyl)-7-hydroxy-3,4,6,8,9,9a-hexahydro-1H-pyrido[1,2-a]pyrazin-2-yl]methanone;
[2-chloro-3-(2-oxa-6-azaspiro[3.3]heptan-6-yl)phenyl]-[rac-(7R,9aS)-7-(4-chlorophenyl)-7-hydroxy-3,4,6,8,9,9a-hexahydro-1H-pyrido[1,2-a]pyrazin-2-yl]methanone;
(2-chloro-3-methoxyphenyl)-[rac-(7R,9aR)-7-(4-chlorophenyl)-7-fluoro-3,4,6,8,9,9a-hexahydro-1H-pyrido[1,2-a]pyrazin-2-yl]methanone;
(2-chloro-3-methoxyphenyl)-[rac-(7R,9aS)-7-(4-chlorophenyl)-7-fluoro-3,4,6,8,9,9a-hexahydro-1H-pyrido[1,2-a]pyrazin-2-yl]methanone;
(2-chloro-3-methoxyphenyl)-[rac-(7R,9aR)-7-(4-chlorophenyl)-7-methoxy-3,4,6,8,9,9a-hexahydro-1H-pyrido[1,2-a]pyrazin-2-yl]methanone;
(2-chloro-3-methoxyphenyl)-[rac-(7R,9aS)-7-(4-chlorophenyl)-7-methoxy-3,4,6,8,9,9a-hexahydro-1H-pyrido[1,2-a]pyrazin-2-yl]methanone;
(2-chloro-3-methoxyphenyl)-[rac-(7R,9aS)-7-methyl-1,3,4,6,7,8,9,9a-octahydropyrido[1,2-a]pyrazin-2-yl]methanone;
(2-chloro-3-methoxyphenyl)-[rac-(7R,9aR)-7-methyl-1,3,4,6,7,8,9,9a-octahydropyrido[1,2-a]pyrazin-2-yl]methanone;
(2-chloro-3-methoxyphenyl)-[rac-(7R,9aS)-7-(2-methylpropoxy)-1,3,4,6,7,8,9,9a-octahydropyrido[1,2-a]pyrazin-2-yl]methanone; and
(1,3-dimethylthieno[2,3-c]pyrazol-5-yl)-[rac-(7R,9aR)-7-(3-chloro-4-fluorophenyl)-1,3,4,6,7,8,9,9a-octahydropyrido[1,2-a]pyrazin-2-yl]methanone;
or a pharmaceutically acceptable salt thereof.

23. The compound of claim 1, selected from the group consisting of:

[(7R,9aR)-7-(4-chlorophenyl)-1,3,4,6,7,8,9,9a-octahydropyrido[1,2-a]pyrazin-2-yl]-(3-phenoxyphenyl)methanone;
[(7R,9aR)-7-(4-chlorophenyl)-1,3,4,6,7,8,9,9a-octahydropyrido[1,2-a]pyrazin-2-yl]-(2-chloro-3-methylphenyl)methanone;
[(7R,9aR)-7-(4-chlorophenyl)-1,3,4,6,7,8,9,9a-octahydropyrido[1,2-a]pyrazin-2-yl]-(2-bromo-3-methoxyphenyl)methanone;
[(7R,9aR)-7-(4-chlorophenyl)-1,3,4,6,7,8,9,9a-octahydropyrido[1,2-a]pyrazin-2-yl]-(2-bromo-3-methoxyphenyl)methanone;hydrochloride;
[(7R,9aR)-7-(4-chlorophenyl)-1,3,4,6,7,8,9,9a-octahydropyrido[1,2-a]pyrazin-2-yl]-[3-(3,5-difluorophenoxy)phenyl]methanone;
[(7R,9aR)-7-phenyl-1,3,4,6,7,8,9,9a-octahydropyrido[1,2-a]pyrazin-2-yl]-(2-bromo-3-methoxyphenyl)methanone;
[(7R,9aR)-7-(4-chlorophenyl)-1,3,4,6,7,8,9,9a-octahydropyrido[1,2-a]pyrazin-2-yl]-(2-chloro-3-methoxyphenyl)methanone;
[(7R,9aR)-7-(4-chlorophenyl)-1,3,4,6,7,8,9,9a-octahydropyrido[1,2-a]pyrazin-2-yl]-(2-methoxyphenyl)methanone;
[(7R,9aR)-7-(4-chlorophenyl)-1,3,4,6,7,8,9,9a-octahydropyrido[1,2-a]pyrazin-2-yl]-[2-(trifluoromethoxy)phenyl]methanone;
[(7R,9aR)-7-(4-chlorophenyl)-1,3,4,6,7,8,9,9a-octahydropyrido[1,2-a]pyrazin-2-yl]-(2,3-dihydro-1-benzofuran-7-yl)methanone;
[(7R,9aR)-7-(4-chlorophenyl)-1,3,4,6,7,8,9,9a-octahydropyrido[1,2-a]pyrazin-2-yl]-(1H-indol-4-yl)methanone;
[(7R,9aR)-7-(4-chlorophenyl)-1,3,4,6,7,8,9,9a-octahydropyrido[1,2-a]pyrazin-2-yl]-(2-chloro-6-fluorophenyl)methanone;
[(7R,9aR)-7-(4-chlorophenyl)-1,3,4,6,7,8,9,9a-octahydropyrido[1,2-a]pyrazin-2-yl]-(2-chlorophenyl)methanone;
[(7R,9aR)-7-(4-chlorophenyl)-1,3,4,6,7,8,9,9a-octahydropyrido[1,2-a]pyrazin-2-yl]-(2-fluoro-3-methylphenyl)methanone;
[(7R,9aR)-7-(4-chlorophenyl)-1,3,4,6,7,8,9,9a-octahydropyrido[1,2-a]pyrazin-2-yl]-(4-chloro-1H-pyrrolo[2,3-b]pyridin-5-yl)methanone;
[(7R,9aR)-7-(4-chlorophenyl)-1,3,4,6,7,8,9,9a-octahydropyrido[1,2-a]pyrazin-2-yl]-(1H-pyrrolo[2,3-b]pyridin-4-yl)methanone;
[(7R,9aR)-7-(4-chlorophenyl)-1,3,4,6,7,8,9,9a-octahydropyrido[1,2-a]pyrazin-2-yl]-[2-chloro-3-(trifluoromethyl)phenyl]methanone;
[(7R,9aR)-7-(4-chlorophenyl)-1,3,4,6,7,8,9,9a-octahydropyrido[1,2-a]pyrazin-2-yl]-(2-chloro-4-fluoro-3-methylphenyl)methanone;
[(7R,9aR)-7-(4-chlorophenyl)-1,3,4,6,7,8,9,9a-octahydropyrido[1,2-a]pyrazin-2-yl]-(3-chloro-2-methylphenyl)methanone;
[(7R,9aR)-7-(4-chlorophenyl)-1,3,4,6,7,8,9,9a-octahydropyrido[1,2-a]pyrazin-2-yl]-(4-chloro-6-methylpyridin-3-yl)methanone;
[(7R,9aR)-7-(4-chlorophenyl)-1,3,4,6,7,8,9,9a-octahydropyrido[1,2-a]pyrazin-2-yl]-(2,4-dimethyl-1,3-benzothiazol-5-yl)methanone;
[(7R,9aR)-7-(4-chlorophenyl)-1,3,4,6,7,8,9,9a-octahydropyrido[1,2-a]pyrazin-2-yl]-(7-chloro-2-methylsulfanyl-[1,3]thiazolo[5,4-b]pyridin-6-yl)methanone;

[(7R,9aR)-7-(4-chlorophenyl)-1,3,4,6,7,8,9,9a-octahydropyrido[1,2-a]pyrazin-2-yl]-(1-benzothiophen-4-yl)methanone;
[(7R,9aR)-7-(4-chlorophenyl)-1,3,4,6,7,8,9,9a-octahydropyrido[1,2-a]pyrazin-2-yl]-(2-bromo-3-methylphenyl)methanone;
[(7R,9aR)-7-(4-chlorophenyl)-1,3,4,6,7,8,9,9a-octahydropyrido[1,2-a]pyrazin-2-yl]-[2-(trifluoromethyl)phenyl]methanone;
[(7R,9aR)-7-(4-chlorophenyl)-1,3,4,6,7,8,9,9a-octahydropyrido[1,2-a]pyrazin-2-yl]-(2-chloro-3-phenoxyphenyl)methanone;
[(7R,9aR)-7-phenyl-1,3,4,6,7,8,9,9a-octahydropyrido[1,2-a]pyrazin-2-yl]-(2-chloro-3-methylphenyl)methanone;
[(7R,9aR)-7-phenyl-1,3,4,6,7,8,9,9a-octahydropyrido[1,2-a]pyrazin-2-yl]-(2-chloro-3-methylphenyl)methanone;hydrochloride;
[(7R,9aR)-7-phenyl-1,3,4,6,7,8,9,9a-octahydropyrido[1,2-a]pyrazin-2-yl]-(2-chloro-5-fluoro-3-methylphenyl)methanone;
[(7R,9aR)-7-phenyl-1,3,4,6,7,8,9,9a-octahydropyrido[1,2-a]pyrazin-2-yl]-[2-bromo-3-(methoxymethyl)phenyl]methanone;
[(7R,9aR)-7-phenyl-1,3,4,6,7,8,9,9a-octahydropyrido[1,2-a]pyrazin-2-yl]-(1H-indol-4-yl)methanone;
[(7R,9aR)-7-phenyl-1,3,4,6,7,8,9,9a-octahydropyrido[1,2-a]pyrazin-2-yl]-(1-methylindol-4-yl)methanone;
[(7R,9aR)-7-phenyl-1,3,4,6,7,8,9,9a-octahydropyrido[1,2-a]pyrazin-2-yl]-(4-chloro-1H-pyrrolo[2,3-b]pyridin-5-yl)methanone;
[(7R,9aR)-7-phenyl-1,3,4,6,7,8,9,9a-octahydropyrido[1,2-a]pyrazin-2-yl]-(2-chloro-3-hydroxyphenyl)methanone;
[(7R,9aR)-7-phenyl-1,3,4,6,7,8,9,9a-octahydropyrido[1,2-a]pyrazin-2-yl]-(3-methylthieno[3,2-c]pyridin-7-yl)methanone;
[(7R,9aR)-7-phenyl-1,3,4,6,7,8,9,9a-octahydropyrido[1,2-a]pyrazin-2-yl]-(1-methyl-2,3-dihydroindol-4-yl)methanone;
[(7R,9aR)-7-phenyl-1,3,4,6,7,8,9,9a-octahydropyrido[1,2-a]pyrazin-2-yl]-(1-propan-2-ylindol-4-yl)methanone;
[(7R,9aR)-7-phenyl-1,3,4,6,7,8,9,9a-octahydropyrido[1,2-a]pyrazin-2-yl]-(2-chloro-3-propan-2-yloxyphenyl)methanone;hydrochloride;
3-[(7R,9aR)-7-phenyl-1,3,4,6,7,8,9,9a-octahydropyrido[1,2-a]pyrazine-2-carbonyl]-2-chlorobenzonitrile;
[(7R,9aR)-7-phenyl-1,3,4,6,7,8,9,9a-octahydropyrido[1,2-a]pyrazin-2-yl]-(4-chloro-1-methylpyrrolo[2,3-b]pyridin-5-yl)methanone;
[(7R,9aR)-7-phenyl-1,3,4,6,7,8,9,9a-octahydropyrido[1,2-a]pyrazin-2-yl]-[2-chloro-3-[(1-methylpyrazol-4-yl)methoxy]phenyl]methanone;
[(7R,9aR)-7-phenyl-1,3,4,6,7,8,9,9a-octahydropyrido[1,2-a]pyrazin-2-yl]-(4-chloro-1-propan-2-ylpyrrolo[2,3-b]pyridin-5-yl)methanone;
[(7S,9aS)-7-(4-chlorophenyl)-1,3,4,6,7,8,9,9a-octahydropyrido[1,2-a]pyrazin-2-yl]-(2-bromo-3-methoxyphenyl)methanone;
[(7R,9aR)-7-phenyl-1,3,4,6,7,8,9,9a-octahydropyrido[1,2-a]pyrazin-2-yl]-(4-chloro-1H-pyrazolo[3,4-b]pyridin-5-yl)methanone;
[(7R,9aR)-7-phenyl-1,3,4,6,7,8,9,9a-octahydropyrido[1,2-a]pyrazin-2-yl]-(1-benzofuran-4-yl)methanone;
[(7R,9aR)-7-phenyl-1,3,4,6,7,8,9,9a-octahydropyrido[1,2-a]pyrazin-2-yl]-(3-chloro-2-methoxypyridin-4-yl)methanone;
[(7R,9aR)-7-(4-chlorophenyl)-1,3,4,6,7,8,9,9a-octahydropyrido[1,2-a]pyrazin-2-yl]-(4-chloro-1-methylpyrrolo[2,3-b]pyridin-5-yl)methanone;
[(7R,9aR)-7-phenyl-1,3,4,6,7,8,9,9a-octahydropyrido[1,2-a]pyrazin-2-yl]-[2-chloro-3-(1,3-thiazol-4-ylmethoxy)phenyl]methanone;
4-[[3-[(7R,9aR)-7-phenyl-1,3,4,6,7,8,9,9a-octahydropyrido[1,2-a]pyrazine-2-carbonyl]-2-chlorophenoxy]methyl]-N-methylbenzamide;
[(7R,9aR)-7-(4-chlorophenyl)-1,3,4,6,7,8,9,9a-octahydropyrido[1,2-a]pyrazin-2-yl]-(4-chloro-1-methylpyrazolo[3,4-b]pyridin-5-yl)methanone;
[(7R,9aR)-7-(3,4-dichlorophenyl)-1,3,4,6,7,8,9,9a-octahydropyrido[1,2-a]pyrazin-2-yl]-(2-bromo-3-methoxyphenyl)methanone;
[(7S,9aS)-7-(3,4-dichlorophenyl)-1,3,4,6,7,8,9,9a-octahydropyrido[1,2-a]pyrazin-2-yl]-(2-bromo-3-methoxyphenyl)methanone;
[(7R,9aR)-7-(4-chlorophenyl)-1,3,4,6,7,8,9,9a-octahydropyrido[1,2-a]pyrazin-2-yl]-[2-chloro-3-(2,2,2-trifluoroethoxy)phenyl]methanone;
[(7R,9aR)-7-(4-chlorophenyl)-1,3,4,6,7,8,9,9a-octahydropyrido[1,2-a]pyrazin-2-yl]-(6-methoxypyridin-2-yl)methanone;
[(7R,9aR)-7-(4-chlorophenyl)-1,3,4,6,7,8,9,9a-octahydropyrido[1,2-a]pyrazin-2-yl]-imidazo[1,2-a]pyridin-5-ylmethanone;
tert-butyl 4-[[3-[(7R,9aR)-7-phenyl-1,3,4,6,7,8,9,9a-octahydropyrido[1,2-a]pyrazine-2-carbonyl]-2-chlorophenoxy]methyl]pyrazole-1-carboxylate;
[(7R,9aR)-7-phenyl-1,3,4,6,7,8,9,9a-octahydropyrido[1,2-a]pyrazin-2-yl]-[2-chloro-3-(1H-pyrazol-4-ylmethoxy)phenyl]methanone;hydrochloride;
[(7R,9aR)-7-phenyl-1,3,4,6,7,8,9,9a-octahydropyrido[1,2-a]pyrazin-2-yl]-[2-chloro-3-(pyridazin-3-ylmethoxy)phenyl]methanone;
[(7R,9aR)-7-phenyl-1,3,4,6,7,8,9,9a-octahydropyrido[1,2-a]pyrazin-2-yl]-[2-chloro-3-(pyridin-4-ylmethoxy)phenyl]methanone;
[(7R,9aR)-7-phenyl-1,3,4,6,7,8,9,9a-octahydropyrido[1,2-a]pyrazin-2-yl]-[2-chloro-3-(pyridin-3-ylmethoxy)phenyl]methanone;
[(7R,9aR)-7-(3-chloro-4-fluorophenyl)-1,3,4,6,7,8,9,9a-octahydropyrido[1,2-a]pyrazin-2-yl]-(2-chloro-3-methoxyphenyl)methanone;
(4-chloro-1H-pyrazolo[3,4-b]pyridin-5-yl)-[rac-(7R,9aR)-7-(3-chloro-4-fluorophenyl)-1,3,4,6,7,8,9,9a-octahydropyrido[1,2-a]pyrazin-2-yl]methanone;
[(7R,9aR)-7-(3-chloro-4-fluorophenyl)-1,3,4,6,7,8,9,9a-octahydropyrido[1,2-a]pyrazin-2-yl]-(4-chloro-1H-pyrazolo[3,4-b]pyridin-5-yl)methanone;
(3-methyl-1H-indazol-5-yl)-[rac-(7R,9aR)-7-(3-chloro-4-fluorophenyl)-1,3,4,6,7,8,9,9a-octahydropyrido[1,2-a]pyrazin-2-yl]methanone;
[(7R,9aR)-7-(3-chloro-4-fluorophenyl)-1,3,4,6,7,8,9,9a-octahydropyrido[1,2-a]pyrazin-2-yl]-(3-methyl-1H-indazol-5-yl)methanone;
[(7R,9aR)-7-(3-chloro-4-fluorophenyl)-1,3,4,6,7,8,9,9a-octahydropyrido[1,2-a]pyrazin-2-yl]-(4-chlorothieno[2,3-b]pyridin-5-yl)methanone;
[(7R,9aR)-7-(3-chloro-4-fluorophenyl)-1,3,4,6,7,8,9,9a-octahydropyrido[1,2-a]pyrazin-2-yl]-[2-chloro-3-(difluoromethoxy)phenyl]methanone;

(4-chloro-3-methyl-1H-indazol-5-yl)-[rac-(7R,9aR)-7-(3-chloro-4-fluorophenyl)-1,3,4,6,7,8,9,9a-octahydro-pyrido[1,2-a]pyrazin-2-yl]methanone;
(4-chloro-3-methyl-1H-indazol-5-yl)-[rac-(7R,9aS)-7-(4-chlorophenyl)-7-hydroxy-3,4,6,8,9,9a-hexahydro-1H-pyrido[1,2-a]pyrazin-2-yl]methanone;
[(7S,9aR)-7-(4-chlorophenyl)-7-hydroxy-3,4,6,8,9,9a-hexahydro-1H-pyrido[1,2-a]pyrazin-2-yl]-(4-chloro-3-methyl-1H-indazol-5-yl)methanone;
(2-chloro-3-methoxyphenyl)-[rac-(7R,9aR)-7-(4-chlorophenyl)-7-hydroxy-3,4,6,8,9,9a-hexahydro-1H-pyrido[1,2-a]pyrazin-2-yl]methanone;
[(7S,9aR)-7-(4-chlorophenyl)-7-hydroxy-3,4,6,8,9,9a-hexahydro-1H-pyrido[1,2-a]pyrazin-2-yl]-(2-chloro-3-methoxyphenyl)methanone;
[2-chloro-3-(difluoromethoxy)phenyl]-[rac-(7R,9aS)-7-(4-chlorophenyl)-7-hydroxy-3,4,6,8,9,9a-hexahydro-1H-pyrido[1,2-a]pyrazin-2-yl]methanone;
[2-chloro-3-(2-oxa-6-azaspiro[3.3]heptan-6-yl)phenyl]-[rac-(7R,9aS)-7-(4-chlorophenyl)-7-hydroxy-3,4,6,8,9,9a-hexahydro-1H-pyrido[1,2-a]pyrazin-2-yl]methanone;
(2-chloro-3-methoxyphenyl)-[rac-(7R,9aS)-7-(4-chlorophenyl)-7-fluoro-3,4,6,8,9,9a-hexahydro-1H-pyrido[1,2-a]pyrazin-2-yl]methanone; and
(2-chloro-3-methoxyphenyl)-[rac-(7R,9aS)-7-(4-chlorophenyl)-7-methoxy-3,4,6,8,9,9a-hexahydro-1H-pyrido[1,2-a]pyrazin-2-yl]methanone;
or a pharmaceutically acceptable salt thereof.

24. The compound of claim 1, selected from the group consisting of:
[(7R,9aR)-7-(4-chlorophenyl)-1,3,4,6,7,8,9,9a-octahydropyrido[1,2-a]pyrazin-2-yl]-(2-chloro-3-methylphenyl)methanone;
[(7R,9aR)-7-(4-chlorophenyl)-1,3,4,6,7,8,9,9a-octahydropyrido[1,2-a]pyrazin-2-yl]-(2-bromo-3-methoxyphenyl)methanone;
[(7R,9aR)-7-(4-chlorophenyl)-1,3,4,6,7,8,9,9a-octahydropyrido[1,2-a]pyrazin-2-yl]-(2-chloro-3-methoxyphenyl)methanone;
[(7R,9aR)-7-(4-chlorophenyl)-1,3,4,6,7,8,9,9a-octahydropyrido[1,2-a]pyrazin-2-yl]-(1H-indol-4-yl)methanone
[(7R,9aR)-7-(4-chlorophenyl)-1,3,4,6,7,8,9,9a-octahydropyrido[1,2-a]pyrazin-2-yl]-(4-chloro-1H-pyrrolo[2,3-b]pyridin-5-yl)methanone
[(7R,9aR)-7-(4-chlorophenyl)-1,3,4,6,7,8,9,9a-octahydropyrido[1,2-a]pyrazin-2-yl]-(1H-pyrrolo[2,3-b]pyridin-4-yl)methanone
[(7R,9aR)-7-(4-chlorophenyl)-1,3,4,6,7,8,9,9a-octahydropyrido[1,2-a]pyrazin-2-yl]-(2-chloro-4-fluoro-3-methylphenyl)methanone
[(7R,9aR)-7-(4-chlorophenyl)-1,3,4,6,7,8,9,9a-octahydropyrido[1,2-a]pyrazin-2-yl]-(2,4-dimethyl-1,3-benzothiazol-5-yl)methanone
[(7R,9aR)-7-(4-chlorophenyl)-1,3,4,6,7,8,9,9a-octahydropyrido[1,2-a]pyrazin-2-yl]-(7-chloro-2-methylsulfanyl-[1,3]thiazolo[5,4-b]pyridin-6-yl)methanone
[(7R,9aR)-7-(4-chlorophenyl)-1,3,4,6,7,8,9,9a-octahydropyrido[1,2-a]pyrazin-2-yl]-(2-bromo-3-methylphenyl)methanone
[(7R,9aR)-7-phenyl-1,3,4,6,7,8,9,9a-octahydropyrido[1,2-a]pyrazin-2-yl]-(2-chloro-3-methylphenyl)methanone
[(7R,9aR)-7-(4-chlorophenyl)-1,3,4,6,7,8,9,9a-octahydropyrido[1,2-a]pyrazin-2-yl]-(4-chloro-1-methylpyrrolo[2,3-b]pyridin-5-yl)methanone
[(7R,9aR)-7-phenyl-1,3,4,6,7,8,9,9a-octahydropyrido[1,2-a]pyrazin-2-yl]-[2-chloro-3-(1,3-thiazol-4-yl-methoxy)phenyl]methanone
[(7R,9aR)-7-(4-chlorophenyl)-1,3,4,6,7,8,9,9a-octahydropyrido[1,2-a]pyrazin-2-yl]-(4-chloro-1-methylpyrazolo[3,4-b]pyridin-5-yl)methanone
[(7R,9aR)-7-(3,4-dichlorophenyl)-1,3,4,6,7,8,9,9a-octahydropyrido[1,2-a]pyrazin-2-yl]-(2-bromo-3-methoxyphenyl)methanone
[(7S,9aS)-7-(3,4-dichlorophenyl)-1,3,4,6,7,8,9,9a-octahydropyrido[1,2-a]pyrazin-2-yl]-(2-bromo-3-methoxyphenyl)methanone
[(7R,9aR)-7-(4-chlorophenyl)-1,3,4,6,7,8,9,9a-octahydropyrido[1,2-a]pyrazin-2-yl]-[2-chloro-3-(2,2,2-trifluoroethoxy)phenyl]methanone; and
[(7R,9aR)-7-phenyl-1,3,4,6,7,8,9,9a-octahydropyrido[1,2-a]pyrazin-2-yl]-[2-chloro-3-(1H-pyrazol-4-yl-methoxy)phenyl]methanone;hydrochloride;
or a pharmaceutically acceptable salt thereof.

25. A process of manufacturing a compound of claim 1, or a pharmaceutically acceptable salt thereof, comprising the steps of:

a) reacting an amine 13, wherein $R^2$, $R^3$, $R^4$, $R^5$, $R^6$ and $R^7$ are as described in claim 1,

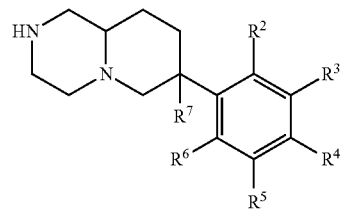

with an acid 14, wherein $R^1$ is as described in claim 1,

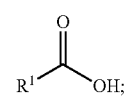

or b) reacting an amine 13, wherein $R^2$, $R^3$, $R^4$, $R^5$, $R^6$ and $R^7$ are as described in claim 1,

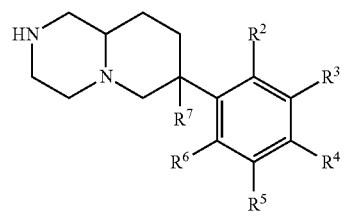

with an acid chloride 15, wherein $R^1$ is as described in claim 1,

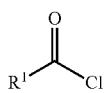

to form said compound, or a pharmaceutically acceptable salt thereof.

26. A compound of claim 1, or a pharmaceutically acceptable salt thereof, when manufactured according to the process comprising the steps of:
b) reacting an amine 13, wherein $R^2$, $R^3$, $R^4$, $R^5$, $R^6$ and $R^7$ are as described in claim 1,

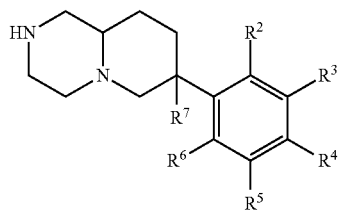

with an acid 14, wherein $R^1$ is as described in claim 1,

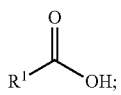

or
b) reacting an amine 13, wherein $R^2$, $R^3$, $R^4$, $R^5$, $R^6$ and $R^7$ are as described in claim 1,

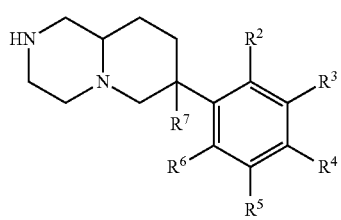

with an acid chloride 15, wherein $R^1$ is as described in claim 1,

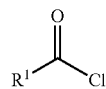

to form said compound, or a pharmaceutically acceptable salt thereof.

27. The compound of claim 1, or a pharmaceutically acceptable salt thereof, wherein said compound or pharmaceutically acceptable salt thereof has an $IC_{50}$ for monoacylglycerol lipase below 10 μM.

28. A pharmaceutical composition comprising:
  (i) a compound of claim 1, or a pharmaceutically acceptable salt thereof; and
  (ii) a therapeutically inert carrier.

29. A method for treating a disorder or condition in a mammal in need thereof, comprising administering an effective amount of a compound of claim 1, or a pharmaceutically acceptable salt thereof, to the mammal, wherein the disorder or condition is a neurodegenerative disease, wherein the neurodegenerative disease is multiple sclerosis, Alzheimer's disease, Parkinson's disease, amyotrophic lateral sclerosis, traumatic brain injury, neurotoxicity, stroke, or epilepsy.

30. The method of claim 29, wherein the mammal is a human.

* * * * *